(12) United States Patent
Simon et al.

(10) Patent No.: US 12,152,075 B2
(45) Date of Patent: Nov. 26, 2024

(54) TREATMENT OF RENAL CELL CARCINOMA

(71) Applicant: Bristol-Myers Squibb Company, Princeton, NJ (US)

(72) Inventors: Jason Samuel Simon, Westfield, NJ (US); Petra B. Ross-Macdonald, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 406 days.

(21) Appl. No.: 17/372,208

(22) Filed: Jul. 9, 2021

(65) Prior Publication Data

US 2022/0002413 A1     Jan. 6, 2022

Related U.S. Application Data

(63) Continuation-in-part of application No. 15/577,661, filed as application No. PCT/US2016/034875 on May 27, 2016, now Pat. No. 11,078,278.

(60) Provisional application No. 62/216,265, filed on Sep. 9, 2015, provisional application No. 62/168,456, filed on May 29, 2015.

(51) Int. Cl.
| | |
|---|---|
| C07K 16/28 | (2006.01) |
| A61K 39/395 | (2006.01) |
| A61P 1/00 | (2006.01) |
| A61P 31/00 | (2006.01) |
| A61P 35/00 | (2006.01) |
| C07K 14/705 | (2006.01) |
| A61K 39/00 | (2006.01) |

(52) U.S. Cl.
CPC .... *C07K 16/2818* (2013.01); *A61K 39/39533* (2013.01); *A61K 39/39558* (2013.01); *A61P 1/00* (2018.01); *A61P 31/00* (2018.01); *A61P 35/00* (2018.01); *C07K 14/70503* (2013.01); *C07K 14/70521* (2013.01); *C07K 14/7056* (2013.01); *C07K 14/70575* (2013.01); *C07K 14/70578* (2013.01); *C07K 16/2803* (2013.01); *A61K 2039/505* (2013.01); *A61K 2039/507* (2013.01); *A61K 2039/545* (2013.01); *A61K 2039/55* (2013.01); *C07K 2317/21* (2013.01); *C07K 2317/76* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,952,199 A | 9/1999 | Davis-Smyth et al. | |
| 5,977,318 A | 11/1999 | Linsley et al. | |
| 6,051,227 A | 4/2000 | Allison et al. | |
| 6,682,736 B1 | 1/2004 | Hanson et al. | |
| 6,808,710 B1 | 10/2004 | Wood et al. | |
| 6,984,720 B1 | 1/2006 | Korman et al. | |
| 7,034,121 B2 | 4/2006 | Carreno et al. | |
| 7,169,901 B2 | 1/2007 | Baca et al. | |
| 7,297,334 B2 | 11/2007 | Baca et al. | |
| 7,423,125 B2 | 9/2008 | Alitalo et al. | |
| 7,488,802 B2 | 2/2009 | Collins et al. | |
| 7,498,414 B2 | 3/2009 | Zhu | |
| 7,595,048 B2 | 9/2009 | Honjo et al. | |
| 7,605,238 B2 | 10/2009 | Korman et al. | |
| 7,943,743 B2 | 5/2011 | Korman et al. | |
| 7,972,596 B2 | 7/2011 | Wu et al. | |
| 8,008,449 B2 | 8/2011 | Korman et al. | |
| 8,034,905 B2 | 10/2011 | Kavile et al. | |
| 8,168,179 B2 | 5/2012 | Honjo et al. | |
| 8,168,757 B2 | 5/2012 | Finnefrock et al. | |
| 8,217,149 B2 | 7/2012 | Irving et al. | |
| 8,354,509 B2 | 1/2013 | Carven et al. | |
| 8,383,796 B2 | 2/2013 | Korman et al. | |
| 8,609,089 B2 | 12/2013 | Langermann et al. | |
| 8,728,474 B2 | 5/2014 | Honjo et al. | |
| 8,779,105 B2 | 7/2014 | Korman et al. | |
| 8,779,108 B2 | 7/2014 | Queva et al. | |
| 8,900,587 B2 | 12/2014 | Carven et al. | |
| 9,067,999 B1 | 6/2015 | Honjo et al. | |
| 9,073,994 B2 | 7/2015 | Honjo et al. | |

(Continued)

FOREIGN PATENT DOCUMENTS

| | | |
|---|---|---|
| WO | WO-0044777 A1 | 8/2000 |
| WO | WO-2004004771 A1 | 1/2004 |

(Continued)

OTHER PUBLICATIONS

Abbas, A.R., et al., "Immune Response in Silica (IRIS): Immune-Specific Genes Identified from a Compendium of Microarray Expression Data," Genes & Immunity 6(4):319-331, Nature Pub. Group, England (Jun. 2005).

Ascierto, P.A., et al., "Biomarkers for Immunostimulatory Monoclonal Antibodies in Combination Strategies for Melanoma and Other Tumor Types," Clinical Cancer Research 19(5):1009-1020, The Association, United States (Mar. 2013).

Ascierto, P.A., et al., "The Additional Facet of Immunoscore: Immunoprofiling as a Possible Predictive Tool for Cancer Treatment," Journal of Translational Medicine 11:54, BioMed Central, England (Mar. 2013).

Brahmer, J.R., et al., "Safety and Activity of Anti-PD-L1 Antibody in Patients with Advanced Cancer," The New England Journal of Medicine 366(26):2455-2465, Massachusetts Medical Society, United States (Jun. 2012).

(Continued)

*Primary Examiner* — Ilia I Ouspenski
(74) *Attorney, Agent, or Firm* — Sterne, Kessler, Goldstein & Fox P.L.L.C.

(57) ABSTRACT

This disclosure provides methods for treating a subject afflicted with a tumor derived from a renal cell carcinoma. The methods comprise administering a first dose to a subject of an anti-PD-1 antibody or antigen-binding portion thereof and/or an anti-PD-L1 antibody or antigen-binding portion thereof, and administering a second dose to the subject, wherein the subject exhibited differential expression in one or more biomarker genes, e.g., CTLA-4, TIGIT, and/or PD-L2, following administration of the first dose.

15 Claims, 21 Drawing Sheets

(56) References Cited

U.S. PATENT DOCUMENTS

| | | | |
|---|---|---|---|
| 9,084,776 | B2 | 7/2015 | Korman et al. |
| 9,102,725 | B2 | 8/2015 | Korman et al. |
| 9,212,224 | B2 | 12/2015 | Cogswell et al. |
| 9,273,135 | B2 | 3/2016 | Korman et al. |
| 9,358,289 | B2 | 6/2016 | Korman et al. |
| 9,387,247 | B2 | 7/2016 | Korman et al. |
| 9,393,301 | B2 | 7/2016 | Honjo et al. |
| 9,402,899 | B2 | 8/2016 | Honjo et al. |
| 9,439,962 | B2 | 9/2016 | Honjo et al. |
| 9,492,539 | B2 | 11/2016 | Korman et al. |
| 9,492,540 | B2 | 11/2016 | Korman et al. |
| 9,580,505 | B2 | 2/2017 | Korman et al. |
| 9,580,507 | B2 | 2/2017 | Korman et al. |
| 9,856,320 | B2 | 1/2018 | Cogswell et al. |
| 10,174,113 | B2 | 1/2019 | Yang |
| 11,078,278 | B2 * | 8/2021 | Simon .............. A61K 39/39533 |
| 2012/0263677 | A1 | 10/2012 | Eagle et al. |
| 2013/0017199 | A1 | 1/2013 | Langermann |
| 2013/0309250 | A1 * | 11/2013 | Cogswell ................ A61P 43/00 530/388.2 |
| 2014/0341917 | A1 | 11/2014 | Nastri et al. |
| 2014/0356353 | A1 | 12/2014 | Queva et al. |
| 2015/0079109 | A1 | 3/2015 | Li et al. |
| 2016/0051672 | A1 | 2/2016 | Stewart et al. |
| 2016/0067336 | A1 | 3/2016 | Fandi et al. |
| 2016/0090417 | A1 | 3/2016 | Cogswell et al. |
| 2016/0244521 | A1 | 8/2016 | White et al. |
| 2016/0312295 | A1 | 10/2016 | Ayers et al. |
| 2016/0312297 | A1 | 10/2016 | Ayers et al. |
| 2017/0051060 | A1 | 2/2017 | Honjo et al. |
| 2017/0088615 | A1 | 3/2017 | Korman et al. |
| 2017/0088626 | A1 | 3/2017 | Jure-Kunkel et al. |
| 2017/0158767 | A1 | 6/2017 | Korman et al. |

FOREIGN PATENT DOCUMENTS

| | | |
|---|---|---|
| WO | WO-2007005874 A2 | 1/2007 |
| WO | WO-2007113648 A2 | 10/2007 |
| WO | WO-2012122444 A1 | 9/2012 |
| WO | WO-2012145493 A1 | 10/2012 |
| WO | WO-2013173223 A1 | 11/2013 |
| WO | WO-2015042246 A1 | 3/2015 |
| WO | WO-2015134605 A1 | 9/2015 |
| WO | WO-2016196389 A1 | 12/2016 |

OTHER PUBLICATIONS

Brahmer., J.R., et al., "Phase I Study of Single-agent Anti-programmed Death-1 (MDX-1106) in Refractory Solid Tumors: Safety, Clinical Activity, Pharmacodynamics, and Immunologic Correlates," Journal of Clinical Oncology 28(19):3167-3175, American Society of Clinical Oncology, United States (Jul. 2010).

Brookmeyer, R., et al., "A Confidence Interval for the Median Survival Time," Biometrics 38(1):29-41, International Biometric Society (Mar. 1982).

Brown, J.A., et al., "Blockade of Programmed Death-1 Ligands on Dendritic Cells Enhances T Cell Activation and Cytokine Production," The Journal of Immunology 170(3):1257-1266, The American Association of Immunologists, United States (Feb. 2003).

Carbone, D.P., et al., "A phase III, Randomized, Open-Label Trial of Nivolumab (anti-PD-1; BMS-936558, ONO-4538) Versus Investigator's Choice Chemotherapy (ICC) as First-Line Therapy for Stage IV or Recurrent PD-L1+ Non-Small Cell Lung Cancer (NSCLC)," Journal of Clinical Oncology 32(15) (May 2014).

Chaussabel, D., et al., "A Modular Analysis Framework for Blood Genomics Studies: Application to Systemic Lupus Erythematosus," Immunity 29(1):150-164, Cell Press, United States (Jul. 2008).

Clopper, C.J., et al., "Testing Rating Scale Unidimensionality Using the Principal Component Analysis (PCA)/t-Test Protocol with the Rasch Model: The Primacy of Theory over Statistics," Biometrika 26:404-413 (1934).

Dai, M., et al., "Evolving Gene/transcript Definitions Significantly Alter the Interpretation of Genechip Data," Nucleic Acids Research 33(20):e175, Oxford University Press, England (Nov. 2005).

Debarros, A., et al., "CD70-CD27 Interactions Provide Survival and Proliferative Signals That Regulate T Cell Receptor-driven Activation of Human yo Peripheral Blood Lymphocytes," European Journal of Immunology 41(1):195-201, Wiley-VCH, Germany (Jan. 2011).

Drake., et al., J Clin Oneal 31: 2013, Abstract 4514.

Elhilali, M.M., et al., "Placebo-associated Remissions in a Multicentre, Randomized, Double-blind Trial of Interferon gamma-1b for the Treatment of Metastatic Renal Cell Carcinoma. The Canadian Urologic Oncology Group," BJU International 86(6):613-618, Blackwell Science, England (Oct. 2000).

GenBank, "C-type lectin domain family 2 member B [Homo sapiens]," Accession No. NP_005118.2, accessed at https://www.ncbi.nlm.nih.gov/protein/NP_005118, Feb. 6, 2018.

GenBank, "cytotoxic T-lymphocyte-associated protein 4 [Homo sapiens]," Accession No. AAB59385.1, accessed on https://www.ncbi.nlm.nih.gov/protein/AAB59385, Nov. 1, 1994.

GenBank, "Human hPD-1 (hPD-1) mRNA, complete eds," Accession No. U64863.1, accessed on https://www.ncbi.nlm.nih.gov/nuccore/U64863, Oct. 12, 2005.

GenBank, "MHC class I polypeptide-related sequence B isoform 1 precursor [Homo sapiens]," Accession No. NP_005922.2, accessed at https://www.ncbi.nlm.nih.gov/protein/NP_005922, Apr. 15, 2018.

GenBank, "natural killer cell receptor 2B4 isoform 1 precursor [Homo sapiens]," Accession No. NP_057466.1, accessed at https://www.ncbi.nlm.nih.gov/protein/NP_057466, Apr. 30, 2018.

GenBank, "NK-tumor recognition protein isoform a [Homo sapiens]," Accession No. NP_005376.2, accessed at https://www.ncbi.nlm.nih.gov/protein/NP_005376, Apr. 1, 2018.

GenBank, "programmed cell death 1 ligand 2 precursor [Homo sapiens]," Accession No. NP_079515.2, accessed at https://www.ncbi.nlm.nih.gov/protein/NP_079515, May 1, 2018.

GenBank, "protein NKG7 [Homo sapiens]," Accession No. NP_005592.1, accessed at https://www.ncbi.nlm.nih.gov/protein/NP_005592, Apr. 29, 2018.

GenBank, "RecName: Full=Programmed cell death 1 ligand 1; Short=PD-L1; Short=PDCD1 ligand 1; Short-Programmed death ligand 1; AltName: Full=B7 homolog 1; Short=B7-H1; AltName: CD_antigen-CD274; Flags: Precursor," Accession No. Q9NZQ7.1, accessed on https://www.ncbi.nlm.nih.gov/protein/Q9NZQ7, Nov. 2, 2016.

GenBank, "T-cell immunoreceptor with 1g and ITIM domains precursor [Homo sapiens]," Accession No. NP_776160.2, accessed at https://www.ncbi.nlm.nih.gov/protein/NP_776160, Jan. 18, 2018.

GenBank, "transcription factor PU.1 isoform 1 [Homo sapiens]," Accession No. NP_001074016.1, accessed at https://www.ncbi.nlm.nih.gov/protein/NP_001074016, Mar. 29, 2018.

GenBank, "transmembrane protein PVRIG [Homo sapiens]," Accession No. NP_076975.2, accessed at https://www.ncbi.nlm.nih.gov/protein/NP_076975, Dec. 11, 2017.

GenBank, "tumor necrosis factor ligand superfamily member 13B isoform 1 [Homo sapiens]," Accession No. NP_006564.1, accessed at https://www.ncbi.nlm.nih.gov/protein/NP_006564, Apr. 15, 2018.

GenBank, "tumor necrosis factor ligand superfamily member 8 isoform 1 [Homo sapiens]," Accession No. NP_001235.1, accessed at https://www.ncbi.nlm.nih.gov/protein/NP_001235.1, Apr. 9, 2018.

GenBank, "Tumor Necrosis Factor Ligand Superfamily Member 8 Isoform 2 [Homo sapiens]," Accession NumberNP_001239219.1, accessed at https://www.ncbi.nlm.nih.gov/protein/356582497/, Apr. 9, 2018.

GenBank, "tumor necrosis factor receptor superfamily member 14 isoform 1 precursor [Homo sapiens]," Accession No. NP_003811.2, accessed at https://www.ncbi.nlm.nih.gov/protein/NP_003811, Apr. 9, 2018.

Gupta, K., et al., "Epidemiologic and Socioeconomic Burden of Metastatic Renal Cell Carcinoma (mRCC): A Literature Review," Cancer Treatment Reviews 34(3):193-205, Elsevier, Netherlands (May 2008).

Heng, D.Y., et al., "Prognostic Factors for Overall Survival in Patients with Metastatic Renal Cell Carcinoma Treated with Vas-

(56) References Cited

OTHER PUBLICATIONS cular Endothelial Growth Factor-targeted Agents: Results from a Large, Multicenter Study," Journal of Clinical Oncology 27(34):5794-5799, American Society of Clinical Oncology, United States (Dec. 2009).

Herbst, R.S., et al., "A Study of MPDL3280A, an Engineered PD-L1 Antibody in Patients with Locally Advanced or Metastatic Tumors," Journal of Clinical Oncology 31(Suppl):Abstract 3000, American Society of Clinical Oncology, United States (2013).

Herbst., R.S., et al., "Predictive Correlates of Response to the Anti-PD-L1 Antibody MPDL3280A in Cancer Patients," Nature 515(7528):563-567, Nature Publishing Group, England (Nov. 2014).

Hooi, F.S., et al., "Improved Survival with Ipilimumab in Patients with Metastatic Melanoma," The New England Journal of Medicine 363(8):711-723, Massachusetts Medical Society, United States (Aug. 2010).

Hudes, G., et al., "Temsirolimus, Interferon Alfa, or Both for Advanced Renal-cell Carcinoma," The New England Journal of Medicine 356(22):2271-2281, Massachusetts Medical Society, United States (May 2007).

Inman, B.A., et al., "Novel Immunotherapeutic Strategies in Development for Renal Cell Carcinoma," European Urology 63(5):881-889, Elsevier Science, Switzerland (May 2013).

International Preliminary Report on Patentability, including the Written Opinion of the International Searching Authority, for International Application No. PCT/US2016/034875, mailed on Dec. 5, 2017, 7 pages.

International Search Report and Written Opinion for International Application No. PCT/US2016/034875, mailed on Aug. 19, 2016, 10 pages.

Irizarry, R.A., et al., "Summaries of Affymetrix GeneChip Probe Level Data," Nucleic Acids Research 31(4):e15, Oxford University Press, England (Feb. 2003).

Ji, R.R., et al., "An Immune-Active Tumor Microenvironment Favors Clinical Response to Ipilimumab," Cancer Immunology, Immunotherapy 61(7):1019-1031, Springer International, Germany (Jul. 2012).

Johnson, D.B., et al., "Severe Cutaneous and Neurologic Toxicity in Melanoma Patients during Vemurafenib Administration Following Anti-PD-1 Therapy," Cancer Immunology Research 1(6):373-377, American Association for Cancer Research, United States (Dec. 2013).

Khleif, S., et al., "MED14736, An Anti-PD-L1 Antibody with Modified Fe Domain: Preclinical Evaluation and Early Clinical Results from a Phase 1 Study in Patients with Advanced Solid Tumors," Abstract 802, in Proceedings from the European Cancer Congress 2013, Amsterdam, The Netherlands (Sep. 27-Oct. 1, 2013).

Motzer, R.J., et al., "Nivolumab for Metastatic Renal Cell Carcinoma (mRCC): Results of a Randomized, Dose-ranging Phase II Trial," Journal of Clinical Oncology 32:5s, (Suppl; Abstract 5009, Clinical Science Symposium) (May 2014).

Motzer, R.J., et al., "Efficacy of Everolimus in Advanced Renal Cell Carcinoma: A Double-blind, Randomised, Placebo-controlled Phase III Trial," Lancet 372(9637):449-456, Elsevier, England (Aug. 2008).

Mulders, P., "Vascular Endothelial Growth Factor and mTOR Pathways in Renal Cell Carcinoma: Differences and Synergies of Two Targeted Mechanisms," BJU International 104(11):1585-1589, Blackwell Science, England (Dec. 2009).

NCI Drug Dictionary, anti-PD-1 Fusion Protein AMP-224, accessed on Dec. 14, 2014, retrieved from the Internet URL: https://www.cancer.gov/publications/dictionaries/cancer-drug?cdrid=700595.

NCI Drug Dictionary, anti-PD-1 monoclonal antibody MEDI0680, accessed on Dec. 14, 2014, retrieved from the Internet URL: https://www.cancer.gov/publications/dictionaries/cancer-drug?cdrid=756047.

NCI Drug Dictionary, pembrolizumab, accessed on Dec. 14, 2014, retrieved from the Internet URL: https://www.cancer.gov/drugdictionary?cancer-drug?cdrid-695789.

Pei-Show Juo., The Concise Dictionary of Biomedicine and Molecular Biology, 2nd Edition, CRC Press, United States (2002).

Peng, W., et al., "Blockade of the PD-1 Pathway Enhances the Efficacy of Adoptive Cell Therapy against Cancer," Oncoimmunology 2(2):e22691, Taylor & Francis, United States (Feb. 2013).

Philips, G.K. and Atkins, M., "Therapeutic Uses of Anti-PD-1 and Anti-PD-L1 Antibodies," International Immunology 27(1):39-46, Oxford University Press, England (Jan. 2015).

Wolchok, J.D., et al., "Nivolumab Plus Ipilimumab in Advanced Melanoma," The New England Journal of Medicine 369(2):122-133, Massachusetts Medical Society, United States (Jul. 2013).

Rini, B.I., et al., "Phase 1 Dose-escalation Trial of Tremelimumab Plus Sunitinib in Patients with Metastatic Renal Cell Carcinoma," Cancer 117(14):758-767, Wiley, United States (Feb. 2011).

Rizvi, N.A., et al., "Mutational Landscape Determines Sensitivity to PD-1 Blockade in Non-Small Cell Lung Cancer," Science 348(6230):124-128, (Apr. 2015).

Robert, C., et al., "Nivolumab in Previously Untreated Melanoma without BRAF Mutation," The New England Journal of Medicine 372:320-330, (Jan. 2015).

Rodig, N., et al., "Endothelial Expression of PD-L1 and PD-L2 Down Regulates CD8+ T Cell Activation and Cytolysis," European Journal of Immunology 33:3117-3126, (2003).

Siegel, R., et al., "Cancer Statistics, 2014," CA: A Cancer Journal for Clinicians 64(1):9-29, Wiley, United States (Jan. 2014).

Sjoblom, T., et al., "The Consensus Coding Sequences of Human Breast and Colorectal Cancers," Science 314(5797):268-274, American Association for the Advancement of Science, United States (Oct. 2006).

Sznol., et al., J Clin Oneal 32: Jun. 2014, Abstract LBA9003.

Tilford, C.A., et al., "Gene Set Enrichment Analysis," Methods in Molecular Biology 563:99-121, Humana Press, United States (2009).

Topalian, S.L., et al., "Safety, Activity and Immune Correlates of Anti-PD-1 Antibody in Cancer," The New England Journal of Medicine 366(26):2443-2454, Massachusetts Medical Society, United States (Jun. 2012).

Topalian, S.L., et al., "Targeting the PD-1/B7-H1(PD-L1) Pathway to Activate Anti-tumor Immunity," Current Opinion in Immunology 24(2):207-212, Elsevier, England (Apr. 2012).

Tumeh, P.C., et al., "PD-1 blockade induces responses by inhibiting adaptive immune resistance," Nature 515(7528):568-71, Nature Publishing Group, England (Nov. 2014).

Wang, C., et al., "In Vitro Characterization of the Anti-PD-1 Antibody Nivolumab, BMS-936558, and in Vivo Toxicology in Non-human Primates," Cancer Immunology Research 2(9):846-856, American Association for Cancer Research, United States (Sep. 2014).

Winograd, R., et al., "Induction of T-cell Immunity Overcomes Complete Resistance to PD-1 and CTLA-4 Blockade and Improves Survival in Pancreatic Carcinoma," Cancer Immunol Res 3(4):399-411, American Association for Cancer Research, United States (Apr. 2015).

Ji, R.R., et al., "An immune-active tumor microenvironment favors clinical response to ipilimumab," Cancer Immunol Immunother 61(7):1019-1031, Springer Science+Business Media, Germany (Jul. 2012).

Choueiri, T.K., et al., "Immunomodulatory activity of nivolumab in metastatic renal cell carcinoma (mRCC): Association of biomarkers with clinical outcomes," Journal of Clinical Oncology 33(15):Abstract 4500, American Society of Clinical Oncology (May 2015).

Wolchok, J.D., et al., "Nivolumab plus ipilimumab in advanced melanoma," N Engl J Med 369(2):122-133, Massachusetts Medical Society, United States (Jul. 2013).

\* cited by examiner

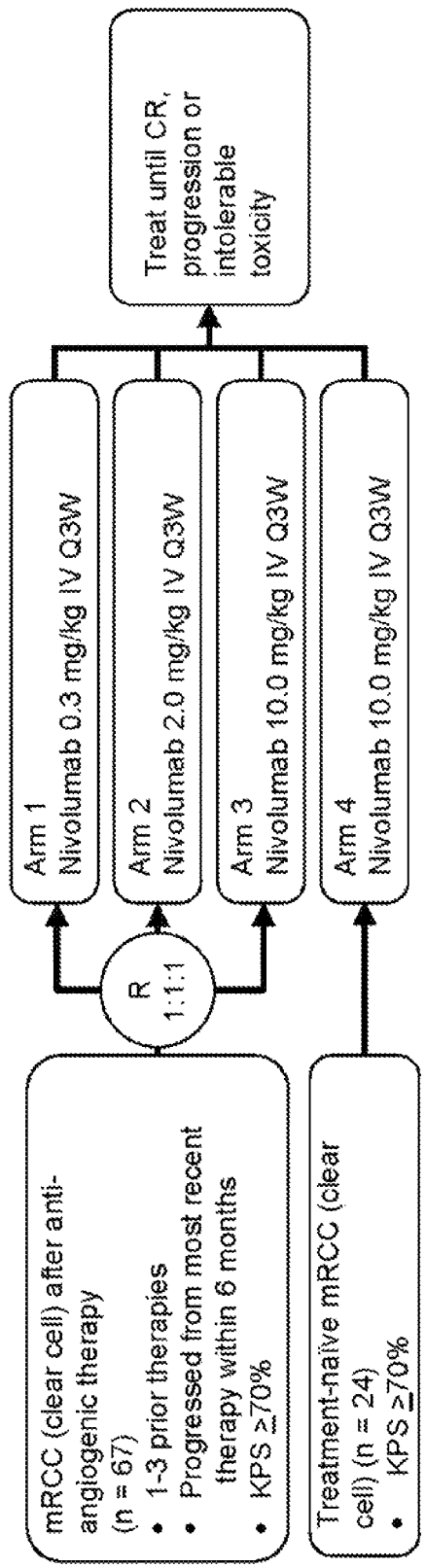
FIG. 1 – Study Design and Objectives

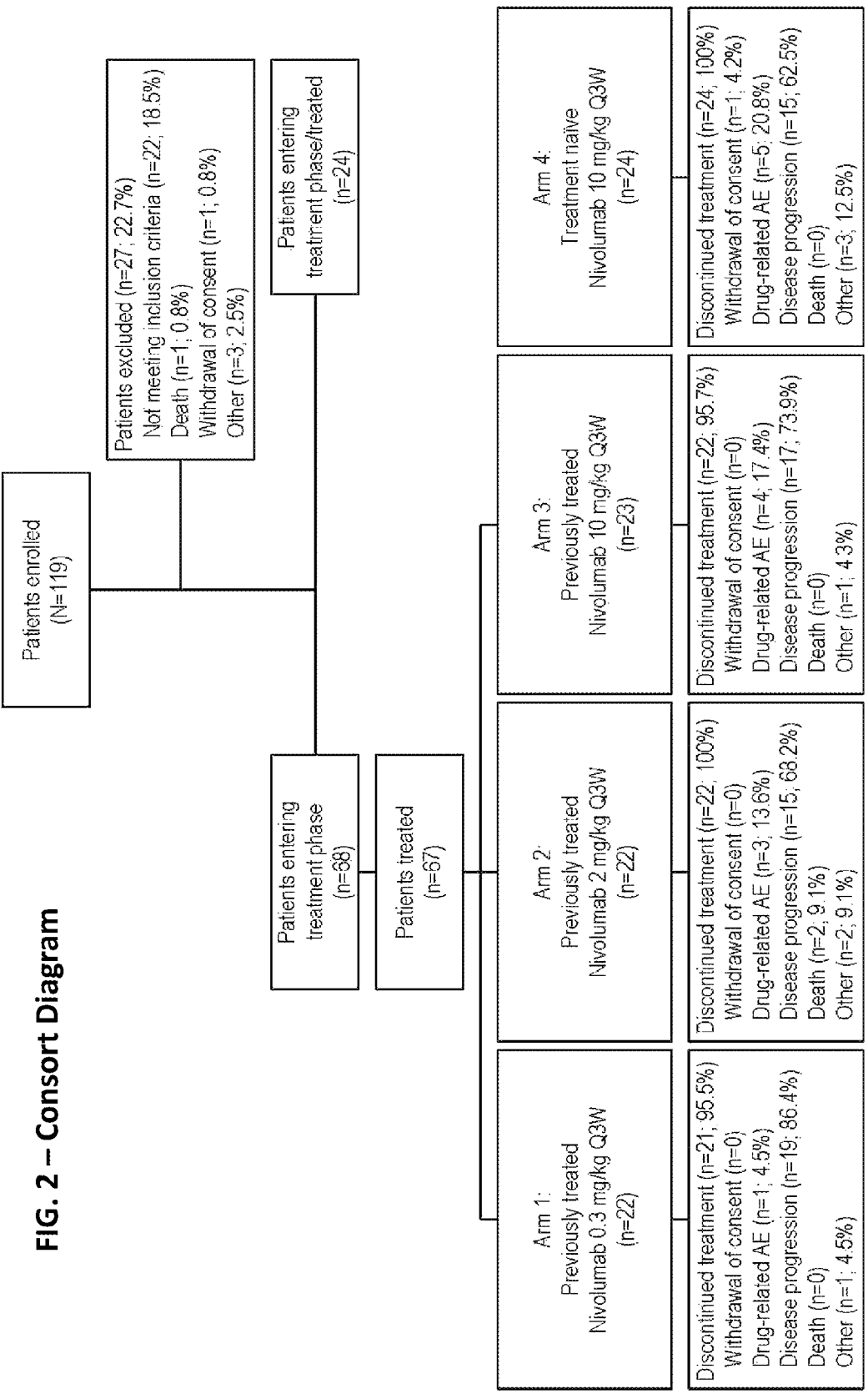
FIG. 2 – Consort Diagram

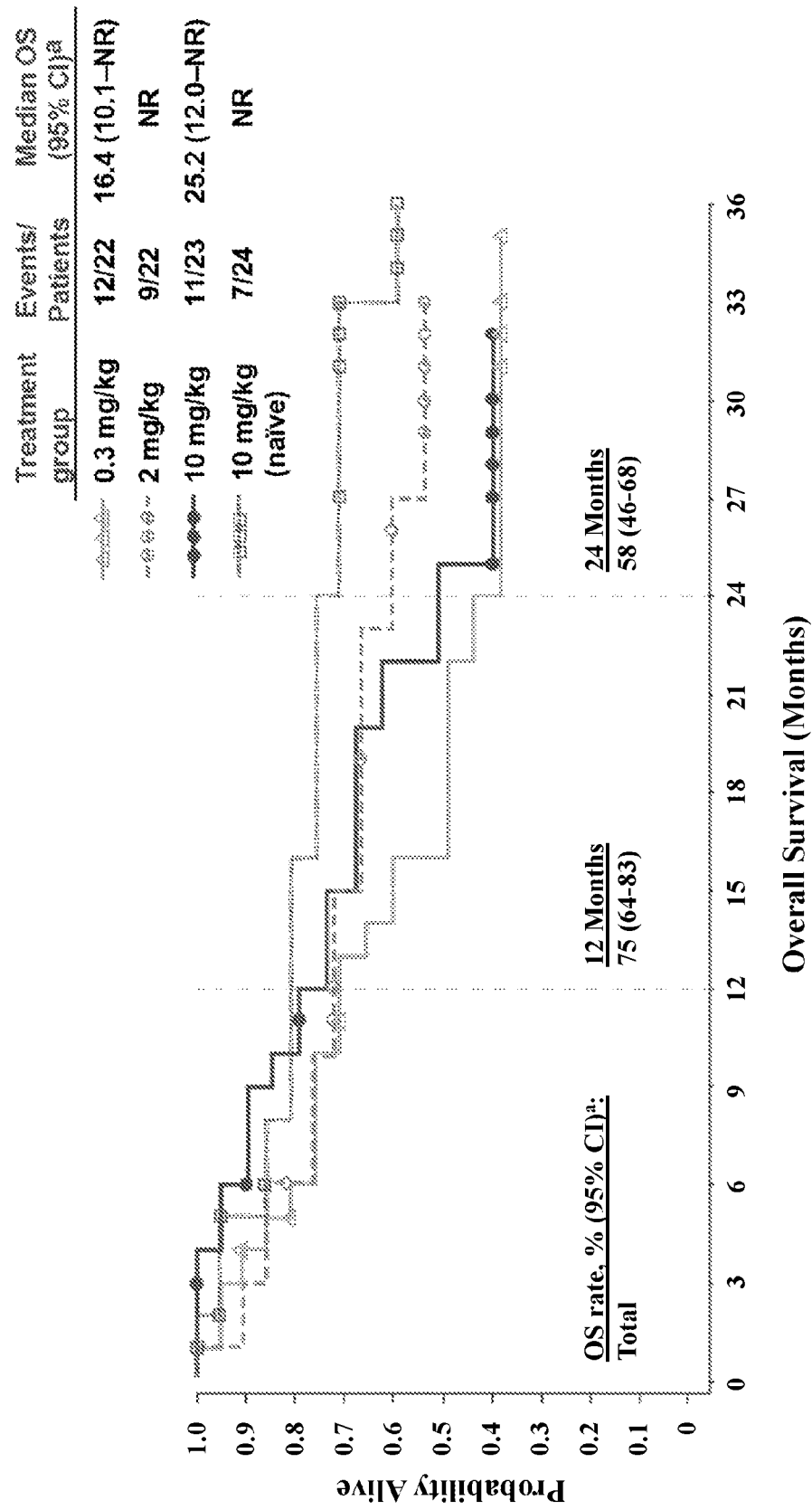

Evaluation of Tumor-Associated Lymphocytes
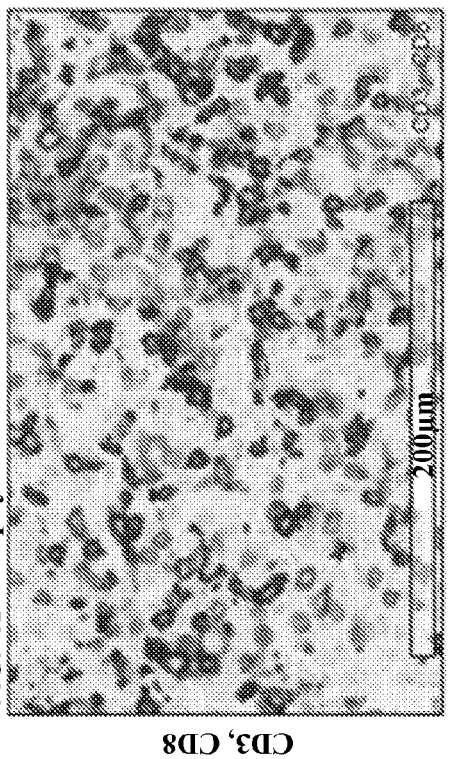
FIG. 4B Biopsy at C2D8 of Nivolumab
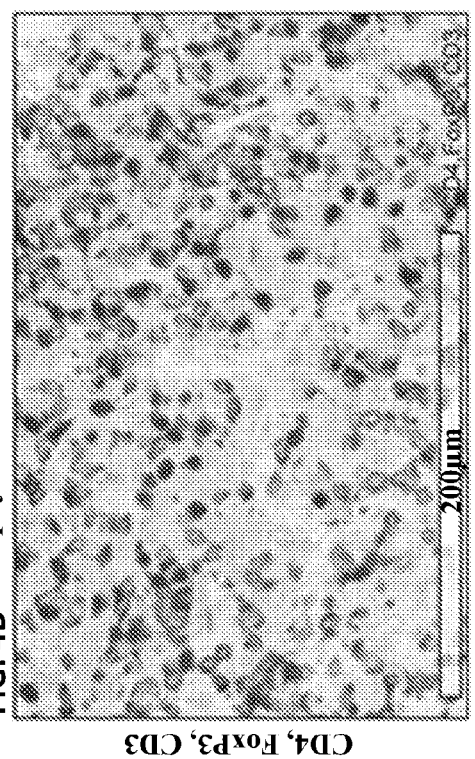
FIG. 4D Biopsy at C2D8 of Nivolumab
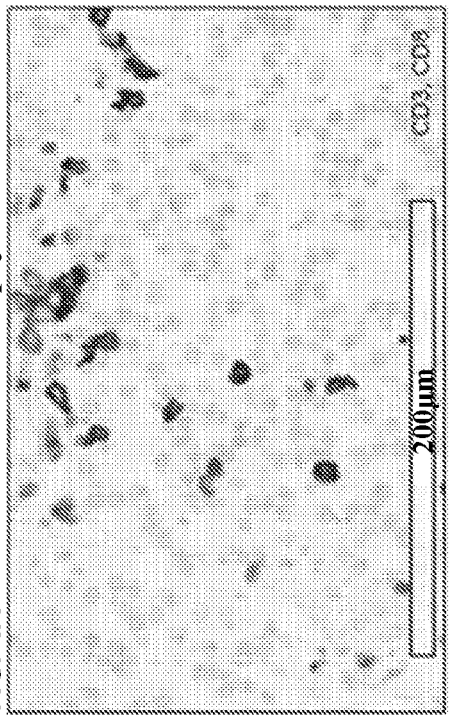
FIG. 4A Baseline Biopsy
FIG. 4C Baseline Biopsy

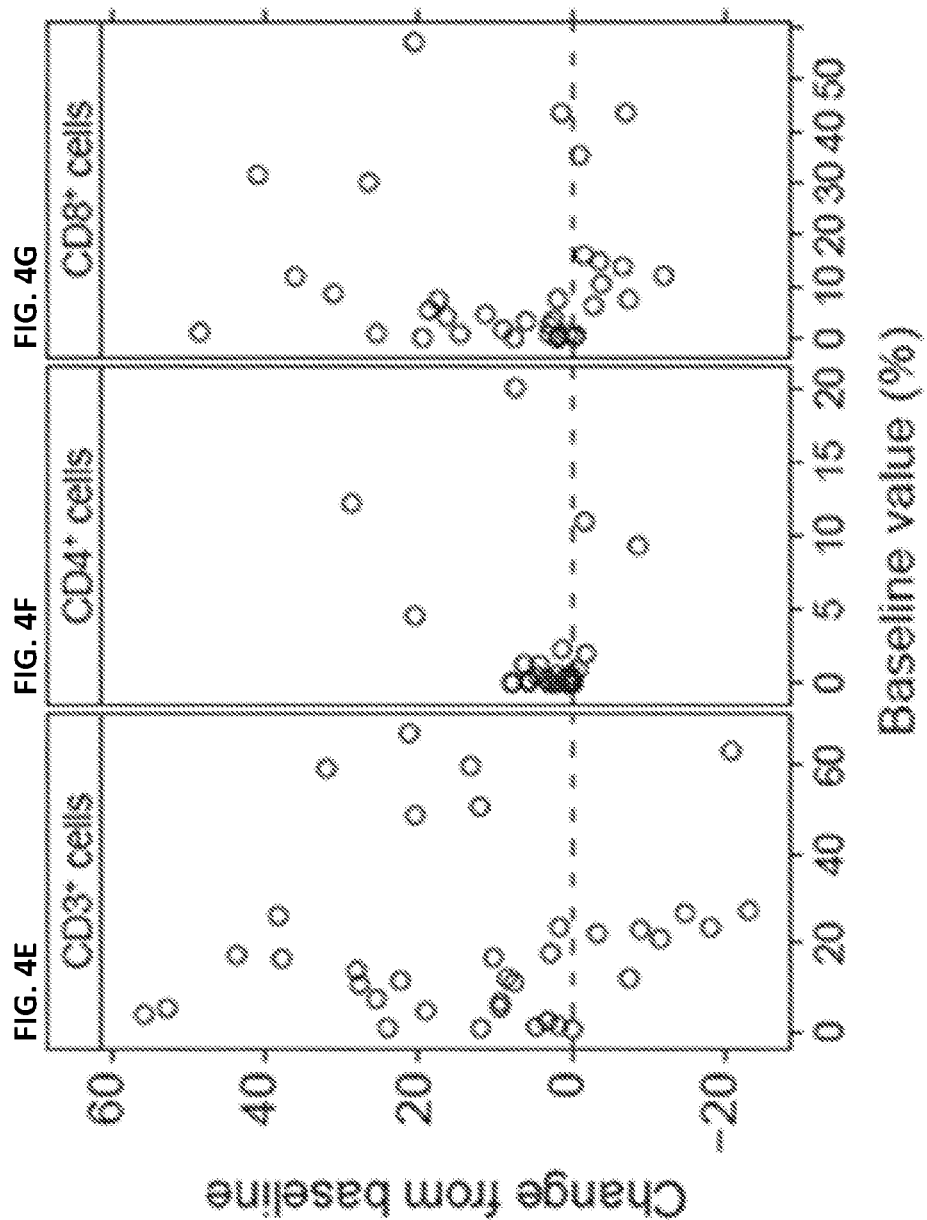

Evaluation of Tumor-Associated Lymphocytes

CFB of percent CD3+ cells

CFB of percent CD4+ cells

CFB of percent CD8+ cells

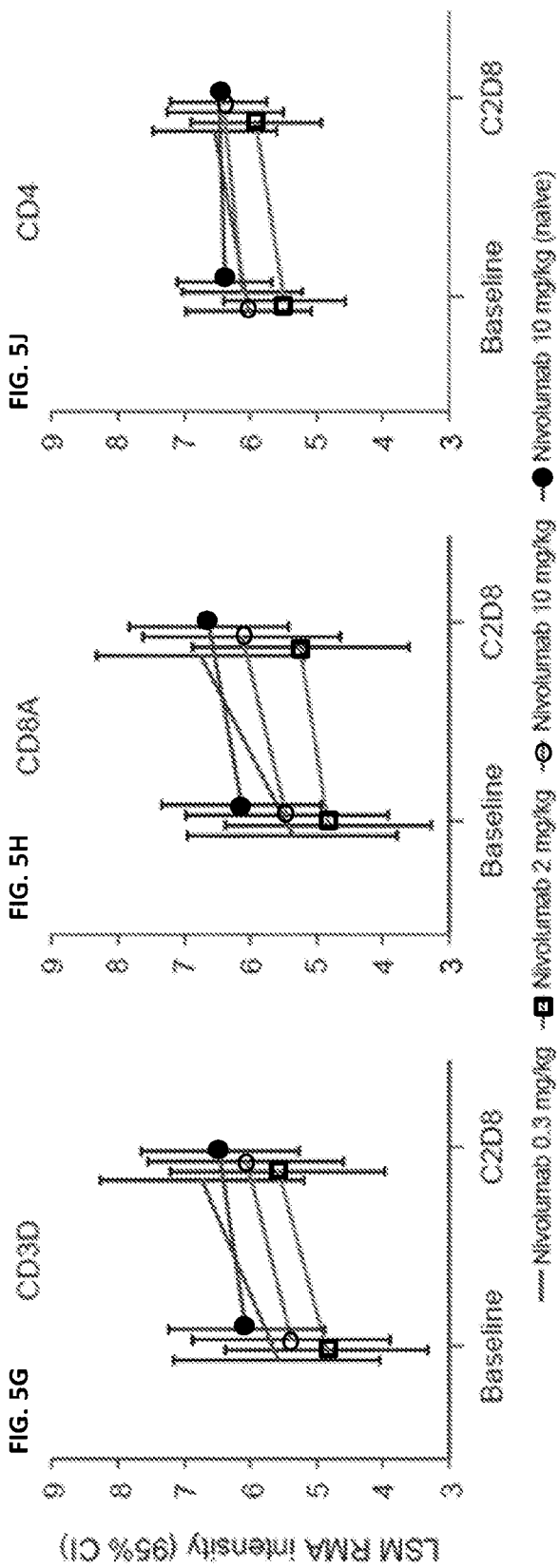

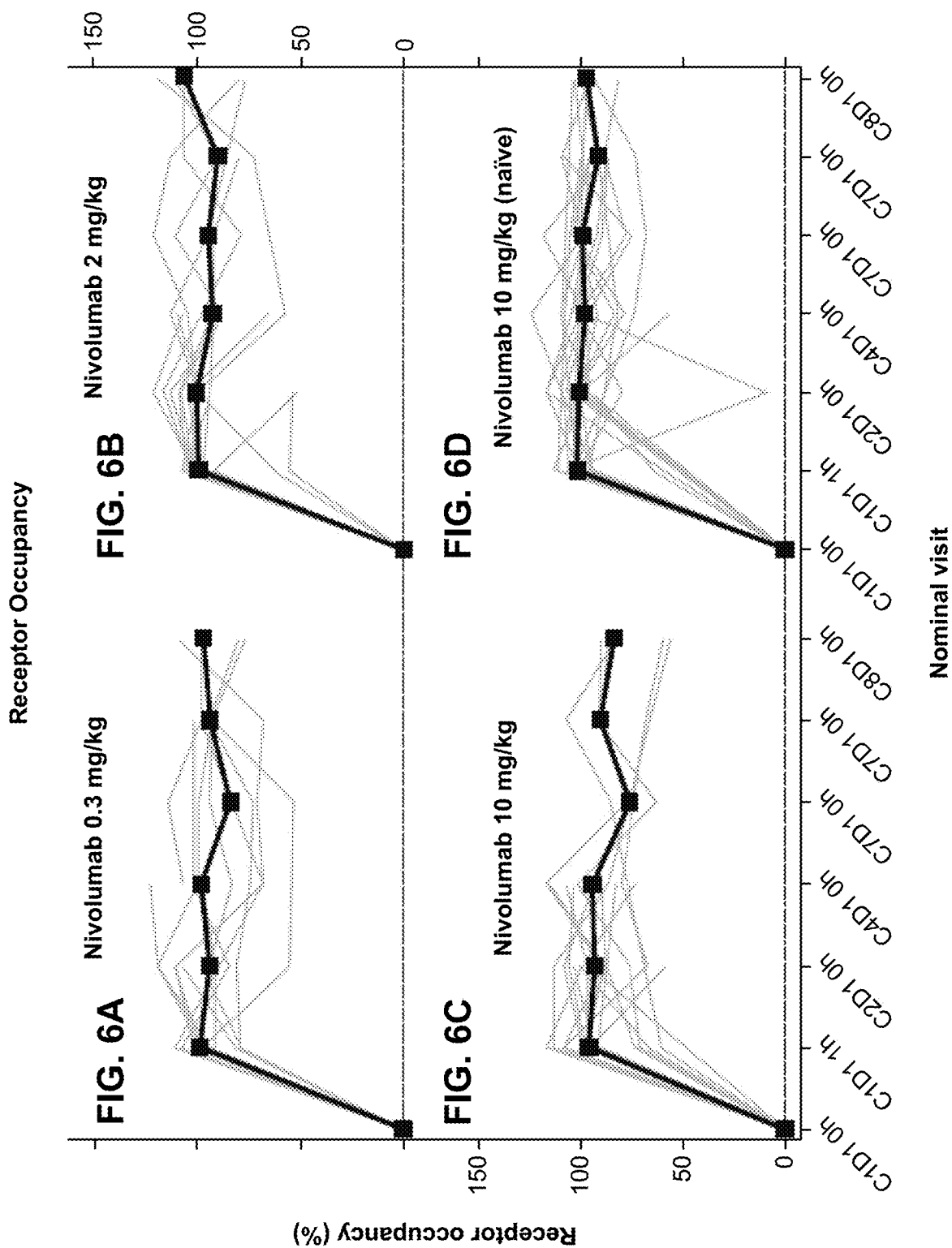

FIG. 8A – Gene Expression and Tumor Burden Reduction: Baseline
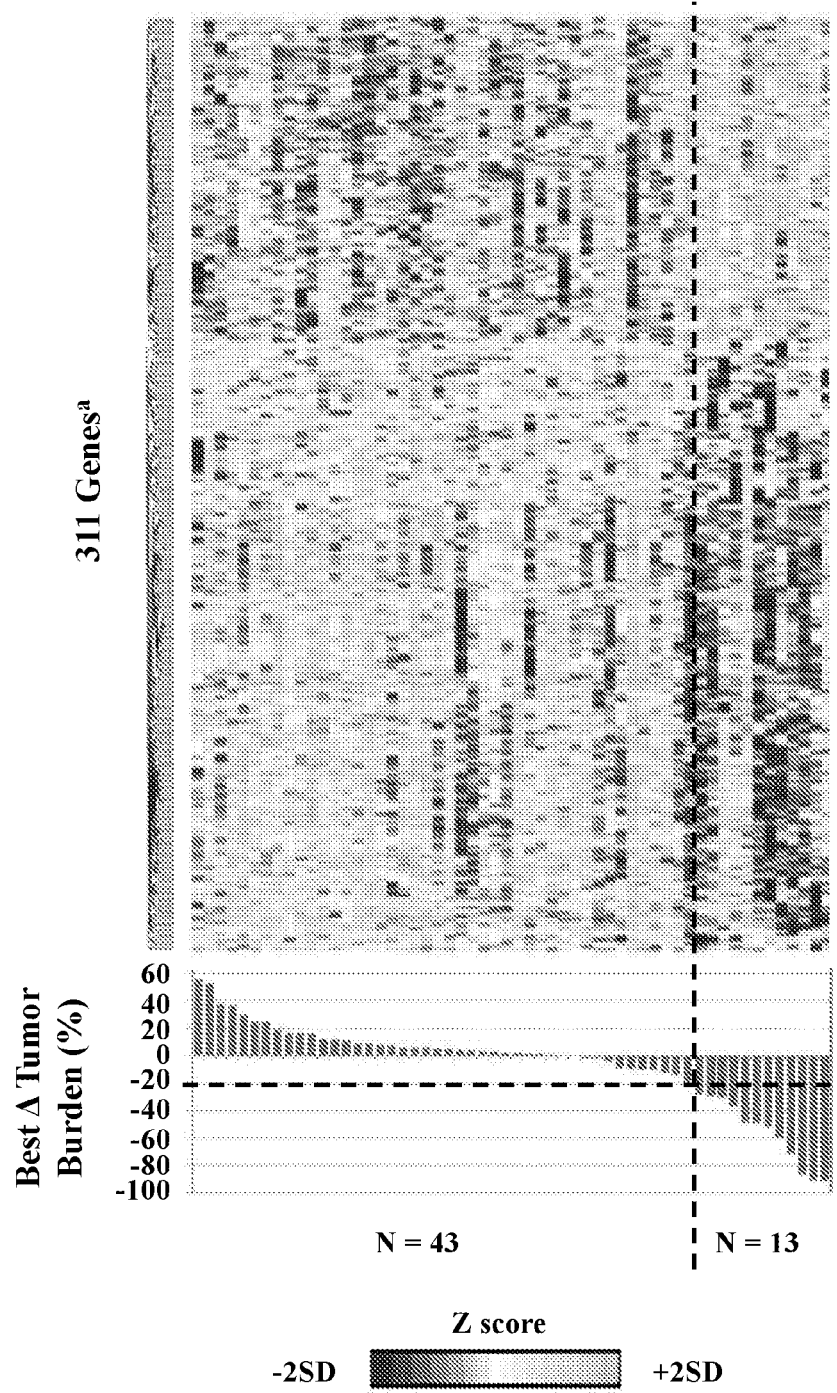
[a]$P < 0.01$, >1.3-fold, false discovery rate <16%.

FIG. 8B - Gene Expression and Tumor Burden Reduction: On Treatment
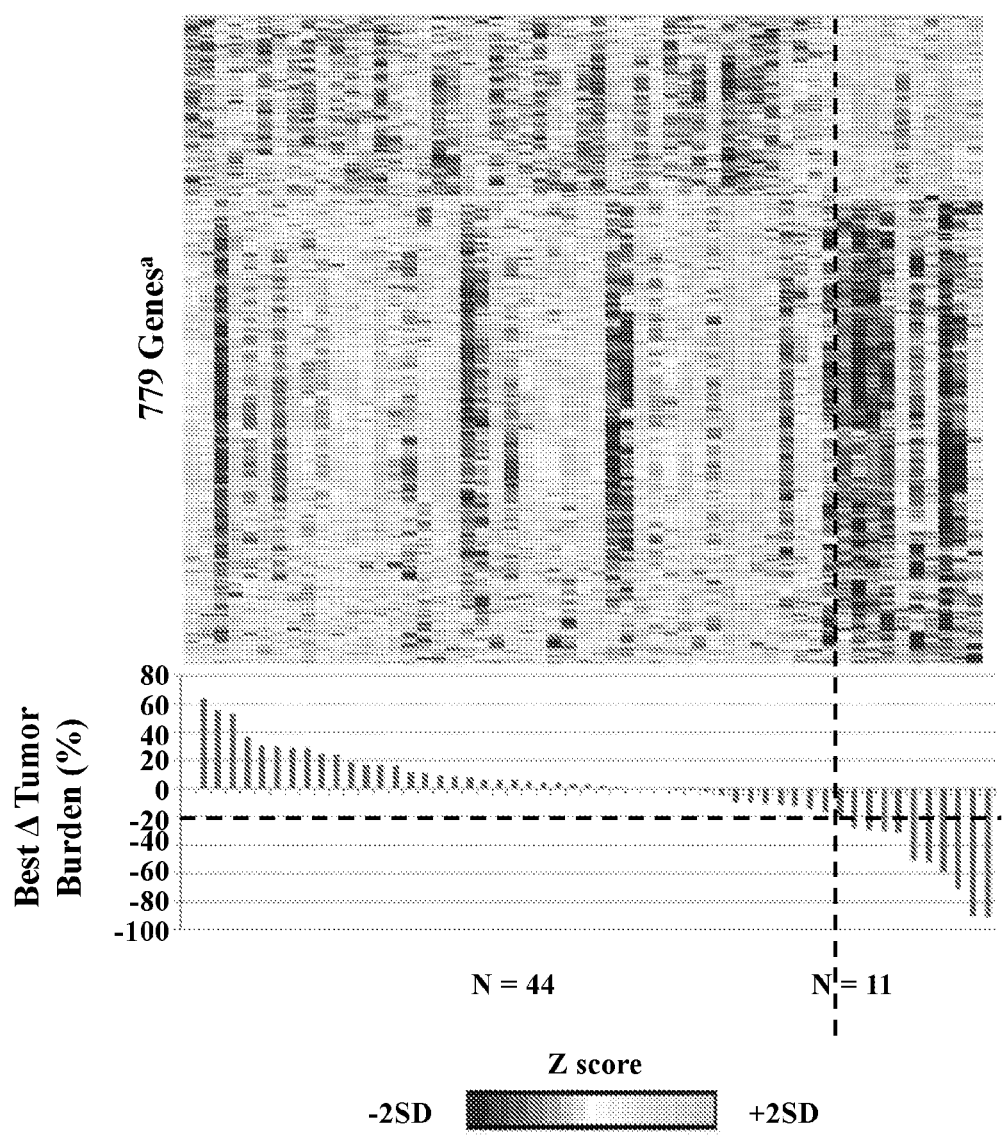
[a]$P < 0.01$, >1.3-fold, false discovery rate <16%.

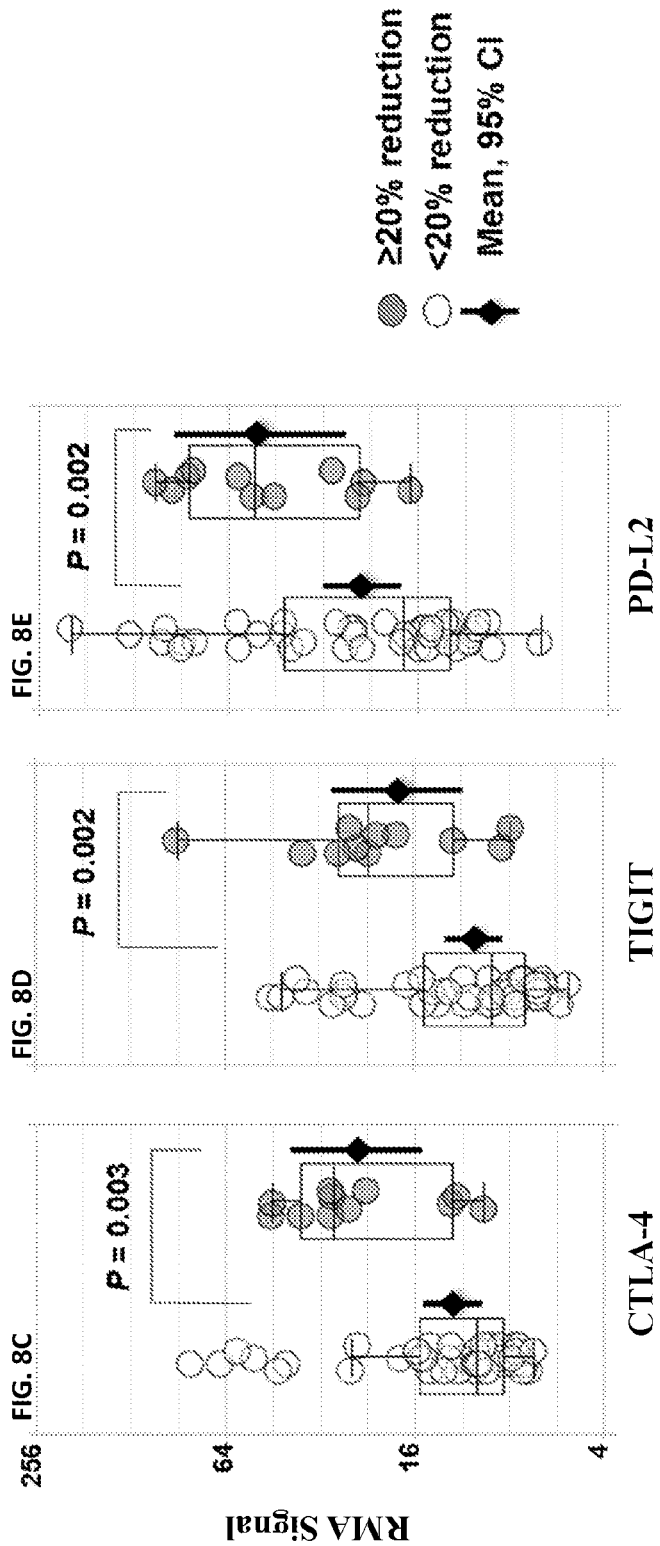

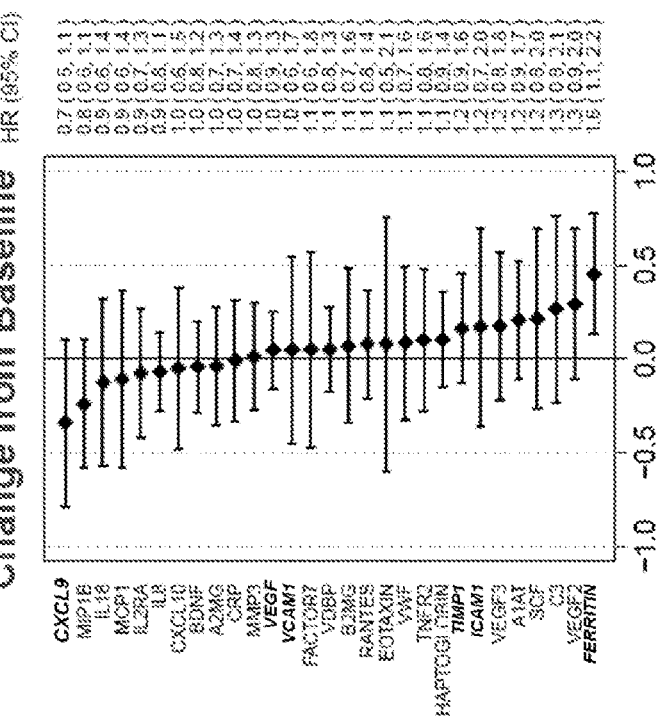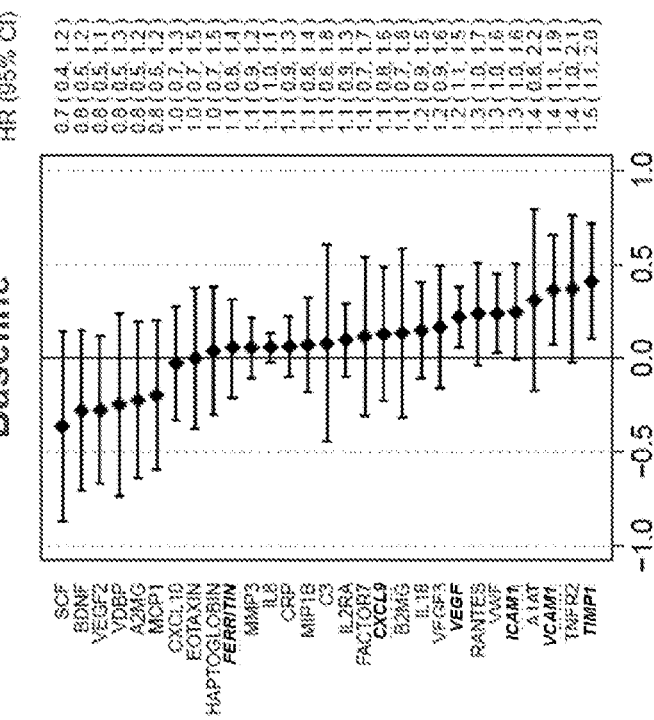
Serum Soluble Factors and Overall Survival[a]
FIG. 9A
FIG. 9B
[a]All analyses are exploratory, not confirmatory. Cox proportional hazards model accounts for dose and naïve/previously treated status. Sample sized range from 74-90, and HRs are for comparing Q3 vs. Q1.
HR, hazard ratio; CI, confidence interval; OS, overall survival.

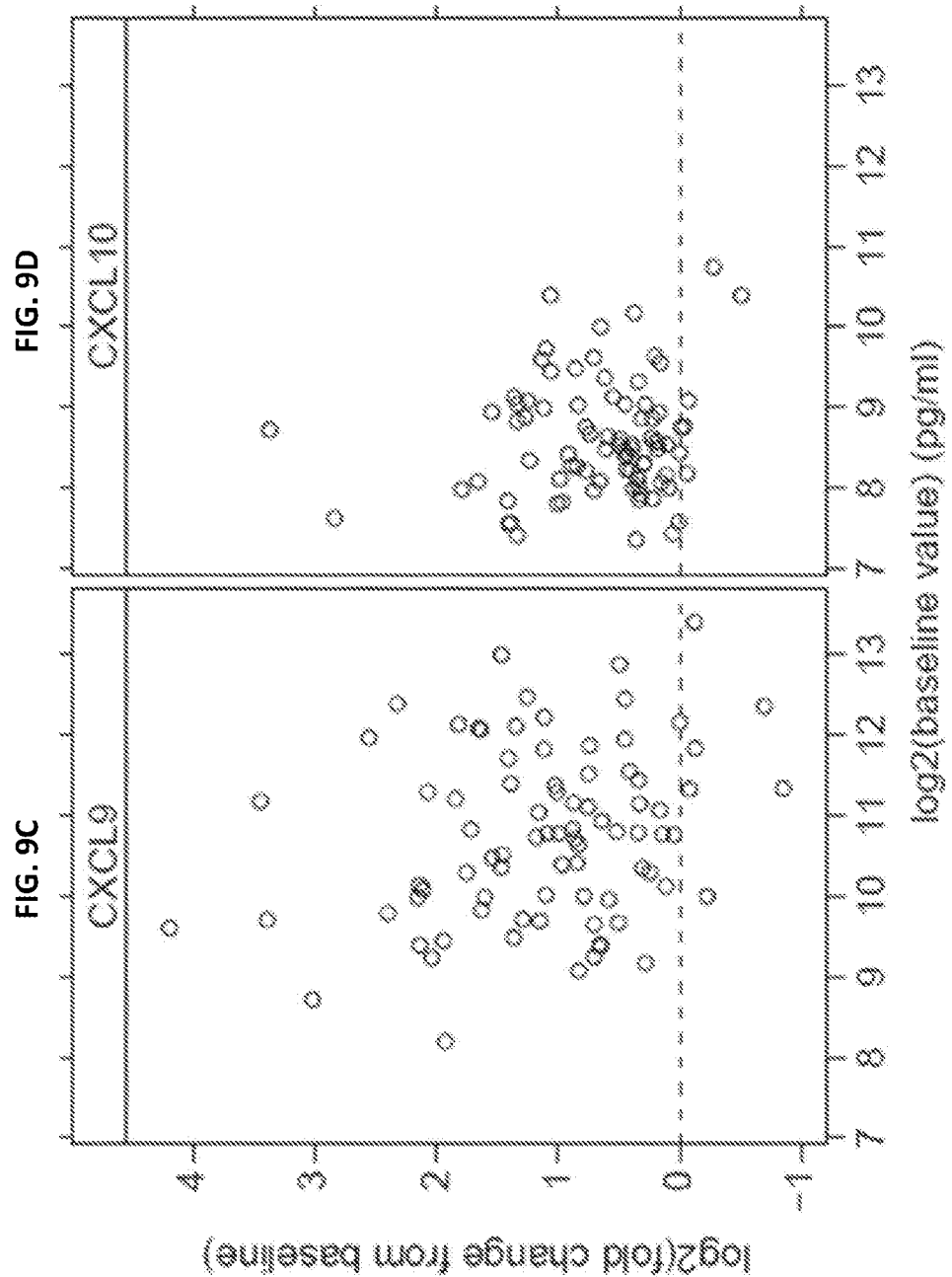

Effect of Nivolumab on Chemokine Markers

CXCL9

CXCL10

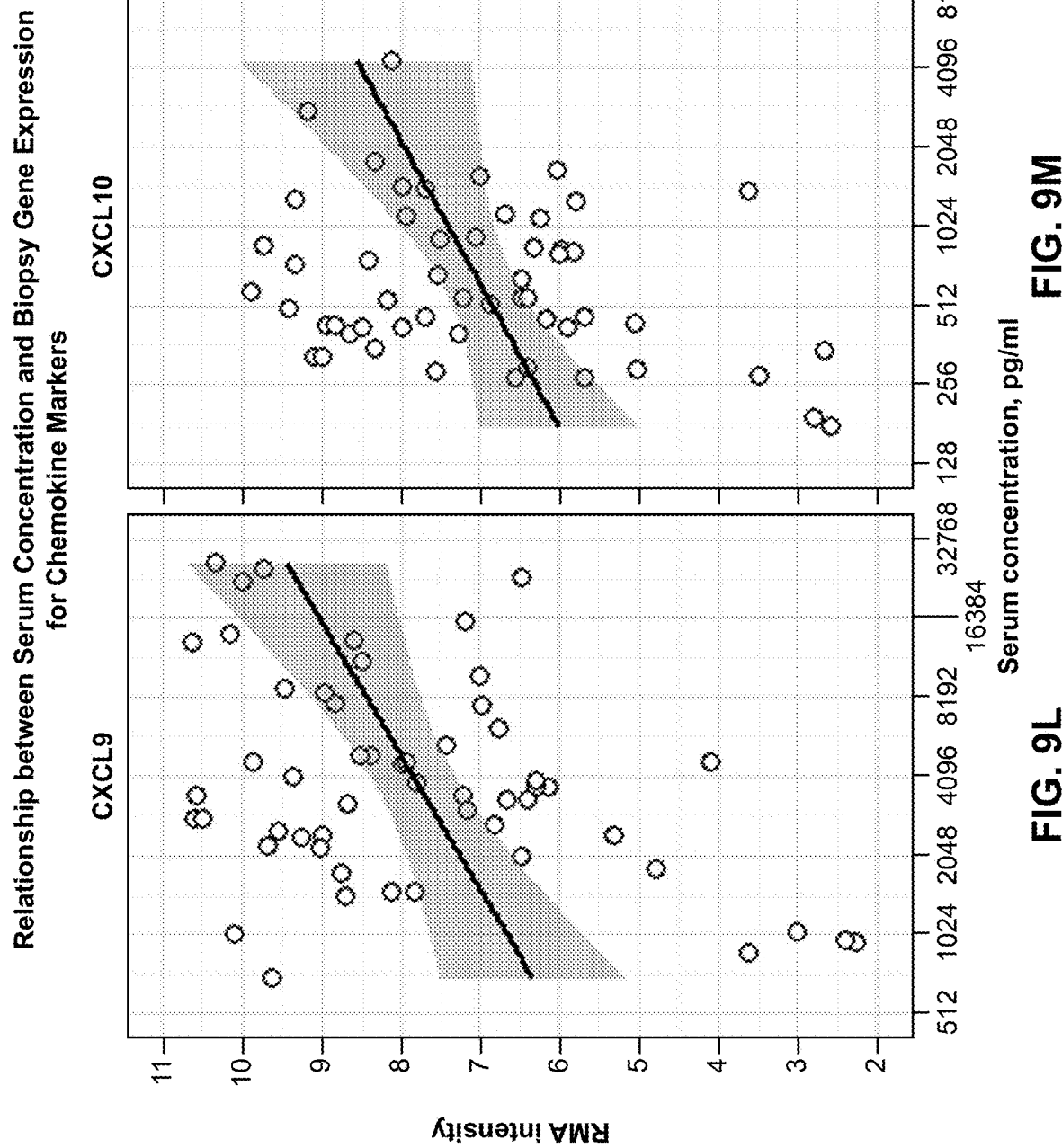

FIG. 10A – T-cell receptor sequencing
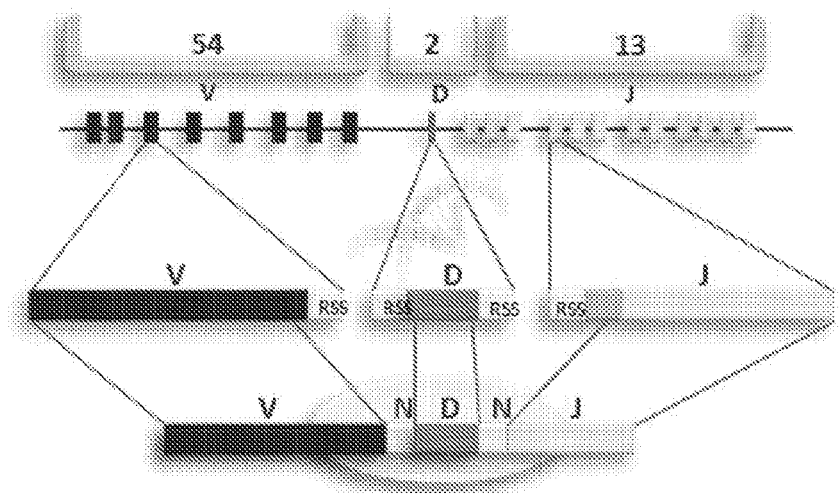
FIG. 10B – High Clonality TCR Repertoire
FIG. 10C – Low Clonality TCR Repertoire
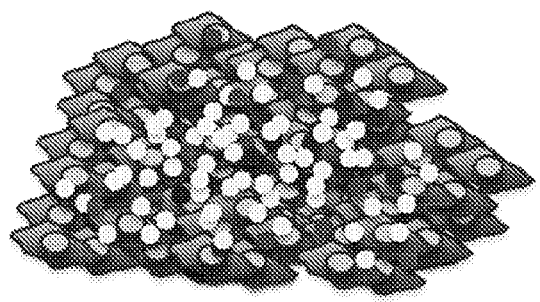 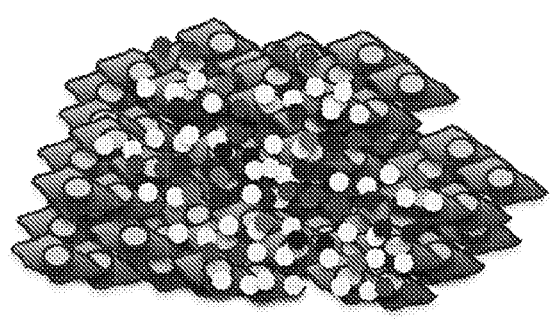
 Tumor Cell
 T-cell Clone

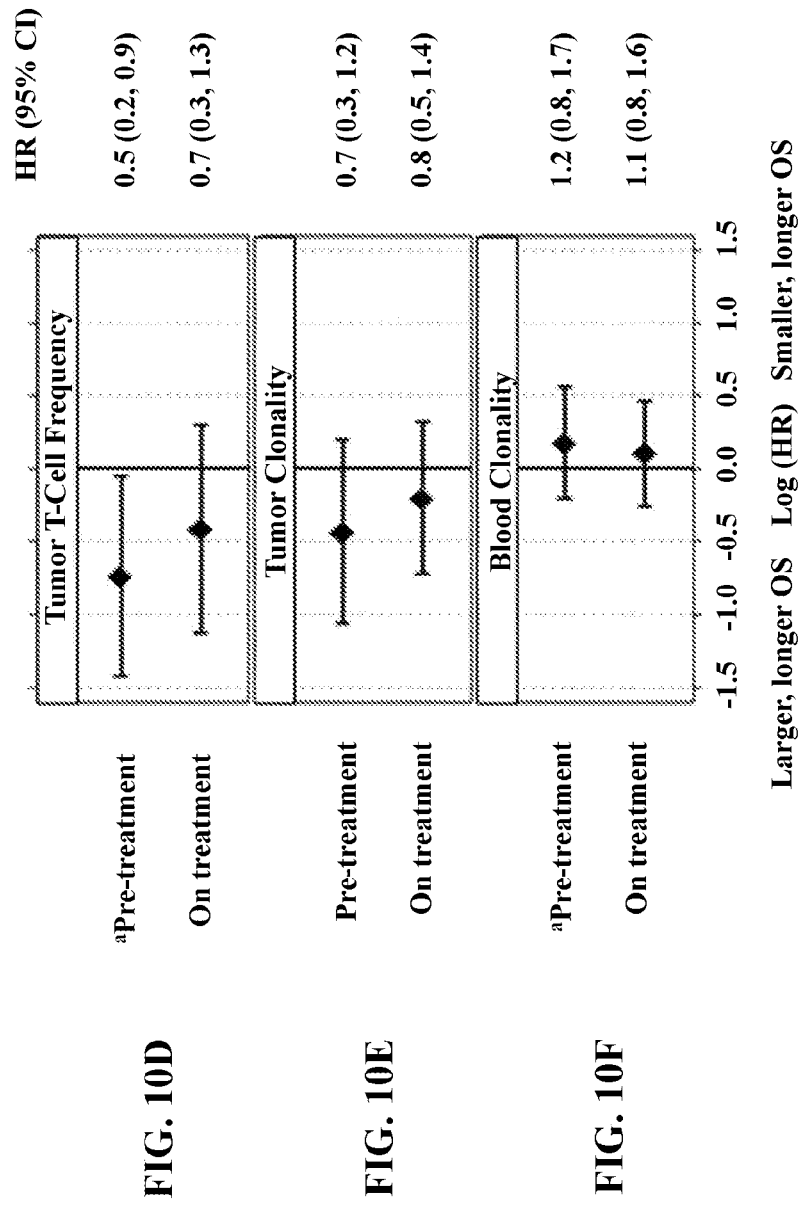

TREATMENT OF RENAL CELL CARCINOMA

CROSS-REFERENCE TO RELATED APPLICATIONS

This application is a division of U.S. application Ser. No. 15/577,661, which is the national phase entry of International Application No. PCT/US2016/034875, filed May 27, 2016, which claims the priority benefit of U.S. Provisional Application Nos. 62/168,456, filed May 29, 2015, and 62/216,265, filed Sep. 9, 2015, each of which is incorporated by reference herein by reference in its entirety.

Throughout this application, various publications are referenced in parentheses by author name and date, or by Patent No. or Patent Publication No. Full citations for these publications can be found at the end of the specification immediately preceding the claims. The disclosures of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention.

FIELD OF THE INVENTION

This invention relates to improving therapeutic efficacy of an anti-PD-1 antibody or an anti-PD-L1 in the treatment of a subject suffering from a tumor derived from a renal cell carcinoma (RCC).

BACKGROUND OF THE INVENTION

Human cancers harbor numerous genetic and epigenetic alterations, generating neoantigens potentially recognizable by the immune system (Sjoblom et al. (2006) *Science* 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

Intensive efforts to develop specific immune checkpoint pathway inhibitors have begun to provide new immunotherapeutic approaches for treating cancer, including the development of an antibody (Ab), ipilimumab (YERVOY®), that binds to and inhibits CTLA-4 for the treatment of patients with advanced melanoma (YERVOY® FDA Full Prescribing Information, revised August 2015) and the development of antibodies such as nivolumab (OPDIVO®) and pembrolizumab (KEYTRUDA®) that bind specifically to the Programmed Death-1 (PD-1) receptor and block the inhibitory PD-1/PD-1 ligand pathway (see OPDIVO® FDA Full Prescribing Information, revised March 2015; KEYTRUDA® FDA Full Prescribing Information, revised June 2015).

PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to downregulate T cell activation and cytokine secretion upon binding to PD-1.

Nivolumab (formerly designated 5C4, BMS-936558, MDX-1106, or ONO-4538), now approved as OPDIVO®, is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al. (2014) *Cancer Immunol Res.* 2(9): 846-56). Nivolumab has shown activity in a variety of advanced solid tumors.

Renal cancer (also known as kidney cancer) is a cancer that originates in the kidneys. The most common type of kidney cancer is renal cell carcinoma (RCC). RCC can often be cured by surgical resection if it is diagnosed and treated when still localized to the kidney and to the immediately surrounding tissue (Stage I), and radical resection is the accepted, often curative, therapy for Stage II as well as Stage III RCC. In contrast, when distant metastases are present (Stage IV), disease-free survival is poor. Moreover, the prognosis for any treated RCC patient with progressing, recurring, or relapsing disease is also poor, regardless of cell type or stage. Approximately 25%-30% of RCC patients have metastatic disease at diagnosis, and median survival for metastatic RCC is only about 24 months (Gupta et al. (2008) *Cancer Treat Rev* 34(3):193-205; NCCN GUIDELINES®, Version 3.2014—Kidney Cancer; Heng et al. (2009) *J Clin Oncol.* 27:5794-9). Responses to cytotoxic chemotherapy generally have not exceeded 10% for any regimen that has been studied in adequate numbers of patients.

SUMMARY OF THE INVENTION

The present disclosure relates to a method for treating a subject afflicted with a tumor derived from a RCC comprising: (i) administering to the subject a first dose of an antibody or an antigen-binding portion thereof that binds specifically to PD-1 or PD-L1 and inhibits PD-1 activity ("anti-PD-1 antibody or antigen-binding portion thereof") or PD-L1 activity ("anti-PD-L1 antibody or antigen-binding portion thereof"), respectively; and (ii) administering a second dose of the anti-PD-1 antibody or antigen-binding portion thereof or the anti-PD-L1 antibody or antigen-binding portion thereof to the subject wherein after the administration of the first dose, the subject exhibits differential expression of PVRIG, NKG7, CD244, NKTR, TNFSF8, TNFSF13B, TNFRSF14, SPI1, CLEC2B, CTLA-4, TIGIT, PD-L2, or any combination thereof.

The present disclosure also relates to a method for treating a subject afflicted with a tumor derived from an RCC comprising administering, to the subject who exhibits differential expression of PVRIG, NKG7, CD244, NKTR, TNFSF8, TNFSF13B, TNFRSF14, SPI1, CLEC2B, CTLA-4, TIGIT, PD-L2, or any combination thereof after administration of a first dose of an anti-PD-1 antibody or antigen-binding portion thereof or an anti-PD-L1 antibody or antigen-binding portion thereof, a second dose of the anti-PD-1 antibody or antigen-binding portion thereof or the anti-PD-L1 antibody or antigen-binding portion thereof.

In one embodiment, the present disclosure relates to a method of treating a subject afflicted with a tumor derived from an RCC comprising: (i) determining an expression level of PVRIG, NKG7, CD244, NKTR, TNFSF8, TNFSF13B, TNFRSF14, SPI1, CLEC2B, CTLA-4, TIGIT, PD-L2, or any combination thereof in a sample of the subject after the subject is administered with a first dose of an anti-PD-1 antibody or antigen-binding portion thereof or an anti-PD-L1 antibody or antigen-binding portion thereof, wherein the subject exhibits differential expression of PVRIG, NKG7, CD244, NKTR, TNFSF8, TNFSF13B, TNFRSF14, SPI1, CLEC2B, CTLA-4, TIGIT, PD-L2, or any combination thereof after the administration of the first dose and (ii) administering to the subject a second dose of the anti-PD-1 antibody or antigen-binding portion thereof or the anti-PD-L1 antibody or antigen-binding portion thereof.

In another embodiment, the present disclosure relates to a method of treating a subject afflicted with a tumor derived from an RCC comprising: (i) administering to the subject a first dose of an anti-PD-1 antibody or antigen-binding portion thereof or an anti-PD-L1 antibody or antigen-binding portion thereof, (ii) determining an expression level of PVRIG, NKG7, CD244, NKTR, TNFSF8, TNFSF13B, TNFRSF14, SPI1, CLEC2B, CTLA-4, TIGIT, PD-L2, or any combination thereof in a sample of the subject after (i), wherein the subject exhibits differential expression of PVRIG, NKG7, CD244, NKTR, TNFSF8, TNFSF13B, TNFRSF14, SPI1, CLEC2B, CTLA-4, TIGIT, PD-L2, or any combination thereof compared to the expression level prior to (i); and (ii) administering to the subject a second dose of the anti-PD-1 antibody or antigen-binding portion thereof or the anti-PD-L1 antibody or antigen-binding portion thereof.

In other embodiments, the present disclosure relates to a method for identifying a subject afflicted with an RCC who is suitable for an anti-PD-1 antibody or anti-PD-L1 antibody therapy comprising measuring an expression level of PVRIG, NKG7, CD244, NKTR, TNFSF8, TNFSF13B, TNFRSF14, SPI1, CLEC2B, CTLA-4, TIGIT, PD-L2, or any combination thereof in a sample of the subject, wherein the subject exhibits differential expression of PVRIG, NKG7, CD244, NKTR, TNFSF8, TNFSF13B, TNFRSF14, SPI1, CLEC2B, CTLA-4, TIGIT, PD-L2, or any combination thereof after administration of a first dose of an anti-PD-1 antibody or antigen-binding portion thereof or an anti-PD-L1 antibody or antigen-binding portion thereof and wherein the subject is administered a second dose of the anti-PD-1 antibody or antigen-binding portion thereof or the anti-PD-L1 antibody or antigen-binding portion thereof.

In some embodiments, the present disclosure relates to a method for identifying a subject afflicted with an RCC suitable for an anti-PD-1 antibody or anti-PD-L1 antibody therapy comprising: (i) administering to the subject a first dose of an anti-PD-1 antibody or antigen-binding portion thereof or an anti-PD-L1 antibody or antigen-binding portion thereof, and (ii) measuring an expression level of PVRIG, NKG7, CD244, NKTR, TNFSF8, TNFSF13B, TNFRSF14, SPI1, CLEC2B, CTLA-4, TIGIT, PD-L2, or any combination thereof in a sample of the subject after (i), wherein the subject exhibits differential expression of PVRIG, NKG7, CD244, NKTR, TNFSF8, TNFSF13B, TNFRSF14, SPI1, CLEC2B, CTLA-4, TIGIT, PD-L2, or any combination thereof compared to the expression level prior to (i); wherein the subject is administered a second dose of the anti-PD-1 antibody or antigen-binding portion thereof or the anti-PD-L1 antibody or antigen-binding portion thereof.

In certain embodiments, the present disclosure relates to a kit for treating a subject afflicted with a tumor derived from an RCC, the kit comprising: (a) an anti-PD-1 antibody or antigen-binding portion thereof or an anti-PD-L1 antibody or antigen-binding portion thereof (b) instructions for determining differential expression of PVRIG, NKG7, CD244, NKTR, TNFSF8, TNFSF13B, TNFRSF14, SPI1, CLEC2B, CTLA-4, TIGIT, PD-L2, or any combination thereof after administration of a first dose of the anti-PD-1 antibody or antigen-binding portion thereof or an anti-PD-L1 antibody or antigen-binding portion thereof and for administering a second dose of the anti-PD-1 antibody or antigen-binding portion thereof or an anti-PD-L1 antibody or antigen-binding portion thereof if the subject exhibits differential expression of PVRIG, NKG7, CD244, NKTR, TNFSF8, TNFSF13B, TNFRSF14, SPI1, CLEC2B, CTLA-4, TIGIT, PD-L2, or any combination thereof. In certain embodiments, the kit further comprises an agent to determine differential expression of PVRIG, NKG7, CD244, NKTR, TNFSF8, TNFSF13B, TNFRSF14, SPI1, CLEC2B, CTLA-4, TIGIT, PD-L2, or any combination thereof prior to administering the second dose.

In certain embodiments, the differential expression of PVRIG, NKG7, CD244, NKTR, TNFSF8, TNFSF13B, TNFRSF14, SPI1, CLEC2B, CTLA-4, TIGIT, PD-L2, or any combination thereof in the subject is relative to the expression level of PVRIG, NKG7, CD244, NKTR, TNFSF8, TNFSF13B, TNFRSF14, SPI1, CLEC2B, CTLA-4, TIGIT, and/or PD-L2 before the administration of the first dose of an anti-PD-1 antibody or antigen-binding portion thereof or an anti-PD-L1 antibody or antigen-binding portion thereof (i.e., at baseline). In one embodiment, the differential expression is an increased expression after the administration.

In other embodiments, the differential expression of PVRIG, NKG7, CD244, NKTR, TNFSF8, TNFSF13B, TNFRSF14, SPI1, CLEC2B, CTLA-4, TIGIT, PD-L2, or any combination thereof is relative to the expression level of PVRIG, NKG7, CD244, NKTR, TNFSF8, TNFSF13B, TNFRSF14, SPI1, CLEC2B, CTLA-4, TIGIT, and/or PD-L2 in non-responders. In yet other embodiments, the differential expression in the subject is a higher expression of PVRIG, NKG7, CD244, NKTR, TNFSF8, TNFSF13B, TNFRSF14, SPI1, CLEC2B, CTLA-4, TIGIT, PD-L2 or any combination thereof in one or more non-responders.

In certain embodiments, the subject exhibits differential expression of PVRIG, NKG7, CD244, NKTR, TNFSF8, TNFSF13B, TNFRSF14, SPI1, CLEC2B, CTLA-4, PD-L2, or both after the administration of the first dose.

In some embodiments, after the administration of the first dose and/or the second dose, the subject further exhibits a characteristic selected from the group consisting of: (i) an increased expression of one or more serum markers of Interferon-γ activation; (ii) an increased tumor gene expression; (iii) a decreased clonality of T cell Receptor in serum; (iv) an increased T cell count in the tumor; and (v) any combination thereof.

In some embodiments, the differential expression is measured by comparing the expression of PVRIG, NKG7, CD244, NKTR, TNFSF8, TNFSF13B, TNFRSF14, SPI1, CLEC2B, CTLA-4, TIGIT, PD-L2, or any combination thereof prior to the administration of the first dose and after the administration of the first dose. In other embodiments, the differential expression is measured by comparing the expression of PVRIG, NKG7, CD244, NKTR, TNFSF8, TNFSF13B, TNFRSF14, SPI1, CLEC2B, CTLA-4, TIGIT, PD-L2, or any combination thereof in responding subjects ("responders") and in non-responding ("non-responders") subjects. In certain embodiments, the expression of PVRIG, NKG7, CD244, NKTR, TNFSF8, TNFSF13B, TNFRSF14, SPI1, CLEC2B, CTLA-4, TIGIT, PD-L2, or any combination thereof is a protein expression measured by an immunohistochemistry, an ELISA, a western blot, a protein array, or any combination thereof. In another embodiment, the expression of PVRIG, NKG7, CD244, NKTR, TNFSF8, TNFSF13B, TNFRSF14, SPI1, CLEC2B, CTLA-4, TIGIT, PD-L2, or any combination thereof is a nucleotide expression measured by an in situ hybridization, a DNA or RNA array or nucleotide hybridization technique, a tumor sequencing technique, a quantitative polymerase chain reaction (PCR), or any combination thereof. In certain embodiments, the tumor further expresses PD-L1.

In some embodiments, the anti-PD-1 antibody or antigen-binding portion thereof cross-competes with nivolumab for binding to human PD-1. In certain embodiments, the anti-PD-1 antibody or antigen-binding portion thereof is a chimeric, humanized, or human monoclonal antibody, or a portion thereof. In some embodiments, the anti-PD-1 antibody or antigen-binding portion thereof comprises a heavy chain constant region which is of a human IgG1 or IgG4 isotype. In one particular embodiment, the anti-PD-1 antibody is nivolumab. In another embodiment, the anti-PD-1 antibody is pembrolizumab.

In other embodiments, the anti-PD-L1 antibody or antigen-binding portion thereof cross-competes with BMS-936559, MPDL3280A, MEDI4736, or MSB0010718C for binding to human PD-L1. In certain embodiments, the anti-PD-L1 antibody or antigen-binding portion thereof is a chimeric, humanized, or human monoclonal antibody, or a portion thereof. In some embodiments, the anti-PD-L1 antibody or antigen-binding portion thereof comprises a heavy chain constant region which is of a human IgG1 or IgG4 isotype. In one embodiment, the anti-PD-L1 antibody is BMS-936559. In another embodiment, the anti-PD-L1 antibody is MPDL3280A. In a further embodiment, the anti-PD-L1 antibody is MEDI4736. In another embodiment, the anti-PD-L1 antibody is MSB0010718C.

In certain embodiments, the first dose is a therapeutic dose and the second dose is a therapeutic dose. In other embodiments, the first dose is a subtherapeutic dose and the second dose is a therapeutic dose. In some embodiments, the first dose is administered at a dose ranging from at least about 80 mg to at least about 800 mg or at least about 0.1 mg/kg to at least about 10.0 mg/kg body weight. In some embodiments, the second dose is administered at a dose ranging from at least about 80 mg to at least about 800 mg or at least about 0.1 mg/kg to at least about 10.0 mg/kg body weight. In one particular embodiment, the first dose is administered at a dose of at least about 3 mg/kg body weight or 240 mg once about every 2 weeks.

In some embodiments, the subject is administered at least two doses, at least three doses, at least four doses, at least five doses, at least six doses, at least seven doses, at least eight doses, at least nine doses, at least ten doses, at least 12 doses, at least 20 doses, or at least 30 doses prior to measuring the increased expression of PVRIG, NKG7, CD244, NKTR, TNFSF8, TNFSF13B, TNFRSF14, SPI1, CLEC2B, CTLA-4, TIGIT, PD-L2, or any combination thereof. In certain embodiments, the anti-PD-1 antibody or antigen-binding portion or the anti-PD-L1 antibody or antigen-binding portion thereof is administered for as long as a clinical benefit is observed or until unmanageable toxicity or disease progression occurs.

In some embodiments, the subject shows an increase in the number of CD4+ tumor associated lymphocytes in the tumor, an increase in the number of CD8+ tumor associated lymphocytes in the tumor, an increased expression level of chemokine (C-X-C motif) ligand-9 (CXCL9) in a serum, an increased expression level of CXCL10 in a serum, or any combination thereof after the administration of the second dose.

In certain embodiments, the subject exhibits an overall survival of at least about 18 months, at least about 19 months, at least about 20 months, at least about 21 months, at least about 22 months, at least about 23 months, at least about 2 years, at least about 3 years, at least about 4 years, or at least about 5 years after the administration.

In some embodiments, the method further comprises administering one or more additional anti-cancer agents. In certain embodiments, the anti-cancer agent is selected from the group consisting of an antibody or antigen-binding portion thereof that binds specifically to CTLA-4 ("anti-CTLA-4 antibody or antigen-binding portion thereof") and inhibits CTLA-4 activity, a chemotherapy, a platinum-based doublet chemotherapy, a tyrosine kinase inhibitor, an anti-VEGF inhibitor, or any combination thereof. In a particular embodiment, the anti-cancer agent is an antibody or antigen-binding portion thereof that binds specifically to CTLA-4 and inhibits CTLA-4 activity. In one embodiment, the anti-cancer agent is ipilimumab.

In some aspects, the invention is directed to a method of identifying a subject afflicted with a tumor who is suitable for an anti-PD-1 antibody or an anti-PD-L1 antibody therapy comprising measuring an expression level of one or more genes selected from the group consisting of MICB, PVRIG, SPI1, CLEC2B, NKG7, or any combination thereof in a sample of the subject prior to the anti-PD-1 antibody or anti-PD-L1 antibody therapy. In some embodiments, the method further comprises administering to the subject a first dose of an anti-PD-1 antibody or antigen-binding portion thereof or an anti-PD-L1 antibody or antigen-binding portion thereof.

In another aspect, the invention is directed to a method for identifying a subject afflicted with a tumor who is suitable for an anti-PD-1 antibody or anti-PD-L1 antibody therapy comprising measuring an expression level of MICB, PVRIG, SPI1, CLEC2B, NKG7, or any combination thereof in a sample of the subject prior to the anti-PD-1 antibody or anti-PD-L1 antibody therapy, wherein the subject exhibits increased expression of MICB, PVRIG, SPI1, CLEC2B, NKG7, or any combination thereof relative to a reference expression level of MICB, PVRIG, SPI1, CLEC2B, and/or NKG7, and wherein the subject is administered a first dose of an anti-PD-1 antibody or antigen-binding portion thereof or an anti-PD-L1 antibody or antigen-binding portion thereof.

In another aspect, the invention is directed to a method for treating a subject afflicted with a tumor comprising administering, to the subject who exhibits increased expression of MICB, PVRIG, SPI1, CLEC2B, NKG7, or any combination thereof, relative to a reference expression level of MICB, PVRIG, SPI1, CLEC2B, and/or NKG7, a first dose of an anti-PD-1 antibody or antigen-binding portion thereof or an anti-PD-L1 antibody or antigen-binding portion thereof.

In another aspect, the invention is directed to method for treating a subject afflicted with a tumor comprising administering a first dose of an anti-PD-1 antibody or antigen-binding portion thereof or an anti-PD-L1 antibody or antigen-binding portion thereof to the subject, wherein the subject exhibits increased expression of MICB, PVRIG, SPI1, CLEC2B, NKG7, or any combination thereof, relative to a reference expression level of MICB, PVRIG, SPI1, CLEC2B, and/or NKG7.

In another aspect, the invention is directed to method for treating a subject afflicted with a tumor comprising: (i) measuring an expression level of one or more genes selected from the group consisting of MICB, PVRIG, SPI1, CLEC2B, NKG7, or any combination thereof, and (ii)

administering to the subject a first dose of an anti-PD-1 antibody or antigen-binding portion thereof or an anti-PD-L1 antibody or antigen-binding portion thereof to the subject, wherein the subject exhibits an increased expression of MICB, PVRIG, SPI1, CLEC2B, NKG7, or any combination thereof, relative to a reference expression level of MICB, PVRIG, SPI1, CLEC2B, and/or NKG7.

In another aspect, the invention is directed to a method of treating a subject afflicted with a tumor comprising: (i) determining an expression level of MICB, PVRIG, SPI1, CLEC2B, NKG7, or any combination thereof in a sample of the subject, wherein the subject exhibits increased expression of MICB, PVRIG, SPI1, CLEC2B, NKG7, or any combination thereof relative to a reference expression level of MICB, PVRIG, SPI1, CLEC2B, and/or NKG7; and (ii) administering to the subject a first dose of an anti-PD-1 antibody or antigen-binding portion thereof or an anti-PD-L1 antibody or antigen-binding portion thereof.

BRIEF DESCRIPTION OF THE DRAWINGS

FIG. 1 shows a schematic of a study design and objectives directed to treatment of mRCC. Abbreviations include Karnofsky performance score (KPS), metastatic renal cell carcinoma (mRCC), ratio (R), intravenously (IV), every three weeks (Q3W), and complete response (CR).

FIG. 2 shows a consort diagram of the study outlined in FIG. 1. FIG. 2 summarizes the patient outcomes for each of Arms 1, 2, 3, and 4, including the occurrence rate of drug related adverse events (AEs).

FIG. 3 shows a graphical representation of the overall survival (OS) of patients treated with 0.3 mg/kg (triangles; Arm 1), 2 mg/kg (open circles; Arm 2), or 10 mg/kg (closed circles; Arm 3) body weight nivolumab and naïve patients treated with 10 mg/kg body weight nivolumab (squares; Arm 4). OS rates are shown with their corresponding 95% confidence interval (CI) values at 12 months and 24 months. The number of events per patient and the median OS (95% CI) for each treatment group are also shown. OS point estimates were derived from Kaplan-Meier analyses, and 95% CIs were derived using Greenwood's formula. "Naïve" subjects have not received any prior therapy, as described below. Point estimates are derived from Kaplan-Meier analyses. 95% CLs are derived from Greenwood's formula. NR means not reached.

FIGS. 4A-4D show images of immunohistochemistry (IHC) for CD3+, CD4+, and CD8+ cells at baseline and cycle 2 day 8 (C2D8) in sample tumor tissue. Scale bars are denoted on the images. FIG. 4A shows CD3 and CD8 staining at baseline. FIG. 4B shows CD3 and CD8 staining from biopsied tissue collected at C2D8 of nivolumab treatment. FIG. 4C shows CD4, FoxP3, and CD3 staining at baseline. FIG. 4D shows CD4, FoxP3, and CD3 staining from biopsied tissue collected at C2D8 of nivolumab treatment. FIGS. 4E-4G show the changes from baseline percentage of cells that are CD3+(FIG. 4E), CD4+(FIG. 4F), or CD8+(FIG. 4G) in tumor biopsies. Data are included for patients with IHC data at both baseline and cycle 2 day 8 in all treatment groups combined (N=36) (FIGS. 4E-4G).

FIGS. 5G, 5H, and 5J show expression levels for genes CD3D (915_at), CD8A (925_at) and CD4 (920_at) in tumor biopsies, respectively. Values presented are least-squares means (LSM) of robust multi-array average (RMA) intensity for the treatment group and time point indicated. Data were obtained from an extended linear model that included fixed effects of treatment group, time on study, process batch and sex (the latter because women were not equally represented in samples from each trial treatment group) as categorical variables, and treatment-by-time on study interactions, and that modeled within-patient correlations by a spatial exponential structure with Euclidean distance. Error bars indicate 95% CIs.

FIGS. 6A-6D show graphical representations of the receptor occupancy for total lymphocytes in sample collected from previously treated subjects receiving 0.3 mg/kg (FIG. 6A; Arm 1), 2 mg/kg (FIG. 6B; Arm 2), and 10 mg/kg (FIG. 6C; Arm 3) nivolumab and treatment-naïve subjects receiving 10 mg/kg nivolumab (FIG. 6D; Arm 4). Light gray lines represent individual time profiles; bold lines connect medians at individual time points. The x-axis shows the time-point, wherein, e.g., "C1D1 0 h" indicates that the sample measured was collected at cycle 1, day 1, 0 hours. The y-axis shows the percentage of receptor occupancy.

FIG. 8A and FIG. 8B are heat maps representing microarray expression data, which show relative gene expression in subjects pre-treatment and on-treatment, respectively. In FIG. 8A, the upper panel shows 311 transcripts that were found to be differentially expressed (P<0.01, >1.3× difference, and a false discovery rate <16%) at baseline in patients who displayed a greater than 20% reduction in tumor burden as compared to those patients with a less than 20% reduction in tumor burden. In FIG. 8B, the upper panel shows 779 genes that were found to be differentially expressed (P<0.01, >1.3× difference, and a false discovery rate <16%) on treatment, as compared to pre-treatment, in patients who displayed a greater than or equal to 20% reduction in tumor burden as compared to those patients with a less than 20% reduction. Shading shows the Z score for each gene, from −2 to +2 standard deviations (SD). The lower panels of both FIG. 8A and FIG. 8B are graphical representations of the best change (A) in tumor burden (%) for each patient in the upper panel, with the horizontal dashed line marking the 20% reduction in tumor burden, and the vertical line separating those subjects with less than 20% reduction in tumor burden from those with more than 20% reduction in tumor burden. FIGS. 8C-8E show the relative expressions of three immune checkpoint genes, CTLA-4 (FIG. 8C), TIGIT (FIG. 8D), and PD-L2 (FIG. 8E) on-treatment as compared to baseline. Each circle represents the robust multi-array average (RMA) signal (e.g., an indicator of relative expression) of a single subject, wherein the white circles represent subjects exhibiting a less than 20% reduction in tumor burden, and wherein the grey circles represent subjects exhibiting a greater than or equal to 20% reduction in tumor burden (FIGS. 8C-8E). Vertical bars indicate the mean and 95% confidence interval (CI). Significance in FIGS. 8C-8E is shown as a p value above each panel. Data shown in FIGS. 8C-8E are largest reduction in tumor burden from baseline.

FIGS. 9A-9H and 9J-9M show the effect of nivolumab on chemokine markers. FIGS. 9A and 9B illustrate the relationship between serum soluble factors and overall survival at baseline (FIG. 9A) and the corresponding changes from baseline (FIG. 9B). The hazard ratio (HR) in FIGS. 9A and 9B is shown on the right, which compares an increment equivalent to the $75^{th}$ percentile (Q3) of the soluble factor to the $25^{th}$ percentile (Q1), with the 95% confidence interval in parentheses. The log hazard ratio is indicated on the x-axis of each of FIGS. 9A and 9B. All analyses are exploratory, not confirmatory. The Cox proportional hazards model used accounts for dose and naïve/previously treated status. The sample size ranged from 74-90.

FIGS. 9C and 9D are graphical representations of the fold changes from baseline at cycle 2 day 8 in serum concentrations of CXCL9 (FIG. 9C) and CXCL10 (FIG. 9D) in all treatment groups (N=83). Both the x- and y-axes are on the log base-2 scale. Each circle represents the fold change from baseline measured in a single subject.

FIG. 9F and FIG. 9G are scatter plot matrices of fold changes from baseline (log base-2 scale) in CXCL10 v. CXCL9 (FIG. 9F) and CXCL9 v. CXCL10 (FIG. 9G) among 83 patients who had serum data at baseline and cycle 2 day 8. FIGS. 9E and 9H give kernel density estimates and histograms summarizing the univariate distributions of CXCL9 (FIG. 9E) and CXCL10 (FIG. 9H), individually.

FIGS. 9J and 9K show graphical representations of gene expression levels for CXCL9 (4283_at) (FIG. 9J) and CXCL10 (3627_at) (FIG. 9K) in fresh tumor tissue samples taken at baseline and at cycle 2 day 9 (C2D8). Values presented are least squares means of RMA intensity for the treatment group and time point indicated (FIGS. 9J and 9K). Error bars indicate 95% CIs (FIGS. 9J and 9K). Data is presented for samples collected from subjects in the 0.3 (solid line), 2 (squares), and 10 (open circles) mg/kg nivolumab treatment groups and the 10 mg/kg (naïve) nivolumab treatment group (closed circles) (FIGS. 9J and 9K).

FIGS. 9L and 9M show graphical representations of the relationship between serum concentration and biopsy gene expression for CXCL9 (FIG. 9L) and CXCL10 (FIG. 9M). Values presented are least squares means of RMA intensity for the treatment group and the serum concentration (pg/ml) (FIGS. 9L and 9M). The data for individual subjects are indicates by open circles, with a trend line superimposed (FIGS. 9L and 9M).

FIG. 10A shows a schematic of T cell receptor (TCR) recombination as exploited by TCR sequencing to measure T cell clonality, including the process of T cell V(D)J recombination, whereby an Ig/TCR transcript is created by expression of one V domain, the D domain, and one J domain. FIG. 10B shows representative drawings of a high clonality TCR repertoire (FIG. 10B); FIG. 10C shows representative drawings of a low clonality TCR repertoire.

FIGS. 10D-10F show graphical representations of a univariate Cox proportional hazards analyses of pre-treatment and on treatment tumor cell frequency (FIG. 10D), tumor clonality (FIG. 10E), and blood clonality (FIG. 10F). Log hazard ratio (HR) is shown on the x-axis with relative overall survival (OS). To the right of each of FIGS. 10D-10F is the corresponding HR (95% confidence interval [CI]).

DETAILED DESCRIPTION OF THE INVENTION

Figure 5D:
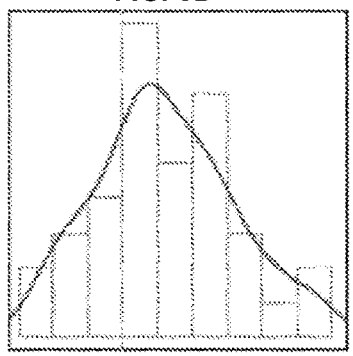
FIGS. 5D, 5E, and 5F give kernel density estimates and histograms summarizing the univariate distributions for the individual cell-type percentages for CD3+, CD4+, and CD8+ cells, respectively.
Figure 5A:
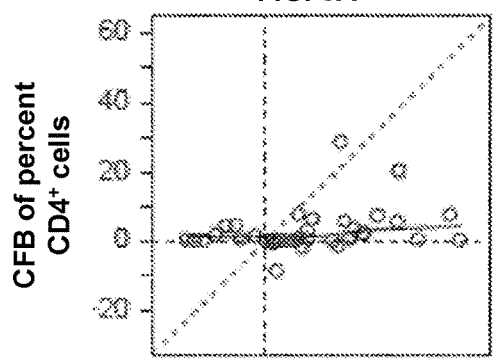
FIG. 5A shows scatter-plot matrices of change from baseline (CFB) of CD3+v. CD4+ cell percentages among the 36 patients.
Figure 5E:
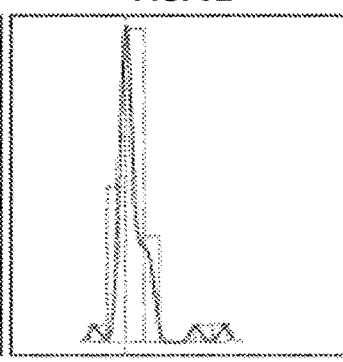
Figure 5B:
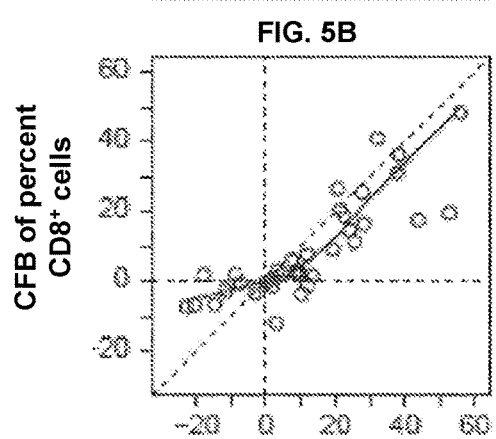
FIG. 5B shows scatter-plot matrices of change from baseline (CFB) of CD3+v. CD8+ cell percentages among the 36 patients.
Figure 5C:
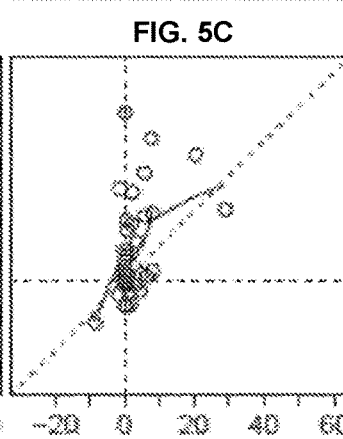
FIG. 5C shows scatter-plot matrices of change from baseline (CFB) of CD4+v. CD8+ cell percentages among the 36 patients.
Figure 5F:
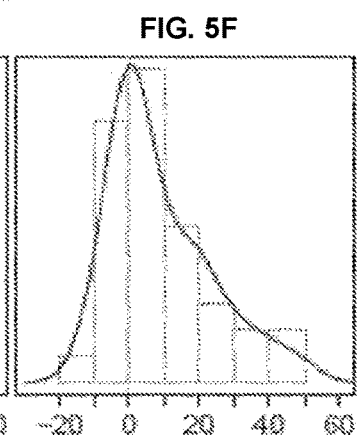

The present invention relates to methods of enhancing the clinical efficacy of an anti-PD-1 or anti-PD-L1 immunotherapy in the treatment of a subject suffering from a tumor derived from a renal cell carcinoma (RCC). In particular, the invention includes methods for treating mRCC in a subject comprising administering to the subject a dose of an anti-PD-1 antibody or antigen-binding portion thereof and/or an anti-PD-L1 antibody or antigen-binding portion thereof, wherein the subject is determined to have differential expression of one or more gene, e.g., CTLA-4, TIGIT, PD-L2, or any combination thereof, during the anti-PD-1 antibody or anti-PD-L1 antibody therapy. In other embodiments, the invention includes methods for treating an RCC in a subject comprising administering to the subject a dose of an anti-PD-1 antibody or antigen-binding portion thereof and/or an anti-PD-L1 antibody or antigen-binding portion thereof, wherein the subject is determined to have differential expression of one or more gene, e.g., PVRIG, NKG7, CD244, NKTR, TNFSF8, TNFSF13B, TNFRSF14, SPI1, CLEC2B, CTLA-4, TIGIT, PD-L2, or any combination thereof, during the anti-PD-1 antibody or anti-PD-L1 antibody therapy.

I. Terms

In order that the present disclosure can be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

As described herein, any concentration range, percentage range, ratio range or integer range is to be understood to include the value of any integer within the recited range and, when appropriate, fractions thereof (such as one tenth and one hundredth of an integer), unless otherwise indicated.

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of a composition comprising a therapeutic agent to a subject, using any of the various methods and delivery systems known to those skilled in the art. Routes of administration for the anti-PD-1 antibody and/or the anti-PD-L1 antibody include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. Non-parenteral routes include a topical, epidermal or mucosal route of administration, for example, orally, intranasally, vaginally, rectally, sublingually or topically. Administering can also be performed, for example, once, a plurality of times, and/or over one or more extended periods.

An "adverse event" (AE) as used herein is any unfavorable and generally unintended or undesirable sign (including an abnormal laboratory finding), symptom, or disease associated with the use of a medical treatment. For example, an adverse event can be associated with activation of the immune system or expansion of immune system cells (e.g., T cells) in response to a treatment. A medical treatment can have one or more associated AEs and each AE can have the same or different level of severity. Reference to methods capable of "altering adverse events" means a treatment regime that decreases the incidence and/or severity of one or more AEs associated with the use of a different treatment regime.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region is comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. In some embodiments, the constant region of the antibodies can be substituted or mutated to alter the effector function.

An immunoglobulin can derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes. The term "antibody" includes, by way of example, both naturally occurring and non-naturally occurring antibodies; monoclonal and polyclonal Abs; chimeric and humanized antibodies; human or nonhuman antibodies; wholly synthetic antibodies; and single chain antibodies. A nonhuman antibody can be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

An "isolated antibody" refers to an antibody that is substantially free of other antibodies having different antigenic specificities (e.g., an isolated antibody that binds specifically to PD-1 is substantially free of antibodies that bind specifically to antigens other than PD-1). An isolated antibody that binds specifically to PD-1 or PD-L1 can, however, have cross-reactivity to other antigens, such as PD-1 or PD-L1 molecules, respectively, from different species. Moreover, an isolated antibody can be substantially free of other cellular material and/or chemicals.

The term "monoclonal antibody" ("mAb") refers to a non-naturally occurring preparation of antibody molecules of single molecular composition, i.e., antibody molecules whose primary sequences are essentially identical, and which exhibits a single binding specificity and affinity for a particular epitope. A mAb is an example of an isolated antibody. MAbs can be produced by hybridoma, recombinant, transgenic or other techniques known to those skilled in the art.

A "human antibody" (HuAb) or a "human monoclonal antibody" (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized antibody" refers to an antibody in which some, most or all of the amino acids outside the CDR domains of a non-human antibody are replaced with corresponding amino acids derived from human immunoglobulins. In one embodiment of a humanized form of an antibody, some, most, or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen" antibody refers to an antibody that binds specifically to the antigen. For example, an anti-PD-1 antibody binds specifically to PD-1, an anti-PD-L1 antibody binds specifically to PD-L1, and an anti-CTLA-4 antibody binds specifically to CTLA-4.

An "antigen-binding portion" of an antibody (also called an "antigen-binding fragment") refers to one or more fragments of an antibody that retain the ability to bind specifically to the antigen bound by the whole antibody.

A "cancer" refers to a broad group of various diseases characterized by the uncontrolled growth of abnormal cells in the body. Unregulated cell division and growth results in the formation of malignant tumors that invade neighboring tissues and can also metastasize to distant parts of the body through the lymphatic system or bloodstream. A "cancer" or "cancer tissue" can include a tumor. In some embodiments, the cancer is a kidney cancer.

The vast majority of patients suffering from a kidney cancer, about 90% of kidney cancer patients, have an RCC, also referred to as a renal cell adenocarcinoma. RCC accounts for about 3% of all cancers in the United States, and an estimated 63,920 patients will be diagnosed with renal cancer and 13,860 will die of the disease in the U.S. in 2014 (Siegel et al. (2014) *CA Cancer J Clin* 64(1):9-29). Metastatic disease is found in about 30% of subjects at diagnosis.

RCC includes several subtypes with physiological and clinical differences. The most common RCC subtypes include clear cell RCC (about 70% of all RCCs), papillary RCC or chromophilic RCC (about 10% of all RCCs), and chromophobe RCC (about 5% of all RCCs). The remaining subtypes include, but are not limited to, oncocytoma, collecting duct RCC, multilocular cystic RCC, medullary carcinoma, mucinous tubular and spindle carcinoma, and neuroblastoma-associated RCC, as well as unclassified RCCs, which don't fit into one group or comprise more than one type of subtype. In one particular embodiment, the mRCC is a clear cell RCC or comprises a clear-cell component. In other embodiments, the renal cancer is an advanced, metastatic, and/or refractory cancer. In certain embodiments, the RCC is a metastatic (mRCC). Kidney cancers can also include less common forms, including, but not limited to, transitional cell carcinomas (about 5-10% of kidney cancer patients), Wilms tumors or nephroblastomas (very rare in adults, but accounts for 5% of all cancers in children), and renal sarcomas (less than 1% of kidney cancer patients).

"Cytotoxic T-Lymphocyte Antigen-4" (CTLA-4) refers to an immunoinhibitory receptor belonging to the CD28 family. CTLA-4 is expressed exclusively on T cells in vivo, and binds to two ligands, CD80 and CD86 (also called B7-1 and B7-2, respectively). The term "CTLA-4" as used herein includes human CTLA-4 (hCTLA-4), variants, isoforms, and species homologs of hCTLA-4, and analogs having at least one common epitope with hCTLA-4. The complete hCTLA-4 sequence can be found under GenBank Accession No. AAB59385.

The term "immunotherapy" refers to the treatment of a subject afflicted with, or at risk of contracting or suffering a recurrence of, a disease by a method comprising inducing, enhancing, suppressing or otherwise modifying an immune response.

"Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease.

"PD-L1 positive" as used herein can be interchangeably used with "PD-L1 expression of at least about 5%." PD-L1 expression can be measured by any methods known in the art. In some embodiments, the PD-L1 expression is measured by an automated IHC. A PD-L1 positive tumor can thus have at least about 5%, at least about 10%, or at least about 20% of tumor cells expressing PD-L1 as measured by an automated IHC. In certain embodiments, "PD-L1 positive" means that there are at least 100 cells that express PD-L1 on the surface of the cells.

"Programmed Death-1" (PD-1) refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

"Programmed Death Ligand-1" (PD-L1; B7 homolog-1; B7-H1; or CD274) and "Programmed Death Ligand-2" (PD-L2; B7-DC; or CD273) are two cell surface glycoprotein ligands for PD-1 that downregulate T-cell activation and cytokine secretion upon binding to PD-1. The terms "PD-L1" and "PD-L2" as used herein include human PD-L1 (hPD-L1) and human PD-L2 (hPD-L2) and variants, isoforms, and species homologs thereof, and analogs having at least one common epitope with hPD-L1 and/or hPD-L2. The complete hPD-L1 sequence can be found under GenBank Accession No. Q9NZQ7. The complete hPD-L2 sequence can be found under GenBank Accession No. NP_079515.

"T-cell Immunoreceptor with Ig and ITIM Domains" ("TIGIT"; V-Set and Immunoglobulin Domain-Containing Protein-9 (VSIG9); and VSTM3) refers to a protein that binds the poliovirus receptor (PVR), causing increased secretion of interleukin-10 (IL10) and decreased secretion of IL12B and suppresses T-cell activation by promoting the generation of mature immunoregulatory dendritic cells. TIGIT is expressed on various types of T cells including follicular B helper T cells (TFH), and it is also believed to facilitate the interaction between TFH and dendritic cells to regulate T cell-dependent B cell responses. The term "TIGIT" as used herein refers to the human TIGIT (hTIGIT)

and variants, isoforms, and species homologs thereof, and analogs having at least one common epitope with hTIGIT. The complete hTIGIT sequence can be found under GenBank Accession No. NP 776160.

"MHC class I polypeptide-related sequence B" ("MICB"; PERB11.2) refers to a protein that is a ligand for the NKG2D type II receptor (KLRK1). NKG2D recognizes the induced-self proteins MICA, MICB, RAET1E/ULBP4, RAET1G/ULBP5, RAET1H/ULBP2, RAET1/ULBP1, RAET1L/ULBP6, and RAET1N/ULBP3, which appear on the surface of stressed, malignant transformed, and infected cells. Binding of these ligands activates the cytolytic response of natural killer (NK) cells, CD8 αβ T cells, and γδ T cells which express the NKG2D receptor. The term "MICB" as used herein refers to the human MICB (hMICB) and variants, isoforms, and species homologs thereof, and analogs having at least one common epitope with hMICB. The complete hMICB sequence can be found under GenBank Accession No. NP_005922.

"Natural killer cell granule protein 7" ("NKG7"; GIG1; GMP-17; p15-TIA-1) refers to a protein that is expressed in natural killer cells and T cells. The term "NKG7" as used herein refers to the human NKG7 (h NKG7) and variants, isoforms, and species homologs thereof, and analogs having at least one common epitope with hNKG7. The complete hNKG7 sequence can be found under GenBank Accession No. NP_005592.

"Poliovirus receptor related immunoglobulin domain containing" ("PVRIG"; CD112R) refers to a protein from an mRNA that is preferentially transcribed in T lymphocytes and NK cells. Like TIGIT, PVRIG is a receptor for CD112, and both receptors are considered suppressive for T cell activation. The term "PVRIG" as used herein refers to the human PVRIG (hPVRIG) and variants, isoforms, and species homologs thereof, and analogs having at least one common epitope with hPVRIG. The complete hPVRIG sequence can be found under GenBank Accession No. NP 076975.

"Spi-1 proto-oncogene" ("SPI1"; OF; PU.1; SFPI1; SPI-1; SPI-A) refers to a protein that is a transcription factor that activates gene expression during myeloid and B-lymphoid cell development. SPI1 expression is present at high levels in mature myeloid cells. Myeloid leukaemias are associated with downregulated activity of myeloid transcription factors, and mutations in the SPI1 gene were identified in 7% of patients with AML in one study. The term "SPI1" as used herein refers to the human SPI1 (hSPI1) and variants, isoforms, and species homologs thereof, and analogs having at least one common epitope with hSPI1. The complete hSPI1 sequence can be found under GenBank Accession No. NP 001074016.

"C-type lectin domain family 2 member B" ("CLEC2B"; AICL; IFNRG1; CLECSF2; HP10085) refers to a protein that is a myeloid-specific activating receptor that binds NKp80 (KLRF1) on natural killer (NK) cells. NKp80-CLEC2B interactions may contribute to the initiation and maintenance of immune responses at sites of inflammation. The term "CLEC2B" as used herein refers to the human CLEC2B (hCLEC2B) and variants, isoforms, and species homologs thereof, and analogs having at least one common epitope with hCLEC2B. The complete hCLEC2B sequence can be found under GenBank Accession No. NP 005118.

"CD244 molecule" ("CD244"; 2B4; NAIL; Nmrk; NKR2B4; SLAMF4) refers to a protein expressed on natural killer (NK) cells (and some T cells) that mediates non-major histocompatibility complex restricted killing. The interaction between NK-cell and target cells via this receptor is thought to modulate NK-cell cytolytic activity. The term "CD244" as used herein refers to the human CD244 (hCD244) and variants, isoforms, and species homologs thereof, and analogs having at least one common epitope with hCD244. The complete hCD244 sequence can be found under GenBank Accession No. NP_057466.

"Natural killer cell triggering receptor" ("NKTR"; p104) refers to a protein present on the surface of natural killer cells that facilitates their binding to targets. Its expression is regulated by IL2 activation of the cells. The term "NKTR" as used herein refers to the human NKTR (hNKTR) and variants, isoforms, and species homologs thereof, and analogs having at least one common epitope with hNKTR. The complete hNKTR sequence can be found under GenBank Accession No. NP_005376.

"Tumor necrosis factor superfamily member 13b" ("TNFSF13B"; DTL; BAFF; BLYS; CD257; TALL1; THANK; ZTNF4; TALL-1; TNLG7A; TNFSF20) refers to a protein ligand for receptors TNFRSF13B/TACI, TNFRSF17/BCMA, and TNFRSF13C/BAFFR. This cytokine is expressed in B cell lineage cells, and acts as a potent B cell activator. It has been also shown to play an important role in the proliferation and differentiation of B cells. The term "TNFSF13B" as used herein refers to the human TNFSF13B (hTNFSF13B) and variants, isoforms, and species homologs thereof, and analogs having at least one common epitope with hTNFSF13B. The complete hTNFSF13B sequence can be found under GenBank Accession No. NP_006564.

"Tumor necrosis factor receptor superfamily member 14" ("TNFRSF14"; TR2; ATAR; HVEA; HVEM; CD270; LIGHTR) refers to a protein that functions in signal transduction pathways that activate inflammatory and inhibitory T-cell immune response. The term "TNFRSF14" as used herein refers to the human TNFRSF14 (hTNFRSF14) and variants, isoforms, and species homologs thereof, and analogs having at least one common epitope with hTNFRSF14. The complete hTNFRSF14 sequence can be found under GenBank Accession No. NP_003811.

"Tumor necrosis factor superfamily member 8" ("TNFSF8"; CD153; CD30 ligand (CD30L, CD30LG)) refers to a protein that is a cytokine with pleiotropic biologic activities. TNFSF8 is a ligand for TNFRSF8/CD30, which is a cell surface antigen and a marker for Hodgkin lymphoma and related hematologic malignancies. The engagement of this cytokine expressed on B cell surface plays an inhibitory role in modulating Ig class switch. The term "TNFSF8" as used herein refers to the human TNFSF8 (h TNFSF8) and variants, isoforms, and species homologs thereof, and analogs having at least one common epitope with h TNFSF8. The complete hTNFSF8 sequences can be found under GenBank Accession Nos. NP_001235.1 and NP_001239219.1.

A "subject" includes any human or nonhuman animal. The term "nonhuman animal" includes, but is not limited to, vertebrates such as nonhuman primates, sheep, dogs, and rodents such as mice, rats and guinea pigs. In some embodiments, the subject is a human. The terms, "subject" and "patient" are used interchangeably herein. A "responding" subject, or a "responder," is a subject who has responded to a treatment, e.g., a subject who has responded to a treatment with an anti-PD-1 antibody or antigen-binding portion thereof or an anti-PD-L1 antibody or antigen-binding portion thereof. A "non-responding" subject, or a "non-responder," is a subject who has not responded to a treatment, e.g., a subject who has not responded to a treatment with an anti-PD-1 antibody or antigen-binding portion thereof or an anti-PD-L1 antibody or antigen-binding portion thereof.

A "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. A "subtherapeutic amount" as used herein refers to a dosage of a drug or therapeutic agent that is significantly lower than the approved dosage. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

A subject may be characterized as having one or more "prior therapies" or as being "treatment naïve." As used herein, unless otherwise indicated, a "prior therapy" refers to any previous systemic therapy for RCC. A "treatment naïve" subject is one that has never received any previous systemic therapy in the metastatic or adjuvant setting.

As used herein, the term "first dose" includes a single dose, but can be more than one dose, i.e., multiple doses (at least two doses, at least three doses, or more) that are administered prior to the administration of "a second dose" if the multiple doses are administered to determine the susceptibility of the patient for an anti-PD-1 antibody or anti-PD-L1 antibody therapy, i.e., differential expression of certain proteins (e.g., PVRIG, NKG7, CD244, NKTR, TNFSF8, TNFSF13B, TNFRSF14, CTLA-4, TIGIT, PD-L2, or any combination thereof). The term "first dose" can also be a therapeutic dose, a dose higher than a therapeutic dose, or a subtherapeutic dose.

The term "second dose" as used herein can also include a single dose or multiple doses that are administered after the first dose (single dose or multiple doses). The second dose can be a therapeutic dose.

The use of the term "fixed dose" with regard to a composition of the invention means that two or more different antibodies in a single composition are present in the composition in particular (fixed) ratios with each other. In some embodiments, the fixed dose is based on the weight (e.g., mg) of the antibodies. In certain embodiments, the fixed dose is based on the concentration (e.g., mg/ml) of the antibodies. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody to mg second antibody. For example, the 3:1 ratio of a first antibody and a second antibody can mean that a vial can contain about 240 mg of the first antibody and 80 mg of the second antibody or about 3 mg/ml of the first antibody and 1 mg/ml of the second antibody.

The use of the term "flat dose" with regard to the composition of the invention means a dose that is administered to a patient without regard for the weight or body surface area (BSA) of the patient. The flat dose is therefore not provided as a mg/kg dose, but rather as an absolute amount of the agent (e.g., the anti-CTLA-4 antibody and/or anti-PD-1 antibody). For example, a 60 kg person and a 100 kg person would receive the same dose of the composition (e.g., 240 mg of an anti-PD-1 antibody and 80 mg of an anti-CTLA-4 antibody in a single fixed dosing formulation vial containing both 240 mg of an anti-PD-1 antibody and 80 mg of an anti-CTLA-4 antibody (or two fixed dosing formulation vials containing 120 mg of an anti-PD-1 antibody and 40 mg of an anti-CTLA-4 antibody, etc.)).

The term "weight based dose" as referred to herein means that a dose that is administered to a patient is calculated based on the weight of the patient. For example, when a patient with 60 kg body weight requires 3 mg/kg of an anti-PD-1 antibody in combination with 1 mg/kg of an anti-CTLA-4 antibody, one can draw the appropriate amounts of the anti-PD-1 antibody (i.e., 180 mg) and the anti-CTLA-4 antibody (i.e., 60 mg) at once from a 3:1 ratio fixed dosing formulation of an anti-PD-1 antibody and an anti-CTLA-4 antibody.

"Pre-treatment" or "baseline," as used herein, refers to the status of a subject prior to administration of a particular therapy, e.g., prior to administration of an anti-cancer agent, e.g., an immunotherapy, e.g., an anti-PD-1 antibody or an antigen binding portion thereof or an anti-PD-L1 antibody or an antigen binding portion thereof. "Pre-treatment" can refer to the status of a treatment naïve subject or to a subject who has had one or more prior therapies. Accordingly, it is possible that a subject may be considered to be "pre-treatment" even though the subject received some form of treatment or therapy at some time prior to the present treatment or therapy. Furthermore, "pre-treatment" can refer to any moment up until the moment that a treatment is administered. For example, "pre-treatment" can include weeks, days, hours, minutes, or seconds before administration of the treatment. In one particular embodiment, a "pre-treatment" sample can be collected from a subject immediately before administration of a first dose of the treatment or therapy. "Pre-treatment" and "baseline" are used interchangeably herein. As used herein, a differential expression of one or more marker genes at baseline can be determined by comparing the expression level of the one or more marker genes in a particular subject with a reference expression level of the one or more marker genes. In some embodiments, the reference expression level of the one or more marker genes is an expression level of the one or more marker genes by a non-responder to an anti-PD1 antibody or an anti-PD-L1 antibody therapy. In another embodiment, the reference expression level of the one or more marker genes is an expression level of the one or more marker genes by a subject who exhibited less than 20% tumor reduction. In other embodiments, the reference expression level of the one or more marker genes is an expression level of the one or more marker genes as measured in the average population. In other embodiments, the reference expression level of the one or more marker genes is an expression level of the one or more marker genes by subjects who exhibited less than 20% tumor reduction as shown in table 6A ("No Response: Mean RMA value at baseline").

"On-treatment," as used herein, refers to the status of a subject who has received one or more initial dose of a particular therapy, e.g., an anti-cancer agent, e.g., an immunotherapy, e.g., an anti-PD-1 antibody or an antigen binding portion thereof or an anti-PD-L1 antibody or an antigen binding portion thereof. "On-treatment" can refer to a subject who has only received a single dose or a subject who has received multiple doses of the anti-PD-1 antibody or an antigen binding portion thereof or the anti-PD-L1 antibody or an antigen binding portion thereof. In some aspects, "on-treatment" refers to a subject who is receiving an ongoing regimen of a particular therapy, e.g., the subject is being treated with an anti-PD-1 antibody or an antigen binding portion thereof or an anti-PD-L1 antibody or an antigen binding portion thereof. In certain embodiments, the "on-treatment" sample can be collected from a subject on about day 1, on about day 2, on about day 3, on about day 4, on about day 5, on about day 6, on about day 7, on about day 8, on about day 9, on about day 10, on about day 11, on about day 12, on about day 13, on about day 14, on about day 15, on about day 16, on about day 17, on about day 18, on about day 19, on about day 20, on about day 21, or any combination thereof, wherein the treatment is administered on day 1. In certain embodiments, the treatment is administration of an anti-PD-1 antibody or an antigen binding portion thereof or an anti-PD-L1 antibody or an antigen binding portion thereof. In some embodiments, the anti-PD-1 antibody or an antigen binding portion thereof or the anti-PD-L1 antibody or an antigen binding portion thereof is administered on day 1 of every 21-day cycle. In certain embodiments, the on-treatment sample is collected from the subject on about day 1, on about day 2, on about day 3, on about day 4, on about day 5, on about day 6, on about day 7, on about day 8, on about day 9, on about day 10, on about day 11, on about day 12, on about day 13, on about day 14, on about day 15, on about day 16, on about day 17, on about day 18, on about day 19, on about day 20, or on about day 21 of the 21 day cycle, or any combination thereof. In one particular embodiment, the on-treatment sample is collected on day 1 of cycle 1, day 1 of cycle 2, day 8 of cycle 2, on day 1 of cycle 4, or any combination thereof. In one embodiment, the on-treatment sample is collect on day 8 of cycle 2.

Pre-treatment and on-treatment samples may be collected in the form of a tumor biopsy (e.g., a core needle biopsy), partial or complete surgical resection, blood draw, or any other method known in the art. In certain embodiments, tumor sites selected for biopsy have not received previous radiation therapy.

By way of example, an "anti-cancer agent" promotes cancer regression in a subject or prevents further tumor growth. In certain embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective," "effectiveness," and "efficacy" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount of an anti-cancer agent can inhibit cell growth, inhibit tumor growth, or reduce tumor size by at least about 5%, at least about 10%, by at least about 15%, at least about 20%, by at least about 25%, by at least about 30%, by at least about 40%, by at least about 50%, by at least about 60%, by at least about 70%, or by at least about 80%, by at least about 90%, by at least about 95%, or by at least about 100% relative to untreated subjects, relative to baseline, or, in certain embodiments, relative to patients treated with a standard-of-care therapy. In other embodiments of the invention, tumor regression can be observed and continue for a period of at least about 20 days, at least about 40 days, or at least about 60 days. Notwithstanding these ultimate measurements of therapeutic effectiveness, evaluation of immunotherapeutic drugs must also make allowance for "immune-related" response patterns.

An "immune-related" response pattern refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents can require long-term monitoring of the effects of these agents on the target disease.

A therapeutically effective amount of a drug or therapeutic agent includes a "prophylactically effective amount," which is any amount of the drug or therapeutic agent that, when administered alone or in combination with an anti-neoplastic agent to a subject at risk of developing a cancer (e.g., a subject having a pre-malignant condition) or of suffering a recurrence of cancer, inhibits the development or recurrence of the cancer. In certain embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

"Differential expression," as used herein in, refers to any expression level which is different than a reference expression level. Differential expression can refer to increased or decreased expression relative to a reference expression level. In some embodiments, differential expression can refer to the relative expression of a gene after treatment, e.g., on treatment, as compared to before treatment, e.g., at baseline. In other embodiments, differential expression can refer to the relative expression of a gene in responders as compared to non-responders.

The terms "once about every week," "once about every two weeks," or any other similar dosing interval terms as used herein mean approximate numbers. "Once about every week" can include every seven days ±one day, i.e., every six days to every eight days. "Once about every two weeks" can include every fourteen days ±three days, i.e., every eleven days to every seventeen days. Similar approximations apply, for example, to once about every three weeks, once about every four weeks, once about every five weeks, once about every six weeks and once about every twelve weeks. In some embodiments, a dosing interval of once about every six weeks or once about every twelve weeks means that the first dose can be administered any day in the first week, and then the next dose can be administered any day in the sixth or twelfth week, respectively. In other embodiments, a dosing interval of once about every six weeks or once about every twelve weeks means that the first dose is administered on a particular day of the first week (e.g., Monday) and then the next dose is administered on the same day of the sixth or twelfth weeks (i.e., Monday), respectively.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% or 20% (i.e., ±10% or ±20%). For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

Various aspects of the invention are described in further detail in the following subsections.

II. Methods of the Invention

This disclosure provides a method of treating a subject afflicted with a tumor derived from an RCC, wherein the method comprises (i) administering to the subject a first dose of an anti-PD-1 antibody or an antigen-binding portion thereof and/or an anti PD-L1 antibody or an antigen-binding portion thereof; and (ii) administering a second dose of the anti-PD-1 antibody or antigen-binding portion thereof or the anti-PD-L1 antibody or antigen-binding portion thereof to the subject, wherein after the administration of the first dose, the subject exhibits an increased or decreased expression of one or more genes which is differentially regulated following treatment with an anti-PD-1 antibody, e.g., PVRIG, NKG7, CD244, NKTR, TNFSF8, TNFSF13B, TNFRSF14, SPI1, CLEC2B, CTLA-4, TIGIT, PD-L2, or any combination thereof. The invention shows that certain genes are up- or down-regulated in a patient suffering from an RCC following initial treatment with an anti-PD-1 antibody or an antigen-binding portion thereof and/or an anti PD-L1 antibody or an antigen-binding portion thereof. Further, some genes are differentially expressed in subjects who ultimately are responsive (responders) to the treatment as compared to subjects who are not responsive (non-responders). Surprisingly, differential expression of certain genes has been found to correlate with increased patient responsiveness to anti-PD-1/anti-PD-L1 immunotherapy, e.g., reduced tumor burden. For example, as described herein, PVRIG, NKG7, CD244, NKTR, TNFSF8, TNFSF13B, TNFRSF14, SPI1, CLEC2B, CTLA-4, TIGIT, and PD-L2 were observed to be upregulated following treatment with an anti-PD-1 antibody to a greater extent in patients who ultimately experienced a ≥20% reduction in tumor size, as compared to patient who experienced a <20% reduction in tumor size. Accordingly, certain aspects of the present invention describe methods for enhancing the treatment of patients suffering from an RCC, comprising (i) administering to a patient a first dose of an anti-PD-1 antibody or antigen-binding portion thereof and/or an anti PD-L1 antibody or antigen-binding portion thereof; (ii) determining the expression of one or more differentially expressed genes (e.g., MICB, PVRIG, NKG7, CD244, NKTR, TNFSF8, TNFSF13B, TNFRSF14, SPI1, CLEC2B, CTLA-4, TIGIT, and/or PD-L2); and (iii) administering a second dose of the anti-PD-1 antibody or antigen-binding portion thereof and/or the anti PD-L1 antibody or antigen-binding portion thereof to a patient who exhibits differential expression of the selected one or more differentially expressed genes. In some embodiments, determining includes obtaining or receiving a report from a laboratory that the patient expresses one or more differentially expressed genes (e.g., increased expression of PVRIG, NKG7, CD244, NKTR, TNFSF8, TNFSF13B, TNFRSF14, SPI1, CLEC2B, CTLA-4, TIGIT, and/or PD-L2).

In some embodiments, the invention is directed to methods of (i) measuring or detecting the expression level of one or more differentially expressed genes (e.g., increased or decreased expression of PVRIG, NKG7, CD244, NKTR, TNFSF8, TNFSF13B, TNFRSF14, SPI1, CLEC2B, CTLA-4, TIGIT, and/or PD-L2) in a sample obtained from a subject, wherein the subject has been administered a first dose of an anti-PD-1 antibody or antigen-binding portion thereof and/or an anti PD-L1 antibody or antigen-binding portion thereof; and (ii) recommending to a health care provider to administer a second dose of an anti-PD-1 antibody or antigen-binding portion thereof and/or an anti PD-L1 antibody or antigen-binding portion thereof. The phrase "recommending a healthcare provider to administer a dose" includes, but is not limited to, sending a report that the patient who needs an anti-PD-1 antibody or anti-PD-L1 antibody therapy expresses one or more differentially expressed genes (e.g., increased or decreased expression of PVRIG, NKG7, CD244, NKTR, TNFSF8, TNFSF13B, TNFRSF14, SPI1, CLEC2B, CTLA-4, TIGIT, and/or PD-L2) after administration of a dose of the anti-PD-1 antibody or antigen-binding portion thereof and/or an anti PD-L1 antibody or antigen-binding portion thereof. In another embodiment, the invention is directed to methods of (i) measuring or detecting the expression level of one or more differentially expressed genes (e.g., increased or decreased expression of PVRIG, NKG7, CD244, NKTR, TNFSF8, TNFSF13B, TNFRSF14, SPI1, CLEC2B, CTLA-4, TIGIT, and/or PD-L2) in a sample obtained from a subject, wherein the subject has been administered a first dose of an anti-PD-1 antibody or antigen-binding portion thereof and/or an anti PD-L1 antibody or antigen-binding portion thereof; and (ii) sending a report to a health care provider to administer a second dose of an anti-PD-1 antibody or antigen-binding portion thereof and/or an anti PD-L1 antibody or antigen-binding portion thereof.

Other embodiments are directed to methods of identifying a subject afflicted with an RCC suitable for an anti-PD-1 antibody or anti-PD-L1 antibody therapy, comprising administering to the subject a first dose of an anti-PD-1 antibody or an antigen-binding portion thereof and/or an anti PD-L1 antibody or an antigen-binding portion thereof, and determining an expression level of one or more differentially expressed genes (e.g., increased or decreased expression of PVRIG, NKG7, CD244, NKTR, TNFSF8, TNFSF13B, TNFRSF14, SPI1, CLEC2B, CTLA-4, TIGIT, PD-L2, or any combination thereof) in a sample of the subject after administration of the first dose, wherein the subject exhibits differential expression of the one or more differentially expressed genes (e.g., PVRIG, NKG7, CD244, NKTR, TNFSF8, TNFSF13B, TNFRSF14, SPI1, CLEC2B, CTLA- 4, TIGIT, PD-L2, or any combination thereof) compared to the expression level prior to administration of the first dose; wherein the subject is administered a second dose of the anti-PD-1 antibody or antigen-binding portion thereof or the anti-PD-L1 antibody or antigen-binding portion thereof.

In some embodiments, the disclosure provides a method for treating a subject afflicted with a tumor derived from an RCC comprising administering, to the subject who exhibits an differential expression of one or more differentially expressed genes (e.g., PVRIG, NKG7, CD244, NKTR, TNFSF8, TNFSF13B, TNFRSF14, SPI1, CLEC2B, CTLA-4, TIGIT, PD-L2, or any combination thereof) after administration of a first dose of an anti-PD-1 antibody or an antigen-binding portion thereof or an anti-PD-L1 antibody or an antigen-binding portion thereof, a second dose of the anti-PD-1 antibody or antigen-binding portion thereof or the anti-PD-L1 antibody or antigen-binding portion thereof. In other embodiments, the disclosure provides a method of treating a subject afflicted with a tumor derived from an RCC, comprising: (i) determining an expression level of one or more differentially expressed genes (e.g., increased or decreased expression of PVRIG, NKG7, CD244, NKTR, TNFSF8, TNFSF13B, TNFRSF14, SPI1, CLEC2B, CTLA-4, TIGIT, PD-L2, or any combination thereof) in a sample of the subject after the subject is administered with a first dose of an anti-PD-1 antibody or an antigen-binding portion thereof or an anti-PD-L1 antibody or an antigen-binding portion thereof, wherein the subject exhibits differential expression of the one or more differentially expressed genes (e.g., PVRIG, NKG7, CD244, NKTR, TNFSF8, TNFSF13B, TNFRSF14, SPI1, CLEC2B, CTLA-4, TIGIT, PD-L2, or any combination thereof) after the administration of the first dose and (ii) administering to the subject a second dose of the anti-PD-1 antibody or antigen-binding portion thereof or the anti-PD-L1 antibody or antigen-binding portion thereof. In certain embodiments, the disclosure provides a method of treating a subject afflicted with a tumor derived from an RCC comprising: (i) administering to the subject a first dose of an anti-PD-1 antibody or antigen-binding portion thereof or an anti-PD-L1 antibody or antigen-binding portion thereof, (ii) determining an expression level of one or more differentially expressed genes (e.g., increased or decreased expression of PVRIG, NKG7, CD244, NKTR, TNFSF8, TNFSF13B, TNFRSF14, SPI1, CLEC2B, CTLA-4, TIGIT, PD-L2, or any combination thereof) in a sample of the subject after (i), wherein the subject exhibits differential expression of the one or more differentially expressed genes (e.g., PVRIG, NKG7, CD244, NKTR, TNFSF8, TNFSF13B, TNFRSF14, SPI1, CLEC2B, CTLA-4, TIGIT, PD-L2, or any combination thereof) compared to the expression level prior to (i); and (ii) administering to the subject a second dose of the anti-PD-1 antibody or antigen-binding portion thereof or the anti-PD-L1 antibody or antigen-binding portion thereof.

In other embodiments, the invention is directed to a method for identifying a subject afflicted with an RCC who is suitable for an anti-PD-1 antibody or anti-PD-L1 antibody therapy ("responder") comprising determining an expression level of one or more differentially expressed genes (e.g., increased or decreased expression of PVRIG, NKG7, CD244, NKTR, TNFSF8, TNFSF13B, TNFRSF14, SPI1, CLEC2B, CTLA-4, TIGIT, PD-L2, or any combination thereof) in a sample of the subject, wherein the subject exhibits differential expression of the one or more differentially expressed genes (e.g., PVRIG, NKG7, CD244, NKTR, TNFSF8, TNFSF13B, TNFRSF14, SPI1, CLEC2B, CTLA-4, TIGIT, PD-L2, or any combination thereof) after administration of a first dose of an anti-PD-1 antibody or antigen-binding portion thereof or an anti-PD-L1 antibody or antigen-binding portion thereof. The subject can be administered a second dose of the anti-PD-1 antibody or antigen-binding portion thereof or the anti-PD-L1 antibody or antigen-binding portion thereof. In another embodiment, the invention is directed to a method for identifying a subject afflicted with an RCC suitable for an anti-PD-1 antibody or anti-PD-L1 antibody therapy comprising: (i) administering to the subject a first dose of an anti-PD-1 antibody or antigen-binding portion thereof or an anti-PD-L1 antibody or antigen-binding portion thereof, and (ii) determining an expression level of one or more differentially expressed genes (e.g., increased or decreased expression of PVRIG, NKG7, CD244, NKTR, TNFSF8, TNFSF13B, TNFRSF14, SPI1, CLEC2B, CTLA-4, TIGIT, PD-L2, or any combination thereof) in a sample of the subject after (i), wherein the subject exhibits differential expression of the one or more differentially expressed genes (e.g., PVRIG, NKG7, CD244, NKTR, TNFSF8, TNFSF13B, TNFRSF14, SPI1, CLEC2B, CTLA-4, TIGIT, PD-L2, or any combination thereof) compared to the expression level prior to (i); wherein the subject is administered a second dose of the anti-PD-1 antibody or antigen-binding portion thereof or the anti-PD-L1 antibody or antigen-binding portion thereof.

In certain aspects, the invention is directed to an anti-PD-1 antibody or antigen-binding portion thereof or an anti-PD-L1 antibody or antigen-binding portion thereof for use in treating a tumor derived from an RCC in a patient, wherein the patient has exhibited (or determined to exhibit) differential expression of one or more differentially expressed genes (e.g., PVRIG, NKG7, CD244, NKTR, TNFSF8, TNFSF13B, TNFRSF14, SPI1, CLEC2B, CTLA-4, TIGIT, PD-L2, or any combination thereof) after receiving a first dose of an anti-PD-1 antibody or antigen-binding portion thereof or an anti-PD-L1 antibody or antigen-binding portion thereof.

In another aspect, the invention is directed to an anti-PD-1 antibody or antigen-binding portion thereof or an anti-PD-L1 antibody or antigen-binding portion thereof for use in treating a tumor derived from an RCC in a patient, wherein the patient previously received a first dose of the anti-PD-1 antibody or antigen-binding portion thereof or an anti-PD-L1 antibody or antigen-binding portion thereof, and wherein after receiving the first dose, the patient exhibited differential expression of one or more differentially expressed genes (e.g., PVRIG, NKG7, CD244, NKTR, TNFSF8, TNFSF13B, TNFRSF14, SPI1, CLEC2B, CTLA-4, TIGIT, PD-L2, or any combination thereof).

This disclosure provides a method of treating a subject afflicted with a tumor derived from an RCC, wherein the method comprises (i) administering to the subject a first dose of an anti-PD-1 antibody or an antigen-binding portion thereof and/or an anti PD-L1 antibody or an antigen-binding portion thereof; and (ii) administering a second dose of the anti-PD-1 antibody or antigen-binding portion thereof or the anti-PD-L1 antibody or antigen-binding portion thereof to the subject, wherein after the administration of the first dose, the subject exhibits an increased or decreased expression of one or more genes which is differentially regulated following treatment with an anti-PD-1 antibody, e.g., PVRIG, NKG7, CD244, NKTR, TNFSF8, TNFSF13B, TNFRSF14, SPI1, CLEC2B, CTLA-4, TIGIT, PD-L2, or any combination thereof. The invention shows that certain genes are up- or down-regulated in a patient suffering from an RCC following initial treatment with an anti-PD-1 antibody or an antigen-binding portion thereof and/or an anti PD-L1 antibody or an antigen-binding portion thereof. Further, some genes are differentially expressed in subjects who ultimately are responsive (responders) to the treatment as compared to subjects who are not responsive (non-responders). Surprisingly, differential expression of certain genes has been found to correlate with increased patient responsiveness to anti-PD-1/anti-PD-L1 immunotherapy, e.g., reduced tumor burden. For example, as described herein, PVRIG, NKG7, CD244, NKTR, TNFSF8, TNFSF13B, TNFRSF14, SPI1, CLEC2B, CTLA-4, TIGIT, and PD-L2 were observed to be upregulated following treatment with an anti-PD-1 antibody to a greater extent in patients who ultimately experienced a ≥20% reduction in tumor size, as compared to patient who experienced a <20% reduction in tumor size. Accordingly, certain aspects of the present invention describe methods for enhancing the treatment of patients suffering from an RCC, comprising (i) administering to a patient a first dose of an anti-PD-1 antibody or antigen-binding portion thereof and/or an anti PD-L1 antibody or antigen-binding portion thereof; (ii) determining the expression of one or more differentially expressed genes (e.g., MICB, PVRIG, NKG7, CD244, NKTR, TNFSF8, TNFSF13B, TNFRSF14, SPI1, CLEC2B, CTLA-4, TIGIT, and/or PD-L2); and (iii) administering a second dose of the anti-PD-1 antibody or antigen-binding portion thereof and/or the anti PD-L1 antibody or antigen-binding portion thereof to a patient who exhibits differential expression of the selected one or more differentially expressed genes. In some embodiments, determining includes obtaining or receiving a report from a laboratory that the patient expresses one or more differentially expressed genes (e.g., increased expression of PVRIG, NKG7, CD244, NKTR, TNFSF8, TNFSF13B, TNFRSF14, SPI1, CLEC2B, CTLA-4, TIGIT, and/or PD-L2).

In another aspect, the invention is directed to an anti-PD-1 antibody or antigen-binding portion thereof or an anti-PD-L1 antibody or antigen-binding portion thereof for use in treating a tumor derived from an RCC in a patient, wherein the patient exhibited (i) an increased expression of one or more serum markers of Interferon-γ activation; (ii) an increased tumor gene expression; (iii) a decreased clonality of T cell Receptor in serum; (iv) an increased T cell count in the tumor; or (v) any combination thereof after receiving a first dose of an anti-PD-1 antibody or antigen-binding portion thereof or an anti-PD-L1 antibody or antigen-binding portion thereof.

In another aspect, the invention is directed to an anti-PD-1 antibody or antigen-binding portion thereof or an anti-PD-L1 antibody or antigen-binding portion thereof for use in treating a tumor derived from an RCC in a patient, wherein the patient exhibited an increased expression level of CXCL9, CXCL10, or both after receiving a first dose and/or a second dose of an anti-PD-1 antibody or antigen-binding portion thereof or an anti-PD-L1 antibody or antigen-binding portion thereof.

This disclosure further provides a method of treating a subject afflicted with a tumor derived from an RCC, wherein the method comprises (i) measuring an expression level of one or more genes selected from the group consisting of MICB, PVRIG, SPI1, CLEC2B, NKG7, or any combination thereof, and (ii) administering to the subject a first dose of an antibody or an anti-PD-1 antibody or antigen-binding portion thereof or an anti-PD-L1 antibody or antigen-binding portion thereof to the subject, wherein the subject exhibits an increased expression of MICB, PVRIG, SPI1, CLEC2B, NKG7, or any combination thereof, relative to a reference expression level of MICB, PVRIG, SPI1, CLEC2B, and/or NKG7. The invention shows that certain genes are differentially expressed at baseline in a patient suffering from an RCC as compared to the average expression level of the same genes. Further, some genes are differentially expressed in subjects who ultimately are responsive (responders) to the treatment as compared to subjects who are not responsive (non-responders). Surprisingly, differential expression of certain genes has been found to correlate with increased patient responsiveness to anti-PD-1/anti-PD-L1 immunotherapy, e.g., reduced tumor burden. For example, as described herein, MICB, PVRIG, SPI1, CLEC2B, and NKG7 were observed to be more highly expressed in patients who ultimately experienced a ≥20% reduction in tumor size, as compared to patients who experienced a <20% reduction in tumor size. Accordingly, certain aspects of the present invention describe methods for enhancing the treatment of patients suffering from an RCC, comprising (i) determining the expression of one or more differentially expressed genes (e.g., MICB, PVRIG, SPI1, CLEC2B, and/or NKG7) and (ii) administering to a patient a first dose of an anti-PD-1 antibody or antigen-binding portion thereof and/or an anti PD-L1 antibody or antigen-binding portion thereof to a patient who exhibits differential expression of the selected one or more differentially expressed genes. In some embodiments, determining includes obtaining or receiving a report from a laboratory that the patient expresses one or more differentially expressed genes (e.g., increased expression of MICB, PVRIG, SPI1, CLEC2B, and/or NKG7).

In some aspects, the invention is directed to a method of identifying a subject afflicted with a tumor who is suitable for an anti-PD-1 antibody or an anti-PD-L1 antibody therapy comprising measuring an expression level of one or more genes selected from the group consisting of MICB, PVRIG, SPI1, CLEC2B, NKG7, or any combination thereof in a sample of the subject prior to the anti-PD-1 antibody or anti-PD-L1 antibody therapy. In some embodiments, the method further comprises administering to the subject a first dose of an anti-PD-1 antibody or antigen-binding portion thereof or an anti-PD-L1 antibody or antigen-binding portion thereof.

In another aspect, the invention is directed to a method for identifying a subject afflicted with a tumor who is suitable for an anti-PD-1 antibody or anti-PD-L1 antibody therapy comprising measuring an expression level of MICB, PVRIG, SPI1, CLEC2B, NKG7, or any combination thereof in a sample of the subject prior to the anti-PD-1 antibody or anti-PD-L1 antibody therapy, wherein the subject exhibits increased expression of MICB, PVRIG, SPI1, CLEC2B, NKG7, or any combination thereof relative to a reference expression level of MICB, PVRIG, SPI1, CLEC2B, and/or NKG7 by subjects who exhibited less than 20% tumor reduction as shown in table 6A ("No Response: Mean RMA value at baseline"), and wherein the subject is administered a first dose of an anti-PD-1 antibody or antigen-binding portion thereof or an anti-PD-L1 antibody or antigen-binding portion thereof.

In another aspect, the invention is directed to a method for treating a subject afflicted with a tumor comprising administering, to the subject who exhibits increased expression of MICB, PVRIG, SPI1, CLEC2B, NKG7, or any combination thereof, relative to a reference expression level of MICB, PVRIG, SPI1, CLEC2B, and/or NKG7 by subjects who exhibited less than 20% tumor reduction as shown in table 6A ("No Response: Mean RMA value at baseline"), a first dose of an anti-PD-1 antibody or antigen-binding portion thereof or an anti-PD-L1 antibody or antigen-binding portion thereof.

In another aspect, the invention is directed to method for treating a subject afflicted with a tumor comprising administering a first dose of an anti-PD-1 antibody or antigen-binding portion thereof or an anti-PD-L1 antibody or antigen-binding portion thereof to the subject, wherein the subject exhibits increased expression of MICB, PVRIG, SPI1, CLEC2B, NKG7, or any combination thereof, relative to a reference expression level of MICB, PVRIG, SPI1, CLEC2B, and/or NKG7 by subjects who exhibited less than 20% tumor reduction as shown in table 6A ("No Response: Mean RMA value at baseline").

In another aspect, the invention is directed to method for treating a subject afflicted with a tumor comprising: (i) measuring an expression level of one or more genes selected from the group consisting of MICB, PVRIG, SPI1, CLEC2B, NKG7, or any combination thereof, and (ii) administering to the subject a first dose of an antibody or an anti-PD-1 antibody or antigen-binding portion thereof or an anti-PD-L1 antibody or antigen-binding portion thereof to the subject, wherein the subject exhibits an increased expression of MICB, PVRIG, SPI1, CLEC2B, NKG7, or any combination thereof, relative to a reference expression level of MICB, PVRIG, SPI1, CLEC2B, and/or NKG7 by subjects who exhibited less than 20% tumor reduction as shown in table 6A ("No Response: Mean RMA value at baseline").

In another aspect, the invention is directed to a method of treating a subject afflicted with a tumor comprising: (i) determining an expression level of MICB, PVRIG, SPI1, CLEC2B, NKG7, or any combination thereof in a sample of the subject, wherein the subject exhibits increased expression of MICB, PVRIG, SPI1, CLEC2B, NKG7, or any combination thereof relative to a reference expression level of MICB, PVRIG, SPI1, CLEC2B, and/or NKG7 by subjects who exhibited less than 20% tumor reduction as shown in table 6A ("No Response: Mean RMA value at baseline"); and (ii) administering to the subject a first dose of an anti-PD-1 antibody or antigen-binding portion thereof or an anti-PD-L1 antibody or antigen-binding portion thereof.

The expression level of MICB, PVRIG, SPI1, CLEC2B, NKG7, or any combination thereof can be measured using any methods known in the art. In some embodiments, the expression of MICB, PVRIG, SPI1, CLEC2B, NKG7, or any combination thereof is a protein expression measured by an immunohistochemistry, an ELISA, a western blot, a protein array or any combination thereof. In other embodiments, the expression of MICB, PVRIG, SPI1, CLEC2B, NKG7, or any combination thereof is a nucleotide expression measured by an in situ hybridization, a DNA or RNA array or nucleotide hybridization technique, a tumor sequencing technique, a quantitative polymerase chain reaction (PCR), or any combination thereof.

In some embodiments, the expression level of MICB, PVRIG, SPI1, CLEC2B, NKG7, or any combination thereof is higher (e.g., increased) relative to a reference expression level of MICB, PVRIG, SPI1, CLEC2B, and/or NKG7 by subjects who exhibited less than 20% tumor reduction as shown in table 6A ("No Response: Mean RMA value at baseline"). In some embodiments, the reference expression level of MICB, PVRIG, SPI1, CLEC2B, NKG7, or any combination thereof the expression level of MICB, PVRIG, SPI1, CLEC2B, NKG7, or any combination thereof by a non-responder to an anti-PD1 antibody or an anti-PD-L1 antibody therapy. In another embodiment, the reference expression level of MICB, PVRIG, SPI1, CLEC2B, NKG7, or any combination thereof is the expression level of MICB, PVRIG, SPI1, CLEC2B, NKG7, or any combination thereof by a subject who exhibited less than 20% tumor reduction.

In other embodiments, the reference expression level of MICB, PVRIG, SPI1, CLEC2B, NKG7, or any combination thereof is the expression level of MICB, PVRIG, SPI1, CLEC2B, NKG7, or any combination thereof as measured in the average population. In other embodiments, the reference expression level of MICB, PVRIG, SPI1, CLEC2B, NKG7, or any combination thereof is the expression level by subjects who exhibited less than 20% tumor reduction as shown in table 6A ("No Response: Mean RMA value at baseline").

In some embodiments, the expression level of MICB, PVRIG, SPI1, CLEC2B, NKG7, or any combination thereof is increased (e.g., higher), relative to a reference expression level of MICB, PVRIG, SPI1, CLEC2B, and/or NKG7, by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 3 fold, at least about 4 fold, at least about 5 fold, at least about 6 fold, at least about 7 fold, at least about 8 fold, at least about 9 fold, at least about 10 fold, at least about 15 fold, at least about 20 fold, at least about 25 fold, at least about 30 fold, at least about 35 fold, at least about 40 fold, at least about 45 fold, at least about 50 fold, at least about 60 fold, at least about 70 fold, at least about 80 fold, at least about 90 fold, or at least about 100 fold. In one particular embodiment, the expression level of MICB is increased by about 1.3 fold relative to the expression level of MICB for subjects who exhibited less than 20% tumor reduction as shown in table 6A ("No Response: Mean RMA value at baseline"). In one particular embodiment, the expression level of PVRIG is increased by about 1.7 fold relative to the expression level of PVRIG for subjects who exhibited less than 20% tumor reduction as shown in table 6A ("No Response: Mean RMA value at baseline"). In one particular embodiment, the expression level of NKG7 is increased by about 2 fold relative to the expression level of NKG7 for subjects who exhibited less than 20% tumor reduction as shown in table 6A ("No Response: Mean RMA value at baseline"). In one particular embodiment, the expression level of SPI1 is increased by about 1.3 fold relative to the expression level of SPI1 for subjects who exhibited less than 20% tumor reduction as shown in table 6A ("No Response: Mean RMA value at baseline") for subjects who exhibited less than 20% tumor reduction as shown in table 6A ("No Response: Mean RMA value at baseline"). In one particular embodiment, the expression level of CLEC2B is increased by about 1.9 fold relative to the expression level of CLEC2B for subjects who exhibited less than 20% tumor reduction as shown in table 6A ("No Response: Mean RMA value at baseline").

The present methods are aimed to improve the treatment of RCCs which are among the most common tumors to show spontaneous regression (Elhilali et al. (2000) *BJU Int* 86:613-8; Inman et al. (2013) *Eur Urol* 63:881-9) while the traditional chemotherapy and radiotherapy had proven disappointing. The present methods disclosed herein increase the efficacy of anti-PD-1 and anti-PD-L1 immunotherapy by identifying a patient who is likely to respond better to an anti-PD-1 antibody or antigen binding portion thereof and/or an anti-PD-L1 antibody antigen binding portion thereof. The methods of this disclosure can be used to treat various stages of RCC, stages I, II, III, or IV. In stage I, the tumor can be 7 centimeters or smaller and is found only in the kidney. In stage II, however, the tumor can be larger than 7 centimeters and is found only in the kidney. In stage III, the tumor can be any size and cancer is found only in the kidney and in one or more nearby lymph nodes; or cancer is found in the main blood vessels of the kidney or in the layer of fatty tissue around the kidney. Cancer may also be found in one or more nearby lymph nodes. In stage IV, cancer has been spread beyond the layer of fatty tissue around the kidney and may be found in the adrenal gland above the kidney with cancer, or in nearby lymph nodes; or to other organs, such as the lungs, liver, bones, or brain, and may have spread to lymph nodes. In other embodiments, RCC that is treatable by the present methods is a recurrent RCC.

In some embodiments, the first dose is a flat dose or a weight based dose. In other embodiments, the second dose is a flat dose or a weight based dose.

Therapeutic administration of the anti-PD-1 antibody or antigen-binding portion thereof and/or the anti-PD-L1 antibody or antigen-binding portion thereof, as described herein, can effectively increase the duration of survival of the subject. In certain embodiments, therapeutic administration of the anti-PD-1 antibody or antigen-binding portion thereof and/or the anti-PD-L1 antibody or antigen-binding portion thereof to a subject results in the subject exhibiting an overall survival of at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months (e.g. 2 years), at least about 25 months, at least about 26 months, at least about 27 months, at least about 28 months, at least about 29 months, at least about 30 months, at least about 31 months, at least about 32 months, at least about 33 months, at least about 34 months, at least about 35 months, at least about 3 years, at least about 4 years, at least about 5 years, at least about 6 years, at least about 7 years, at least about 8 years, at least about 9 years, at least about 10 years, or at least about 20 years after the administration of the anti-PD-1 antibody or antigen-binding portion thereof and/or the anti-PD-L1 antibody or antigen-binding portion thereof. The overall survival of the anti-PD-1 antibody or anti-PD-L1 antibody therapy responder is better than non-responders who are not determined to have the increased or decreased expression of the one or more biomarker genes (e.g., increased or decreased expression of PVRIG, NKG7, CD244, NKTR, TNFSF8, TNFSF13B, TNFRSF14, SPI1, CLEC2B, CTLA-4, TIGIT, PD-L2, or any combination thereof).

In other embodiments, the administration of the anti-PD-1 antibody or antigen-binding portion thereof and/or the anti-PD-L1 antibody or antigen-binding portion thereof can effectively decrease the size of the tumor. Tumor size can be reduced after a first dose of the anti-PD-1 antibody or antigen-binding portion thereof and/or the anti-PD-L1 antibody or antigen-binding portion thereof, after a second dose of the anti-PD-1 antibody or antigen-binding portion thereof and/or the anti-PD-L1 antibody or antigen-binding portion thereof, or both. Tumor reduction can be measured by comparing the tumor size (e.g., the tumor burden) after administration of the anti-PD-1 antibody or antigen-binding portion thereof and/or the anti-PD-L1 antibody or antigen-binding portion thereof (on-treatment) to the tumor size at baseline (pre-treatment). In some embodiments, the tumor is reduced by at least about 10%, at least about 20%, at least about 30%, at least about 40%, at least about 50%, at least about 60%, at least about 70%, at least about 80%, at least about 90%, at least about 95%, or about 100%. In certain embodiments, after the administration of the second dose, the tumor is reduced by at least about 10%, at least about 20%, at least about 30%, at least about 40%, at least about 50%, at least about 60%, at least about 70%, at least about 80%, at least about 90%, at least about 95%, or about 100%.

In certain embodiments, the therapy of the present invention effectively increases the duration of progression free survival (PFS) of the subject. For example, the PFS of the subject can be increased by at least about 2 weeks, at least about 1 month, at least about 2 months, at least about 3 months, at least about 4 months, at least about 6 months, or at least about 1 year when compared to another subject treated with only standard-of-care therapy. For example, the PFS of the subject can be increased by at least about 2 weeks, at least about 1 month, at least about 2 months, at least about 3 months, at least about 4 months, at least about 6 months, or at least about 1 year when the subject exhibits an increased or decreased expression of PVRIG, NKG7, CD244, NKTR, TNFSF8, TNFSF13B, TNFRSF14, SPI1, CLEC2B, CTLA-4, TIGIT, PD-L2, or any combination thereof after the administration of a first dose of the anti-PD-1 antibody or antigen-binding portion thereof and/or the anti-PD-L1 antibody or antigen-binding portion thereof, and wherein the subject is then administered a second dose, as compared to another subject treated with only standard-of-care therapy.

II. A. Differentially Expressed Genes (or Proteins Thereof)

The present disclosure provides methods of treating a subject afflicted with a tumor derived from an RCC after determining that the subject is eligible or responsive to an anti-PD-1 antibody or antigen binding portion thereof or an anti-PD-L1 antibody antigen binding portion thereof. The subject's eligibility or responsiveness can be determined by measuring or detecting (or ordering a test and receiving a report providing) the expression of the one or more differentially expressed genes (or proteins thereof). In one embodiment, a subject is eligible or responsive to an anti-PD-1 antibody or anti-PD-L1 antibody therapy if the subject shows differential expression of CTLA-4, TIGIT, PD-L2, or any combination thereof. In another embodiment, a subject is eligible or responsive to an anti-PD-1 antibody or anti-PD-L1 antibody therapy if the subject shows differential, e.g., increased, expression of MICB, PVRIG, NKG7, or any combination thereof at baseline, e.g., prior to treatment with an anti-PD-1 antibody. In another embodiment, a subject is eligible or responsive to an anti-PD-1 antibody or anti-PD-L1 antibody therapy if the subject shows differential, e.g., increased, expression of TGIT, PVRIG, NKG7, CD244, NKTR, TNFSF8, TNFSF13B, TNFRSF14, SPI1, CLEC2B, or any combination thereof on treatment, e.g., after treatment with a first dose of an anti-PD-1 antibody or anti-PD-L1 antibody. In another embodiment, the subject shows differential expression of CTLA-4, TIGIT, PD-L2, CXCL9, CXCL10, and PD-L1, and any combination thereof after the administration of the first dose.

In some embodiments, the subject exhibits differential expression at baseline of MICB. In other embodiments, the subject exhibits differential expression at baseline of PVRIG. In other embodiments, the subject exhibits differential expression at baseline of NKG7. In other embodiments, the subject exhibits differential expression at baseline of SPI1. In other embodiments, the subject exhibits differential expression at baseline of CLEC2B. In some embodiments, the subject exhibits differential expression at baseline of MICB and PVRIG. In some embodiments, the subject exhibits differential expression at baseline of MICB and NKG7. In some embodiments, the subject exhibits differential expression at baseline of NKG7 and PVRIG. In some embodiments, the subject exhibits differential expression at baseline of NKG7, MICB, and PVRIG.

In some embodiments, the subject exhibits differential expression of CTLA-4 after the administration of the first dose. In other embodiments, the subject exhibits differential expression of TIGIT after the administration of the first dose. In yet other embodiments, the subject exhibits differential expression of PD-L2 after the administration of the first dose. In some embodiments, the subject exhibits differential expression of CTLA-4 and PD-L2 after the administration of the first dose. In some embodiments, the subject exhibits differential expression of CTLA-4 and TIGIT after the administration of the first dose. In some embodiments, the subject exhibits differential expression of TIGIT and PD-L2 after the administration of the first dose. In other embodiments, the subject exhibits differential expression of CTLA-4, PD-L2, and TIGIT after the administration of the first dose. In one particular embodiment, the subject exhibits differential, e.g., increased, expression of CXCL9 after the administration of the first dose. In another embodiment, the subject exhibits differential, e.g., increased, expression of CXCL10 after the administration of the first dose. In another embodiment, the subject exhibits differential expression of PD-L1 after the administration of the first dose.

In some embodiments, the subject exhibits differential, e.g., increased, expression of PVRIG after the administration of the first dose. In some embodiments, the subject exhibits differential, e.g., increased, expression of NKG7 after the administration of the first dose. In some embodiments, the subject exhibits differential, e.g., increased, expression of CD244 after the administration of the first dose. In some embodiments, the subject exhibits differential, e.g., increased, expression of NKTR after the administration of the first dose. In some embodiments, the subject exhibits differential, e.g., increased, expression of TNFSF8 after the administration of the first dose. In some embodiments, the subject exhibits differential, e.g., increased, expression of TNFSF13B after the administration of the first dose. In some embodiments, the subject exhibits differential, e.g., increased, expression of TNFRSF14 after the administration of the first dose. In some embodiments, the subject exhibits differential, e.g., increased, expression of SPI1 after the administration of the first dose. In some embodiments, the subject exhibits differential, e.g., increased, expression of CLEC2B after the administration of the first dose. In one embodiment, the subject exhibits differential, e.g., increased, expression of PVRIG and NKG7 after the administration of the first dose. In one particular embodiment, the subject exhibits differential, e.g., increased, expression of PVRIG and NKG7 at baseline and differentia, e.g., increased, expression of PVRIG and NKG7 after the administration of the first dose.

Other biomarker genes or proteins identified herein may be used in the present methods, either in addition to or in replacement of CTLA-4, TIGIT, and/or PD-L2. In some embodiments, the subject exhibits differential expression of one or more genes (or protein) selected from Table 2 (below) after the administration of the first dose. In other embodiments, the subject exhibits differential expression of one or more genes or proteins selected from Table 3 (below). In other embodiments, the subject exhibits differential expression of one or more genes or proteins selected from Table 4 (below). In other embodiments, the subject exhibits differential expression of one or more genes or proteins selected from Table 5 (below). In other embodiments, the subject exhibits differential expression of one or more genes or proteins selected from Table 6A and/or Table 6B (below). In other embodiments, the subject exhibits differential expression of one or more genes or proteins selected from Table 7A and/or Table 7B (below). In other embodiments, the subject exhibits differential expression of one or more genes or proteins selected from Table 8A and or Table 8B (below).

In certain embodiments, the one or more differentially expressed genes, of which expression can be increased or decreased, include, but are not limited to, one or more genes encoding stem cell factor (SCF), vascular epithelial growth factor-3 (VEGF-3), brain-derived neurotrophic factor, vascular epithelial growth factor (VEGF), vascular epithelial growth factor-2 (VEGF-2), regulated on activation, normal T cell expressed and secreted (RANTES; chemokine (C-C motif) ligand 5 [CCL5]), vitamin D binding protein, von Willebrand factor (vWF), α-2 macroglobulin, intercellular adhesion molecule-1 (ICAM-1), monocyte chemotactic protein-1 (MCP-1; CCL2), α-1 antitrypsin, CXCL10 (IP10), vascular cell adhesion protein-1 (VCAM-1), eotaxin, tumor necrosis factor receptor-II (TNF RII), haptoglobin, tissue inhibitor of metalloproteinases-1 (TIMP-1), ferritin, IL2-RA, matrix metalloproteinase-3 (MMP-3), C reactive protein (CRP), IL-18, factor VII, β-2-microglobulin, complement 3, CXCL9 (MIG), macrophage inflammatory protein (MIP-1β; CCL4), or any combination thereof. In some embodiments, the differential expression of the one or more genes is relative to the expression of the genes prior to administration of the first dose (baseline). In one particular embodiment, the subject exhibits an increase in the expression of CXCL9, CXCL10, or both after administration of the first dose. In other embodiments, the differential expression of the one or more genes is measured by comparing the expression of the one or more genes in a responder to the expression of the one or more genes in a non-responder.

In other embodiments, the one or more differentially expressed genes, of which expression can be increased or decreased, include, but are not limited to, one or more genes selected from Table 6A, Table 7A, and Table 8A.

In addition, certain genes identified herein were observed to have higher expression levels after administration of a first dose of an anti-PD-1 antibody (on-treatment) in those subjects with a >20% reduction in tumor burden.

In addition, certain genes identified herein were observed to have lower expression levels after administration of a first dose of an anti-PD-1 antibody (on-treatment) in those subjects with a >20% reduction in tumor burden. Accordingly, these marker genes may also be used in the disclosed methods. In some embodiments, the subject exhibits a lower expression level of one or more cellular component organization genes, signaling genes, genes previously identified to be downregulated by ipilimumab in melanoma, or any combination thereof as compared to the average expression of the one or more genes in all subjects receiving the first dose.

The expression level of one or more genes identified herein at baseline (pre-treatment) can indicate a responsiveness to anti-PD-1 or an anti-PD-L1 immunotherapy. In some embodiments, prior to administration of a first dose of an anti-PD-1 antibody (baseline) the subject exhibits a lower expression level of a gene selected from NPNT, RNF152, PLLP, GALNT14, LINC00472, EPB41L1, RBPMS2, ZNF462, NFIB, SERHL, MTUS1, TDRP, TTC28, PLEKHA1, FRK, CABLES1, STON1, METTL20, TACC2, BTD, SLC24A5, UNC119B, GLCE, BTBD3, FAM117B, FAM213A, DAB2IP, RBPMS, CCDC110, DZIP3, ZNF704, DNAJC19, PTPRF, SMADS, RPL22, MBLAC1, ERMP1, TJP2, DLG3, ZNRF3, AFG3L2, RPRD2, ZHX2, IPO11∥IPO11-LRRC70, MOAP1, HSDL2, LRPPRC, SAMM50, GALK2, FGD4, C5ORF54, WWTR1, MTPAP, MRPS27, ARHGAP5, ERLIN2, MARCH6, UQCRB, FBXO3, TOMM20, LCLAT1, PEX12, GFM2, HECTD1, COQ7, LARS, LIN7C, NAPEPLD, PEX19, SCAPER, WASL, ASCC1, ZKSCAN1, MAN2A1, EIF1AX, EIF4EBP2, TTC33, AP3M2, MRPL40, MPP5, APP, THNSL1, USP53, TCAIM, ABI2, MSH3, TNFAIP1, ZNF791, SEC22A, LIPT2, PARD3, MIEF1, TBL1XR1, FBXL20, KLHL24, DCTN5, ZNF260, VAPB, CLUAP1, COX15, TMEM194B, SCAMPI, SLC25A3, ZNF12, ZMYM4, ZNF512, SERINC4, TPRG1L, and any combination thereof. In some embodiments, prior to administration of a first dose of an anti-PD-1 antibody (baseline) the subject exhibits a higher expression level of a gene selected from NANOS3, LINC01119, KCNA10, CLEC4G, TMEM105, LGALS8-AS1, ADAMTS6, RTL1, MSGN1, E2F4, SPATA31D1, FAM163B, ZSWIM1, TSPAN16, CEACAM3, C19ORF35, C11ORF24, SP9, MSLN, GALR3, TMEM190, TROAP, RP11-797H7.5, ABCB11, GDF10, KIAA1683, TMEM196, SRMS, KCNA6, C5AR2, FLJ44635, EVC, SNORA53, MUC6, SPRN, OSBP2, ZAP70, APOBEC3H, C11ORF94, MUTYH, PLEKHM2, SLC35G6, OTOS, SPRNP1, A1BG, RP11-72304.2, SYTL4, AGER, WNT5B, GFI1B, ITPRIPL1, TRAPPC1, AURKB, SLFN11, TMEM132A, KCNAB2, MYO1G, SPANXD (SPANXE), OR56A1, SIX3, SSTR4, BMP5, TMEM117, CD300E, TIMM17B, ANKRD9, ANKRD13D, ARHGEF19, CSRNP1, QRFP, TCP11, KRTAP10-3, KRTAP10-1, TMEM86B, GPR1, C11ORF88, LILRA4, TAS2R31, CIDEC, MIIP, CARD17, ZNF215, RTKN2, MYO9B, DOK1, ZNF414, TRPT1, BHLHE22, FLT3LG, RP11-290F20.1, GOLGA6L7P, SCARNA20, C2CD4C, DBNL, REG3A, LOC100288637, CDC34, ASGR2, CD7, RALGDS, CCDC22, CYTH4, C17ORF62, LINC00158, METRNL, LILRB5, IKBKE, HSH2D, KIF26B, KIFC1, MICB, SPI1, TWIST2, ROS1, LRRC29, USP15, GPR97, ELF4, MSX2, GPBAR1, CYTH1, RNF175, REG1B, CRYAA, DOK2, PPP2R2C, S100A11, LSM10, PBX4, IRS4, PTK2B, CD82, DRAP1, TCEAL5, FBXO6, SH3BP1, KCND2, DENND3, TKTL1, SAT1, IL1A, TBC1D10C, KCNN4, GBP2, FCRL3, PRAM1, EHBP1L1, FXYD5, PSTPIP1, PLEKHO1, SNORA34, SCGB1A1, PENK, CATSPER1, IL15RA, CEP128, E2F7, EGFL6, TXNDC2, VASP, HAS2, WAS, FMNL1, GADD45B, DKK2, PPAPDC1A, LTB, HIST1H3 G, ZNF101, KIAA1551, RABGAP1L, EFHD2, CTSZ, FAM20A, IGFL2, ARHGAP9, CCDC109B, IRF1, PVRIG, CTSW, CFD, BATF, MYO1F, GFPT2, TAGAP, GJB6, EVI2B, CLEC2B, SAMSN1, CLMP, PLEK, RAC2, NKG7, BIN2, SP140, CILP, IL1R2, CD3E, GBP5, GZMB, MMP3, AIM2, and any combination thereof.

The present disclosure provides that a subject can be identified as being more responsive to immunotherapy treatment with an anti-PD-1 antibody or antigen-binding portion thereof and/or an anti-PD-L1 antibody or antigen-binding portion thereof by measuring the expression level of certain genes prior to administration of the immunotherapy. In some embodiments, the method of the present invention includes a method for identifying a subject afflicted with an RCC who is suitable for an anti-PD-1 antibody or anti-PD-L1 antibody therapy comprising determining the expression level of one or more genes upregulated by ipilimumab in melanoma, immune system genes (e.g., IL15RA, IL1R2, and/or IRF1), myeloid lineage genes (e.g., IL1A, LINC00158, PRAM1, and/or SPI1), lymphoid lineage genes (e.g., CD3E, AIM2, GZMB, NKG7, CD7, and/or CTSW), or any combination thereof, and administering an anti-PD-1 antibody or antigen-binding portion thereof and/or an anti-PD-L1 antibody or antigen-binding portion thereof if the expression of the one or more genes is increased relative to the average expression level of the one or more genes in a select population (e.g., all RCC subjects). In other embodiments, the method comprises determining the expression level of one or more genes downregulated by ipilimumab in melanoma establishment of protein localization genes, genes coding negative regulators of epithelial cell proliferation involved in lung morphogenesis, or any combination thereof and determining that those subjects with low expression of the one or more genes relative to the average expression level of the one or more genes in a select population (e.g., all RCC subjects) may be less responsive to an anti-PD-1 or anti-PD-L1 immunotherapy.

The expression level of the one or more genes, e.g., MICB, PVRIG, NKG7, CD244, NKTR, TNFSF8, TNFSF13B, TNFRSF14, CTLA-4, TIGIT, and/or PD-L2, can be measured at any time, e.g., before administration of the first dose of the anti-PD-1 antibody or antigen-binding portion thereof and/or the anti-PD-L1 antibody or antigen-binding portion thereof (pre-treatment); after the first dose of the anti-PD-1 antibody or antigen-binding portion thereof and/or the anti-PD-L1 antibody or antigen-binding portion thereof (on-treatment); and/or after the second dose of the anti-PD-1 antibody or antigen-binding portion thereof and/or the anti-PD-L1 antibody or antigen-binding portion thereof (on-treatment). In some embodiments, the baseline expression level of the one or more genes, e.g., the increased or decreased expression of MICB, PVRIG, SPI1, CLEC2B, and/or NKG7, is measured by comparing the expression of the one or more genes, e.g., MICB, PVRIG, SPI1, CLEC2B, and/or NKG7, in one subject with the expression of the one or more genes, e.g., MICB, PVRIG, SPI1, CLEC2B, and/or NKG7, with another subject or with the average expression of the one or more genes across a selected population of subjects (e.g., the average expression of the one or more genes by subjects affected with a tumor derived from an RCC). In some embodiments, the expression level of the one or more genes, e.g., the increased or decreased expression of PVRIG, NKG7, CD244, NKTR, TNFSF8, TNFSF13B, TNFRSF14, SPI1, CLEC2B, CTLA-4, TIGIT, and/or PD-L2, is measured by comparing the expression of the one or more genes, e.g., PVRIG, NKG7, CD244, NKTR, TNFSF8, TNFSF13B, TNFRSF14, SPI1, CLEC2B, CTLA-4, TIGIT, PD-L2, or any combination thereof, prior to the administration of the first dose (pre-treatment) and after administration of the first dose (on-treatment). In other embodiments, the expression level of the one or more genes, e.g., PVRIG, NKG7, CD244, NKTR, TNFSF8, TNFSF13B, TNFRSF14, SPI1, CLEC2B, CTLA-4, TIGIT, and/or PD-L2, is measured pre-treatment and after administration of a second dose of the anti-PD-1 antibody or antigen-binding portion thereof and/or the anti-PD-L1 antibody or antigen-binding portion thereof. In one embodiment, the expression level of the one or more genes, e.g., MICB, PVRIG, NKG7, CD244, NKTR, TNFSF8, TNFSF13B, TNFRSF14, SPI1, CLEC2B, CTLA-4, TIGIT, and/or PD-L2, is measured at one or more time points selected from the group consisting of: pre-treatment, on about day 1, on about day 2, on about day 3, on about day 4, on about day 5, on about day 6, on about day 7, on about day 8, on about day 9, on about day 10, on about day 11, on about day 12, on about day 13, on about day 14, on about day 15, on about day 16, on about day 17, on about day 18, on about day 19, on about day 20, and on about day 21 of each 21-day cycle, wherein the anti-PD-1 antibody or antigen-binding portion thereof and/or the anti-PD-L1 antibody or antigen-binding portion thereof is administered on day 1 of each 21-day cycle. In some embodiments, the expression level of the one or more genes, e.g., MICB, PVRIG, NKG7, CD244, NKTR, TNFSF8, TNFSF13B, TNFRSF14, SPI1, CLEC2B, CTLA-4, TIGIT, and/or PD-L2, is measured during one or more 21-day cycles selected from the group consisting of: cycle 1, cycle 2, cycle 3, cycle 4, cycle 5, cycle 6, cycle 7, cycle 8, cycle 9, cycle 10, cycle 11, cycle 12, cycle 13, cycle 14, cycle 15, cycle 16, cycle 17, cycle 18, cycle 19, cycle 20, cycle 21, cycle 22, cycle 23, cycle 24, cycle 25, and after cycle 25, wherein the first dose of the anti-PD-1 antibody or antigen-binding portion thereof and/or the anti-PD-L1 antibody or antigen-binding portion thereof is administered on day 1 of cycle 1. In one particular embodiment, the expression level of MICB, PVRIG, NKG7, CD244, NKTR, TNFSF8, TNFSF13B, TNFRSF14, SPI1, CLEC2B, CTLA-4, TIGIT, and/or PD-L2 is measured pre-treatment and on about day 8 of cycle 2, wherein the anti-PD-1 antibody or antigen-binding portion thereof and/or the anti-PD-L1 antibody or antigen-binding portion thereof is administered on day 1 of each 21-day cycle.

Any higher or lower expression of a particular gene at baseline, as compared to the reference expression of the particular gene, can be indicative of subject's responsiveness to the anti-PD-1/anti-PD-L1 therapy. In some embodiments, a subject is considered to have increased, e.g., higher or greater, expression of one or more genes, e.g., MICB, PVRIG, SPI1, CLEC2B, and/or NKG7, if the baseline expression of the one or more genes by a particular subject is at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 3.5 fold, at least about 4 fold, at least about 4.5 fold, at least about 5 fold, at least about 6 fold, at least about 7 fold, at least about 8 fold, at least about 9 fold, at least about 10 fold, at least about 20 fold, at least about 30 fold, at least about 40 fold, at least about 50 fold, or at least about 100 fold greater than the reference expression level of the one or more genes, e.g., MICB, PVRIG, SPI1, CLEC2B, and/or NKG7. In other embodiments, a subject is considered to have decreased, e.g., lower, expression of one or more genes, e.g., MICB, PVRIG, SPI1, CLEC2B, and/or NKG7, if the baseline expression of the one or more genes by a particular subject is less than about 99%, less than about 98%, less than about 97%, less than about 96%, less than about 95%, less than about 90%, less than about 85%, less than about 80%, less than about 75%, less than about 70%, less than about 65%, less than about 60%, less than about 55%, less than about 50%, less than about 40%, less than about 30%, less than about 20%, less than about 10%, less than about 5%, or less than about 1% that of the average expression of the one or more genes, e.g., MICB, PVRIG, SPI1, CLEC2B, and/or NKG7.

Any increase or decrease in the expression of a particular gene following administration of a first dose of the anti-PD-1/anti-PD-L1 therapy can be indicative of subject's responsiveness to the anti-PD-1/anti-PD-L1 therapy. In some embodiments, a subject is considered to have increased expression of one or more genes, e.g., PVRIG, NKG7, CD244, NKTR, TNFSF8, TNFSF13B, TNFRSF14, SPI1, CLEC2B, CTLA-4, TIGIT, and/or PD-L2, if the on-treatment expression of the one or more genes is at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 3.5 fold, at least about 4 fold, at least about 4.5 fold, at least about 5 fold, at least about 6 fold, at least about 7 fold, at least about 8 fold, at least about 9 fold, at least about 10 fold, at least about 20 fold, at least about 30 fold, at least about 40 fold, at least about 50 fold, or at least about 100 fold greater than the expression level of the one or more genes, e.g., PVRIG, NKG7, CD244, NKTR, TNFSF8, TNFSF13B, TNFRSF14, SPI1, CLEC2B, CTLA-4, TIGIT, and/or PD-L2, at baseline (pre-treatment). In other embodiments, a subject is considered to have decreased expression of one or more genes if the on-treatment expression of the one or more genes is less than about 99%, less than about 98%, less than about 97%, less than about 96%, less than about 95%, less than about 90%, less than about 85%, less than about 80%, less than about 75%, less than about 70%, less than about 65%, less than about 60%, less than about 55%, less than about 50%, less than about 40%, less than about 30%, less than about 20%, less than about 10%, less than about 5%, or less than about 1% that of the expression of the one or more genes at baseline (pre-treatment).

The expression of one or more genes, e.g., MICB, PVRIG, NKG7, CD244, NKTR, TNFSF8, TNFSF13B, TNFRSF14, SPI1, CLEC2B, CTLA-4, TIGIT, or PD-L2, can be measured using any method known in the art. In some embodiments, the increase or decrease in gene expression is detected by measuring a corresponding protein expression. For example, the expression of the one or more genes, e.g., MICB, PVRIG, NKG7, CD244, NKTR, TNFSF8, TNFSF13B, TNFRSF14, SPI1, CLEC2B, CTLA-4, TIGIT, PD-L2, or any combination thereof, can be a protein expression measured by an immunohistochemistry, an ELISA, a western blot, a protein array or any combination thereof. In other embodiments, the increase or decrease in gene expression is detected by measuring corresponding messenger RNA (mRNA) levels. For example, the expression of the one or more genes, e.g., MICB, PVRIG, NKG7, CD244, NKTR, TNFSF8, TNFSF13B, TNFRSF14, SPI1, CLEC2B, CTLA-4, TIGIT, PD-L2, or any combination thereof, can be a nucleotide expression (e.g., mRNA) measured by an in situ hybridization, a DNA or RNA array or nucleotide hybridization technique, a northern blot, a tumor sequencing technique, a quantitative polymerase chain reaction (PCR), or any combination thereof.

The expression levels of the one or more genes can be measured using a sample obtained from the subject. In certain embodiments, the sample comprises tumor tissue. In some embodiments, the sample comprises the primary tumor or a metastatic lymph node. In one particular embodiment, the sample comprises a biopsy of a primary tumor or biopsy of a metastatic lymph node. In other embodiments, the sample comprises patient serum or blood.

In certain embodiments, the tumor further expresses PD-L1. The PD-L1 status of a tumor in a subject can be measured prior to administering any composition and utilizing any method disclosed herein. In some embodiments, a tumor is said to be "PD-L1 positive" if the PD-L1 expression level of a tumor (e.g., the percentage of tumor cells expressing PD-L1) is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, or greater than 20%. In one embodiment, the PD-L1 expression level of a PD-L1 positive tumor is at least about 1%. In other embodiments, the PD-L1 expression level of a PD-L1 positive tumor is at least about 5%. In a certain embodiment, the PD-L1 expression level of a PD-L1 positive tumor is at least about 10%.

In one embodiment, a test tissue sample can be obtained from the subject who is in need of the therapy. In another embodiment, the assessment of the expression of one or more biomarker genes, e.g., MICB, PVRIG, NKG7, CD244, NKTR, TNFSF8, TNFSF13B, TNFRSF14, SPI1, CLEC2B, CTLA-4, TIGIT, PD-L2, PD-L1, CXCL9, and/or CXCL10, can be achieved without obtaining a test tissue sample. In some embodiments, selecting a suitable patient includes (i) optionally providing a test tissue sample obtained from a subject with cancer of the tissue, the test tissue sample comprising tumor cells and/or tumor-infiltrating inflammatory cells; and (ii) assessing the expression level of the one or more biomarker genes or the proportion of cells in the test tissue sample that express PD-L1 on the surface of the cells based on an assessment that the proportion of cells in the test tissue sample that express PD-L1 on the cell surface is higher than a predetermined threshold level.

In any of the methods comprising the measurement of gene expression in a test tissue sample as disclosed herein, however, it should be understood that any step comprising the provision of a test tissue sample obtained from a subject is an optional step. It should also be understood that in certain embodiments, the "measuring" or "assessing" step to determine the expression level of one or more genes, e.g., MICB, PVRIG, NKG7, CD244, NKTR, TNFSF8, TNFSF13B, TNFRSF14, SPI1, CLEC2B, CTLA-4, TIGIT, PD-L2, CXCL9, and/or CXCL10, or to identify, or determine the number or proportion of, cells in the test tissue sample that express a gene, e.g., PD-L1, on the cell surface is performed by a transformative method of assaying for gene expression, for example by performing a reverse transcriptase-polymerase chain reaction (RT-PCR) assay or an IHC assay. In certain other embodiments, no transformative step is involved and the expression of the one or more genes is assessed by, for example, reviewing a report of test results from a laboratory. In certain embodiments, the steps of the methods up to, and including, assessing gene expression provides an intermediate result that can be provided to a physician or other healthcare provider for use in selecting a suitable candidate for the anti-PD-1 antibody or anti-PD-L1 antibody therapy. In certain embodiments, the steps that provide the intermediate result is performed by a medical practitioner or someone acting under the direction of a medical practitioner. In other embodiments, these steps are performed by an independent laboratory or by an independent person such as a laboratory technician.

In addition to the increased or decreased expression of the one or more genes, the subject can exhibit one or more additional characteristics indicative of increased responsiveness to the immunotherapy after the administration of the first dose. Those characteristics can be selected from the group consisting of: (i) an increased expression of one or more serum markers of Interferon-γ activation; (ii) an increased tumor gene expression; (iii) a decreased clonality of T cell Receptor in serum; (iv) an increased T cell count in the tumor; and (v) any combination thereof. In one particular embodiment, the one or more characteristics indicative of increased responsiveness to the immunotherapy is increased expression of one or more serum markers of Interferon-γ activation (e.g., AIM2, CASP1, CCL8, and/or IRF9). In another embodiment, the one or more characteristics indicative of increased responsiveness to the immunotherapy is increased expression of one or more tumor gene. In another embodiment, the one or more characteristics indicative of increased responsiveness to the immunotherapy is a decreased clonality of T cell Receptor in serum. In another embodiment, the one or more characteristics indicative of increased responsiveness to the immunotherapy is an increased T cell count in the tumor.

The expression level of the one or more serum markers of interferon-γ can be measured using any of the methods disclosed herein. In some embodiments, the expression of the one or more serum markers of interferon-γ, e.g., AIM2, CASP1, CCL8, and/or IRF9, is increased following administration of a first dose of an anti-PD-1 antibody, an anti-PD-L1 antibody, a fragment thereof, or any combination thereof by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 3.5 fold, at least about 4 fold, at least about 4.5 fold, at least about 5 fold, at least about 6 fold, at least about 7 fold, at least about 8 fold, at least about 9 fold, at least about 10 fold, at least about 20 fold, at least about 30 fold, at least about 40 fold, at least about 50 fold, or at least about 100 fold relative to the expression level of the one or more serum markers of interferon-γ at baseline (pre-treatment).

The expression level of the tumor genes can also be measured using any of the methods disclosed herein. In some embodiments, the expression of the tumor genes is increased following administration of a first dose of an anti-PD-1 antibody or antigen-binding portion thereof and/or an anti-PD-L1 antibody or antigen-binding portion thereof by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 3.5 fold, at least about 4 fold, at least about 4.5 fold, at least about 5 fold, at least about 6 fold, at least about 7 fold, at least about 8 fold, at least about 9 fold, at least about 10 fold, at least about 20 fold, at least about 30 fold, at least about 40 fold, at least about 50 fold, or at least about 100 fold relative to the expression level of the tumor genes at baseline (pre-treatment).

In some embodiments, the administration of the anti-PD-1 antibody or antigen-binding portion thereof and/or the anti-PD-L1 antibody or antigen-binding portion thereof results in a decrease in serum (e.g., blood) T cell receptor (TCR) clonality. Subject serum T cell receptor clonality can be measured by any method known in the art, including, but not limited to, targeted next-generation sequencing of T cell receptors amplified from blood. These methods take advantage of the fact that during early T cell development, genes encoding the Ig and TCR molecules are formed by stepwise rearrangement of variable (V), diversity (D), and joining (J) gene segments, through a process referred to as V(D)J recombination (FIG. 10A). During this process, nucleotides are deleted and randomly inserted at the joining sites, yielding a diverse population of unique antigen receptors. As a result, circulating T cells can be sequenced at the Ig/TCR genes to identify the repertoire of T cell clones in a given subject, indicative of the diversity of T cells within the subject's serum. Accordingly, a high T cell clonality indicates a less diverse T cell population, and a low T cell clonality indicates a more diverse T cell population (FIG. 10A). In certain embodiments, the administration of the anti-PD-1 antibody or antigen-binding portion thereof and/or the anti-PD-L1 antibody or antigen-binding portion thereof results in a decrease in serum TCR clonality of at least about 2%, at least about 5%, at least about 7%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 80%, or at least about 90% relative to the serum TCR clonality at baseline. In one particular embodiment, the administration of the anti-PD-1 antibody or antigen-binding portion thereof and/or the anti-PD-L1 antibody or antigen-binding portion thereof results in a decrease in serum TCR clonality of at least about 50% relative to the serum TCR clonality at baseline.

In certain embodiments, the administration of the anti-PD-1 antibody or antigen-binding portion thereof and/or the anti-PD-L1 antibody or antigen-binding portion thereof results in an increase in tumor associated lymphocytes, e.g., T cell infiltration of the renal cancer tissue or tumor, relative to baseline, as indicated by an increase in the T cell count in the tumor. T cell infiltration can be characterized by an increased infiltration of $CD4^+$ T cells, $CD8^+$ T cells, or both into the renal cancer tissue or a tumor derived therefrom. This increase in T cell infiltration can be at least about 10%, at least about 20%, at least about 30%, at least about 40%, at least about 50%, at least about 60%, at least about 70%, at least about 80%, or at least about 90% greater than the level of T cell infiltration at baseline. In other embodiments, the administration of the anti-PD-1 antibody or antigen-binding portion thereof and/or the anti-PD-L1 antibody or antigen-binding portion thereof results in increased T cell proliferation. T cell proliferation can be increased by at least about 10%, at least about 20%, at least about 30%, at least about 40%, at least about 50%, at least about 60%, at least about 70%, at least about 80%, or at least about 90% relative to T cell proliferation at baseline. The disclosed methods can also, in certain embodiments, lead to a decrease in T-regulatory cells compared to baseline. T cell infiltration and/or proliferation and T-regulator cell counts can be measured by any method known in the art, including but not limited to, targeted next-generation sequencing of T cell receptors amplified from tumor or blood, immunohistochemistry, flow cytometry, or any combination thereof.

In other embodiments, the disclosed methods for treating RCC decreases the number of monocytic myeloid-derived suppressor cells or increases the number of granulocytic myeloid cells, relative to baseline. In one embodiment, the monocytic myeloid-derived suppressor cells are characterized by $CD11b^+/Ly6C^{hi}/Ly6G^-$ expression or $CD11b^+/Ly6C^{low}v/Ly6G^-$ expression. In another embodiment, the granulocytic myeloid cells are characterized by $CD11b^+/Ly6C^-/Ly6G^+$ expression. The number of monocytic myeloid-derived suppressor cells can decrease by at least about 5%, at least about 10%, at least about 15%, at least about 20%, at least about 25%, at least about 30%, at least about 40%, at least about 50%, at least about 60%, at least about 70%, at least about 80%, or at least about 90%, relative to baseline. The number of granulocytic myeloid cells can increase by at least about 5%, at least about 10%, at least about 20%, at least about 30%, at least about 40%, at least about 50%, at least about 60%, at least about 70%, at least about 80%, or at least about 90%, relative to baseline.

In one particular embodiment, the subject exhibits an increase in the number of CD4+ tumor associated lymphocytes in the tumor, an increase in the number of CD8+ tumor associated lymphocytes in the tumor, an increased expression level of CXCL9 in a serum, an increased expression level of CXCL10 in a serum, or any combination thereof after the administration of the first dose of the anti-PD-1 antibody or antigen-binding portion thereof and/or the anti-PD-L1 antibody or antigen-binding portion thereof. In another embodiment, the subject exhibits an increase in the number of CD4+ tumor associated lymphocytes in the tumor, an increase in the number of CD8+ tumor associated lymphocytes in the tumor, an increased expression level of CXCL9 in a serum, an increased expression level of CXCL10 in a serum, or any combination thereof after the administration of the second dose of the anti-PD-1 antibody or antigen-binding portion thereof and/or the anti-PD-L1 antibody or antigen-binding portion thereof.

II. B. Anti-PD-1 and Anti-PD-L1 Antibodies

PD-1 is a key immune checkpoint receptor expressed by activated T and B cells, which mediates immunosuppression. PD-1 is a member of the CD28 family of receptors, which includes CD28, CTLA-4, ICOS, PD-1, and BTLA. Two cell surface glycoprotein ligands for PD-1 have been identified, PD-L1 and PD-L2, which are expressed on antigen-presenting cells as well as many human cancers and have been shown to down regulate T cell activation and cytokine secretion upon binding to PD-1. Inhibition of the PD-1/PD-L1 interaction mediates potent antitumor activity in preclinical models.

Anti-PD-1 antibodies suitable for use in the disclosed methods are antibodies that bind to PD-1 with high specificity and affinity, block the binding of PD-L1, and inhibit the immunosuppressive effect of the PD-1 signaling pathway. In any of the therapeutic methods disclosed herein, an anti-PD-1 or anti-PD-L1 "antibody" includes an antigen-binding portion that binds to the PD-1 or PD-L1 receptor, respectively, and exhibits the functional properties similar to those of whole antibodies in inhibiting ligand binding and upregulating the immune system.

In other embodiments, the anti-PD-1 antibody or antigen binding portion thereof or the anti-PD-L1 antibody antigen binding portion thereof is a chimeric, humanized or, human monoclonal antibody or a portion thereof. In certain embodiments for treating a human subject, the antibody is a humanized antibody. In other embodiments for treating a human subject, the antibody is a human antibody. antibodies of an IgG1, IgG2, IgG3 or IgG4 isotype can be used.

In certain embodiments, the anti-PD-1 antibody or anti-gen binding portion thereof or the anti-PD-L1 antibody antigen binding portion thereof comprises a heavy chain constant region which is of a human IgG1 or IgG4 isotype. In certain other embodiments, the sequence of the IgG4 heavy chain constant region of the anti-PD-1 antibody or antigen binding portion thereof or the anti-PD-L1 antibody antigen binding portion thereof contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al. (2014) *Cancer Immunol Res.* 2(9):846-56). In yet other embodiments, the antibody comprises a light chain constant region which is a human kappa or lambda constant region. In other embodiments, the anti-PD-1 antibody or antigen binding portion thereof or the anti-PD-L1 antibody antigen binding portion thereof is a mAb or an antigen-binding portion thereof.

HuMAbs that bind specifically to PD-1 with high affinity have been disclosed in U.S. Pat. Nos. 8,008,449 and 8,779,105. Other anti-PD-1 mAbs have been described in, for example, U.S. Pat. Nos. 6,808,710, 7,488,802, 8,168,757 and 8,354,509, and PCT Publication No. WO 2012/145493. Each of the anti-PD-1 HuMAbs disclosed in U.S. Pat. No. 8,008,449 has been demonstrated to exhibit one or more of the following characteristics: (a) binds to human PD-1 with a $K_D$ of $1\times10^{-7}$ M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates antibody responses; and (j) inhibits tumor cell growth in vivo. Anti-PD-1 antibodies usable in the present invention include mAbs that bind specifically to human PD-1 and exhibit at least one, preferably at least five, of the preceding characteristics. In some embodiments, the anti-PD-1 antibody is nivolumab. In one embodiment, the anti-PD-1 antibody is pembrolizumab.

In certain embodiments, the anti-PD-1 antibody or antigen-binding portion thereof cross-competes with nivolumab for binding to human PD-1. In one embodiment, the anti-PD-1 antibody is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al. (2014) *Cancer Immunol Res.* 2(9):846-56). In other embodiments, the anti-PD-1 antibody or fragment thereof binds to the same epitope as nivolumab. In certain embodiments, the anti-PD-1 antibody has the same CDRs as nivolumab.

In another embodiment, the anti-PD-1 antibody or fragment thereof cross-competes with pembrolizumab. In some embodiments, the anti-PD-1 antibody or fragment thereof binds to the same epitope as pembrolizumab. In certain embodiments, the anti-PD-1 antibody has the same CDRs as pembrolizumab. In another embodiment, the anti-PD-1 antibody is pembrolizumab. Pembrolizumab (also known as "KEYTRUDA®," lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. Nos. 8,354,509 and 8,900,587; see also http://www.cancer.gov/drugdictionary?cdrid=695789 (last accessed: Dec. 14, 2014). Pembrolizumab has been approved by the FDA for the treatment of relapsed or refractory melanoma.

In other embodiments, the anti-PD-1 antibody or fragment thereof cross-competes with MEDI0608. In still other embodiments, the anti-PD-1 antibody or fragment thereof binds to the same epitope as MEDI0608. In certain embodiments, the anti-PD-1 antibody has the same CDRs as MEDI0608. In some embodiments, the anti-PD-1 antibody is MEDI0608 (formerly AMP-514), which is a monoclonal antibody. MEDI0608 is described, for example, in U.S. Pat. No. 8,609,089B2 or in http://www.cancer.gov/drugdictionary?cdrid=756047 (last accessed Dec. 14, 2014).

In certain embodiments, an immune checkpoint inhibitor is AMP-224, which is a B7-DC Fc fusion protein. AMP-224 is discussed in U.S. Publ. No. 2013/0017199 or in http://www.cancer.gov/publications/dictionaries/cancer-drug?cdrid=700595 (last accessed Jul. 8, 2015).

In other embodiments, the anti-PD-1 antibody or fragment thereof cross-competes with BGB-A317. In some embodiments, the anti-PD-1 antibody or fragment thereof binds the same epitope as BGB-A317. In certain embodiments, the anti-PD-1 antibody has the same CDRs as BGB-A317. In certain embodiments, the anti-PD-1 antibody is BGB-A317, which is a humanized monoclonal antibody. BGB-A317 is described in U.S. Publ. No. 2015/0079109.

Anti-PD-1 antibodies usable in the disclosed methods also include isolated antibodies that bind specifically to human PD-1 and cross-compete for binding to human PD-1 with nivolumab (see, e.g., U.S. Pat. Nos. 8,008,449 and 8,779,105; WO 2013/173223). The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of nivolumab by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 as, nivolumab are mAbs. For administration to human subjects, these cross-competing antibodies are preferably chimeric antibodies, or more preferably humanized or human antibodies. Such chimeric, humanized or human mAbs can be prepared and isolated by methods well known in the art.

Anti-PD-1 antibodies usable in the methods of the disclosed invention also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an antibody.

Anti-PD-1 antibodies suitable for use in the disclosed compositions are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and upregulating the immune system. In certain embodiments, the anti-PD-1 antibody or antigen-binding portion thereof cross-competes with nivolumab for binding to human PD-1. In other embodiments, the anti-PD-1 antibody or antigen-binding portion thereof is a chimeric, humanized or human monoclonal antibody or a portion thereof. In certain embodiments, the antibody is a humanized antibody. In other embodiments, the antibody is a human antibody. Antibodies of an IgG1, IgG2, IgG3 or IgG4 isotype can be used.

In certain embodiments, the anti-PD-1 antibody or antigen-binding portion thereof comprises a heavy chain constant region which is of a human IgG1 or IgG4 isotype. In certain other embodiments, the sequence of the IgG4 heavy chain constant region of the anti-PD-1 antibody or antigen-binding portion thereof contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al. (2014)). In yet other embodiments, the antibody comprises a light chain constant region which is a human kappa or lambda constant region. In other embodiments, the anti-PD-1 antibody or antigen-binding portion thereof is a mAb or an antigen-binding portion thereof.

In certain embodiments of any of the therapeutic methods described herein comprising administration of an anti-PD-1 antibody, the anti-PD-1 antibody is nivolumab. In other embodiments, the anti-PD-1 antibody is pembrolizumab. In other embodiments, the anti-PD-1 antibody is chosen from the human antibodies 17D8, 2D3, 4H1, 4A11, 7D3 and 5F4 described in U.S. Pat. No. 8,008,449. In still other embodiments, the anti-PD-1 antibody is MEDI0608 (formerly AMP-514), AMP-224, or BGB-A317.

Anti-PD-1 antibodies usable in the methods of the disclosed invention also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an antibody.

In certain embodiments, an anti-PD-1 antibody used in the methods can be replaced with another PD-1 or anti-PD-L1 antagonist. For example, because an anti-PD-L1 antibody prevents interaction between PD-1 and PD-L1, thereby exerting similar effects to the signaling pathway of PD-1, an anti-PD-L1 antibody can replace the use of an anti-PD-1 antibody in the methods disclosed herein. Therefore, in one embodiment, the present invention is directed to a method for treating a subject afflicted with a non-squamous NSCLC comprising administering to the subject a therapeutically effective amount an anti-PD-L1 antibody.

In certain embodiments, the anti-PD-L1 antibody is BMS-936559 (formerly 12A4 or MDX-1105) (see, e.g., U.S. Pat. No. 7,943,743; WO 2013/173223).

In other embodiments, the anti-PD-L1 antibody is MPDL3280A (also known as RG7446) (see, e.g., Herbst et al. (2013) *J Clin Oncol* 31(suppl):3000. Abstract.; U.S. Pat. No. 8,217,149).

In other embodiments, the anti-PD-L1 antibody is MEDI4736 (also called Durvalumab; Khleif (2013) In: Proceedings from the European Cancer Congress 2013; Sep. 27-Oct. 1, 2013; Amsterdam, The Netherlands. Abstract 802, See U.S. Pat. No. 8,779,108 or US 2014/0356353, filed May 6, 2014).

In further embodiments, the anti-PD-L1 antibody is MSB0010718C (also called Avelumab; See US 2014/0341917).

Because anti-PD-1 and anti-PD-L1 target the same signaling pathway and have been shown in clinical trials to exhibit similar levels of efficacy in a variety of cancers, including RCC (see Brahmer et al. (2012) *N Engl J Med* 366:2455-65; Topalian et al. (2012a) *N Engl J Med* 366: 2443-54; WO 2013/173223), an anti-PD-L1 antibody can be substituted for the anti-PD-1 antibody in any of the therapeutic methods disclosed herein. In certain embodiments, the anti-PD-L1 antibody is BMS-936559 (formerly 12A4 or MDX-1105) (see, e.g., U.S. Pat. No. 7,943,743; WO 2013/173223). In other embodiments, the anti-PD-L1 antibody is MPDL3280A (also known as RG7446) (see, e.g., Herbst et al. (2013) *J Clin Oncol* 31(suppl):3000. Abstract; U.S. Pat. No. 8,217,149) or MEDI4736 (Khleif (2013) In: Proceedings from the European Cancer Congress 2013; Sep. 27-Oct. 1, 2013; Amsterdam, The Netherlands. Abstract 802). In certain embodiments, the antibodies that cross-compete for binding to human PD-L1 with, or bind to the same epitope region of human PD-L1 as the above-references PD-L1 antibodies are mAbs. For administration to human subjects, these cross-competing antibodies can be chimeric antibodies, or can be humanized or human antibodies. Such chimeric, humanized or human mAbs can be prepared and isolated by methods well known in the art.

In some embodiments, an immune checkpoint inhibitor, e.g., an anti-PD-1 antagonist, used in the present invention is a PD-1 Fc fusion protein.

The anti-PD-1 antibody or antigen binding portion thereof or the anti-PD-L1 antibody antigen binding portion thereof of the present invention can be administered to a subject at a dose (either a first dose or a second dose) selected from the group consisting of about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5.5 mg/kg, about 6.5 mg/kg, about 7.5 mg/kg, about 8.0 mg/kg, about 8.5 mg/kg, about 9.0 mg/kg, about 9.5 mg/kg, about 10 mg/kg, about 11 mg/kg, about 12 mg/kg, about 13 mg/kg, about 14 mg/kg, about 15 mg/kg, about 20 mg/kg, or greater than about 20 mg/kg. In other embodiments, the anti-PD-1 antibody or antigen binding portion thereof or the anti-PD-L1 antibody antigen binding portion thereof, can be administered at a dose selected from the group consisting of about 0.1 to about 20.0 mg/kg, about 0.1 to about 15.0 mg/kg, about 0.1 to about 10.0 mg/kg, about 0.1 to about 9.5 mg/kg, about 0.1 to about 9.0 mg/kg, about 0.1 to about 8.5 mg/kg, about 0.1 to about 8.0 mg/kg, about 0.1 to about 7.5 mg/kg, about 0.1 to about 7.0 mg/kg, about 0.1 to about 6.5 mg/kg, about 0.1 to about 6.0 mg/kg, about 0.1 to about 5.5 mg/kg, about 0.1 to about 5.0 mg/kg, about 0.1 to about 4.5 mg/kg, about 0.1 to about 4.0 mg/kg, about 0.1 to about 3.5 mg/kg, about 0.1 to about 3.0 mg/kg, about 0.3 to about 10.0 mg/kg, about 0.3 to about 9.0 mg/kg, about 0.3 to about 6.0 mg/kg, about 0.3 to about 3.0 mg/kg, about 3.0 to about 10.0 mg/kg, about 3.0 to about 9.0 mg/kg, or about 3.0 to about 6.0 mg/kg. In certain embodiments, a subject is administered 0.3 mg/kg of an anti-PD-1 antibody, e.g., nivolumab, or an anti-PD-L1 antibody. In other embodiments, a subject is administered 2.0 mg/kg of an anti-PD-1 antibody, e.g., nivolumab, or an anti-PD-L1 antibody. In other embodiments, a subject is administered 10 mg/kg of an anti-PD-1 antibody, e.g., nivolumab, or an anti-PD-L1 antibody.

II. C. Combination Therapies with Anti-PD-1 and/or Anti-PD-L1 Antibodies

In some embodiments, the methods disclosed herein further comprise administering one or more additional anti-cancer agents. In certain embodiments, the one or more anti-cancer agents have been administered to the subject prior to the administration of the anti-PD-1 antibody or antigen-binding portion thereof and/or the anti-PD-L1 antibody or antigen-binding portion thereof. In certain embodiments, the one or more anti-cancer agents were not effective in treating the cancer. In some embodiments, the other anti-cancer agent is any anti-cancer agent described herein or known in the art. In certain embodiments, the anti-PD-1 antibody or anti-PD-L1 antibody can be combined with another immunotherapy. In certain embodiments, immunotherapy involving blockade of immune checkpoints is administered as a monotherapy. In other embodiments, immunotherapy involving blockade of immune checkpoints is administered in combination with other therapies.

When the anti-PD-1 antibody or anti-PD-L1 antibody is combined with another anti-cancer agent, the anti-PD-1 antibody or anti-PD-L1 antibody and the second anti-cancer agent can be administered at a fixed dose. In some embodiments, the dosage of the anti-PD-1 antibody or anti-PD-L1 antibody and the second anti-cancer agent can be flat doses or fixed doses.

In some embodiments, the anti-cancer agent is selected from the group consisting of an antibody or antigen-binding portion thereof that binds specifically to CTLA-4 ("anti-CTLA-4 antibody or antigen-binding portion thereof") and inhibits CTLA-4 activity, a chemotherapy, a platinum-based doublet chemotherapy, a TKI, an anti-VEGF inhibitor, or any combination thereof. In one embodiment, the other anti-cancer agent is an anti-CTLA antibody. In another embodiment, the other anti-cancer agent is a chemotherapy or a platinum-based doublet chemotherapy (PT-DC). In certain embodiments, the other anti-cancer agent is an EGFR-targeted TKI. In one embodiment, the other anti-cancer agent is an anti-VEGF antibody. In other embodiments, the anti-cancer agent is a platinum agent (e.g., cisplatin, carboplatin), a mitotic inhibitor (e.g., paclitaxel, albumin-bound paclitaxel, docetaxel, taxotere, docecad), a fluorinated Vinca alkaloid (e.g., vinflunine, javlor), vinorelbine, vinblastine, etoposide, or pemetrexed gemcitabin. In one embodiment, the other anti-cancer agent is 5-flurouracil (5-FU). In certain embodiments, the other anti-cancer agent is any other anti-cancer agent known in the art. In some embodiments, two or more additional anti-cancer agents are administered in combination with the anti-PD-1 antibody or antigen-binding portion thereof and/or the anti-PD-L1 antibody or antigen-binding portion thereof. In some embodiments, administration of the anti-PD-1 antibody or antigen-binding portion thereof and/or the anti-PD-L1 antibody or antigen-binding portion thereof is combined with surgical resection, radiation therapy, and or any other standard-of-care treatment of RCC known in the art.

1. Anti-CTLA-4 Antibodies

In certain embodiments, an anti-PD-1 antibody or anti-PD-L1 antibody is combined with an anti-CTLA-4 antibody. CTLA-4 interaction with B7 transduces a signal leading to inactivation of T-cells bearing the CTLA-4 receptor. Disruption of this interaction effectively induces, enhances, or prolongs the activation of such T cells, thereby inducing, enhancing, or prolonging an immune response. Previous studies have found that RCC patients treated with a combination of an anti-PD-1 antibody (e.g., nivolumab) and an anti-CTLA-4 antibody (e.g., ipilimumab) exhibit increased objective response rates (ORRs) relative to treatment with nivolumab alone. See International Application No. PCT/US2015/018727, which is incorporated by reference herein in its entirety. In some embodiments, the anti-PD-1 antibody or antigen-binding portion thereof and/or the anti-PD-L1 antibody or antigen-binding portion thereof are administered to a subject in combination with an anti-cancer agent, wherein the anti-cancer agent is an antibody or antigen-binding portion thereof that binds specifically to CTLA-4 and inhibits CTLA-4 activity. In one particular embodiment, the anti-cancer agent is ipilimumab.

HuMAbs that bind specifically to CTLA-4 with high affinity have been disclosed in U.S. Pat. Nos. 6,984,720 and 7,605,238. Other anti-CTLA-4 mAbs have been described in, for example, U.S. Pat. Nos. 5,977,318, 6,051,227, 6,682,736, and 7,034,121. The anti-CTLA-4 HuMAbs disclosed in U.S. Pat. Nos. 6,984,720 and 7,605,238 have been demonstrated to exhibit one or more of the following characteristics: (a) binds specifically to human CTLA-4 with a binding affinity reflected by an equilibrium association constant ($K_a$) of at least about $10^7$ $M^{-1}$, or about $10^9$ $M^{-1}$, or about $10^{10}$ $M^{-1}$ to $10^{11}$ $M^{-1}$ or higher, as determined by Biacore analysis; (b) a kinetic association constant ($k_a$) of at least about $10^3$, about $10^4$, or about $10^5$ $m^{-1}$ $s^{-1}$; (c) a kinetic disassociation constant ($k_d$) of at least about $10^3$, about $10^4$, or about $10^5$ $m^{-1}$ $s^{-1}$; and (d) inhibits the binding of CTLA-4 to B7-1 (CD80) and B7-2 (CD86). Anti-CTLA-4 antibodies usable in the present method include mAbs that bind specifically to human CTLA-4 and exhibit at least one, at least two or, in one embodiment, at least three of the preceding characteristics.

An exemplary clinical anti-CTLA-4 antibody useful for the combination is the human mAb 10D1 (now known as ipilimumab and marketed as YERVOY®) as disclosed in U.S. Pat. No. 6,984,720. Ipilimumab is an anti-CTLA-4 antibody that can be used in the methods disclosed herein. Ipilimumab is a fully human, IgG1 monoclonal antibody that blocks the binding of CTLA-4 to its B7 ligands, thereby stimulating T cell activation and improving overall survival (OS) in patients with advanced melanoma (Hodi et al. (2010) *N Engl J Med* 363:711-23). Concurrent therapy with nivolumab and ipilimumab in a Phase 1 clinical trial produced rapid and deep tumor regression in a substantial proportion of patients with advanced melanoma, and was significantly more effective than either antibody alone (Wolchok et al. (2013) *N Engl J Med* 369(2):122-33; WO 2013/173223).

Another anti-CTLA-4 antibody usable in the present methods is tremelimumab (also known as CP-675,206). Tremelimumab is human IgG2 monoclonal anti-CTLA-4 antibody. Tremelimumab is described in WO/2012/122444, U.S. Publ. No. 2012/263677, or WO Publ. No. 2007/113648 A2.

Anti-CTLA-4 antibodies usable in the disclosed methods also include isolated antibodies that bind specifically to human CTLA-4 and cross-compete for binding to human CTLA-4 with ipilimumab or tremelimumab or bind to the same epitope region of human CTLA-4 as ipilimumab or tremelimumab. In certain embodiments, the antibodies that cross-compete for binding to human CTLA-4 with, or bind to the same epitope region of human CTLA-4 as does ipilimumab or tremelimumab, are antibodies comprising a heavy chain of the human IgG1 isotype. For administration to human subjects, these cross-competing antibodies are preferably chimeric antibodies, or more preferably humanized or human antibodies. Usable anti-CTLA-4 antibodies also include antigen-binding portions of the above antibodies such as Fab, F(ab')$_2$, Fd or Fv fragments.

In some embodiments, the method of the present invention further comprises administering an anti-CTLA-4 antibody or antigen-binding portion thereof to the subject. The anti-CTLA-4 antibody or antigen-binding portion thereof can be administered before, after, or concurrently with the anti-PD-1 antibody or antigen-binding portion thereof and/or the anti-PD-L1 antibody or antigen-binding portion thereof, or any combination thereof. In some embodiments, the anti-CTLA-4 antibody or antigen-binding portion thereof is administered before the anti-PD-1 antibody or antigen-binding portion thereof and/or the anti-PD-L1 antibody or antigen-binding portion thereof. In other embodiments, the anti-CTLA-4 antibody or antigen-binding portion thereof is administered after the anti-PD-1 antibody or antigen-binding portion thereof and/or the anti-PD-L1 antibody or antigen-binding portion thereof. In other embodiments, the anti-CTLA-4 antibody or antigen-binding portion thereof is administered at the same time as the anti-PD-1 antibody or antigen-binding portion thereof and/or the anti-PD-L1 antibody or antigen-binding portion thereof.

2. Combinations with Other Standard-of-Care Treatments

In certain embodiments, the anti-PD-1 antibody or antigen-binding portion thereof and/or the anti-PD-L1 antibody or antigen-binding portion thereof are administered in combination with any other known standard-of-care treatment of RCC. In some embodiments, the anti-PD-1 antibody or antigen-binding portion thereof and/or the anti-PD-L1 antibody or antigen-binding portion thereof are administered in combination with one or more of surgical resection, including radical nephrectomy, partial nephrectomy, cytoreductive nephrectomy, and nephron-sparing surgery; radiotherapy; chemotherapy; treatment with cytokines IL-2 and IFNα, e.g., IFN-2b and PegIFN-2b; mTOR inhibitors, e.g., everolimus and temsirolimus; or any combination thereof.

Standard-of-care therapies for different types of cancer are well known by persons of skill in the art. For example, the National Comprehensive Cancer Network (NCCN), an alliance of 21 major cancer centers in the USA, publishes the NCCN Clinical Practice Guidelines in Oncology (NCCN GUIDELINES®) that provide detailed up-to-date information on the standard-of-care treatments for a wide variety of cancers (see NCCN GUIDELINES®, 2014).

For clinically localized RCC (Stage IA and IB), surgical resection, including radical nephrectomy and nephron-sparing surgery, is an effective therapy. Partial nephrectomy is generally not suitable for patients with locally advanced tumors (Stage II and III), in which case radical nephrectomy is preferred. Where the tumor is confined to the renal parenchyma, the 5-year survival rate is 60-70%, but this is lowered considerably in Stage IV disease where metastases have spread. Stage IV RCC is relatively resistant to radiotherapy and chemotherapy, although patients can benefit from surgery, and cytoreductive nephrectomy before systemic therapy is recommended for patients with a potentially surgically resectable primary and multiple resectable metastases.

In some embodiments, the standard of care that can be combined with the anti-PD-1 or anti-PD-L1 therapy includes IL-2 and interferon (IFN) a, e.g., IFN-2b and PegIFN-2b.

The recognition of the importance of hypoxia inducible factor alpha (HIFα) signaling in the pathogenesis of clear-cell RCC has led to widespread study of two classes of targeted therapies, anti-angiogenic TKIs and mTOR inhibitors, in 1L and 2L treatments (Mulders (2009) *BJU Int* 104:1585-89). Targeting of angiogenesis is rational because constitutive HIFα activation leads to the upregulation or activation of several proteins including vascular endothelial growth factor (VEGF), which can subsequently lead to tumor proliferation and neovasculature formation. Moreover, blockade of VEGF activity may modulate the immune environment and stimulate an antitumor response. Targeting of the mTOR pathway is important because activation of the upstream PI3K/Akt/mTOR signaling pathway is one method by which constitutive HIFα activation or upregulation occurs (Mulders (2009) *BJU Int* 104:1585-89).

Agents that target angiogenesis include VEGF-receptor (VEGFr) TKIs (e.g., sorafenib, sunitinib, pazopanib, axitinib, and tivozanib) and VEGF-binding mAbs (e.g., bevacizumab), while agents that target the mTOR pathway include the mTOR inhibitors (e.g., everolimus and temsirolimus) (Mulders (2009) *BJU Int* 104:1585-89; NCCN GUIDELINES®, Version 3.2014—Kidney Cancer). However, durable responses are rare as most patients develop resistance and eventually progressive disease, and OS improvement has only been shown in one phase 3 trial in poor-risk patients: temsirolimus (TORISEL®) showed a statistically significant benefit for OS in patients with advanced RCC compared to IFNα (10.9 months versus 7.3 months) (Hudes et al. (2007) *N Engl J Med* 356(22):2271-81). Everolimus (AFINITOR®) has also demonstrated a 2.1-month improvement in median progression-free survival (PFS) versus placebo, but with no OS improvement (Motzer et al. (2008) *Lancet* 372:449-56). Among the five approved anti-angiogenic agents (sorafenib, sunitinib, pazopanib, axitinib, and bevacizumab) and two approved mTOR inhibitors (temsirolimus, everolimus), only everolimus is approved specifically for use after the failure of treatment with anti-angiogenic therapy. In the U.S., everolimus is indicated for the treatment of advanced RCC after failure of first-line treatment with sunitinib or sorafenib, whereas in the EU, everolimus is more broadly indicated for patients with advanced RCC, whose disease has progressed on or after treatment with VEGF-targeted therapy. No recommendation exists for patients progressing on mTOR inhibitors.

In certain embodiments, the anti-PD-1 antibody or antigen binding portion thereof or the anti-PD-L1 antibody antigen binding portion thereof can be administered to a subject suffering from a renal cancer in addition to (e.g., co-administered), prior to, or following a standard-of-care therapy, or any combination thereof. In some embodiments, the antibodies of the present invention can be administered before the subject is administered one or more standard-of-care therapies. In other embodiments, the antibodies of the present invention can be administered after the subject has received one or more standard-of-care therapies. In other embodiments, the antibodies of the present invention can be administered at the same time (e.g., concurrently or as part of the same course of treatment) as one or more standard-of-care therapies. In certain embodiments, a subject is administered an anti-PD-1 antibody or antigen binding portion thereof or an anti-PD-L1 antibody antigen binding portion thereof and an anti-angiogenic TKI. In one particular embodiment, the TKI is selected from sunitinib, pazopanib, sorafenib, axitinib, or tivozanib.

Vascular endothelial growth factor ("VEGF") is an endothelial cell-specific mitogen and an inducer of angiogenesis. VEGF has a prominent role in angiogenesis and tumor growth and development. In some embodiments of this invention, the anti-PD-1 antibody or antigen-binding portion thereof and/or the anti-PD-L1 antibody or antigen-binding portion thereof are administered in combination with an anti-VEGF antagonist. In certain embodiments, the anti-VEGF antagonist is an anti-VEGF antibody or an antigen-binding molecule or fragment thereof. In certain embodiments, the anti-VEGF antibody is bevacizumab (described in U.S. Pat. No. 7,169,901), or any other VEGF antibody known in the art including ranibizumab (U.S. Pat. No. 7,297,334), VGX-100 (U.S. Pat. No. 7,423,125), r84 (U.S. Pat. No. 8,034,905), aflibercept (U.S. Pat. No. 5,952, 199), IMC-18F1 (U.S. Pat. No. 7,972,596), IMC-1C11 (PCT/US2000/02180), and ramucirumab (U.S. Pat. No. 7,498,414).

In some embodiments, the anti-PD-1 antibody or antigen-binding portion thereof and/or the anti-PD-L1 antibody or antigen-binding portion thereof are administered in combination with any chemotherapy known in the art. In certain embodiments, the chemotherapy is a platinum based-chemotherapy. Platinum-based chemotherapies are coordination complexes of platinum. In some embodiments, the platinum-based chemotherapy is a platinum-doublet chemotherapy. In one embodiment, the chemotherapy is administered at the approved dose for the particular indication. In other embodiments, the chemotherapy is administered at any dose disclosed herein. In some embodiments, the platinum-based chemotherapy is cisplatin, carboplatin, oxaliplatin, satraplatin, picoplatin, Nedaplatin, Triplatin, Lipoplatin, or combinations thereof. In certain embodiments, the platinum-based chemotherapy is any other platinum-based chemotherapy known in the art. In some embodiments, the chemotherapy is the nucleotide analog gemcitabine. In an embodiment, the chemotherapy is a folate antimetabolite. In an embodiment, the folate antimetabolite is pemetrexed. In certain embodiments the chemotherapy is a taxane. In other embodiments, the taxane is paclitaxel. In other embodiments, the chemotherapy is a nucleoside analog. In one embodiment, the nucleoside analog is gemcitabine. In some embodiments, the chemotherapy is any other chemotherapy known in the art. In certain embodiments, at least one, at least two or more chemotherapeutic agents are administered in combination with the anti-PD-1 antibody or antigen-binding portion thereof and/or the anti-PD-L1 antibody or antigen-binding portion thereof. In some embodiments, the anti-PD-1 antibody or antigen-binding portion thereof and/ or the anti-PD-L1 antibody or antigen-binding portion thereof are administered in combination with gemcitabine and cisplatin. In some embodiments, the anti-PD-1 antibody or antigen-binding portion thereof and/or the anti-PD-L1 antibody or antigen-binding portion thereof are administered in combination with pemetrexed and cisplatin. In certain embodiments, the anti-PD-1 antibody or antigen-binding portion thereof and/or the anti-PD-L1 antibody or antigen-binding portion thereof are administered in combination with gemcitabine and pemetrexed. In one embodiment, the anti-PD-1 antibody or antigen-binding portion thereof and/ or the anti-PD-L1 antibody or antigen-binding portion thereof are administered in combination with paclitaxel and carboplatin. In an embodiment, an anti-CTLA-4 antibody is additionally administered.

In certain embodiments, the anti-PD-1 antibody or antigen-binding portion thereof and/or the anti-PD-L1 antibody or antigen-binding portion thereof are administered in combination with a TKI. In certain embodiments, the tyrosine kinase inhibitor is pazopanib, sorafenib, sunitinib, axitinib, tivozanib, gefitinib, erlotinib, any combination thereof, or any other tyrosine kinase inhibitor known in the art. In some embodiments, the tyrosine kinase inhibitor act on the epidermal growth factor receptor (EGFR). In an embodiment, an anti-CTLA-4 antibody is additionally administered.

III. Pharmaceutical Compositions and Dosages

Therapeutic agents of the present invention can be constituted in a composition, e.g., a pharmaceutical composition containing an antibody or antigen-binding portion thereof and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. In one embodiment, the carrier for a composition containing an antibody is suitable for intravenous, intramuscular, subcutaneous, parenteral, spinal or epidermal administration (e.g., by injection or infusion), whereas the carrier for a composition containing a TKI is suitable for non-parenteral, e.g., oral, administration. In one particular embodiment, the anti-PD-1 antibody or antigen-binding portion thereof or the anti-PD-L1 antibody or antigen-binding portion thereof is formulated for intravenous administration. A pharmaceutical composition of the invention can include one or more pharmaceutically acceptable salts, anti-oxidant, aqueous and non-aqueous carriers, and/or adjuvants such as preservatives, wetting agents, emulsifying agents and dispersing agents.

Dosage regimens are adjusted to provide the optimum desired response, e.g., a maximal therapeutic response and/ or minimal adverse effects. For administration of an anti-PD-1 antibody or antigen-binding portion thereof and/or an anti-PD-L1 antibody or antigen-binding portion thereof, as a monotherapy or in combination with another anti-cancer agent, the dosage can range from about 0.01 to about 20 mg/kg, about 0.1 to about 10 mg/kg, about 0.1 to about 5 mg/kg, about 1 to about 5 mg/kg, about 2 to about 5 mg/kg, about 7.5 to about 12.5 mg/kg, or about 0.1 to about 30 mg/kg of the subject's body weight. For example, dosages can be about 0.1, about 0.3, about 1, about 2, about 3, about 5, or about 10 mg/kg body weight, or about 0.3, about 1, about 2, about 3, or about 5 mg/kg body weight. In one particular embodiment, the first dose is administered at a dose ranging from at least about 0.1 mg/kg to at least about 10.0 mg/kg body weight. In another embodiment, the second dose is administered at a dose ranging from at least about 0.1 mg/kg to at least about 10.0 mg/kg body weight.

In some embodiments, the dosage of the anti-PD-1 antibody or antigen-binding portion thereof and/or the anti-PD-L1 antibody or antigen-binding portion thereof comprises a dose ranging from at least about 10 mg to at least about 1200 mg, at least about 10 mg to at least about 1100 mg, at least about 10 mg to at least about 1000 mg, at least about 10 mg to at least about 900 mg, at least about 10 mg to at least about 800 mg, at least about 10 mg to at least about 700 mg, at least about 10 mg to at least about 600 mg, at least about 10 mg to at least about 500 mg, at least about 10 mg to at least about 400 mg, at least about 10 mg to at least about 300 mg, at least about 10 mg to at least about 200 mg, at least about 10 mg to at least about 100 mg, at least about 20 mg to at least about 1200 mg, at least about 30 mg to at least about 1100 mg, at least about 40 mg to at least about 1000 mg, at least about 50 mg to at least about 900 mg, at least about 60 mg to at least about 800 mg, at least about 70 mg to at least about 800 mg, at least about 80 mg to at least about 800 mg, at least about 90 mg to at least about 800 mg, at least about 100 mg to at least about 1000 mg, at least about 100 mg to at least about 900 mg, at least about 100 mg to at least about 800 mg, at least about 100 mg to at least about 700 mg, at least about 100 mg to at least about 600 mg, or at least about 100 mg to at least about 500 mg. In one particular embodiment, the first dose is administered at a dose ranging from at least about 80 mg to at least about 800 mg. In another embodiment, the second dose is administered at a dose ranging from at least about 80 mg to at least about 800 mg.

In some embodiments, the first dose and/or the second dose of the anti-PD-1 antibody or antigen-binding portion thereof and/or the anti-PD-L1 antibody or antigen-binding portion thereof comprises a dose of at least about 10 mg, at least about 20 mg, at least about 30 mg, at least about 40 mg, at least about 50 mg, at least about 60 mg, at least about 70 mg, at least about 80 mg, at least about 90 mg, at least about 100 mg, at least about 110 mg, at least about 120 mg, at least about 130 mg, at least about 140 mg, at least about 150 mg, at least about 160 mg, at least about 170 mg, at least about 180 mg, at least about 190 mg, at least about 200 mg, at least about 220 mg, at least about 240 mg, at least about 260 mg, at least about 280 mg, at least about 300 mg, at least about 350 mg, at least about 400 mg, at least about 450 mg, at least about 500 mg, at least about 550 mg, at least about 600 mg, at least about 650 mg, at least about 700 mg, at least about 800 mg, at least about 900 mg, at least about 1000 mg, or at least about 1500 mg.

In some embodiments, the first dose is administered at a dose ranging from at least about 80 mg to at least about 800 mg or at least about 0.1 mg/kg to at least about 10.0 mg/kg body weight. In other embodiments, the second dose is administered at a dose ranging from at least about 80 mg to at least about 800 mg or at least about 0.1 mg/kg to at least about 10.0 mg/kg body weight.

The dosing schedule is typically designed to achieve exposures that result in sustained receptor occupancy (RO) based on typical pharmacokinetic properties of an antibody. An exemplary treatment regime entails administration about once per week, once about every 2 weeks, once about every 3 weeks, once about every 4 weeks, once about a month, once about every 3-6 months or longer. In certain embodiments, an anti-PD-1 antibody or antigen-binding portion thereof and/or an anti-PD-L1 antibody or antigen-binding portion thereof is administered to the subject once about every 2 weeks. In other embodiments, the antibody or antigen-binding portion thereof is administered once about every 3 weeks. The dosage and scheduling can change during a course of treatment. For example, a dosing schedule for anti-PD-1 or anti-PD-L1 monotherapy can comprise administering the Ab: (i) about every 2 weeks in about 6-week cycles; (ii) about every 4 weeks for about six dosages, then about every three months; (iii) about every 3 weeks; (iv) about 3 to about 10 mg/kg once followed by about 1 mg/kg every about 2-3 weeks. Considering that an IgG4 antibody typically has a half-life of 2-3 weeks, a dosage regimen for an anti-PD-1 antibody or an anti-PD-L1 antibody of the invention comprises at least about 0.3 to at least about 10 mg/kg body weight, at least about 1 to at least about 5 mg/kg body weight, or at least about 1 to at least about 3 mg/kg body weight via intravenous administration, with the antibody being given every about 14-21 days in up to about 6-week or about 12-week cycles until complete response or confirmed progressive disease. In certain embodiments, an anti-PD-1 or an anti-PD-L1 monotherapy is administered at 3 mg/kg every 2 weeks until progressive disease or unacceptable toxicity. In some embodiments, the antibody treatment, or any combination treatment disclosed herein, is continued for at least about 1 month, at least about 3 months, at least about 6 months, at least about 9 months, at least about 1 year, at least about 18 months, at least about 24 months, at least about 3 years, at least about 5 years, or at least about 10 years.

When used in combinations with other cancer agents, the dosage of an anti-PD-1 antibody can be lowered compared to the monotherapy dose. Dosages of nivolumab that are lower than the typical 3 mg/kg, but not less than 0.001 mg/kg, are subtherapeutic dosages. The subtherapeutic doses of an anti-PD-1 antibody used in the methods herein are higher than 0.001 mg/kg and lower than 3 mg/kg. In some embodiments, a subtherapeutic dose is about 0.001 mg/kg-about 1 mg/kg, about 0.01 mg/kg-about 1 mg/kg, about 0.1 mg/kg-about 1 mg/kg, or about 0.001 mg/kg-about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. Receptor-occupancy data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%). In some embodiments, 0.3 mg/kg dosing can allow for sufficient exposure to lead to maximal biologic activity. Receptor-occupancy data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%) (Brahmer et al. (2010) J Clin Oncol 28:3167-75). Thus, 0.3 mg/kg dosing can allow for sufficient exposure to lead to maximal biologic activity.

Although higher nivolumab monotherapy dosing up to about 10 mg/kg every two weeks has been achieved without reaching the maximum tolerated does (MTD), the significant toxicities reported in other trials of checkpoint inhibitors plus anti-angiogenic therapy (see, e.g., Johnson et al. (2013) Cancer Immunol Res 1:373-77; Rini et al. (2011) Cancer 117:758-67) support the selection of a nivolumab dose lower than 10 mg/kg.

In certain embodiments, the dose of an anti-PD-1 antibody or an anti-PD-L1 antibody is a fixed dose in a pharmaceutical composition. In other embodiments, the method of the present invention can be used with a flat dose (a dose given to a patient irrespective of the body weight of the patient). For example, a flat dose of a nivolumab can be about 240 mg. For example, a flat dose of pembrolizumab can be about 200 mg. In some embodiments, the anti-PD-1 antibody or antigen-binding portion thereof is administered at a dose of about 240 mg. In embodiments, the anti-PD-1 antibody or antigen-binding portion thereof is administered at a dose of about 360 mg. In embodiments, the anti-PD-1 antibody or antigen-binding portion thereof is administered at a dose of about 480 mg. In one embodiment, 360 mg of the anti-PD-1 antibody or antigen binding fragment is administered once every 3 weeks. In another embodiment, 480 mg of the anti-PD-1 antibody or antigen binding fragment is administered once every 4 weeks.

In certain embodiments, the anti-PD-1 antibody or antigen-binding portion thereof and/or the anti-PD-L1 antibody or antigen-binding portion thereof is administered at a dose of 0.3 mg/kg, 2 mg/kg, or 10 mg/kg once every 3 weeks. In other embodiments, the anti-PD-1 antibody or antigen-binding portion thereof and/or the anti-PD-L1 antibody or antigen-binding portion thereof is administered at a dose of about 5 mg/kg once about every 3 weeks. In one particular embodiment, the first dose is administered at a dose of at least about 3 mg/kg body weight or 240 mg once about every 2 weeks.

For combinations of the anti-PD-1 antibody or antigen-binding portion thereof and/or the anti-PD-L1 antibody or antigen-binding portion thereof with other anti-cancer agents, these agents are administered at their approved dosages. Treatment is continued as long as clinical benefit is observed or until unacceptable toxicity or disease progression occurs. Nevertheless, in certain embodiments, the dosages of these anti-cancer agents administered are significantly lower than the approved dosage, i.e., a subtherapeutic dosage, of the agent is administered in combination with the anti-PD-1 antibody or antigen-binding portion thereof and/or the anti-PD-L1 antibody or antigen-binding portion thereof. The anti-PD-1 antibody or antigen-binding portion thereof and/or the anti-PD-L1 antibody or antigen-binding portion thereof can be administered at the dosage that has been shown to produce the highest efficacy as monotherapy in clinical trials, e.g., about 3 mg/kg of nivolumab administered once about every three weeks (Topalian et al. (2012) *N Engl J Med* 366:2443-54; Topalian et al. (2012) *Curr Opin Immunol* 24:207-12), or at a significantly lower dose, i.e., at a subtherapeutic dose. In one particular embodiment, the first dose of the anti-PD-1 antibody or antigen-binding portion thereof and/or the anti-PD-L1 antibody or antigen-binding portion thereof is a therapeutic dose and the second dose is a therapeutic dose. In another embodiment, the first dose is a subtherapeutic dose and the second dose is a therapeutic dose. In certain embodiments, the anti-PD-1 antibody or antigen-binding portion thereof and/or the anti-PD-L1 antibody or antigen-binding portion thereof is administered at about 3 mg/kg once about every two weeks.

Actual dosage levels of the active ingredient or ingredients in the pharmaceutical compositions of the present invention can be varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present invention can be administered via one or more routes of administration using one or more of a variety of methods well known in the art. As will be appreciated by the skilled artisan, the route and/or mode of administration will vary depending upon the desired results.

In some embodiments, both an anti-PD-1 antibody or antigen-binding portion thereof and an anti-PD-L1 antibody or antigen-binding portion thereof are administered to a patient. The anti-PD-1 antibody or antigen-binding portion thereof and the anti-PD-L1 antibody or antigen-binding portion can be administered concurrently or in sequence (e.g., the anti-PD-1 antibody or antigen-binding portion thereof administered first and the anti-PD-L1 antibody or antigen-binding portion administered second or the anti-PD-L1 antibody or antigen-binding portion administered first and the anti-PD-1 antibody or antigen-binding portion thereof administered second).

In certain aspects of the methods disclosed herein, the subject is administered a first dose of an anti-PD-1 antibody or antigen-binding portion and an anti-PD-L1 antibody or antigen-binding portion thereof, and the expression level of one or more genes, e.g., CTLA-4, TIGIT, PD-L2, or any combination thereof, is measured following the administration of the first dose. In some embodiments, the subject is administered at least two doses, at least three doses, at least four doses, at least five doses, at least six doses, at least seven doses, at least eight doses, at least nine doses, at least ten doses, at least 12 doses, at least 20 doses, or at least 20 doses prior to measuring the expression level of the one or more target genes, e.g., the increased expression of CTLA-4, TIGIT, PD-L2, or any combination thereof.

A subject may continue to receive the anti-PD-1 antibody or antigen-binding portion and/or the anti-PD-L1 antibody or antigen-binding portion thereof for any reasonable duration of time. In some embodiments, the anti-PD-1 antibody or antigen-binding portion or the anti-PD-L1 antibody or antigen-binding portion thereof is administered for as long as a clinical benefit is observed or until unmanageable toxicity or disease progression occurs. In other embodiments, the anti-PD-1 antibody or antigen-binding portion or the anti-PD-L1 antibody or antigen-binding portion thereof is administered for at least about 1 year, at least about 2 years, at least about 3 years, at least about 4 years, at least about 5 years, at least about 6 years, at least about 7 years, at least about 8 years, at least about 9 years, at least about 10 years, at least about 15 years, at least about 20 years, or more than 20 years. In some embodiments, the anti-PD-1 antibody or antigen-binding portion or the anti-PD-L1 antibody or antigen-binding portion thereof is administered until a complete response is observed.

IV. Kits

Also within the scope of the present invention are kits for treating a subject afflicted with a tumor derived from an RCC. Kits typically include a label indicating the intended use of the contents of the kit and instructions for use. The term label includes any writing, or recorded material supplied on or with the kit, or which otherwise accompanies the kit. Accordingly, this disclosure provides a kit for treating a subject afflicted with a tumor derived from an RCC, the kit comprising: (a) an anti-PD-1 antibody or antigen-binding portion thereof or an anti-PD-L1 antibody or antigen-binding portion thereof; (b) instructions for determining an increased expression of one or more genes, e.g., MICB, PVRIG, NKG7, CD244, NKTR, TNFSF8, TNFSF13B, TNFRSF14, SPI1, CLEC2B, CTLA-4, TIGIT, PD-L2, or any combination thereof, after administration of a first dose of the anti-PD-1 antibody or antigen-binding portion thereof or the anti-PD-L1 antibody or antigen-binding portion thereof and for administering a second dose of the anti-PD-1 antibody or antigen-binding portion thereof or the anti-PD-L1 antibody or antigen-binding portion thereof in the methods of claims described herein if the subject exhibits differential expression of CTLA-4, TIGIT, PD-L2, or any combination thereof. In other embodiments, the disclosure provides a kit for treating a subject afflicted with a tumor derived from an RCC, the kit comprising: (a) an anti-PD-1 antibody or antigen-binding portion thereof or an anti-PD-L1 antibody or antigen-binding portion thereof; (b) instructions for determining an expression of one or more genes, e.g., MICB, PVRIG, SPI1, CLEC2B, NKG7, or any combination thereof, at baseline and for administering a first dose of the anti-PD-1 antibody or antigen-binding portion thereof or the anti-PD-L1 antibody or antigen-binding portion thereof in the methods of claims described herein if the subject exhibits increased expression of MICB, PVRIG, SPI1, CLEC2B, NKG7, or any combination thereof, relative to the average expression level of MICB, PVRIG, SPI1, CLEC2B, and/or NKG7. In some embodiments, the kit further comprises an agent to determine the differential expression of PVRIG, NKG7, CD244, NKTR, TNFSF8, TNFSF13B, TNFRSF14, SPI1, CLEC2B, CTLA-4, TIGIT, PD-L2, or any combination thereof prior to administering the second dose and/or an agent to determine the differential expression of MICB, PVRIG, SPI1, CLEC2B, NKG7, or any combination thereof at baseline. In certain embodiments, the anti-PD-1 antibody and/or the anti-PD-L1 AB can be co-packaged in unit dosage form. In certain embodiments for treating human patients, the kit comprises an anti-human PD-1 antibody, e.g., nivolumab or pembrolizumab, and/or an anti-human PD-L1 antibody, e.g., BMS-936559, MPDL3280A, MEDI4736, or MSB0010718C. In other embodiments, the kit comprises an anti-human CTLA-4 antibody disclosed herein, e.g., ipilimumab or tremelimumab.

The present invention is further illustrated by the following example, which should not be construed as further limiting. The contents of all references cited throughout this application are expressly incorporated herein by reference.

EXAMPLES

Example 1

An open-label, parallel, four-group, phase 1b study of nivolumab (Bristol-Myers Squibb, Lawrenceville, NJ; Ono Pharmaceutical Company Limited, Osaka City, Japan) to treat mRCC (clean cell) was conducted. Previously treated patients (after anti-angiogenic therapy; n=67) were randomized 1:1:1 to receive one of three nivolumab doses: 0.3 (Arm 1), 2 (Arm 2), or 10 mg/kg (Arm 3); and treatment-naïve patients (n=24) received 10 mg/kg (Arm 4) of nivolumab (FIG. 1). In all groups, nivolumab was administered to the patients as an intravenous infusion on day 1 of a treatment cycle every 3 weeks until the patients showed complete response, progressive disease, intolerable AEs, or withdrawal of consent occurred (FIG. 1). Patients were permitted to continue nivolumab treatment beyond confirmed disease progression if the investigator determined the patient was experiencing clinical benefit and the patient tolerated treatment.

I. Patients

Eligible patients had histologic confirmation of mRCC with a clear-cell component, measurable disease as defined by Response Evaluation Criteria in Solid Tumors (RECIST) v1.1, a Karnofsky performance score of ≥70%, presence of soft-tissue tumor lesions that could be biopsied both at baseline and on-treatment, and adequate organ and marrow function. To be eligible for enrollment in treatment groups 1-3 (previously treated cohorts; Arms 1-3), patients must have been treated with at least one but not more than three previous systemic therapies for RCC with progression occurring following the most recent therapy within 6 months prior to study enrollment (FIG. 1). To be eligible for the treatment-naïve group, patients must not have received any previous systemic therapy in the metastatic or adjuvant setting. Exclusion criteria included active central nervous system metastases within 30 days of study enrollment; active or prior autoimmune disease; active use of systemic corticosteroids; prior malignancy unless complete remission occurred ≥2 years prior to study enrollment; and previous treatment with anti-CTLA-4, anti-PD-1, anti-PD-L1, anti-PD-L2, anti-CD137, anti-CD40, or anti-OX40 antibodies.

II. Study Assessments

A. Objectives and Assessments

The primary objective of this study was to investigate the pharmacodynamic immunomodulatory activity of nivolumab on CD4+ and CD8+ tumor-associated lymphocytes, and serum chemokines CXCL9 and CXL10 in patients with clear-cell mRCC. Secondary objectives were to assess the efficacy, safety, and tolerability of nivolumab. Exploratory objectives included analyses of additional serum-soluble factors in serum, gene expression profiling in the tumor and whole blood, PD-L1 expression by tumor membrane staining, clinical activity according to PD-L1 expression prior to treatment, and receptor occupancy.

Patients were evaluated for response (RECIST v1.1) every 6 weeks for the first 12 months from randomization, then every 12 weeks until documented disease progression. Patients who discontinued treatment for reasons other than tumor progression continued to have tumor assessments according to the treatment schedule.

Patients were required to provide fresh biopsies both at screening and on treatment as a condition of protocol participation. Tumor sites selected for biopsy must not have received previous radiation therapy. It was preferred that patients have at least one soft-tissue lesion large enough to undergo repeat core needle biopsies (one biopsy at baseline and one biopsy at cycle 2 day 8). However, patients may also have had two distinct soft-tissue lesions eligible for core needle or excisional biopsies. One lesion was to be biopsied at baseline and the other was to be biopsied at cycle 2 day 8.

B. Biomarker Assessments

Assessment of immune cells was performed by using two validated multiplex IHC assays provided by Mosaic Laboratories (Lake Forest, CA) on formalin-fixed, paraffin-embedded sections. The assays selected were one dual stain, CD3+/CD8+, and one triple stain, CD3+/CD4+/FOXP3+. Each multiplex IHC assay was designed and validated to be compatible with Clinical Laboratory Improvement Amendments guideline class I test validation. A representative 20× field of staining was spectrally imaged using the NUANCE® Multispectral Imaging System with software v.2.4.0 (Caliper Life Sciences, Hopkinton, MA) attached to a NIKON® 90i microscope. The multispectral image was acquired between 420 and 720 nm using 20-nm wavelength steps. Image cubes were analyzed using INFORM® software v1.2 (Caliper Life Sciences). Image cubes were unmixed using the spectral absorbance patterns for each chromogen and hematoxylin.

Nivolumab binding to PD-1 molecules on circulating T cells was investigated by flow cytometric analysis of serially collected blood samples. The assay was optimized from the receptor occupancy assay as described previously (Brahmer et al. (2010) *J Clin Oncol* 28:3167-75). Briefly, PD-1 occupancy by infused nivolumab was estimated as the ratio of the percent of total T cells, CD4+ T cells, and CD8+ T cells stained with antidrug antibody (anti-huIgG4) after in vitro saturation with isotype control antibody (indicating in vivo binding) to that observed after nivolumab saturation (indicating total available binding sites). To obtain these measures, individual aliquots of each whole blood sample were preincubated (30 minutes at 4° C.) with a saturating concentration (50 µg/ml) of either isotype control or nivolumab, washed extensively, and then co-stained with anti-CD3 PerCP, anti-CD4 FITC, anti-CD8 APC, and murine anti-huIgG4 PE (SouthernBiotech, Birmingham, AL).

The biopsies obtained from metastatic lesions at baseline and cycle 2 day 8 were used for the quantification of tumor-associated lymphocytes, for evaluation of the expression of PD-L1 and PD-1 proteins, and for evaluation of gene expression. IHC (Mosaic Laboratories) was used to assess the number and composition of tumor-associated lymphocytes, including CD4+ and CD8+ cells (Table 1). The expression of PD-L1 on the surface of tumor cells was assessed in these biopsies and in archival samples, when available, at a central laboratory with the use of an automated IHC assay (Bristol-Myers Squibb/Dako IHC assay using the 28-8 antibody), as described previously (Sznol et al. (2014) *J Clin Oncol* 32:Abstract LBA9003). The level of PD-L1 expression was determined by the cell-surface PD-L1 staining of any intensity in a section containing at least 100 tumor cells that could be evaluated. RNA was extracted from the fresh biopsies in parallel to IHC and also from whole blood at cycle 1 day 1 (prior to nivolumab infusion), cycle 1 day 2, and cycle 2 day 8. RNA was labeled by WT-Pico OVATION® (NuGEN, San Carlos, CA). Gene expression profiling was performed using the HG-U219 array plate on the GENETITAN® platform (Affymetrix, Santa Clara, CA). The robust multi-array average (RMA) algorithm (Irizarry et al. (2003) *Nucleic Acids Res* 31:e15) was used to establish intensity values for each of 18,562 loci (BrainArray v.10) (Dai et al. (2005) *Nucleic Acids Res* 33:e175). Data have been deposited in ArrayExpress (E-MTAB-3218 and E-MTAB-3219).

TABLE 1

Assessments of Immunomodulatory Activity.

| Analysis | Sample | Assay | Time Points |
|---|---|---|---|
| PD-L1 expression | FFPE tumor biopsy | IHC (BMS/Dako; 28-8 antibody) | Baseline |
| Soluble factors | Serum | LUMINX ™ (Myriad RBM) | Baseline, C2D8 |
| Gene expression profiling | Tumor biopsy | AFFYMETRIX ® Human Genome U219 | Baseline, C2D8 |
| T-cell receptor sequencing | Frozen tumor biopsy, PBMC | IMMUNOSEQ ™ (Adaptive Biotechnologies) | Baseline, C2D8 |

Note
Baseline refers to tumor biopsies collected during screening or peripheral bold collected on day 1 of the first cycle, prior to nivolumab infusion. C2D8, cycle 2 day 8; FFPE, formalin-fixed, paraffin-embedded; PBMC, peripheral blood mononuclear cells.

The assessment of serum chemokines (CXCL9, CXCL10) and other serum-soluble factors (Table 9) at baseline, cycle 1 day 1, cycle 2 day 1, cycle 2 day 8, and cycle 4 day 1 was performed for all treated patients for whom serum was available using a multiplex panel based on LUMINEX® technology (Myriad Rules-Based Medicine, Austin, TX).

TABLE 2

108 Genes From an Analysis of Tumor Biopsies

| Probeset (BrainArray v.10) | ENTREZ Gene ID | HUGO Gene Symbol | P value for baseline v. C2D8 | Baseline: Mean RMA value | C2D8: Mean RMA value | C2D8 v. Baseline: Fold Change |
|---|---|---|---|---|---|---|
| BrAr: LOC118932_at | LOC118932 | ANKRD22 | 0.0006207 | 3.73 | 4.3 | 1.48 |
| BrAr: LOC54518_at | LOC54518 | APBB1IP | 0.00018251 | 8.4 | 8.83 | 1.34 |
| BrAr: LOC200316_at | LOC200316 | APOBEC3F | 0.00010417 | 4.43 | 4.93 | 1.42 |
| BrAr: LOC60489_at | LOC60489 | APOBEC3G | 0.00135835 | 5.77 | 6.32 | 1.46 |
| BrAr: LOC80833_at | LOC80833 | APOL3 | 0.00151848 | 8.11 | 8.58 | 1.39 |
| BrAr: LOC80830_at | LOC80830 | APOL6 | 0.00408546 | 5.15 | 5.53 | 1.3 |
| BrAr: LOC116984_at | LOC116984 | ARAP2 | 0.00119885 | 4.93 | 5.37 | 1.36 |
| BrAr: LOC283897_at | LOC283897 | C16orf54 | 0.0094305 | 5.84 | 6.42 | 1.5 |
| BrAr: LOC132720_at | LOC132720 | C4ORF32 | 0.00690996 | 5.01 | 5.41 | 1.32 |
| BrAr: LOC834_at | LOC834 | CASP1 | 0.00036764 | 6.35 | 6.76 | 1.33 |
| BrAr: LOC6351_at | LOC6351 | CCL4 | 0.00966536 | 7.88 | 8.33 | 1.37 |
| BrAr: LOC6352_at | LOC6352 | CCL5 | 0.00164617 | 6.82 | 7.65 | 1.77 |
| BrAr: LOC919_at | LOC919 | CD247 | 0.00434502 | 3.8 | 4.32 | 1.43 |
| BrAr: LOC29126_at | LOC29126 | CD274 | 0.00151105 | 3.79 | 4.18 | 1.31 |
| BrAr: LOC915_at | LOC915 | CD3D | 0.00637029 | 5.48 | 6.21 | 1.66 |
| BrAr: LOC916_at | LOC916 | CD3E | 0.00891231 | 4.76 | 5.54 | 1.72 |
| BrAr: LOC917_at | LOC917 | CD3G | 0.00874864 | 5.3 | 6 | 1.62 |
| BrAr: LOC962_at | LOC962 | CD48 | 0.00951571 | 7.06 | 7.75 | 1.61 |
| BrAr: LOC963_at | LOC963 | CD53 | 0.0061421 | 7.31 | 7.75 | 1.36 |
| BrAr: LOC969_at | LOC969 | CD69 | 0.00398662 | 3.47 | 4.1 | 1.55 |
| BrAr: LOC971_at | LOC971 | CD72 | 0.00320178 | 2.71 | 3.18 | 1.39 |
| BrAr: LOC925_at | LOC925 | CD8A | 0.0024245 | 5.45 | 6.19 | 1.67 |
| BrAr: LOC926_at | LOC926 | CD8B | 0.00505758 | 2.63 | 3.17 | 1.46 |
| BrAr: LOC160364_at | LOC160364 | CLEC12A | 0.00277043 | 3.65 | 4.12 | 1.39 |
| BrAr: LOC7373_at | LOC7373 | COL14A1 | 0.00689524 | 6.63 | 6.25 | 0.77 |
| BrAr: LOC1307_at | LOC1307 | COL16A1 | 0.0007086 | 4.95 | 4.55 | 0.76 |
| BrAr: LOC11151_at | LOC11151 | CORO1A | 0.00977025 | 4.41 | 4.79 | 1.3 |
| BrAr: LOC8530_at | LOC8530 | CST7 | 0.00163984 | 5.57 | 6.37 | 1.74 |
| BrAr: LOC1493_at | LOC1493 | CTLA4 | 0.0083113 | 3.36 | 3.77 | 1.33 |
| BrAr: LOC1520_at | LOC1520 | CTSS | 0.00510613 | 8.01 | 8.45 | 1.35 |
| BrAr: LOC6373_at | LOC6373 | CXCL11 | 0.00144838 | 4.68 | 5.63 | 1.93 |
| BrAr: LOC4283_at | LOC4283 | CXCL9 | 0.00079598 | 7.1 | 8.38 | 2.43 |
| BrAr: LOC10663_at | LOC10663 | CXCR6 | 8.4691E−05 | 5.16 | 5.93 | 1.71 |
| BrAr: LOC80231_at | LOC80231 | CXORF21 | 0.00929267 | 3.01 | 3.44 | 1.34 |

TABLE 2-continued

108 Genes From an Analysis of Tumor Biopsies

| Probeset (BrainArray v.10) | ENTREZ Gene ID | HUGO Gene Symbol | P value for baseline v. C2D8 | Baseline: Mean RMA value | C2D8: Mean RMA value | C2D8 v. Baseline: Fold Change |
|---|---|---|---|---|---|---|
| BrAr: LOC27071_at | LOC27071 | DAPP1 | 0.0022226 | 3.92 | 4.42 | 1.41 |
| BrAr: LOC1734_at | LOC1734 | DIO2 | 0.00979853 | 4.66 | 4.14 | 0.7 |
| BrAr: LOC81704_at | LOC81704 | DOCK8 | 0.00102282 | 5.03 | 5.43 | 1.32 |
| BrAr: LOC94240_at | LOC94240 | EPSTI1 | 0.00022911 | 5.63 | 6.22 | 1.51 |
| BrAr: LOC125704_at | LOC125704 | FAM69C | 0.00014377 | 3.67 | 3.27 | 0.76 |
| BrAr: LOC2207_at | LOC2207 | FCER1G | 0.00055515 | 8.61 | 9.05 | 1.35 |
| BrAr: LOC10875_at | LOC10875 | FGL2 | 0.00314134 | 7.21 | 7.65 | 1.35 |
| BrAr: LOC2533_at | LOC2533 | FYB | 0.00755475 | 6.66 | 7.13 | 1.39 |
| BrAr: LOC2633_at | LOC2633 | GBP1 | 5.3598E−05 | 5.87 | 6.72 | 1.81 |
| BrAr: LOC115361_at | LOC115361 | GBP4 | 0.00020926 | 6.08 | 6.76 | 1.6 |
| BrAr: LOC115362_at | LOC115362 | GBP5 | 0.00017365 | 6.13 | 7.06 | 1.9 |
| BrAr: LOC2643_at | LOC2643 | GCH1 | 0.00041451 | 6.6 | 7.25 | 1.57 |
| BrAr: LOC29909_at | LOC29909 | GPR171 | 0.00072124 | 4.68 | 5.42 | 1.68 |
| BrAr: LOC3001_at | LOC3001 | GZMA | 0.00054429 | 7.54 | 8.32 | 1.72 |
| BrAr: LOC3002_at | LOC3002 | GZMB | 0.0041206 | 5.16 | 5.99 | 1.78 |
| BrAr: LOC2999_at | LOC2999 | GZMH | 0.00020686 | 5.85 | 6.81 | 1.94 |
| BrAr: LOC29851_at | LOC29851 | ICOS | 0.0041205 | 4.1 | 4.57 | 1.39 |
| BrAr: LOC3620_at | LOC3620 | IDO1 | 0.00105399 | 4.74 | 5.76 | 2.02 |
| BrAr: LOC64135_at | LOC64135 | IFIH1 | 0.00633078 | 6.53 | 6.91 | 1.31 |
| BrAr: LOC3433_at | LOC3433 | IFIT2 | 0.0009791 | 6.25 | 6.68 | 1.35 |
| BrAr: LOC8519_at | LOC8519 | IFITM1 | 0.00329708 | 8.06 | 8.47 | 1.33 |
| BrAr: LOC3458_at | LOC3458 | IFNG | 0.00252908 | 2.58 | 3.14 | 1.47 |
| BrAr: LOC3488_at | LOC3488 | IGFBP5 | 0.00686955 | 8.88 | 8.41 | 0.72 |
| BrAr: LOC10261_at | LOC10261 | IGSF6 | 0.00738051 | 7.64 | 8.05 | 1.32 |
| BrAr: LOC22806_at | LOC22806 | IKZF3 | 0.00348126 | 4.3 | 5.11 | 1.76 |
| BrAr: LOC3553_at | LOC3553 | IL1B | 0.00541195 | 4.48 | 4.86 | 1.3 |
| BrAr: LOC3560_at | LOC3560 | IL2RB | 0.00461433 | 4.18 | 4.82 | 1.56 |
| BrAr: LOC3561_at | LOC3561 | IL2RG | 0.00616889 | 6.25 | 6.99 | 1.66 |
| BrAr: LOC3659_at | LOC3659 | IRF1 | 4.7581E−06 | 5.05 | 5.59 | 1.46 |
| BrAr: LOC3689_at | LOC3689 | ITGB2 | 0.00726197 | 7.44 | 7.95 | 1.42 |
| BrAr: LOC3702_at | LOC3702 | ITK | 0.00081966 | 2.89 | 3.36 | 1.39 |
| BrAr: LOC3759_at | LOC3759 | KCNJ2 | 0.0098923 | 5.87 | 6.28 | 1.33 |
| BrAr: LOC3820_at | LOC3820 | KLRB1 | 0.0017051 | 4.05 | 4.57 | 1.43 |
| BrAr: LOC3824_at | LOC3824 | KLRD1 | 0.00602459 | 4.33 | 4.77 | 1.36 |
| BrAr: LOC10219_at | LOC10219 | KLRG1 | 0.00509516 | 4.13 | 4.6 | 1.39 |
| BrAr: LOC51056_at | LOC51056 | LAP3 | 0.00062969 | 7.18 | 7.65 | 1.38 |
| BrAr: LOC3936_at | LOC3936 | LCP1 | 0.00788663 | 7.8 | 8.33 | 1.45 |
| BrAr: LOC3957_at | LOC3957 | LGALS2 | 0.00048367 | 7.7 | 8.37 | 1.59 |
| BrAr: LOC10859_at | LOC10859 | LILRB1 | 0.00234176 | 4.14 | 4.62 | 1.39 |
| BrAr: LOC4065_at | LOC4065 | LY75 | 0.00385138 | 5.56 | 5.99 | 1.35 |
| BrAr: LOC55686_at | LOC55686 | MREG | 0.0024365 | 5.82 | 6.41 | 1.51 |
| BrAr: LOC3071_at | LOC3071 | NCKAP1L | 0.0088131 | 4.18 | 4.75 | 1.48 |
| BrAr: LOC4818_at | LOC4818 | NKG7 | 0.00083844 | 6.27 | 6.97 | 1.62 |
| BrAr: LOC53829_at | LOC53829 | P2RY13 | 1.4924E−05 | 6 | 6.54 | 1.46 |
| BrAr: LOC56937_at | LOC56937 | PMEPA1 | 0.00349819 | 7.06 | 6.65 | 0.75 |
| BrAr: LOC5551_at | LOC5551 | PRF1 | 0.00344285 | 4.11 | 4.7 | 1.5 |
| BrAr: LOC5579_at | LOC5579 | PRKCB | 0.00760977 | 4.05 | 4.54 | 1.4 |
| BrAr: LOC5698_at | LOC5698 | PSMB9 | 0.00174273 | 9.27 | 9.65 | 1.31 |
| BrAr: LOC9050_at | LOC9050 | PSTPIP2 | 2.3187E−05 | 3.51 | 4.28 | 1.71 |
| BrAr: LOC5784_at | LOC5784 | PTPN14 | 0.00924443 | 5.31 | 4.91 | 0.76 |
| BrAr: LOC5880_at | LOC5880 | RAC2 | 0.00321482 | 5.86 | 6.41 | 1.46 |
| BrAr: LOC5920_at | LOC5920 | RARRES3 | 0.0044999 | 9.51 | 9.94 | 1.34 |
| BrAr: LOC64108_at | LOC64108 | RTP4 | 0.00041451 | 4.67 | 5.11 | 1.36 |
| BrAr: LOC219285_at | LOC219285 | SAMD9L | 0.00853322 | 5.6 | 5.99 | 1.31 |
| BrAr: LOC64092_at | LOC64092 | SAMSN1 | 0.0037497 | 5.63 | 6.03 | 1.32 |
| BrAr: LOC54440_at | LOC54440 | SASH3 | 0.00070534 | 3.98 | 4.49 | 1.42 |
| BrAr: LOC388325_at | LOC388325 | SCIMP | 0.00491723 | 4.83 | 5.37 | 1.45 |
| BrAr: LOC6401_at | LOC6401 | SELE | 0.00242864 | 3.65 | 3.21 | 0.73 |
| BrAr: LOC4068_at | LOC4068 | SH2D1A | 0.00569087 | 3.28 | 3.85 | 1.49 |
| BrAr: LOC57823_at | LOC57823 | SLAMF7 | 0.00970256 | 5.22 | 6.02 | 1.74 |
| BrAr: LOC6772_at | LOC6772 | STAT1 | 0.00462175 | 8.1 | 8.6 | 1.42 |
| BrAr: LOC6775_at | LOC6775 | STAT4 | 0.0051167 | 3.92 | 4.37 | 1.37 |
| BrAr: LOC6890_at | LOC6890 | TAP1 | 0.00475158 | 6.41 | 6.8 | 1.31 |
| BrAr: LOC57451_at | LOC57451 | TENM2 | 0.00026164 | 2.73 | 2.29 | 0.73 |
| BrAr: LOC387357_at | LOC387357 | THEMIS | 0.00431695 | 3.89 | 4.48 | 1.51 |
| BrAr: LOC51311_at | LOC51311 | TLR8 | 0.00447705 | 4.77 | 5.24 | 1.39 |
| BrAr: LOC28755_at | LOC28755 | TRAC | 0.00397501 | 6.07 | 6.89 | 1.76 |
| BrAr: LOC50852_at | LOC50852 | TRAT1 | 0.00410059 | 3.66 | 4.35 | 1.61 |
| BrAr: LOC10537_at | LOC10537 | UBD | 0.00031032 | 8.92 | 9.82 | 1.87 |

TABLE 2-continued

108 Genes From an Analysis of Tumor Biopsies

| Probeset (BrainArray v.10) | ENTREZ Gene ID | HUGO Gene Symbol | P value for baseline v. C2D8 | Baseline: Mean RMA value | C2D8: Mean RMA value | C2D8 v. Baseline: Fold Change |
| --- | --- | --- | --- | --- | --- | --- |
| BrAr: LOC7351_at | LOC7351 | UCP2 | 0.00078162 | 7.18 | 7.63 | 1.36 |
| BrAr: LOC7409_at | LOC7409 | VAV1 | 0.00355556 | 4.48 | 4.94 | 1.37 |
| BrAr: LOC8875_at | LOC8875 | VNN2 | 0.00439216 | 4.63 | 5.07 | 1.36 |
| BrAr: LOC7453_at | LOC7453 | WARS | 0.00106922 | 7 | 7.58 | 1.5 |
| BrAr: LOC79413_at | LOC79413 | ZBED2 | 0.0011301 | 2.63 | 3.18 | 1.47 |

Note:
These are genes for which the null hypothesis was rejected and the change over time averaged over treatment groups was >1.3-fold.

Patients who received the study drug were included in the safety population. Safety assessments were conducted at every visit and were evaluated according to the National Cancer Institute Common Terminology Criteria for Adverse Events, version 4.0 (National Cancer Institute, 2009). Safety was assessed by the incidence of adverse events (AEs) and select AEs that may be related to the mechanism of action of nivolumab. Select AEs of interest were defined as events with potential immunologic causes and those that required more frequent monitoring or intervention with immune suppression.

C. Statistical Analysis

This study was not designed to statistically test a specific hypothesis; therefore the sample size was not based on statistical power calculations. The study was designed to explore the pharmacodynamic effects of nivolumab in patients with mRCC, and using this information, to generate hypotheses for testing of selected biomarkers in subsequent clinical studies.

Efficacy analyses included best overall response (complete response (CR), partial response (PR), stable disease (SD), progressive disease (PD)), Progression Free Survival (PFS), and overall survival (OS), as well as objective response rate (ORR), which was the proportion of patients whose best response was a CR or PR. The 95% CIs for assessment of ORR were estimated using the Clopper-Pearson method (Clopper et al. (1934) *Biometrika* 26:404-13). PFS was defined as the time from first dosing date to the date of first documented disease progression. PFS and OS functions were estimated by the Kaplan-Meier method with 95% CIs estimated using Greenwood's formula (Brookmeyer et al. (1982) *Biometrics* 38:29-41).

The pharmacodynamic effects of nivolumab on tumor-associated lymphocytes and serum chemokines and in tumors were described using summary statistics and changes or percent changes from baseline tabulated by cycle, visit, and dose. Analyses of the relationship of gene expression to pharmacodynamic parameters (treatment group and time on study) were based on an extended linear model, fit by restricted maximum likelihood (NLME version 3.1-109 under R 3.0.1 for Linux) (Pinheiro et al. (2013) R package version 3.1-109 [Computer software]). For blood samples, the model included fixed effects of treatment group and time on study as categorical variables, and treatment-by-time on study interactions. For tumor biopsy samples, the model also included fixed effects of process batch and sex (the latter because women were not equally represented in samples from each trial treatment group). Within-patient correlations were modeled by a spatial exponential structure with Euclidean distance. A multi-contrast conditional F test was used to compare the null hypothesis that all time-related fixed-effect parameters were zero versus an alternative hypothesis that gene expression changed over time in at least one treatment group. The q value of each test (expected proportion of false positives incurred at that p value) was also estimated. Results presented are genes for which this null hypothesis was rejected (p for time on study <0.01), and the change over time averaged over treatment groups was >1.3-fold (biopsy; 108 genes in Table 2) or >1.2-fold (blood; 59 genes in Table 3). Analyses of the relationships of gene expression to Response parameters (Maximal reduction in tumor burden of >20%) were based on an extended linear model, fit by restricted maximum likelihood (NLME version 3.1-109 under R 3.0.1 for Linux) (Pinheiro et al. (2013) R package version 3.1-109 [Computer software]). The model included fixed effects of Response, time on study, process batch and sex as categorical variables, and Response-by-time on study interactions. Within-patient correlations were modeled by a spatial exponential structure with Euclidean distance. A multi-contrast conditional F test was used to compare the null hypothesis that all Response-related fixed-effect parameters were zero versus an alternative hypothesis that gene expression differed at at least one time in at least one Response group. The q value of each test (expected proportion of false positives incurred at that p value) was also estimated. Results presented are genes for which this null hypothesis was rejected (p for a difference between Response groups at any time point <0.05), and the difference between Response groups at a given time met p<0.01 and was >1.25-fold (311 genes at baseline, Table 6A; 779 genes at C1D28, Table 7A). For a subset of the 779 genes, the interaction between Response and time also met p<0.01 and the change upon treatment in Responders was >1.25-fold (56 genes in Table 8A). The sets of transcripts meeting each of the above significance criteria were evaluated for enrichment (Tilford et al. 2009, *Gene set enrichment analysis*, In Protein Networks and Pathways, Nikolsky, Y. and Bryant, J. (Eds.), New York: Humana Press, pp. 99-122) (p values provided were Bonferroni corrected) of 1,539 genes from immune cell lineages (Abbas et al. (2005) *Genes Immun* 6:319-31) and for biological impact (MetaCore; Thomson Reuters, New York, NY).

TABLE 3

59 Transcripts From Whole Blood Analysis.

| Probeset (BrainArray v.10) | ENTREZ Gene ID | HUGO Gene Symbol | P value for C1D2 v. C1D1 | C1D1: Mean RMA value | C1D2: Mean RMA value | C1D2 v. C1D1: Fold Change |
|---|---|---|---|---|---|---|
| BrAr: LOC3983_at | LOC3983 | ABLIM1 | 4.75997E−05 | 4.67 | 4.39 | 0.82 |
| BrAr: LOC9447_at | LOC9447 | AIM2 | 0.0014429 | 4.7 | 5.02 | 1.25 |
| BrAr: LOC29123_at | LOC29123 | ANKRD11 | 0.004165336 | 6.64 | 6.32 | 0.81 |
| BrAr: LOC118932_at | LOC118932 | ANKRD22 | 3.93174E−05 | 3.21 | 3.52 | 1.24 |
| BrAr: LOC1236_at | LOC1236 | CCR7 | 2.93852E−05 | 7.88 | 7.41 | 0.72 |
| BrAr: LOC939_at | LOC939 | CD27 | 1.28677E−05 | 6.3 | 5.97 | 0.79 |
| BrAr: LOC917_at | LOC917 | CD3G | 0.005433463 | 6.09 | 5.63 | 0.73 |
| BrAr: LOC91351_at | LOC91351 | DDX60L | 5.63444E−09 | 6.8 | 7.1 | 1.23 |
| BrAr: LOC1975_at | LOC1975 | EIF4B | 0.005759727 | 5.09 | 4.74 | 0.78 |
| BrAr: LOC94240_at | LOC94240 | EPSTI1 | 9.11328E−09 | 4.88 | 5.49 | 1.53 |
| BrAr: LOC51513_at | LOC51513 | ETV7 | 6.46465E−05 | 2.72 | 3.02 | 1.23 |
| BrAr: LOC441168_at | LOC441168 | FAM26F | 2.57221E−07 | 4.75 | 5.1 | 1.27 |
| BrAr: LOC26270_at | LOC26270 | FBXO6 | 4.64598E−10 | 4.08 | 4.53 | 1.37 |
| BrAr: LOC2272_at | LOC2272 | FHIT | 0.004291588 | 5.06 | 4.77 | 0.82 |
| BrAr: LOC2633_at | LOC2633 | GBP1 | 2.4785E−10 | 4.33 | 4.9 | 1.48 |
| BrAr: LOC115361_at | LOC115361 | GBP4 | 3.84104E−06 | 2.87 | 3.15 | 1.21 |
| BrAr: LOC115362_at | LOC115362 | GBP5 | 1.12749E−09 | 5.15 | 5.69 | 1.46 |
| BrAr: LOC2643_at | LOC2643 | GCH1 | 2.83232E−08 | 4.25 | 4.61 | 1.29 |
| BrAr: LOC2710_at | LOC2710 | GK | 0.000283034 | 4.45 | 4.81 | 1.29 |
| BrAr:LOC2745_at | LOC2745 | GLRX | 0.001989618 | 5.55 | 5.81 | 1.21 |
| BrAr: LOC3430_at | LOC3430 | IFI35 | 1.64598E−05 | 6.18 | 6.52 | 1.27 |
| BrAr: LOC10561_at | LOC10561 | IFI44 | 0.00021054 | 3.86 | 4.19 | 1.25 |
| BrAr: LOC2537_at | LOC2537 | IFI6 | 0.000341067 | 6.34 | 6.66 | 1.25 |
| BrAr: LOC64135_at | LOC64135 | IFIH1 | 0.002562623 | 5.05 | 5.32 | 1.2 |
| BrAr: LOC3434_at | LOC3434 | IFIT1 | 2.30102E−05 | 6.22 | 6.65 | 1.35 |
| BrAr: LOC3433_at | LOC3433 | IFIT2 | 5.89582E−05 | 5.08 | 5.38 | 1.23 |
| BrAr: LOC3437_at | LOC3437 | IFIT3 | 0.002092781 | 6.56 | 6.85 | 1.23 |
| BrAr: LOC3575_at | LOC3575 | IL7R | 5.15074E−07 | 7.84 | 7.3 | 0.69 |
| BrAr: LOC3665_at | LOC3665 | IRF7 | 1.9346E−06 | 7.21 | 7.56 | 1.27 |
| BrAr: LOC9636_at | LOC9636 | ISG15 | 0.001134979 | 6.47 | 6.76 | 1.23 |
| BrAr: LOC51056_at | LOC51056 | LAP3 | 0.003108231 | 2.77 | 3.11 | 1.26 |
| BrAr: LOC100128751_at | LOC100128751 | LOC100128751 | 0.008038775 | 6.23 | 5.93 | 0.81 |
| BrAr: LOC100131541_at | LOC100131541 | LOC100131541 | 0.005861658 | 4.52 | 4.1 | 0.74 |
| BrAr: LOC4118_at | LOC4118 | MAL | 7.17596E−06 | 6.53 | 6.24 | 0.82 |
| BrAr: LOC4775_at | LOC4775 | NFATC3 | 0.000709543 | 6.33 | 5.96 | 0.77 |
| BrAr: LOC57185_at | LOC57185 | NIPAL3 | 0.001814472 | 4.43 | 4.08 | 0.78 |
| BrAr: LOC9934_at | LOC9934 | P2RY14 | 5.87145E−05 | 3.3 | 3.73 | 1.35 |
| BrAr: LOC286530_at | LOC286530 | P2RY8 | 0.005584607 | 7.21 | 6.93 | 0.82 |
| BrAr: LOC54625_at | LOC54625 | PARP14 | 2.23537E−07 | 4.12 | 4.42 | 1.24 |
| BrAr: LOC83666_at | LOC83666 | PARP9 | 1.66909E−05 | 5.27 | 5.63 | 1.28 |
| BrAr: LOC5359_at | LOC5359 | PLSCR1 | 3.57775E−07 | 5.9 | 6.26 | 1.29 |
| BrAr: LOC5423_at | LOC5423 | POLB | 0.000820428 | 5.98 | 6.24 | 1.2 |
| BrAr: LOC9050_at | LOC9050 | PSTPIP2 | 9.27591E−13 | 5.6 | 6.02 | 1.34 |
| BrAr: LOC55647_at | LOC55647 | RAB20 | 0.000477973 | 3.3 | 3.61 | 1.24 |
| BrAr: LOC6095_at | LOC6095 | RORA | 0.007747422 | 5.01 | 4.69 | 0.8 |
| BrAr: LOC64108_at | LOC64108 | RTP4 | 0.000207057 | 3.23 | 3.51 | 1.21 |
| BrAr: LOC219285_at | LOC219285 | SAMD9L | 2.81577E−05 | 4.33 | 4.65 | 1.24 |
| BrAr: LOC9997_at | LOC9997 | SCO2 | 2.04163E−05 | 7.18 | 7.63 | 1.37 |
| BrAr: LOC710_at | LOC710 | SERPING1 | 0.001824018 | 3.05 | 3.4 | 1.27 |
| BrAr: LOC6772_at | LOC6772 | STAT1 | 8.03115E−10 | 4.89 | 5.29 | 1.32 |
| BrAr: LOC6890_at | LOC6890 | TAP1 | 3.26126E−05 | 7.72 | 8.01 | 1.22 |
| BrAr: LOC7130_at | LOC7130 | TNFAIP6 | 3.48335E−05 | 7.18 | 7.58 | 1.31 |
| BrAr: LOC28755_at | LOC28755 | TRAC | 7.80813E−05 | 8.32 | 7.98 | 0.79 |
| BrAr: LOC28638_at | LOC28638 | TRBC2 | 5.36988E−05 | 9.33 | 9.05 | 0.82 |
| BrAr: LOC10346_at | LOC10346 | TRIM22 | 1.69393E−06 | 5.42 | 5.82 | 1.32 |
| BrAr: LOC1890_at | LOC1890 | TYMP | 0.002083458 | 5.8 | 6.15 | 1.27 |
| BrAr: LOC9246_at | LOC9246 | UBE2L6 | 2.71549E−10 | 7.9 | 8.26 | 1.28 |
| BrAr: LOC10791_at | LOC10791 | VAMP5 | 7.41239E−05 | 5.92 | 6.3 | 1.3 |
| BrAr: LOC7453_at | LOC7453 | WARS | 0.000887265 | 6.67 | 7.01 | 1.26 |

Note:
These are transcripts for which the null hypothesis was rejected and the change over time averaged over treatment groups was >1.2-fold.

Within the analyses of the relationship of gene expression to pharmacodynamic parameters (treatment group and time on study) possible treatment group-specific effects were examined. Among genes where the null hypothesis was rejected (p for time on study, <0.01), a second multi-contrast test of all time-by-treatment interaction parameters was used to test whether the pattern of expression change differed between at least two treatment groups. If this null hypothesis was rejected (p<0.01 for interaction between dose and time on study or between previous treatment status and time on study), then we examined the effect size in each treatment group. Genes for which the change over time for at least one treatment group was >1.3-fold (biopsy; 37 probesets) or >1.2-fold (blood; 24 probesets) are presented in Tables 4 and 5. In all cases, the change over time for at least two of the other treatment groups did not meet those criteria.

TABLE 4

Genes From an Analysis of Tumor Biopsies With >1.3-fold Differences Between Treatment Groups Over Time.

| Probeset (BrainArray v.10) | ENTREZ Gene ID | HUGO Gene Symbol | P value for change upon treatment | P value for change upon treatment differing between Dose groups | P value for change upon treatment differing between pretreated and Naïve | Comment |
|---|---|---|---|---|---|---|
| 139886_at | LOC139886 | SPIN4 | 0.000227 | 0.909 | 0.000207 | Possible effect of Pretreatment |
| 165215_at | LOC165215 | FAM171B | 0.000309 | 0.306 | 0.00119 | Possible effect of Pretreatment |
| 677841_at | LOC677841 | SNORA74B | 0.000915 | 0.289 | 0.00276 | Possible effect of Pretreatment |
| 158405_at | LOC158405 | KIAA1958 | 0.00116 | 0.677 | 0.00843 | Possible effect of Pretreatment |
| 81839_at | LOC81839 | VANGL1 | 0.00126 | 0.225 | 0.00993 | Possible effect of Pretreatment |
| 7056_at | LOC7056 | THBD | 0.00158 | 0.861 | 0.00528 | Possible effect of Pretreatment |
| 80256_at | LOC80256 | FAM214B | 0.00163 | 0.758 | 0.00298 | Possible effect of Pretreatment |
| 29984_at | LOC29984 | RHOD | 0.00244 | 0.591 | 0.00417 | Possible effect of Pretreatment |
| 283899_at | LOC283899 | INO80E | 0.00844 | 0.72 | 0.00597 | Possible effect of Pretreatment |
| 838_at | LOC838 | CASP5 | 0.0000112 | 0.00368 | 0.224 | Possible effect of Dose |
| 22934_at | LOC22934 | RPIA | 0.0000468 | 0.000416 | 0.589 | Possible effect of Dose |
| 7920_at | LOC7920 | ABHD16A | 0.0000576 | 0.000157 | 0.591 | Possible effect of Dose |
| 649_at | LOC649 | BMP1 | 0.0000881 | 0.00834 | 0.123 | Possible effect of Dose |
| 5136_at | LOC5136 | PDE1A | 0.00013 | 0.000293 | 0.705 | Possible effect of Dose |
| 441631_at | LOC441631 | TSPAN11 | 0.000144 | 0.00141 | 0.184 | Possible effect of Dose |
| 57167_at | LOC57167 | SALL4 | 0.000197 | 0.00235 | 0.785 | Possible effect of Dose |
| 57451_at | LOC57451 | TENM2 | 0.000262 | 0.00167 | 0.2 | Possible effect of Dose |
| 4131_at | LOC4131 | MAP1B | 0.000373 | 0.00715 | 0.0496 | Possible effect of Dose |
| 5793_at | LOC5793 | PTPRG | 0.000387 | 0.00696 | 0.0644 | Possible effect of Dose |
| 6750_at | LOC6750 | SST | 0.00044 | 0.00744 | 0.959 | Possible effect of Dose |
| 131375_at | LOC131375 | LYZL4 | 0.000503 | 0.0000613 | 0.17 | Possible effect of Dose |
| 23608_at | LOC23608 | MKRN1 | 0.000583 | 0.00243 | 0.385 | Possible effect of Dose |
| 64175_at | LOC64175 | LEPRE1 | 0.000584 | 0.00701 | 0.468 | Possible effect of Dose |
| 257019_at | LOC257019 | FRMD3 | 0.000625 | 0.00202 | 0.392 | Possible effect of Dose |
| 253512_at | LOC253512 | SLC25A30 | 0.000641 | 0.00153 | 0.266 | Possible effect of Dose |
| 58484_at | LOC58484 | NLRC4 | 0.000701 | 0.00578 | 0.387 | Possible effect of Dose |
| 8458_at | LOC8458 | TTF2 | 0.000977 | 0.00307 | 0.249 | Possible effect of Dose |
| 80381_at | LOC80381 | CD276 | 0.000978 | 0.000694 | 0.821 | Possible effect of Dose |
| 5291_at | LOC5291 | PIK3CB | 0.000992 | 0.00198 | 0.355 | Possible effect of Dose |
| 3908_at | LOC3908 | LAMA2 | 0.00124 | 0.00746 | 0.25 | Possible effect of Dose |
| 6531_at | LOC6531 | SLC6A3 | 0.00141 | 0.00586 | 0.116 | Possible effect of Dose |
| 51257_at | LOC51257 | MAR2 | 0.00162 | 0.00738 | 0.0142 | Possible effect of Dose |
| 221656_at | LOC221656 | KDM1B | 0.00166 | 0.00867 | 0.963 | Possible effect of Dose |
| 3956_at | LOC3956 | LGALS1 | 0.00173 | 0.000595 | 0.161 | Possible effect of Dose |
| 84243_at | LOC84243 | ZDHHC18 | 0.00179 | 0.00933 | 0.252 | Possible effect of Dose |
| 5654_at | LOC5654 | HTRA1 | 0.00181 | 0.00388 | 0.781 | Possible effect of Dose |
| 4920_at | LOC4920 | ROR2 | 0.00186 | 0.000622 | 0.469 | Possible effect of Dose |

Note:
Thirty-seven probesets identified from gene expression analysis.

TABLE 5

Genes From Whole Blood Analysis With >1.2-fold Differences Between Treatment Groups Over Time.

| Probeset (BrainArray v.10) | ENTREZ Gene ID | HUGO Gene Symbol | P value for change upon treatment | P value for change upon treatment differing between Dose groups | P value for change upon treatment differing between pretreated and Naïve | Comment |
|---|---|---|---|---|---|---|
| 3301_at | LOC3301 | DNAJA1 | 0.000300892 | 0.00283273 | 0.1319663 | Possible effect of Dose |
| 27247_at | LOC27247 | NFU1 | 0.003282889 | 0.001166246 | 0.01694071 | Possible effect of Dose |
| 28227_at |  | PPP2R3B || ? | 0.006291189 | 0.006389651 | 0.06670232 | Possible effect of Dose |
|  |  | || ? |  |  |  |  |
| 283537_at | LOC283537 | SLC46A3 | 0.005223015 | 0.003790012 | 0.06725309 | Possible effect of Dose |
| 6643_at | LOC6643 | SNX2 | 0.000891442 | 0.000328151 | 0.04873944 | Possible effect of Dose |

TABLE 5-continued

Genes From Whole Blood Analysis With >1.2-fold Differences Between Treatment Groups Over Time.

| Probeset (BrainArray v.10) | ENTREZ Gene ID | HUGO Gene Symbol | P value for change upon treatment | P value for change upon treatment differing between Dose groups | P value for change upon treatment differing between pretreated and Naïve | Comment |
|---|---|---|---|---|---|---|
| 379013_at | | RNF138 \|\| RNF138P1 | 0.005091024 | 0.000976717 | 0.2653985 | Possible effect of Dose |
| 55855_at | | FAM45B \|\| FAM45A | 0.001326355 | 0.001402364 | 0.04572821 | Possible effect of Dose |
| 30011_at | LOC30011 | SH3KBP1 | 0.00376672 | 0.007403809 | 0.01968723 | Possible effect of Dose |
| 23112_at | LOC23112 | TNRC6B | 0.001041506 | 0.004713658 | 0.01089389 | Possible effect of Dose |
| 23741_at | LOC23741 | EID1 | 0.004571983 | 0.005961323 | 0.064752 | Possible effect of Dose |
| 23215_at | LOC23215 | PRRC2C | 0.008805884 | 0.009225187 | 0.01164823 | Possible effect of Dose |
| 57466_at | LOC57466 | SCAF4 | 0.005837828 | 0.003790088 | 0.01926408 | Possible effect of Dose |
| 100507117_at | LOC100507117 | ASAP1-IT2 | 0.009482807 | 0.006106619 | 0.006915612 | Possible effect of Dose |
| 4775_at | LOC4775 | NFATC3 | 0.000709543 | 0.02451703 | 0.007846956 | Possible effect of Pretreatment |
| 100507117_at | LOC100507117 | ASAP1-IT2 | 0.009482807 | 0.006106619 | 0.006915612 | Possible effect of Pretreatment |
| 23157_at | LOC23157 | | 0.0014221 | 0.2044598 | 0.004195466 | Possible effect of Pretreatment |
| 54737_at | LOC54737 | MPHOSPH8 | 0.004196599 | 0.04784359 | 0.005009904 | Possible effect of Pretreatment |
| 54876_at | LOC54876 | DCAF16 | 1.1088E−05 | 0.02246931 | 0.000732451 | Possible effect of Pretreatment |
| 51176_at | LOC51176 | LEF1 | 0.002074846 | 0.4212703 | 0.007699788 | Possible effect of Pretreatment |
| 26999_at | LOC26999 | CYFIP2 | 0.00204136 | 0.3130331 | 0.00867614 | Possible effect of Pretreatment |
| 81539_at | LOC81539 | SLC38A1 | 0.000962059 | 0.08678283 | 0.007378195 | Possible effect of Pretreatment |
| 9214_at | LOC9214 | FAIM3 | 0.001082093 | 0.5771362 | 0.008717745 | Possible effect of Pretreatment |
| 54900_at | LOC54900 | LAX1 | 0.001028967 | 0.3447576 | 0.008016235 | Possible effect of Pretreatment |
| 3615_at | LOC3615 | IMPDH2 | 0.008047956 | 0.5363073 | 0.008885895 | Possible effect of Pretreatment |

Note:
Twenty-four probesets identified from gene expression analysis.

TABLE 6A

Genes From an Analysis of Tumor Biopsies With ≥1.2-fold or ≤0.8-fold Differences Between Treatment at Baseline.

| Probeset (BrainArray v.10) | ENTREZ Gene ID | HUGO Gene Symbol | P value for Response v. No Response at baseline | No Response: Mean RMA value at baseline | Response: Mean RMA value at baseline | Response v. No response: Fold difference at baseline |
|---|---|---|---|---|---|---|
| BrAr:LOC1_at | LOC1 | A1BG | 0.002439879 | 2.34 | 2.7 | 1.28 |
| BrAr:LOC8647_at | LOC8647 | ABCB11 | 0.009042188 | 2.08 | 2.41 | 1.26 |
| BrAr:LOC10152_at | LOC10152 | ABI2 | 0.002010763 | 6.7 | 6.28 | 0.74 |
| BrAr:LOC11174_at | LOC11174 | ADAMTS6 | 1.69594E−06 | 2.25 | 2.59 | 1.26 |
| BrAr:LOC10939_at | LOC10939 | AFG3L2 | 0.007003315 | 6.23 | 5.69 | 0.68 |
| BrAr:LOC177_at | LOC177 | AGER | 0.000612783 | 3.09 | 3.45 | 1.29 |
| BrAr:LOC9447_at | LOC9447 | AIM2 | 0.000486717 | 4.68 | 6.62 | 3.82 |
| BrAr:LOC338692_at | LOC338692 | ANKRD13D | 0.000854153 | 4.12 | 4.5 | 1.31 |
| BrAr:LOC122416_at | LOC122416 | ANKRD9 | 0.00839715 | 3.61 | 3.99 | 1.3 |
| BrAr:LOC10947_at | LOC10947 | AP3M2 | 0.004540524 | 4.6 | 4.15 | 0.73 |
| BrAr:LOC164668_at | LOC164668 | APOBEC3H | 0.000373208 | 3.44 | 3.81 | 1.28 |
| BrAr:LOC351_at | LOC351 | APP | 0.003579009 | 10.52 | 10.09 | 0.74 |
| BrAr:LOC394_at | LOC394 | ARHGAP5 | 0.003585724 | 5.57 | 5.05 | 0.7 |
| BrAr:LOC64333_at | LOC64333 | ARHGAP9 | 0.001948117 | 3.8 | 4.56 | 1.7 |
| BrAr:LOC128272_at | LOC128272 | ARHGEF19 | 0.000141249 | 4.01 | 4.4 | 1.31 |
| BrAr:LOC51008_at | LOC51008 | ASCC1 | 0.003067675 | 6.6 | 6.15 | 0.73 |
| BrAr:LOC433_at | LOC433 | ASGR2 | 0.008844586 | 3.34 | 3.79 | 1.36 |
| BrAr:LOC9212_at | LOC9212 | AURKB | 0.00323879 | 4.39 | 4.75 | 1.29 |
| BrAr:LOC10538_at | LOC10538 | BATF | 0.003946406 | 3.94 | 4.79 | 1.8 |
| BrAr:LOC27319_at | LOC27319 | BHLHE22 | 0.000832399 | 2.72 | 3.13 | 1.33 |

TABLE 6A-continued

Genes From an Analysis of Tumor Biopsies With ≥1.2-fold or ≤0.8-fold Differences Between Treatment at Baseline.

| Probeset (BrainArray v.10) | ENTREZ Gene ID | HUGO Gene Symbol | P value for Response v. No Response at baseline | No Response: Mean RMA value at baseline | Response: Mean RMA value at baseline | Response v. No response: Fold difference at baseline |
|---|---|---|---|---|---|---|
| BrAr:LOC51411_at | LOC51411 | BIN2 | 0.001478985 | 5.15 | 6.3 | 2.22 |
| BrAr:LOC653_at | LOC653 | BMP5 | 0.003429408 | 2.26 | 2.64 | 1.3 |
| BrAr:LOC22903_at | LOC22903 | BTBD3 | 0.004900034 | 5.7 | 5.01 | 0.62 |
| BrAr:LOC686_at | LOC686 | BTD | 0.000105266 | 4.7 | 3.99 | 0.61 |
| BrAr:LOC53838_at | LOC53838 | C11ORF24 | 0.003520261 | 4.97 | 5.3 | 1.26 |
| BrAr:LOC399949_at | LOC399949 | C11ORF88 | 7.2489E−06 | 2.12 | 2.52 | 1.32 |
| BrAr:LOC143678_at | LOC143678 | C11ORF94 | 2.49371E−05 | 1.99 | 2.35 | 1.28 |
| BrAr:LOC79415_at | LOC79415 | C17ORF62 | 0.006116147 | 5.76 | 6.21 | 1.37 |
| BrAr:LOC374872_at | LOC374872 | C19ORF35 | 0.009042774 | 3.6 | 3.93 | 1.26 |
| BrAr:LOC126567_at | LOC126567 | C2CD4C | 0.000755252 | 2.93 | 3.36 | 1.34 |
| BrAr:LOC27202_at | LOC27202 | C5AR2 | 0.00698718 | 3.44 | 3.79 | 1.27 |
| BrAr:LOC63920_at | LOC63920 | C5ORF54 | 0.008739816 | 4.08 | 3.54 | 0.69 |
| BrAr:LOC91768_at | LOC91768 | CABLES1 | 0.002940092 | 4.9 | 4.14 | 0.59 |
| BrAr:LOC440068_at | LOC440068 | CARD17 | 0.004061575 | 2.66 | 3.06 | 1.32 |
| BrAr:LOC117144_at | LOC117144 | CATSPER1 | 0.005573531 | 3.35 | 3.98 | 1.54 |
| BrAr:LOC55013_at | LOC55013 | CCDC109B | 0.009687793 | 6.15 | 6.92 | 1.7 |
| BrAr:LOC256309_at | LOC256309 | CCDC110 | 0.006222969 | 2.57 | 1.9 | 0.63 |
| BrAr:LOC28952_at | LOC28952 | CCDC22 | 8.79954E−05 | 4.24 | 4.7 | 1.37 |
| BrAr:LOC342510_at | LOC342510 | CD300E | 0.009277761 | 3.72 | 4.1 | 1.3 |
| BrAr:LOC916_at | LOC916 | CD3E | 0.005229998 | 4.67 | 6.1 | 2.7 |
| BrAr:LOC924_at | LOC924 | CD7 | 0.000599999 | 3.22 | 3.68 | 1.37 |
| BrAr:LOC3732_at | LOC3732 | CD82 | 0.007778158 | 3.14 | 3.65 | 1.43 |
| BrAr:LOC997_at | LOC997 | CDC34 | 0.001777585 | 4.04 | 4.48 | 1.36 |
| BrAr:LOC1084_at | LOC1084 | CEACAM3 | 0.00167501 | 3.74 | 4.07 | 1.26 |
| BrAr:LOC145508_at | LOC145508 | CEP128 | 0.000595015 | 3.88 | 4.52 | 1.56 |
| BrAr:LOC1675_at | LOC1675 | CFD | 0.004220607 | 3.35 | 4.19 | 1.79 |
| BrAr:LOC63924_at | LOC63924 | CIDEC | 0.000915451 | 2.49 | 2.89 | 1.32 |
| BrAr:LOC8483_at | LOC8483 | CILP | 0.003154463 | 2.92 | 4.16 | 2.36 |
| BrAr:LOC9976_at | LOC9976 | CLEC2B | 0.000938528 | 7.17 | 8.14 | 1.95 |
| BrAr:LOC339390_at | LOC339390 | CLEC4G | 0.000637875 | 2.52 | 2.85 | 1.25 |
| BrAr:LOC79827_at | LOC79827 | CLMP | 0.002162595 | 3.58 | 4.55 | 1.97 |
| BrAr:LOC23059_at | LOC23059 | CLUAP1 | 0.004273619 | 5.58 | 5.18 | 0.76 |
| BrAr:LOC10229_at | LOC10229 | COQ7 | 0.009767632 | 6.08 | 5.58 | 0.71 |
| BrAr:LOC1355_at | LOC1355 | COX15 | 0.001550291 | 6.25 | 5.85 | 0.76 |
| BrAr:LOC1409_at | LOC1409 | CRYAA ‖ ? | 0.009195632 | 2.83 | 3.32 | 1.41 |
| BrAr:LOC64651_at | LOC64651 | CSRNP1 | 0.001153343 | 4.95 | 5.34 | 1.31 |
| BrAr:LOC1521_at | LOC1521 | CTSW | 0.001728422 | 3.73 | 4.57 | 1.79 |
| BrAr:LOC1522_at | LOC1522 | CTSZ | 0.007645829 | 7.64 | 8.38 | 1.67 |
| BrAr:LOC9267_at | LOC9267 | CYTH1 | 0.004664342 | 5.12 | 5.62 | 1.41 |
| BrAr:LOC27128_at | LOC27128 | CYTH4 | 0.007386637 | 3.49 | 3.94 | 1.37 |
| BrAr:LOC153090_at | LOC153090 | DAB2IP | 0.002227001 | 5.59 | 4.92 | 0.63 |
| BrAr:LOC28988_at | LOC28988 | DBNL | 0.002200102 | 5.51 | 5.93 | 1.34 |
| BrAr:LOC84516_at | LOC84516 | DUNS | 0.001890579 | 6.09 | 5.66 | 0.75 |
| BrAr:LOC22898_at | LOC22898 | DENND3 | 0.001155438 | 3.77 | 4.32 | 1.46 |
| BrAr:LOC27123_at | LOC27123 | DKK2 | 0.000782988 | 2.91 | 3.6 | 1.62 |
| BrAr:LOC1741_at | LOC1741 | DLG3 | 0.001806326 | 5.95 | 5.4 | 0.68 |
| BrAr:LOC131118_at | LOC131118 | DNAJC19 | 0.006866278 | 7.24 | 6.59 | 0.64 |
| BrAr:LOC1796_at | LOC1796 | DOK1 | 0.002452713 | 3.71 | 4.11 | 1.33 |
| BrAr:LOC9046_at | LOC9046 | DOK2 | 0.009504175 | 3.63 | 4.13 | 1.42 |
| BrAr:LOC10589_at | LOC10589 | DRAP1 | 0.001830494 | 6.35 | 6.87 | 1.44 |
| BrAr:LOC9666_at | LOC9666 | DZIP3 | 0.002893835 | 4.96 | 4.32 | 0.64 |
| BrAr:LOC1874_at | LOC1874 | E2F4 | 0.005888969 | 5.01 | 5.34 | 1.26 |
| BrAr:LOC144455_at | LOC144455 | E2F7 | 0.00060632 | 2.54 | 3.2 | 1.58 |
| BrAr:LOC79180_at | LOC79180 | EFHD2 | 0.001533709 | 5.24 | 5.98 | 1.67 |
| BrAr:LOC25975_at | LOC25975 | EGFL6 | 0.006225321 | 2.62 | 3.28 | 1.58 |
| BrAr:LOC254102_at | LOC254102 | EHBP1L1 | 0.001083093 | 3.6 | 4.21 | 1.52 |
| BrAr:LOC1964_at | LOC1964 | EIF1AX | 0.007627306 | 7.33 | 6.88 | 0.73 |
| BrAr:LOC1979_at | LOC1979 | EIF4EBP2 | 0.002832149 | 7.95 | 7.49 | 0.73 |
| B rAr:LO C2000_at | LOC2000 | ELF4 | 0.009430975 | 6.83 | 7.3 | 1.39 |
| BrAr:LOC2036_at | LOC2036 | EPB41L1 | 0.000854408 | 6.9 | 5.9 | 0.5 |
| BrAr:LOC11160_at | LOC11160 | ERLIN2 | 0.002726397 | 5.12 | 4.61 | 0.7 |
| BrAr:LOC79956_at | LOC79956 | ERMP1 | 0.003099694 | 6.44 | 5.84 | 0.66 |
| BrAr:LOC2121_at | LOC2121 | EVC | 0.003766926 | 3.36 | 3.7 | 1.27 |
| BrAr:LOC2124_at | LOC2124 | EVI2B | 0.008272345 | 6.7 | 7.65 | 1.93 |
| BrAr:LOC150864_at | LOC150864 | FAM117B | 0.000508571 | 5.61 | 4.94 | 0.63 |
| BrAr:LOC642968_at | LOC642968 | FAM163B | 0.000315427 | 2.4 | 2.73 | 1.26 |
| BrAr:LOC54757_at | LOC54757 | FAM20A | 0.008983202 | 4.16 | 4.9 | 1.68 |
| BrAr:LOC84293_at | LOC84293 | FAM213A | 0.009083801 | 8.7 | 8.03 | 0.63 |
| BrAr:LOC84961_at | LOC84961 | FBXL20 | 0.001990936 | 5.33 | 4.92 | 0.75 |
| BrAr:LOC26273_at | LOC26273 | FBXO3 | 0.005774007 | 5.24 | 4.72 | 0.7 |
| BrAr:LOC26270_at | LOC26270 | FBXO6 | 0.004151206 | 2.91 | 3.44 | 1.44 |

TABLE 6A-continued

Genes From an Analysis of Tumor Biopsies With ≥1.2-fold or ≤0.8-fold Differences Between Treatment at Baseline.

| Probeset (BrainArray v.10) | ENTREZ Gene ID | HUGO Gene Symbol | P value for Response v. No Response at baseline | No Response: Mean RMA value at baseline | Response: Mean RMA value at baseline | Response v. No response: Fold difference at baseline |
|---|---|---|---|---|---|---|
| BrAr:LOC115352_at | LOC115352 | FCRL3 | 0.008603096 | 3.18 | 3.77 | 1.51 |
| BrAr:LOC121512_at | LOC121512 | FGD4 | 0.006220203 | 5.57 | 5.04 | 0.69 |
| BrAr:LOC392490_at | LOC392490 | FLJ44635 | 0.005825881 | 2.91 | 3.26 | 1.27 |
| BrAr:LOC2323_at | LOC2323 | FLT3LG | 0.001059924 | 3.88 | 4.29 | 1.33 |
| BrAr:LOC752_at | LOC752 | FMNL1 | 0.005673631 | 3.19 | 3.87 | 1.61 |
| BrAr:LOC2444_at | LOC2444 | FRK | 0.007354384 | 5.41 | 4.63 | 0.59 |
| BrAr:LOC53827_at | LOC53827 | FXYD5 | 0.00949403 | 7.52 | 8.12 | 1.52 |
| BrAr:LOC4616_at | LOC4616 | GADD45B | 0.006110882 | 6.38 | 7.07 | 1.61 |
| BrAr:LOC2585_at | LOC2585 | GALK2 | 0.002535719 | 5.6 | 5.06 | 0.69 |
| BrAr:LOC79623_at | LOC79623 | GALNT14 | 0.007555669 | 7.43 | 6.42 | 0.49 |
| BrAr:LOC8484_at | LOC8484 | GALR3 | 0.002225231 | 2.88 | 3.21 | 1.26 |
| BrAr:LOC2634_at | LOC2634 | GBP2 | 0.00169654 | 9.1 | 9.68 | 1.5 |
| BrAr:LOC115362_at | LOC115362 | GBP5 | 0.004448746 | 5.71 | 7.15 | 2.71 |
| BrAr:LOC2662_at | LOC2662 | GDF10 | 9.97246E−05 | 2.18 | 2.53 | 1.27 |
| BrAr:LOC8328_at | LOC8328 | GFI1B | 0.000528856 | 2.71 | 3.07 | 1.29 |
| BrAr:LOC84340_at | LOC84340 | GFM2 | 0.006257568 | 5.52 | 5.03 | 0.71 |
| BrAr:LOC9945_at | LOC9945 | GFPT2 | 0.001612889 | 4.86 | 5.72 | 1.82 |
| BrAr:LOC10804_at | LOC10804 | GJB6 | 0.009481221 | 2.13 | 3.03 | 1.87 |
| BrAr:LOC26035_at | LOC26035 | GLCE | 0.007331368 | 6.44 | 5.76 | 0.62 |
| BrAr:LOC728310_at | LOC728310 | GOLGA6L7P | 0.002663795 | 4.18 | 4.58 | 1.33 |
| BrAr:LOC151306_at | LOC151306 | GPBAR1 | 0.001078179 | 3.82 | 4.3 | 1.4 |
| BrAr:LOC2825_at | LOC2825 | GPR1 | 1.12776E−05 | 2.32 | 2.72 | 1.32 |
| BrAr:LOC222487_at | LOC222487 | GPR97 | 0.006093072 | 3.3 | 3.77 | 1.39 |
| BrAr:LOC3002_at | LOC3002 | GZMB | 0.002027831 | 4.42 | 5.91 | 2.81 |
| BrAr:LOC3037_at | LOC3037 | HAS2 | 0.00079141 | 2.97 | 3.64 | 1.6 |
| BrAr:LOC25831_at | LOC25831 | HECTD1 | 0.004167883 | 6.92 | 6.43 | 0.71 |
| BrAr:LOC8355_at | LOC8355 | HIST1H3G | 0.002866252 | 3.41 | 4.12 | 1.64 |
| BrAr:LOC84263_at | LOC84263 | HSDL2 | 0.006343005 | 6.57 | 6.02 | 0.68 |
| BrAr:LOC84941_at | LOC84941 | HSH2D | 0.005527177 | 3.85 | 4.31 | 1.37 |
| BrAr:LOC147920_at | LOC147920 | IGFL2 | 0.001338112 | 2.98 | 3.74 | 1.69 |
| BrAr:LOC9641_at | LOC9641 | IKBKE | 0.006567351 | 3.51 | 3.96 | 1.37 |
| BrAr:LOC3601_at | LOC3601 | IL15RA | 0.006778476 | 5.15 | 5.78 | 1.55 |
| BrAr:LOC3552_at | LOC3552 | IL1A | 0.000381983 | 2.34 | 2.91 | 1.48 |
| BrAr:LOC7850_at | LOC7850 | IL1R2 | 0.00913524 | 4.99 | 6.31 | 2.51 |
| BrAr:LOC51194_at | LOC51194 | IPO11 ‖ IPO11-LRRC70 | 0.001524954 | 6.28 | 5.73 | 0.68 |
| BrAr:LOC3659_at | LOC3659 | IRF1 | 0.001881433 | 4.94 | 5.72 | 1.72 |
| BrAr:LOC8471_at | LOC8471 | IRS4 | 0.00026598 | 2.09 | 2.6 | 1.43 |
| BrAr:LOC150771_at | LOC150771 | ITPRIPL1 | 0.006231421 | 2.75 | 3.12 | 1.29 |
| BrAr:LOC3744_at | LOC3744 | KCNA10 | 0.000801613 | 2.88 | 3.2 | 1.25 |
| BrAr:LOC3742_at | LOC3742 | KCNA6 | 0.001284042 | 3.59 | 3.94 | 1.27 |
| BrAr:LOC8514_at | LOC8514 | KCNAB2 | 0.008920942 | 3.34 | 3.72 | 1.3 |
| BrAr:LOC3751_at | LOC3751 | KCND2 | 0.000823109 | 2.39 | 2.93 | 1.46 |
| BrAr:LOC3783_at | LOC3783 | KCNN4 | 0.000453519 | 3.34 | 3.91 | 1.49 |
| BrAr:LOC55196_at | LOC55196 | KIAA1551 | 0.000793589 | 7.13 | 7.87 | 1.67 |
| BrAr:LOC80726_at | LOC80726 | KIAA1683 | 0.000217967 | 3.78 | 4.13 | 1.27 |
| BrAr:LOC55083_at | LOC55083 | KIF26B | 0.007631673 | 3.08 | 3.53 | 1.37 |
| BrAr:LOC3833_at | LOC3833 | KIFC1 | 0.008302118 | 3.86 | 4.32 | 1.37 |
| BrAr:LOC54800_at | LOC54800 | KLHL24 | 0.001808739 | 8.36 | 7.93 | 0.75 |
| BrAr:LOC386677_at | LOC386677 | KRTAP10-1 | 0.007741563 | 4.54 | 4.93 | 1.31 |
| BrAr:LOC386682_at | LOC386682 | KRTAP10-3 | 0.003161767 | 3.77 | 4.15 | 1.31 |
| BrAr:LOC51520_at | LOC51520 | LARS | 0.000220464 | 6.63 | 6.16 | 0.72 |
| BrAr:LOC253558_at | LOC253558 | LCLAT1 | 0.008215165 | 6.8 | 6.3 | 0.71 |
| BrAr:LOC100287902_at | LOC100287902 | LGALS8-AS1 | 0.006350303 | 2.37 | 2.7 | 1.25 |
| BrAr:LOC23547_at | LOC23547 | LILRA4 | 0.00040177 | 2.8 | 3.21 | 1.32 |
| BrAr:LOC10990_at | LOC10990 | LILRB5 | 0.006482713 | 3.59 | 4.05 | 1.37 |
| BrAr:LOC55327_at | LOC55327 | LIN7C | 0.003833811 | 7.5 | 7.04 | 0.72 |
| BrAr:LOC54072_at | LOC54072 | LINC00158 | 0.00672404 | 2.28 | 2.74 | 1.37 |
| BrAr:LOC79940_at | LOC79940 | LINC00472 | 0.006488207 | 4.47 | 3.44 | 0.49 |
| BrAr:LOC100134259_at | LOC100134259 | LINC01119 | 0.000625649 | 2.76 | 3.08 | 1.25 |
| BrAr:LOC387787_at | LOC387787 | LIPT2 | 0.008893266 | 3.03 | 2.61 | 0.74 |
| BrAr:LOC100288637_at | LOC100288637 | LOC100288637 | 0.005731863 | 5.25 | 5.69 | 1.35 |
| BrAr:LOC10128_at | LOC10128 | LRPPRC | 0.001065237 | 6.79 | 6.26 | 0.69 |
| BrAr:LOC26231_at | LOC26231 | LRRC29 | 4.34623E−05 | 3.71 | 4.18 | 1.39 |
| BrAr:LOC84967_at | LOC84967 | LSM10 | 0.001372205 | 4.75 | 5.27 | 1.43 |
| BrAr:LOC4050_at | LOC4050 | LTB | 0.005018671 | 4.3 | 5.02 | 1.64 |
| BrAr:LOC4124_at | LOC4124 | MAN2A1 | 0.007495834 | 5.26 | 4.81 | 0.73 |
| BrAr:LOC10299_at | LOC10299 | MARCH6 | 0.004816187 | 8.96 | 8.45 | 0.7 |
| BrAr:LOC255374_at | LOC255374 | MBLAC1 | 0.003068993 | 4.44 | 3.83 | 0.66 |
| BrAr:LOC284207_at | LOC284207 | METRNL | 0.000642659 | 3.35 | 3.8 | 1.37 |
| BrAr:LOC254013_at | LOC254013 | METTL20 | 0.000117399 | 4.43 | 3.69 | 0.6 |

TABLE 6A-continued

Genes From an Analysis of Tumor Biopsies With ≥1.2-fold or ≤0.8-fold Differences Between Treatment at Baseline.

| Probeset (BrainArray v.10) | ENTREZ Gene ID | HUGO Gene Symbol | P value for Response v. No Response at baseline | No Response: Mean RMA value at baseline | Response: Mean RMA value at baseline | Response v. No response: Fold difference at baseline |
|---|---|---|---|---|---|---|
| BrAr:LOC4277_at | LOC4277 | MICB | 0.000321554 | 3.49 | 3.96 | 1.38 |
| BrAr:LOC54471_at | LOC54471 | MIEF1 | 0.000410552 | 4.92 | 4.51 | 0.75 |
| BrAr:LOC60672_at | LOC60672 | MIIP | 0.004931523 | 4.76 | 5.16 | 1.32 |
| BrAr:LOC4314_at | LOC4314 | MIMP3 | 4.97409E−07 | 2.19 | 3.92 | 3.33 |
| BrAr:LOC64112_at | LOC64112 | MOAP1 | 0.008394216 | 7.08 | 6.53 | 0.68 |
| BrAr:LOC64398_at | LOC64398 | MPP5 | 0.006167145 | 6.7 | 6.24 | 0.73 |
| BrAr:LOC64976_at | LOC64976 | MRPL40 | 0.007764465 | 8.23 | 7.77 | 0.73 |
| BrAr:LOC23107_at | LOC23107 | MRPS27 | 0.001414269 | 5.83 | 5.31 | 0.7 |
| BrAr:LOC343930_at | LOC343930 | MSGN1 | 0.000579512 | 2.74 | 3.07 | 1.26 |
| BrAr:LOC4437_at | LOC4437 | MSH3 | 0.00389965 | 5.54 | 5.11 | 0.74 |
| BrAr:LOC10232_at | LOC10232 | MSLN | 0.008092046 | 2.27 | 2.6 | 1.26 |
| BrAr:LOC4488_at | LOC4488 | MSX2 | 0.001329214 | 3.04 | 3.52 | 1.4 |
| BrAr:LOC55149_at | LOC55149 | MTPAP | 0.000627336 | 4.42 | 3.91 | 0.7 |
| BrAr:LOC57509_at | LOC57509 | MTUS1 | 0.003060695 | 6.21 | 5.31 | 0.54 |
| BrAr:LOC4588_at | LOC4588 | MUC6 | 0.004734191 | 3.43 | 3.78 | 1.27 |
| BrAr:LOC4595_at | LOC4595 | MUTYH | 0.000171 | 3.18 | 3.53 | 1.28 |
| BrAr:LOC4542_at | LOC4542 | MYO1F | 0.008571913 | 5.44 | 6.3 | 1.82 |
| BrAr:LOC64005_at | LOC64005 | MYO1G | 5.55979E−05 | 2.55 | 2.93 | 1.3 |
| BrAr:LOC4650_at | LOC4650 | MYO9B | 0.005096816 | 3.22 | 3.64 | 1.33 |
| BrAr:LOC342977_at | LOC342977 | NANOS3 | 0.000396627 | 2.89 | 3.21 | 1.25 |
| BrAr:LOC222236_at | LOC222236 | NAPEPLD | 0.008927534 | 4.79 | 4.33 | 0.72 |
| BrAr:LOC4781_at | LOC4781 | NFIB | 0.008871165 | 7.31 | 6.39 | 0.53 |
| BrAr:LOC4818_at | LOC4818 | NKG7 | 0.003622084 | 5.83 | 6.89 | 2.08 |
| BrAr:LOC255743_at | LOC255743 | NPNT | 0.00344628 | 5.63 | 4.2 | 0.37 |
| BrAr:LOC120796_at | LOC120796 | OR56A1 | 0.000432027 | 3.72 | 4.1 | 1.3 |
| BrAr:LOC23762_at | LOC23762 | OSBP2 | 0.009185113 | 3.02 | 3.36 | 1.27 |
| BrAr:LOC150677_at | LOC150677 | OTOS | 0.000614992 | 3.08 | 3.44 | 1.28 |
| BrAr:LOC56288_at | LOC56288 | PARD3 | 0.005865917 | 5.38 | 4.97 | 0.75 |
| BrAr:LOC80714_at | LOC80714 | PBX4 | 0.000760261 | 3.32 | 3.84 | 1.43 |
| BrAr:LOC5179_at | LOC5179 | PENK | 1.15397E−05 | 2.06 | 2.69 | 1.54 |
| BrAr:LOC5193_at | LOC5193 | PEX12 | 0.002594105 | 4.79 | 4.3 | 0.71 |
| BrAr:LOC5824_at | LOC5824 | PEX19 | 0.006368879 | 6.17 | 5.7 | 0.72 |
| BrAr:LOC5292_at | LOC5292 | PIM1 | 0.007345148 | 4.82 | 5.67 | 1.8 |
| BrAr:LOC5341_at | LOC5341 | PLEK | 0.00929435 | 6.12 | 7.15 | 2.03 |
| BrAr:LOC59338_at | LOC59338 | PLEKHA1 | 0.007269683 | 7.18 | 6.39 | 0.58 |
| BrAr:LOC23207_at | LOC23207 | PLEKHM2 | 0.009858656 | 4.36 | 4.71 | 1.28 |
| BrAr:LOC51177_at | LOC51177 | PLEKHO1 | 0.0074894 | 8.2 | 8.81 | 1.53 |
| BrAr:LOC51090_at | LOC51090 | PLLP | 0.00772165 | 4.78 | 3.58 | 0.44 |
| BrAr:LOC196051_at | LOC196051 | PPAPDCIA | 0.000201087 | 2.24 | 2.96 | 1.64 |
| BrAr:LOC5522_at | LOC5522 | PPP2R2C | 0.008008356 | 2.83 | 3.34 | 1.42 |
| BrAr:LOC84106_at | LOC84106 | PRAM1 | 0.003485915 | 3.62 | 4.21 | 1.51 |
| BrAr:LOC9051_at | LOC9051 | PSTPIP1 | 0.002985194 | 3.37 | 3.99 | 1.53 |
| BrAr:LOC2185_at | LOC2185 | PTK2B | 0.007119679 | 3.8 | 4.32 | 1.43 |
| BrAr:LOC5792_at | LOC5792 | PTPRF | 0.007560515 | 7.18 | 6.56 | 0.65 |
| BrAr:LOC79037_at | LOC79037 | PVRIG | 0.008669818 | 6.44 | 7.26 | 1.77 |
| BrAr:LOC347148_at | LOC347148 | QRFP | 0.002381775 | 2.72 | 3.11 | 1.31 |
| BrAr:LOC9910_at | LOC9910 | RABGAP1L | 0.001179112 | 6.91 | 7.65 | 1.67 |
| BrAr:LOC5880_at | LOC5880 | RAC2 | 0.008956919 | 5.63 | 6.68 | 2.07 |
| BrAr:LOC5900_at | LOC5900 | RALGDS | 0.005206308 | 4.29 | 4.75 | 1.37 |
| BrAr:LOC11030_at | LOC11030 | RBPMS | 0.008856938 | 7.14 | 6.49 | 0.63 |
| BrAr:LOC348093_at | LOC348093 | RBPMS2 | 0.004997179 | 4.52 | 3.52 | 0.5 |
| BrAr:LOC5968_at | LOC5968 | REG1B | 0.003701446 | 2.49 | 2.99 | 1.41 |
| BrAr:LOC5068_at | LOC5068 | REG3A | 0.000511408 | 2.53 | 2.96 | 1.35 |
| BrAr:LOC220441_at | LOC220441 | RNF152 | 0.005124915 | 4.58 | 3.4 | 0.44 |
| BrAr:LOC285533_at | LOC285533 | RNF175 | 0.004745303 | 2.36 | 2.85 | 1.41 |
| BrAr:LOC6098_at | LOC6098 | ROS1 | 0.001421936 | 2.35 | 2.82 | 1.38 |
| BrAr:LOC284751_at | LOC284751 | RP11-290F20.1 | 0.002153538 | 3.64 | 4.05 | 1.33 |
| BrAr:LOC653712_at | LOC653712 | RP11-723O4.2 | 0.006747128 | 3.23 | 3.58 | 1.28 |
| BrAr:LOC441239_at | LOC441239 | RP11-797H7.5 | 0.00892347 | 3.24 | 3.58 | 1.26 |
| BrAr:LOC6146_at | LOC6146 | RPL22 | 0.000447423 | 8.65 | 8.05 | 0.66 |
| BrAr:LOC23248_at | LOC23248 | RPRD2 | 0.000980072 | 6.24 | 5.68 | 0.68 |
| BrAr:LOC219790_at | LOC219790 | RTKN2 | 6.04892E−06 | 2.03 | 2.45 | 1.33 |
| BrAr:LOC388015_at | LOC388015 | RTL1 | 0.000195172 | 2.75 | 3.09 | 1.26 |
| BrAr:LOC6282_at | LOC6282 | S100A11 | 0.009482935 | 9.26 | 9.77 | 1.42 |
| BrAr:LOC25813_at | LOC25813 | SAMM50 | 0.001748454 | 6.05 | 5.51 | 0.69 |
| BrAr:LOC64092_at | LOC64092 | SAMSN1 | 0.008819902 | 5.26 | 6.23 | 1.96 |
| BrAr:LOC6303_at | LOC6303 | SAT1 | 0.002195688 | 9.38 | 9.93 | 1.47 |
| BrAr:LOC9522_at | LOC9522 | SCAMPI | 0.001160461 | 7.53 | 7.17 | 0.78 |
| BrAr:LOC49855_at | LOC49855 | SCAPER | 0.00740715 | 4.81 | 4.34 | 0.72 |
| BrAr:LOC677681_at | LOC677681 | SCARNA20 | 0.003490289 | 2.35 | 2.77 | 1.33 |
| BrAr:LOC7356_at | LOC7356 | SCGB1A1 | 0.008222088 | 2.48 | 3.09 | 1.53 |

TABLE 6A-continued

Genes From an Analysis of Tumor Biopsies With ≥1.2-fold or ≤0.8-fold Differences Between Treatment at Baseline.

| Probeset (BrainArray v.10) | ENTREZ Gene ID | HUGO Gene Symbol | P value for Response v. No Response at baseline | No Response: Mean RMA value at baseline | Response: Mean RMA value at baseline | Response v. No response: Fold difference at baseline |
| --- | --- | --- | --- | --- | --- | --- |
| BrAr:LOC26984_at | LOC26984 | SEC22A | 0.007747092 | 4.57 | 4.14 | 0.74 |
| BrAr:LOC94009_at | LOC94009 | SERHL | 0.006002332 | 4.23 | 3.31 | 0.53 |
| BrAr:LOC619189_at | LOC619189 | SERINC4 | 0.006726625 | 4.09 | 3.75 | 0.79 |
| BrAr:LOC23616_at | LOC23616 | SH3BP1 | 0.000535136 | 3.71 | 4.25 | 1.45 |
| BrAr:LOC6496_at | LOC6496 | SIX3 | 5.00022E−05 | 2.3 | 2.68 | 1.3 |
| BrAr:LOC283652_at | LOC283652 | SLC24A5 | 0.008605602 | 5.26 | 4.56 | 0.61 |
| BrAr:LOC5250_at | LOC5250 | SLC25A3 | 0.008268775 | 9.07 | 8.72 | 0.78 |
| BrAr:LOC643664_at | LOC643664 | SLC35G6 | 0.001852751 | 3.07 | 3.42 | 1.28 |
| BrAr:LOC91607_at | LOC91607 | SLFN11 | 0.009145132 | 5.63 | 6 | 1.29 |
| BrAr:LOC4090_at | LOC4090 | SMAD5 | 0.001746237 | 6.1 | 5.48 | 0.65 |
| BrAr:LOC677815_at | LOC677815 | SNORA34 | 0.002017953 | 4.59 | 5.21 | 1.53 |
| BrAr:LOC677832_at | LOC677832 | SNORA53 | 0.006626719 | 3.18 | 3.52 | 1.27 |
| BrAr:LOC11262_at | LOC11262 | SP140 | 0.009581919 | 3.73 | 4.88 | 2.23 |
| BrAr:LOC100131390_at | LOC100131390 | SP9 | 0.001887466 | 3.92 | 4.25 | 1.26 |
| BrAr:LOC64648_at | LOC64648 | SPANXD ‖ SPANXE | 5.13918E−05 | 2.56 | 2.94 | 1.3 |
| BrAr:LOC389763_at | LOC389763 | SPATA31D1 | 0.000603214 | 2.72 | 3.06 | 1.26 |
| BrAr:LOC6688_at | LOC6688 | SPI1 | 0.009982697 | 4.17 | 4.64 | 1.38 |
| BrAr:LOC503542_at | LOC503542 | SPRN | 0.006440302 | 3.11 | 3.45 | 1.27 |
| BrAr:LOC399833_at | LOC399833 | SPRNP1 | 0.000820016 | 2.66 | 3.02 | 1.28 |
| B rAr:LO C6725 at | LOC6725 | SRMS | 0.001157127 | 2.56 | 2.91 | 1.27 |
| BrAr:LOC6754_at | LOC6754 | SSTR4 | 0.001481682 | 3.49 | 3.87 | 1.3 |
| BrAr:LOC11037_at | LOC11037 | STON1 | 0.005887841 | 4.97 | 4.22 | 0.59 |
| BrAr:LOC94121_at | LOC94121 | SYTL4 | 0.005600715 | 4.69 | 5.05 | 1.28 |
| BrAr:LOC10579_at | LOC10579 | TACC2 | 0.007019696 | 4.72 | 3.99 | 0.6 |
| BrAr:LOC117289_at | LOC117289 | TAGAP | 0.003061103 | 3.99 | 4.87 | 1.84 |
| BrAr:LOC259290_at | LOC259290 | TAS2R31 | 0.000896064 | 2.82 | 3.22 | 1.32 |
| BrAr:LOC374403_at | LOC374403 | TBC1D10C | 0.007740885 | 3.13 | 3.7 | 1.49 |
| BrAr:LOC79718_at | LOC79718 | TBL1XR1 | 0.004717765 | 8.65 | 8.23 | 0.75 |
| BrAr:LOC285343_at | LOC285343 | TCAIM | 0.002451025 | 5.12 | 4.68 | 0.74 |
| BrAr:LOC340543_at | LOC340543 | TCEAL5 | 0.008738975 | 2.25 | 2.77 | 1.44 |
| BrAr:LOC6954_at | LOC6954 | TCP11 | 0.000500883 | 3.37 | 3.76 | 1.31 |
| BrAr:LOC157695_at | LOC157695 | TDRP | 0.003793627 | 5.76 | 4.9 | 0.55 |
| BrAr:LOC79896_at | LOC79896 | THNSL1 | 0.005125473 | 3.74 | 3.3 | 0.74 |
| BrAr:LOC10245_at | LOC10245 | TIMM17B | 0.008928311 | 2.88 | 3.26 | 1.3 |
| BrAr:LOC9414_at | LOC9414 | TJP2 | 0.00524848 | 5.99 | 5.41 | 0.67 |
| BrAr:LOC8277_at | LOC8277 | TKTL1 | 4.21036E−05 | 2.24 | 2.79 | 1.47 |
| BrAr:LOC284186_at | LOC284186 | TMEM105 | 0.003550476 | 2.79 | 3.12 | 1.25 |
| BrAr:LOC84216_at | LOC84216 | TMEM117 | 0.005294472 | 3.45 | 3.83 | 1.3 |
| BrAr:LOC54972_at | LOC54972 | TMEM132A | 0.007470194 | 3.92 | 4.28 | 1.29 |
| BrAr:LOC147744_at | LOC147744 | TMEM190 | 0.00321492 | 3.5 | 3.83 | 1.26 |
| BrAr:LOC100131211_at | LOC100131211 | TMEM194B | 0.001358748 | 4.93 | 4.56 | 0.77 |
| BrAr:LOC256130_at | LOC256130 | TMEM196 | 0.000704047 | 2.16 | 2.51 | 1.27 |
| BrAr:LOC255043_at | LOC255043 | TMEM86B | 0.007769635 | 2.89 | 3.28 | 1.31 |
| BrAr:LOC7126_at | LOC7126 | INFAIP1 | 0.009595017 | 6.07 | 5.64 | 0.74 |
| BrAr:LOC9804_at | LOC9804 | TOMM20 | 0.001452667 | 8.39 | 7.9 | 0.71 |
| BrAr:LOC127262_at | LOC127262 | TPRG1L | 0.009328823 | 6.53 | 6.2 | 0.8 |
| BrAr:LOC58485_at | LOC58485 | TRAPPC1 | 0.003857304 | 7.98 | 8.34 | 1.29 |
| BrAr:LOC10024_at | LOC10024 | TROAP | 0.003342892 | 3.08 | 3.41 | 1.26 |
| BrAr:LOC83707_at | LOC83707 | TRPT1 | 0.005403522 | 5.51 | 5.93 | 1.33 |
| BrAr:LOC26526_at | LOC26526 | TSPAN16 | 0.007917814 | 2.54 | 2.87 | 1.26 |
| BrAr:LOC23331_at | LOC23331 | TTC28 | 0.001645396 | 5.86 | 5.08 | 0.58 |
| BrAr:LOC23548_at | LOC23548 | TTC33 | 0.002813375 | 4.32 | 3.87 | 0.73 |
| BrAr:LOC117581_at | LOC117581 | TWIST2 | 0.000970578 | 3.8 | 4.27 | 1.38 |
| BrAr:LOC84203_at | LOC84203 | TXNDC2 | 5.21975E−07 | 3.54 | 4.2 | 1.59 |
| BrAr:LOC84747_at | LOC84747 | UNC119B | 0.006490817 | 6.96 | 6.26 | 0.62 |
| BrAr:LOC7381_at | LOC7381 | UQCRB | 0.005477408 | 6.42 | 5.91 | 0.7 |
| BrAr:LOC9958_at | LOC9958 | USP15 | 0.002623883 | 6.32 | 6.79 | 1.39 |
| BrAr:LOC54532_at | LOC54532 | USP53 | 0.003345289 | 4.91 | 4.48 | 0.74 |
| BrAr:LOC9217_at | LOC9217 | VAPB | 0.003742321 | 6.89 | 6.49 | 0.76 |
| BrAr:LOC7408_at | LOC7408 | VASP | 0.0085207 | 4.19 | 4.86 | 1.59 |
| BrAr:LOC7454_at | LOC7454 | WAS | 0.002617183 | 4.38 | 5.06 | 1.61 |
| BrAr:LOC8976_at | LOC8976 | WASL | 0.005786824 | 5.95 | 5.5 | 0.73 |
| BrAr:LOC81029_at | LOC81029 | WNT5B | 0.000381404 | 2.8 | 3.17 | 1.29 |
| BrAr:LOC25937_at | LOC25937 | WWTR1 | 0.008239544 | 9.07 | 8.56 | 0.7 |
| BrAr:LOC7535_at | LOC7535 | ZAP70 | 0.003799558 | 3.27 | 3.63 | 1.28 |
| BrAr:LOC22882_at | LOC22882 | ZHX2 | 0.002402316 | 9.6 | 9.06 | 0.68 |
| BrAr:LOC7586_at | LOC7586 | ZKSCAN1 | 0.003865802 | 6.02 | 5.57 | 0.73 |
| BrAr:LOC9202_at | LOC9202 | ZMYM4 | 0.008490749 | 4.95 | 4.6 | 0.78 |
| BrAr:LOC94039_at | LOC94039 | ZNF101 | 0.003583557 | 4.67 | 5.4 | 1.66 |
| BrAr:LOC7559_at | LOC7559 | ZNF12 | 0.003675848 | 7.13 | 6.78 | 0.78 |

TABLE 6A-continued

Genes From an Analysis of Tumor Biopsies With ≥1.2-fold or ≤0.8-fold Differences Between Treatment at Baseline.

| Probeset (BrainArray v.10) | ENTREZ Gene ID | HUGO Gene Symbol | P value for Response v. No Response at baseline | No Response: Mean RMA value at baseline | Response: Mean RMA value at baseline | Response v. No response: Fold difference at baseline |
|---|---|---|---|---|---|---|
| BrAr:LOC7762_at | LOC7762 | ZNF215 | 0.009488907 | 2.82 | 3.22 | 1.32 |
| BrAr:LOC339324_at | LOC339324 | ZNF260 | 0.009438142 | 5.44 | 5.02 | 0.75 |
| BrAr:LOC84330_at | LOC84330 | ZNF414 | 1.51102E−05 | 2.9 | 3.31 | 1.33 |
| BrAr:LOC58499_at | LOC58499 | ZNF462 | 0.000404504 | 6.85 | 5.89 | 0.52 |
| BrAr:LOC84450_at | LOC84450 | ZNF512 | 0.00966092 | 5.28 | 4.92 | 0.78 |
| BrAr:LOC619279_at | LOC619279 | ZNF704 | 0.007056823 | 3.51 | 2.87 | 0.64 |
| BrAr:LOC163049_at | LOC163049 | ZNF791 | 0.008235588 | 5.85 | 5.42 | 0.74 |
| BrAr:LOC84133_at | LOC84133 | ZNRF3 | 0.008712389 | 3.28 | 2.71 | 0.68 |
| BrAr:LOC90204_at | LOC90204 | ZSWIM1 | 0.00049795 | 2.54 | 2.87 | 1.26 |

TABLE 6B

Normalization of select genes presented in Table 6A relative to the mean of all values measured at baseline.

| Categorization of response | RMA intensity value at Baseline | | | | | Expression relative to Mean of all values at Baseline | | | | |
|---|---|---|---|---|---|---|---|---|---|---|
| | MICB | NKG7 | PVRIG | SPI1 | CLEC2B | MICB | NKG7 | PVRIG | SPI1 | CLEC2B |
| ≥20% decrease | 3.66 | 9.01 | 8.56 | 4.62 | 8.24 | 0.96 | 6.86 | 3.64 | 1.18 | 1.62 |
| ≥20% decrease | 3.27 | 5.60 | 6.99 | 4.53 | 8.05 | 0.73 | 0.65 | 1.23 | 1.11 | 1.42 |
| ≥20% decrease | 3.50 | 5.21 | 6.80 | 3.71 | 7.51 | 0.87 | 0.49 | 1.08 | 0.63 | 0.97 |
| ≥20% decrease | 4.38 | 7.17 | 6.16 | 4.86 | 8.41 | 1.59 | 1.92 | 0.69 | 1.39 | 1.82 |
| ≥20% decrease | 4.15 | 6.29 | 7.50 | 3.91 | 9.45 | 1.35 | 1.04 | 1.74 | 0.72 | 3.75 |
| ≥20% decrease | 4.08 | 7.84 | 7.40 | 5.37 | 8.76 | 1.29 | 3.04 | 1.63 | 1.98 | 2.32 |
| ≥20% decrease | 3.93 | 5.77 | 7.85 | 4.67 | 8.38 | 1.16 | 0.73 | 2.23 | 1.22 | 1.78 |
| ≥20% decrease | 4.42 | 8.48 | 8.27 | 5.01 | 7.91 | 1.63 | 4.72 | 2.98 | 1.54 | 1.29 |
| ≥20% decrease | 4.33 | 5.89 | 6.31 | 5.18 | 9.40 | 1.53 | 0.78 | 0.77 | 1.74 | 3.63 |
| ≥20% decrease | 4.31 | 7.32 | 7.28 | 4.76 | 8.87 | 1.52 | 2.11 | 1.50 | 1.30 | 2.51 |
| ≥20% decrease | 4.21 | 7.26 | 7.97 | 5.41 | 8.06 | 1.41 | 2.04 | 2.43 | 2.04 | 1.43 |
| ≥20% decrease | 3.99 | 7.32 | 6.73 | 4.61 | 7.75 | 1.22 | 2.11 | 1.03 | 1.17 | 1.15 |
| ≥20% decrease | 3.96 | 6.74 | 6.55 | 4.94 | 7.86 | 1.18 | 1.41 | 0.91 | 1.47 | 1.24 |
| <20% decrease | 3.52 | 5.54 | 6.09 | 4.16 | 8.65 | 0.87 | 0.62 | 0.66 | 0.85 | 2.15 |
| <20% decrease | 3.94 | 5.08 | 6.66 | 4.85 | 9.68 | 1.17 | 0.45 | 0.97 | 1.39 | 4.39 |
| <20% decrease | 3.86 | 6.89 | 8.63 | 4.57 | 8.40 | 1.10 | 1.57 | 3.82 | 1.14 | 1.80 |
| <20% decrease | 3.80 | 4.86 | 6.45 | 4.57 | 6.22 | 1.06 | 0.39 | 0.84 | 1.13 | 0.40 |
| <20% decrease | 2.97 | 7.26 | 6.49 | 3.51 | 6.22 | 0.60 | 2.04 | 0.87 | 0.55 | 0.40 |
| <20% decrease | 3.60 | 6.54 | 6.84 | 4.58 | 8.96 | 0.93 | 1.23 | 1.11 | 1.15 | 2.67 |
| <20% decrease | 3.77 | 5.33 | 6.41 | 4.87 | 6.49 | 1.04 | 0.53 | 0.82 | 1.40 | 0.48 |
| <20% decrease | 3.72 | 6.02 | 6.60 | 4.15 | 6.20 | 1.01 | 0.86 | 0.93 | 0.85 | 0.39 |
| <20% decrease | 3.41 | 4.50 | 5.27 | 4.39 | 6.83 | 0.81 | 0.30 | 0.37 | 1.00 | 0.61 |
| <20% decrease | 3.20 | 4.50 | 6.13 | 3.87 | 6.70 | 0.70 | 0.30 | 0.68 | 0.70 | 0.56 |
| <20% decrease | 3.82 | 6.61 | 7.09 | 4.27 | 6.01 | 1.08 | 1.29 | 1.32 | 0.92 | 0.34 |
| <20% decrease | 3.90 | 7.03 | 6.91 | 4.04 | 6.47 | 1.14 | 1.74 | 1.16 | 0.79 | 0.48 |
| <20% decrease | 3.86 | 8.18 | 7.40 | 5.11 | 8.06 | 1.11 | 3.86 | 1.64 | 1.65 | 1.42 |
| <20% decrease | 3.38 | 4.78 | 5.74 | 4.25 | 7.64 | 0.79 | 0.36 | 0.52 | 0.91 | 1.07 |
| <20% decrease | 3.21 | 4.32 | 5.78 | 3.76 | 6.81 | 0.71 | 0.26 | 0.53 | 0.65 | 0.60 |
| <20% decrease | 3.23 | 4.90 | 6.10 | 3.96 | 4.81 | 0.72 | 0.40 | 0.66 | 0.75 | 0.15 |
| <20% decrease | 3.35 | 4.63 | 5.75 | 3.73 | 6.53 | 0.78 | 0.33 | 0.52 | 0.64 | 0.49 |
| <20% decrease | 3.95 | 7.92 | 7.31 | 4.45 | 7.03 | 1.18 | 3.22 | 1.53 | 1.05 | 0.70 |
| <20% decrease | 3.82 | 7.04 | 6.57 | 4.68 | 7.51 | 1.07 | 1.75 | 0.92 | 1.23 | 0.97 |
| <20% decrease | 3.69 | 5.30 | 6.18 | 3.66 | 7.68 | 0.98 | 0.52 | 0.70 | 0.60 | 1.10 |
| <20% decrease | 3.61 | 4.64 | 5.04 | 3.93 | 7.73 | 0.93 | 0.33 | 0.32 | 0.73 | 1.14 |
| <20% decrease | 3.28 | 4.57 | 6.23 | 4.08 | 7.18 | 0.74 | 0.32 | 0.72 | 0.81 | 0.77 |
| <20% decrease | 3.03 | 5.97 | 6.18 | 3.77 | 7.09 | 0.62 | 0.83 | 0.70 | 0.65 | 0.73 |
| <20% decrease | 3.74 | 8.02 | 6.95 | 4.51 | 7.96 | 1.02 | 3.43 | 1.20 | 1.09 | 1.33 |
| <20% decrease | 3.70 | 6.66 | 7.10 | 4.21 | 7.78 | 0.99 | 1.34 | 1.32 | 0.89 | 1.18 |
| <20% decrease | 3.46 | 4.28 | 6.10 | 3.64 | 5.38 | 0.84 | 0.26 | 0.66 | 0.60 | 0.22 |
| <20% decrease | 3.68 | 5.79 | 6.64 | 5.67 | 8.13 | 0.98 | 0.74 | 0.96 | 2.44 | 1.50 |
| <20% decrease | 3.74 | 5.25 | 6.65 | 4.11 | 7.35 | 1.02 | 0.50 | 0.97 | 0.83 | 0.88 |
| <20% decrease | 4.21 | 6.09 | 6.19 | 3.56 | 9.35 | 1.41 | 0.90 | 0.71 | 0.57 | 3.48 |
| <20% decrease | 3.92 | 5.12 | 5.93 | 4.21 | 8.16 | 1.15 | 0.46 | 0.59 | 0.89 | 1.53 |
| <20% decrease | 3.70 | 8.71 | 7.66 | 4.33 | 7.47 | 0.99 | 5.55 | 1.96 | 0.97 | 0.95 |
| <20% decrease | 3.80 | 6.52 | 6.39 | 4.31 | 6.95 | 1.06 | 1.22 | 0.81 | 0.95 | 0.66 |
| <20% decrease | 3.37 | 5.00 | 6.43 | 3.60 | 6.07 | 0.79 | 0.42 | 0.83 | 0.58 | 0.36 |
| <20% decrease | 4.18 | 8.19 | 7.50 | 5.31 | 7.32 | 1.38 | 3.87 | 1.75 | 1.91 | 0.86 |
| <20% decrease | 3.37 | 5.57 | 5.46 | 4.13 | 8.18 | 0.79 | 0.63 | 0.43 | 0.84 | 1.55 |

TABLE 6B-continued

Normalization of select genes presented in Table 6A relative to the mean of all values measured at baseline.

| Categorization of response | RMA intensity value at Baseline | | | | | Expression relative to Mean of all values at Baseline | | | | |
|---|---|---|---|---|---|---|---|---|---|---|
| | MICB | NKG7 | PVRIG | SPI1 | CLEC2B | MICB | NKG7 | PVRIG | SPI1 | CLEC2B |
| <20% decrease | 3.43 | 5.86 | 6.98 | 4.78 | 7.87 | 0.82 | 0.77 | 1.22 | 1.32 | 1.25 |
| <20% decrease | 3.88 | 8.44 | 8.10 | 5.15 | 8.14 | 1.13 | 4.61 | 2.66 | 1.70 | 1.51 |
| <20% decrease | 3.55 | 6.40 | 6.12 | 4.12 | 7.70 | 0.89 | 1.12 | 0.67 | 0.83 | 1.12 |
| <20% decrease | 3.28 | 5.88 | 6.11 | 4.37 | 7.42 | 0.74 | 0.78 | 0.67 | 0.99 | 0.92 |
| <20% decrease | 4.10 | 7.58 | 7.09 | 4.51 | 7.41 | 1.31 | 2.54 | 1.32 | 1.10 | 0.91 |
| <20% decrease | 3.59 | 5.26 | 6.57 | 3.92 | 6.42 | 0.92 | 0.51 | 0.92 | 0.72 | 0.46 |
| <20% decrease | 3.49 | 6.97 | 6.36 | 4.20 | 6.34 | 0.86 | 1.66 | 0.79 | 0.88 | 0.43 |
| <20% decrease | 3.61 | 5.32 | 6.31 | 3.99 | 7.62 | 0.93 | 0.53 | 0.77 | 0.76 | 1.05 |
| Mean RMA, all Patients | 3.71 | 6.24 | 6.69 | 4.38 | 7.55 | | | | | |
| Mean RMA, Responders | 4.01 | 6.92 | 7.26 | 4.74 | 8.36 | | | | | |
| Fold-difference in Mean values | 1.23 | 1.60 | 1.48 | 1.28 | 1.76 | | | | | |

TABLE 7A

Genes From an Analysis of Tumor Biopsies With >1.2-fold or <0.8-fold Differences Between Treatment Groups Before and After Treatment.

| Probeset (BrainArray v.10) | ENTREZ Gene ID | HUGO Gene Symbol | P value for Response v. No Response | No Response: Mean RMA value at C2D8 | Response: Mean RMA value at C2D8 | Response v. No response: Fold difference at C2D8 |
|---|---|---|---|---|---|---|
| BrAr:LOC225_at | LOC225 | ABCD2 | 0.0012467 | 2.23 | 2.71 | 1.39 |
| BrAr:LOC171586_at | LOC171586 | ABHD3 | 0.000906661 | 3.82 | 4.6 | 1.72 |
| BrAr:LOC10006_at | LOC10006 | ABI1 | 0.003228742 | 7.56 | 7.88 | 1.25 |
| BrAr:LOC100287036_at | LOC100287036 | AC137932.6 | 0.000569795 | 3.23 | 3.69 | 1.37 |
| BrAr:LOC9744_at | LOC9744 | ACAP1 | 0.002971479 | 3.7 | 4.34 | 1.56 |
| BrAr:LOC38_at | LOC38 | ACAT1 | 0.005640416 | 9.96 | 9.16 | 0.57 |
| BrAr:LOC100_at | LOC100 | ADA | 0.006118173 | 4.22 | 4.84 | 1.53 |
| BrAr:LOC10863_at | LOC10863 | ADAM28 | 0.006146653 | 6 | 6.78 | 1.71 |
| BrAr:LOC101_at | LOC101 | ADAM8 | 0.002707153 | 3.74 | 4.19 | 1.37 |
| BrAr:LOC115_at | LOC115 | ADCY9 | 0.001524858 | 5.91 | 5.29 | 0.65 |
| BrAr:LOC140_at | LOC140 | ADORA3 | 0.001167454 | 5.65 | 6.72 | 2.1 |
| BrAr:LOC10939_at | LOC10939 | AFG3L2 | 0.00101786 | 6.21 | 5.54 | 0.63 |
| BrAr:LOC116987_at | LOC116987 | AGAP1 | 0.009065365 | 5.18 | 4.76 | 0.75 |
| BrAr:LOC177_at | LOC177 | AGER | 0.002217024 | 3 | 3.36 | 1.29 |
| BrAr:LOC192670_at | LOC192670 | AGO4 | 0.001209203 | 4.44 | 4.99 | 1.47 |
| BrAr:LOC23287_at | LOC23287 | AGTPBP1 | 0.007729579 | 6.26 | 6.85 | 1.51 |
| BrAr:LOC199_at | LOC199 | AIF1 | 0.003692163 | 8.56 | 9.3 | 1.67 |
| BrAr:LOC9447_at | LOC9447 | AIM2 | 0.001621524 | 5.17 | 6.99 | 3.54 |
| BrAr:LOC80709_at | LOC80709 | AKNA | 0.001609129 | 3.21 | 3.8 | 1.51 |
| BrAr:LOC1645_at | LOC1645 | AKR1C1 | 0.00526145 | 7.78 | 5.96 | 0.28 |
| BrAr:LOC1646_at | LOC1646 | AKR1C2 | 0.002437391 | 6.33 | 4.63 | 0.31 |
| BrAr:LOC130540_at | LOC130540 | ALS2CR12 | 7.7349E-05 | 3.04 | 3.73 | 1.61 |
| BrAr:LOC154796_at | LOC154796 | AMOT | 0.005299115 | 4.58 | 3.65 | 0.53 |
| BrAr:LOC149992_at | LOC149992 | ANKRD30BP2 | 0.000727269 | 2.94 | 3.41 | 1.38 |
| BrAr:LOC84250_at | LOC84250 | ANKRD32 | 0.000742431 | 5.74 | 6.4 | 1.58 |
| BrAr:LOC57101_at | LOC57101 | ANO2 | 0.000400645 | 2.61 | 3.32 | 1.63 |
| BrAr:LOC162_at | LOC162 | AP1B1 | 0.000507082 | 5.67 | 6.06 | 1.31 |
| BrAr:LOC8905_at | LOC8905 | AP1S2 | 0.002796838 | 8.02 | 8.71 | 1.62 |
| BrAr:LOC10717_at | LOC10717 | AP4B1 | 0.006391273 | 4.67 | 5.07 | 1.32 |
| BrAr:LOC60489_at | LOC60489 | APOBEC3G | 0.005710224 | 6.08 | 7.13 | 2.06 |
| BrAr:LOC164668_at | LOC164668 | APOBEC3H | 0.000140365 | 3.56 | 3.96 | 1.32 |
| BrAr:LOC139322_at | LOC139322 | APOOL | 0.000353552 | 8.31 | 7.81 | 0.71 |
| BrAr:LOC351_at | LOC351 | APP | 0.000185526 | 10.48 | 9.93 | 0.68 |
| BrAr:LOC55843_at | LOC55843 | ARHGAP15 | 0.00219141 | 6.55 | 7.36 | 1.75 |
| BrAr:LOC9938_at | LOC9938 | ARHGAP25 | 0.001914689 | 6.29 | 7.25 | 1.94 |
| BrAr:LOC257106_at | LOC257106 | ARHGAP30 | 0.001105979 | 4.58 | 5.65 | 2.11 |
| BrAr:LOC393_at | LOC393 | ARHGAP4 | 0.005535493 | 4.57 | 5.12 | 1.46 |
| BrAr:LOC394_at | LOC394 | ARHGAP5 | 0.005400379 | 5.57 | 5.05 | 0.7 |
| BrAr:LOC64333_at | LOC64333 | ARHGAP9 | 0.000273055 | 4.02 | 4.95 | 1.9 |
| BrAr:LOC7984_at | LOC7984 | ARHGEF5 | 1.40777E-06 | 7.18 | 5.88 | 0.41 |
| BrAr:LOC10865_at | LOC10865 | ARID5A | 0.000149652 | 4.83 | 5.26 | 1.34 |
| BrAr:LOC115761_at | LOC115761 | ARL11 | 1.2E-05 | 2.99 | 3.59 | 1.51 |
| BrAr:LOC142686_at | LOC142686 | ASB14 | 0.008551171 | 4.02 | 4.36 | 1.27 |

TABLE 7A-continued

Genes From an Analysis of Tumor Biopsies With >1.2-fold or <0.8-fold Differences Between Treatment Groups Before and After Treatment.

| Probeset (BrainArray v.10) | ENTREZ Gene ID | HUGO Gene Symbol | P value for Response v. No Response at C2D8 | No Response: Mean RMA value at C2D8 | Response: Mean RMA value at C2D8 | Response v. No response: Fold difference at C2D8 |
|---|---|---|---|---|---|---|
| BrAr:LOC51008_at | LOC51008 | ASCC1 | 0.002223687 | 6.69 | 6.15 | 0.69 |
| BrAr:LOC430_at | LOC430 | ASCL2 | 0.001842603 | 5.34 | 5.89 | 1.47 |
| BrAr:LOC445_at | LOC445 | ASS1 | 0.004568605 | 6.87 | 5.75 | 0.46 |
| BrAr:LOC476_at | LOC476 | ATP1A1 | 0.009247333 | 11.16 | 10.72 | 0.74 |
| BrAr:LOC481_at | LOC481 | ATP1B1 | 0.003199982 | 10.54 | 9.46 | 0.47 |
| BrAr:LOC489_at | LOC489 | ATP2A3 | 0.001027403 | 3.89 | 4.49 | 1.52 |
| BrAr:LOC506_at | LOC506 | ATP5B | 0.008087795 | 10.21 | 9.58 | 0.65 |
| BrAr:LOC79895_at | LOC79895 | ATP8B4 | 0.006027013 | 4.43 | 5.14 | 1.64 |
| BrAr:LOC10409_at | LOC10409 | BASP1 | 0.005104092 | 8.35 | 9.38 | 2.04 |
| BrAr:LOC10538_at | LOC10538 | BATF | 6.5602E−05 | 4.25 | 5.45 | 2.28 |
| BrAr:LOC11177_at | LOC11177 | BAZ1A | 0.008213807 | 7.05 | 7.59 | 1.45 |
| BrAr:LOC64919_at | LOC64919 | BCLUB | 0.000434645 | 3.28 | 4.55 | 2.41 |
| BrAr:LOC23743_at | LOC23743 | BHMT2 | 0.001978113 | 7.44 | 5.77 | 0.31 |
| BrAr:LOC80114_at | LOC80114 | BICC1 | 7.78561E−05 | 6.48 | 5.37 | 0.46 |
| BrAr:LOC51411_at | LOC51411 | BIN2 | 0.000237264 | 5.55 | 6.93 | 2.6 |
| BrAr:LOC90427_at | LOC90427 | BMF | 0.000637595 | 4.19 | 4.71 | 1.43 |
| BrAr:LOC55589_at | LOC55589 | BMP2K | 0.003980083 | 5.71 | 6.19 | 1.39 |
| BrAr:LOC657_at | LOC657 | BMPR1A | 7.43284E−05 | 6.38 | 5.36 | 0.49 |
| BrAr:LOC663_at | LOC663 | BNIP2 | 0.006852177 | 7.21 | 7.62 | 1.33 |
| BrAr:LOC283870_at | LOC283870 | BRICD5 | 0.00072577 | 4.42 | 4.87 | 1.37 |
| BrAr:LOC339479_at | LOC339479 | BRINP3 | 0.000557819 | 2.41 | 2.77 | 1.28 |
| BrAr:LOC7862_at | LOC7862 | BRPF1 | 0.000158804 | 3.31 | 3.75 | 1.36 |
| BrAr:LOC84446_at | LOC84446 | BRSK1 | 0.00053125 | 3.7 | 4.29 | 1.5 |
| BrAr:LOC695_at | LOC695 | BTK | 0.001125632 | 2.66 | 3.24 | 1.5 |
| BrAr:LOC121273_at | LOC121273 | C12ORF54 | 0.001468421 | 2.36 | 2.68 | 1.25 |
| BrAr:LOC374467_at | LOC144535 | C12ORF55 | 0.003437712 | 2.32 | 2.65 | 1.25 |
| BrAr:LOC283897_at | | C16ORF54 || ? | 0.002932479 | 5.9 | 7.15 | 2.39 |
| BrAr:LOC146556_at | LOC146556 | C16ORF89 | 0.006470581 | 4.38 | 4.95 | 1.49 |
| BrAr:LOC79415_at | LOC79415 | C17ORF62 | 0.000899343 | 5.75 | 6.31 | 1.48 |
| BrAr:LOC55337_at | LOC55337 | C19ORF66 | 0.007514937 | 5.39 | 5.83 | 1.36 |
| BrAr:LOC128346_at | LOC128346 | C1ORF162 | 0.005672875 | 7.33 | 8.19 | 1.81 |
| BrAr:LOC712_at | LOC712 | C1QA | 0.002049065 | 5.86 | 6.83 | 1.96 |
| BrAr:LOC713_at | LOC713 | C1QB | 0.002586781 | 8.65 | 9.6 | 1.94 |
| BrAr:LOC714_at | LOC714 | C1QC | 0.001215013 | 7.71 | 8.66 | 1.93 |
| BrAr:LOC26005_at | LOC26005 | C2CD3 | 1.55638E−05 | 3.24 | 3.74 | 1.41 |
| BrAr:LOC718_at | LOC718 | C3 | 0.000524922 | 10.95 | 10.04 | 0.53 |
| BrAr:LOC719_at | LOC719 | C3AR1 | 0.003525139 | 7.6 | 8.42 | 1.76 |
| BrAr:LOC728_at | LOC728 | C5AR1 | 0.00481309 | 5.14 | 6.19 | 2.06 |
| BrAr:LOC441108_at | LOC441108 | C5ORF56 | 3.09721E−05 | 3.4 | 4.05 | 1.57 |
| BrAr:LOC133874_at | LOC133874 | C5ORF58 | 0.000865267 | 2.35 | 2.84 | 1.41 |
| BrAr:LOC55262_at | LOC55262 | C7ORF43 | 7.45196E−05 | 3.56 | 4.01 | 1.37 |
| BrAr:LOC51719_at | LOC51719 | CAB39 | 0.000708262 | 7.83 | 8.33 | 1.41 |
| BrAr:LOC10486_at | LOC10486 | CAP2 | 0.007405167 | 7.26 | 6.23 | 0.49 |
| BrAr:LOC65981_at | LOC65981 | CAPRIN2 | 0.000250068 | 4.39 | 5.09 | 1.63 |
| BrAr:LOC114769_at | LOC114769 | CARD16 | 0.003494659 | 5.59 | 6.29 | 1.63 |
| BrAr:LOC22900_at | LOC22900 | CARD8 | 0.000173925 | 5.86 | 6.55 | 1.62 |
| BrAr:LOC64170_at | LOC64170 | CARD9 | 1.28773E−05 | 4.38 | 5.22 | 1.79 |
| BrAr:LOC834_at | LOC834 | CASP1 | 0.002724277 | 6.61 | 7.39 | 1.72 |
| BrAr:LOC863_at | LOC863 | CBFA2T3 | 0.005881378 | 2.48 | 2.95 | 1.39 |
| BrAr:LOC865_at | LOC865 | CBFB | 0.002240827 | 6.82 | 7.24 | 1.33 |
| BrAr:LOC23468_at | LOC23468 | CBX5 | 0.00051764 | 8.65 | 8.1 | 0.69 |
| BrAr:LOC343099_at | LOC343099 | CCDC18 | 0.00043805 | 4.4 | 4.92 | 1.44 |
| BrAr:LOC8030_at | LOC8030 | CCDC6 | 0.008058159 | 7.77 | 7.32 | 0.73 |
| BrAr:LOC440193_at | LOC440193 | CCDC88C | 0.00674531 | 3.39 | 3.83 | 1.36 |
| BrAr:LOC6368_at | LOC6368 | CCL23 | 0.000445198 | 2.36 | 2.94 | 1.49 |
| BrAr:LOC6348_at | LOC6348 | CCL3 | 5.02254E−06 | 4.04 | 6.1 | 4.17 |
| BrAr:LOC6351_at | LOC6351 | CCL4 | 0.000127014 | 8.12 | 9.35 | 2.34 |
| BrAr:LOC6352_at | LOC6352 | CCL5 | 0.000764550 | 7.09 | 8.69 | 3.03 |
| BrAr:LOC6355_at | LOC6355 | CCL8 | 8.16358E−05 | 4.01 | 5.79 | 3.43 |
| BrAr:LOC83605_at | LOC83605 | CCM2 | 0.001340517 | 3.95 | 4.35 | 1.32 |
| BrAr:LOC8900_at | LOC8900 | CCNA1 | 0.005854451 | 2.07 | 2.44 | 1.3 |
| BrAr:LOC57018_at | LOC57018 | CCNL1 | 0.001128634 | 6.49 | 7.17 | 1.61 |
| BrAr:LOC81669_at | LOC81669 | CCNL2 | 0.007592021 | 4.52 | 5.06 | 1.45 |
| BrAr:LOC1230_at | LOC1230 | CCR1 | 0.001134927 | 5.62 | 6.83 | 2.33 |
| BrAr:LOC1233_at | LOC1233 | CCR4 | 8.65555E−05 | 3.16 | 3.68 | 1.43 |
| BrAr:LOC1234_at | LOC1234 | CCR5 | 0.001360935 | 4.72 | 6.05 | 2.53 |
| BrAr:LOC9034_at | LOC9034 | CCRL2 | 0.001227378 | 4.29 | 5.39 | 2.14 |
| BrAr:LOC10574_at | LOC10574 | CCT7 | 0.00800504 | 8.44 | 8.11 | 0.8 |
| BrAr:LOC914_at | LOC914 | CD2 | 0.001090516 | 4.38 | 5.59 | 2.31 |
| BrAr:LOC131450_at | LOC131450 | CD200R1 | 0.000220547 | 2.2 | 3.03 | 1.78 |
| BrAr:LOC51744_at | LOC51744 | CD244 | 0.006585776 | 3.48 | 4.13 | 1.57 |

TABLE 7A-continued

Genes From an Analysis of Tumor Biopsies With >1.2-fold or <0.8-fold Differences Between Treatment Groups Before and After Treatment.

| Probeset (BrainArray v.10) | ENTREZ Gene ID | HUGO Gene Symbol | P value for Response v. No Response at C2D8 | No Response: Mean RMA value at C2D8 | Response: Mean RMA value at C2D8 | Response v. No response: Fold difference at C2D8 |
|---|---|---|---|---|---|---|
| BrAr:LOC939_at | LOC939 | CD27 | 9.28841E−05 | 4.35 | 5.72 | 2.58 |
| BrAr:LOC940_at | LOC940 | CD28 | 0.000390203 | 3.66 | 4.68 | 2.03 |
| BrAr:LOC146722_at | LOC146722 | CD300LF | 0.009992266 | 4.51 | 5.11 | 1.52 |
| BrAr:LOC945_at | LOC945 | CD33 | 0.001827574 | 3.32 | 3.86 | 1.46 |
| BrAr:LOC952_at | LOC952 | CD38 | 0.002437251 | 3.53 | 4.86 | 2.52 |
| BrAr:LOC915_at | LOC915 | CD3D | 0.001167151 | 6.07 | 7.73 | 3.15 |
| BrAr:LOC916_at | LOC916 | CD3E | 0.003022968 | 5.37 | 6.95 | 2.98 |
| BrAr:LOC917_at | LOC917 | CD3G | 0.008399115 | 5.89 | 7.19 | 2.48 |
| BrAr:LOC923_at | LOC923 | CD6 | 4.99939E−05 | 2.56 | 2.89 | 1.26 |
| BrAr:LOC968_at | LOC968 | CD68 | 0.004726071 | 8.27 | 9 | 1.65 |
| BrAr:LOC969_at | LOC969 | CD69 | 0.000954582 | 4.05 | 5.6 | 2.93 |
| BrAr:LOC924_at | LOC924 | CD7 | 0.000215612 | 3.3 | 3.8 | 1.42 |
| BrAr:LOC8832_at | LOC8832 | CD84 | 0.008155386 | 6.07 | 7.05 | 1.98 |
| BrAr:LOC942_at | LOC942 | CD86 | 0.007372391 | 4.84 | 5.69 | 1.8 |
| BrAr:LOC925_at | LOC925 | CD8A | 0.005143238 | 6.08 | 7.55 | 2.79 |
| BrAr:LOC926_at | LOC926 | CD8B | 7.12558E−05 | 3.05 | 4.51 | 2.75 |
| BrAr:LOC10225_at | LOC10225 | CD96 | 0.002746719 | 3.96 | 4.92 | 1.94 |
| BrAr:LOC23580_at | LOC23580 | CDC42EP4 | 0.005989914 | 6.31 | 5.89 | 0.74 |
| BrAr:LOC56882_at | LOC56882 | CDC42SE1 | 0.001408363 | 6.9 | 7.46 | 1.47 |
| BrAr:LOC50937_at | LOC50937 | CDON | 0.004412943 | 4.45 | 3.52 | 0.53 |
| BrAr:LOC1050_at | LOC1050 | CEBPA | 0.005882136 | 5.39 | 6.24 | 1.8 |
| BrAr:LOC1952_at | LOC1952 | CELSR2 | 0.002212027 | 5.97 | 5 | 0.51 |
| BrAr:LOC145508_at | LOC145508 | CEP128 | 0.000205356 | 4.02 | 4.74 | 1.65 |
| BrAr:LOC387119_at | LOC387119 | CEP85L | 0.001263933 | 4.68 | 5.13 | 1.36 |
| BrAr:LOC9023_at | LOC9023 | CH25H | 0.001769097 | 2.83 | 3.42 | 1.51 |
| BrAr:LOC26973_at | LOC26973 | CHORDC1 | 0.00935165 | 5.73 | 6.2 | 1.39 |
| BrAr:LOC1145_at | LOC1145 | CHRNE | 7.42355E−05 | 3.34 | 3.76 | 1.34 |
| BrAr:LOC55501_at | LOC55501 | CHST12 | 4.32937E−06 | 3.47 | 4.04 | 1.49 |
| BrAr:LOC11129_at | LOC11129 | CLASRP | 0.005760168 | 4.46 | 5 | 1.45 |
| BrAr:LOC10462_at | LOC10462 | CLEC10A | 0.009296829 | 2.38 | 2.71 | 1.25 |
| BrAr:LOC9976_at | LOC9976 | CLEC2B | 0.000849039 | 7.21 | 8.2 | 1.99 |
| BrAr:LOC29121_at | LOC29121 | CLEC2D | 0.000154789 | 5.14 | 6.39 | 2.37 |
| BrAr:LOC338339_at | LOC338339 | CLEC4D | 0.005230634 | 2.75 | 3.49 | 1.67 |
| BrAr:LOC64581_at | LOC64581 | CLEC7A | 0.006805698 | 4.79 | 5.69 | 1.86 |
| BrAr:LOC1195_at | LOC1195 | CLK1 | 0.006461537 | 7.4 | 7.94 | 1.45 |
| BrAr:LOC23059_at | LOC23059 | CLUAP1 | 0.000805496 | 5.65 | 5.09 | 0.68 |
| BrAr:LOC8418_at | LOC8418 | CMAHP | 5.40572E−05 | 3.29 | 4.21 | 1.9 |
| BrAr:LOC1240_at | LOC1240 | CMKLR1 | 0.00959365 | 4.89 | 5.54 | 1.57 |
| BrAr:LOC129607_at | LOC129607 | CMPK2 | 0.002692027 | 3.44 | 4.06 | 1.54 |
| BrAr:LOC146223_at | LOC146223 | CMTM4 | 0.001695882 | 5.54 | 4.84 | 0.62 |
| BrAr:LOC112616_at | LOC112616 | CMTM7 | 2.28639E−05 | 4.83 | 5.81 | 1.98 |
| BrAr:LOC25904_at | LOC25904 | CNOT10 | 0.005674705 | 4.75 | 5.1 | 1.27 |
| BrAr:LOC28958_at | LOC28958 | COA3 | 0.004529243 | 7.61 | 6.85 | 0.59 |
| BrAr:LOC22837_at | LOC22837 | COBLL1 | 0.004840016 | 5.83 | 5.01 | 0.57 |
| BrAr:LOC27235_at | LOC27235 | COQ2 | 0.005978604 | 5.68 | 6.1 | 1.34 |
| BrAr:LOC11151_at | LOC11151 | CORO1A | 0.003258636 | 4.62 | 5.56 | 1.91 |
| BrAr:LOC58487_at | LOC58487 | CREBZF | 0.004478774 | 5.05 | 5.5 | 1.36 |
| BrAr:LOC56253_at | LOC56253 | CRTAM | 0.000220566 | 3.38 | 4.71 | 2.51 |
| BrAr:LOC1410_at | LOC1410 | CRYAB | 3.55009E−05 | 11.55 | 10.08 | 0.36 |
| BrAr:LOC1441_at | LOC1441 | CSF3R | 0.001115654 | 3.68 | 4.75 | 2.1 |
| BrAr:LOC1445_at | LOC1445 | CSK | 0.000228425 | 5.06 | 5.65 | 1.51 |
| BrAr:LOC8530_at | LOC8530 | CST7 | 0.000603149 | 5.96 | 7.6 | 3.12 |
| BrAr:LOC80169_at | LOC80169 | CTC1 | 0.000709519 | 3.06 | 3.4 | 1.27 |
| BrAr:LOC1493_at | LOC1493 | CTLA4 | 0.003162410 | 3.62 | 4.58 | 1.93 |
| BrAr:LOC1495_at | LOC1495 | CTNNA1 | 0.000660903 | 9.22 | 8.87 | 0.78 |
| BrAr:LOC1508_at | LOC1508 | CTSB | 0.005985191 | 9.97 | 10.5 | 1.45 |
| BrAr:LOC1521_at | LOC1521 | CTSW | 0.000149298 | 3.95 | 5.18 | 2.35 |
| BrAr:LOC1522_at | LOC1522 | CTSZ | 0.002000543 | 7.68 | 8.49 | 1.75 |
| BrAr:LOC284340_at | LOC284340 | CXCL17 | 0.002487037 | 2.67 | 3.08 | 1.33 |
| BrAr:LOC2833_at | LOC2833 | CXCR3 | 0.004868852 | 3.47 | 4.11 | 1.56 |
| BrAr:LOC10663_at | LOC10663 | CXCR6 | 0.002518905 | 5.46 | 6.77 | 2.47 |
| BrAr:LOC158830_at | LOC158830 | CXORF65 | 1.12446E−06 | 2.5 | 3.15 | 1.57 |
| BrAr:LOC1540_at | LOC1540 | CYLD | 0.002044721 | 4.74 | 5.22 | 1.39 |
| BrAr:LOC9267_at | LOC9267 | CYTH1 | 0.000269468 | 5.23 | 5.89 | 1.58 |
| BrAr:LOC27128_at | LOC27128 | CYTH4 | 0.000226778 | 3.49 | 4.11 | 1.54 |
| BrAr:LOC9595_at | LOC9595 | CYTIP | 0.00564827 | 4.85 | 5.99 | 2.19 |
| BrAr:LOC1605_at | LOC1605 | DAG1 | 0.004336404 | 6.94 | 6.5 | 0.73 |
| BrAr:LOC23604_at | LOC23604 | DAPK2 | 0.000168922 | 4.05 | 4.66 | 1.53 |
| BrAr:LOC27071_at | LOC27071 | DAPP1 | 0.003238457 | 4.4 | 5.67 | 2.4 |
| BrAr:LOC23576_at | LOC23576 | DDAH1 | 0.006783001 | 8.12 | 7.17 | 0.52 |
| BrAr:LOC80821_at | LOC80821 | DDHD1 | 0.003836518 | 6.48 | 7.11 | 1.55 |

TABLE 7A-continued

Genes From an Analysis of Tumor Biopsies With >1.2-fold or <0.8-fold Differences Between Treatment Groups Before and After Treatment.

| Probeset (BrainArray v.10) | ENTREZ Gene ID | HUGO Gene Symbol | P value for Response v. No Response at C2D8 | No Response: Mean RMA value at C2D8 | Response: Mean RMA value at C2D8 | Response v. No response: Fold difference at C2D8 |
|---|---|---|---|---|---|---|
| BrAr:LOC780_at | LOC780 | DDR1 | 0.002611921 | 5.78 | 4.89 | 0.54 |
| BrAr:LOC91351_at | LOC91351 | DDX60L | 0.001586639 | 5.53 | 6.33 | 1.73 |
| BrAr:LOC50619_at | LOC50619 | DEF6 | 5.62458E−05 | 2.6 | 3.58 | 1.98 |
| BrAr:LOC79961_at | LOC79961 | DENND2D | 0.00608633 | 7.05 | 7.8 | 1.68 |
| BrAr:LOC22898_at | LOC22898 | DENND3 | 0.008265605 | 3.77 | 4.26 | 1.4 |
| BrAr:LOC1606_at | LOC1606 | DGKA | 0.001067797 | 4.65 | 5.57 | 1.9 |
| BrAr:LOC79132_at | LOC79132 | DHX58 | 5.94837E−05 | 3.22 | 3.57 | 1.27 |
| BrAr:LOC1741_at | LOC1741 | DLG3 | 0.006616897 | 5.92 | 5.37 | 0.68 |
| BrAr:LOC9231_at | LOC9231 | DLG5 | 0.004910244 | 6.33 | 5.88 | 0.73 |
| BrAr:LOC23312_at | LOC23312 | DMXL2 | 0.005117223 | 5.51 | 6.18 | 1.59 |
| BrAr:LOC1759_at | LOC1759 | DNM1 | 0.001682122 | 4.7 | 3.89 | 0.57 |
| BrAr:LOC23268_at | LOC23268 | DNMBP | 0.009281491 | 4.14 | 3.64 | 0.7 |
| BrAr:LOC55619_at | LOC55619 | DOCK10 | 0.009910164 | 6.72 | 7.37 | 1.57 |
| BrAr:LOC1794_at | LOC1794 | DOCK2 | 5.88991E−05 | 4.58 | 5.79 | 2.32 |
| BrAr:LOC1796_at | LOC1796 | DOK1 | 0.000720179 | 3.64 | 4.11 | 1.39 |
| BrAr:LOC9046_at | LOC9046 | DOK2 | 0.00010846 | 3.71 | 4.49 | 1.72 |
| BrAr:LOC79930_at | LOC79930 | DOK3 | 0.005606473 | 4.09 | 4.76 | 1.6 |
| BrAr:LOC25911_at | LOC25911 | DPCD | 0.001635341 | 7.56 | 6.57 | 0.5 |
| BrAr:LOC64174_at | LOC64174 | DPEP2 | 0.002593743 | 4.71 | 5.89 | 2.26 |
| BrAr:LOC286148_at | LOC286148 | DPY19L4 | 0.008414163 | 7.02 | 6.59 | 0.74 |
| BrAr:LOC1806_at | LOC1806 | DPYD | 0.003034131 | 5.56 | 6.24 | 1.6 |
| BrAr:LOC128338_at | LOC128338 | DRAM2 | 0.003935992 | 6.9 | 7.37 | 1.39 |
| BrAr:LOC1829_at | LOC1829 | DSG2 | 0.00052769 | 6.38 | 4.67 | 0.31 |
| BrAr:LOC401124_at | LOC401124 | DTHD1 | 0.004861568 | 2.98 | 3.48 | 1.41 |
| BrAr:LOC1844_at | LOC1844 | DUSP2 | 0.000769069 | 2.79 | 3.14 | 1.28 |
| BrAr:LOC1874_at | LOC1874 | E2F4 | 0.00176138 | 5.04 | 5.43 | 1.31 |
| BrAr:LOC124454_at | LOC124454 | EARS2 | 0.003104123 | 4.38 | 4.02 | 0.78 |
| BrAr:LOC80303_at | LOC80303 | EFHD1 | 0.007117336 | 4.98 | 3.79 | 0.44 |
| BrAr:LOC79180_at | LOC79180 | EFHD2 | 0.007511702 | 5.54 | 6.15 | 1.52 |
| BrAr:LOC1956_at | LOC1956 | EGFR | 1.55289E−05 | 7.23 | 5.74 | 0.36 |
| BrAr:LOC1959_at | LOC1959 | EGR2 | 0.003664288 | 3.56 | 3.97 | 1.33 |
| BrAr:LOC254102_at | LOC254102 | EHBP1L1 | 0.000337433 | 3.59 | 4.32 | 1.66 |
| BrAr:LOC1964_at | LOC1964 | EIF1AX | 0.007746341 | 7.3 | 6.81 | 0.71 |
| BrAr:LOC1979_at | LOC1979 | EIF4EBP2 | 0.002419451 | 7.98 | 7.5 | 0.71 |
| BrAr:LOC79993_at | LOC79993 | ELOVL7 | 0.005737598 | 5.56 | 4.16 | 0.38 |
| BrAr:LOC133418_at | LOC133418 | EMB | 0.007214626 | 4.98 | 5.96 | 1.98 |
| BrAr:LOC23065_at | LOC23065 | EMC1 | 0.004377065 | 6.71 | 6.21 | 0.71 |
| BrAr:LOC9583_at | LOC9583 | ENTPD4 | 0.008166686 | 4.95 | 5.43 | 1.4 |
| BrAr:LOC8320_at | LOC8320 | EOMES | 0.000354844 | 3.2 | 4.36 | 2.24 |
| BrAr:LOC2036_at | LOC2036 | EPB41L1 | 0.002126996 | 6.84 | 5.89 | 0.52 |
| BrAr:LOC57669_at | LOC57669 | EPB41L5 | 0.002790213 | 4.08 | 3.46 | 0.65 |
| BrAr:LOC4072_at | LOC4072 | EPCAM | 5.45391E−05 | 7.61 | 4.64 | 0.13 |
| BrAr:LOC54749_at | LOC54749 | EPDR1 | 0.00366304 | 6.23 | 5.43 | 0.58 |
| BrAr:LOC94240_at | LOC94240 | EPSTI1 | 0.008201474 | 5.88 | 6.88 | 2 |
| BrAr:LOC57488_at | LOC57488 | ESYT2 | 0.00758229 | 6.69 | 6.22 | 0.72 |
| BrAr:LOC2123_at | LOC2123 | EVI2A | 0.004048187 | 7.54 | 8.57 | 2.04 |
| BrAr:LOC2124_at | LOC2124 | EVI2B | 0.000797326 | 7.02 | 8.22 | 2.3 |
| BrAr:LOC84923_at | LOC84923 | FAM104A | 0.001116208 | 6.17 | 6.62 | 1.37 |
| BrAr:LOC81558_at | LOC81558 | FAM117A | 0.00957928 | 4.57 | 5.26 | 1.61 |
| BrAr:LOC55007_at | LOC55007 | FAM118A | 0.000350269 | 5.19 | 5.85 | 1.58 |
| BrAr:LOC25854_at | LOC25854 | FAM149A | 0.006327603 | 6.8 | 5.92 | 0.54 |
| BrAr:LOC348378_at | LOC348378 | FAM159A | 0.000325725 | 2.88 | 3.39 | 1.42 |
| BrAr:LOC729830_at | LOC729830 | FAM160A1 | 0.002194721 | 5.53 | 4.24 | 0.41 |
| BrAr:LOC10712_at | LOC10712 | FAM189B | 0.001562034 | 7.32 | 6.76 | 0.68 |
| BrAr:LOC100131897_at | LOC100131897 | FAM196B | 1.61849E−06 | 3.72 | 4.27 | 1.46 |
| BrAr:LOC51571_at | LOC51571 | FAM49B | 0.007916123 | 7.05 | 7.72 | 1.58 |
| BrAr:LOC374986_at | LOC374986 | FAM73A | 0.009874403 | 6.63 | 6.13 | 0.7 |
| BrAr:LOC286336_at | LOC286336 | FAM78A | 0.000685394 | 3.66 | 4.43 | 1.71 |
| BrAr:LOC286077_at | LOC286077 | FAM83H | 0.006416324 | 4.84 | 3.99 | 0.55 |
| BrAr:LOC10160_at | LOC10160 | FARP1 | 0.005161169 | 6.32 | 5.69 | 0.65 |
| BrAr:LOC356_at | LOC356 | FASLG | 0.004570784 | 3.26 | 3.97 | 1.63 |
| BrAr:LOC2195_at | LOC2195 | FAT1 | 1.39101E−05 | 9.47 | 8.45 | 0.49 |
| BrAr:LOC115290_at | LOC115290 | FBXO17 | 0.002681893 | 5.9 | 5 | 0.54 |
| BrAr:LOC2204_at | LOC2204 | FCAR | 0.008980063 | 2.74 | 3.22 | 1.4 |
| BrAr:LOC2212_at | LOC2212 | FCGR2A | 0.002857455 | 8.33 | 9.14 | 1.76 |
| BrAr:LOC2217_at | LOC2217 | FCGRT | 0.004742303 | 8.92 | 9.38 | 1.38 |
| BrAr:LOC343413_at | LOC343413 | FCRL6 | 0.000105945 | 3.24 | 3.86 | 1.53 |
| BrAr:LOC83706_at | LOC83706 | FERMT3 | 0.000152188 | 4.63 | 5.57 | 1.92 |
| BrAr:LOC26127_at | LOC26127 | FGFR1OP2 | 8.43904E−06 | 7.91 | 8.54 | 1.54 |
| BrAr:LOC81608_at | LOC81608 | FIP1L1 | 0.009198129 | 8.47 | 8.86 | 1.31 |
| BrAr:LOC11328_at | LOC11328 | FKBP9 | 0.00768174 | 6.64 | 6.04 | 0.66 |

TABLE 7A-continued

Genes From an Analysis of Tumor Biopsies With >1.2-fold or <0.8-fold Differences Between Treatment Groups Before and After Treatment.

| Probeset (BrainArray v.10) | ENTREZ Gene ID | HUGO Gene Symbol | P value for Response v. No Response at C2D8 | No Response: Mean RMA value at C2D8 | Response: Mean RMA value at C2D8 | Response v. No response: Fold difference at C2D8 |
|---|---|---|---|---|---|---|
| BrAr:LOC80308_at | LOC80308 | FLAD1 | 0.005616362 | 4.18 | 4.56 | 1.3 |
| BrAr:LOC285150_at | LOC285150 | FLJ33534 | 0.005229915 | 3.31 | 3.67 | 1.29 |
| BrAr:LOC752_at | LOC752 | FMNL1 | 0.00106439 | 3.26 | 4.1 | 1.78 |
| BrAr:LOC64122_at | LOC64122 | FN3K | 0.009685761 | 5.63 | 4.52 | 0.46 |
| BrAr:LOC54874_at | LOC54874 | FNBP1L | 0.001131939 | 7.43 | 6.37 | 0.48 |
| BrAr:LOC2353_at | LOC2353 | FOS | 0.001428641 | 2.71 | 3.51 | 1.74 |
| BrAr:LOC2354_at | LOC2354 | FOSB | 0.001418416 | 3.77 | 4.43 | 1.58 |
| BrAr:LOC2290_at | LOC2290 | FOXG1 | 0.001807998 | 2.34 | 2.75 | 1.33 |
| BrAr:LOC221937_at | LOC221937 | FOXK1 | 0.001511282 | 5.33 | 4.98 | 0.78 |
| BrAr:LOC2444_at | LOC2444 | FRK | 0.001867484 | 5.27 | 4.34 | 0.53 |
| BrAr:LOC79068_at | LOC79068 | FTO | 0.008108023 | 7.8 | 7.23 | 0.68 |
| BrAr:LOC2517_at | LOC2517 | FUCA1 | 0.006928375 | 7.52 | 7.88 | 1.29 |
| BrAr:LOC53827_at | LOC53827 | FXYD5 | 0.003668668 | 7.54 | 8.18 | 1.56 |
| BrAr:LOC2533_at | LOC2533 | FYB | 0.006370513 | 6.8 | 7.83 | 2.04 |
| BrAr:LOC8321_at | LOC8321 | FZD1 | 0.000576837 | 7.17 | 6.39 | 0.58 |
| BrAr:LOC2581_at | LOC2581 | GALC | 0.005135891 | 5.7 | 6.18 | 1.39 |
| BrAr:LOC79623_at | LOC79623 | GALNT14 | 0.007826728 | 7.35 | 5.79 | 0.34 |
| BrAr:LOC2634_at | LOC2634 | GBP2 | 0.001383408 | 9.45 | 10.08 | 1.55 |
| BrAr:LOC115362_at | LOC115362 | GBP5 | 0.000985486 | 6.53 | 8.25 | 3.3 |
| BrAr:LOC25929_at | LOC25929 | GEMIN5 | 0.005334583 | 5.54 | 5.15 | 0.76 |
| BrAr:LOC2672_at | LOC2672 | GFI1 | 0.000154364 | 4.06 | 4.84 | 1.71 |
| BrAr:LOC2673_at | LOC2673 | GFPT1 | 0.00319937 | 7.1 | 6.69 | 0.75 |
| BrAr:LOC170575_at | LOC170575 | GIMAP1 | 0.00022359 | 4.09 | 4.6 | 1.43 |
| BrAr:LOC26157_at | LOC26157 | GIMAP2 | 0.005839193 | 6.59 | 7.43 | 1.79 |
| BrAr:LOC55303_at | LOC55303 | GIMAP4 | 0.003717962 | 8.38 | 9.15 | 1.7 |
| BrAr:LOC168537_at | LOC168537 | GIMAP7 | 0.003685418 | 7.91 | 8.87 | 1.94 |
| BrAr:LOC256710_at | LOC256710 | GLIPR1L1 | 0.00202765 | 3.42 | 3.82 | 1.32 |
| BrAr:LOC152007_at | LOC152007 | GLIPR2 | 0.002267318 | 6.52 | 7.44 | 1.89 |
| BrAr:LOC169792_at | LOC169792 | GLIS3 | 0.009408735 | 4.64 | 4.11 | 0.69 |
| BrAr:LOC9535_at | LOC9535 | GMFG | 0.007629464 | 8.78 | 9.52 | 1.66 |
| BrAr:LOC51291_at | LOC51291 | GMIP | 4.20642E−05 | 3.43 | 4.19 | 1.69 |
| BrAr:LOC2769_at | LOC2769 | GNA15 | 0.00246765 | 3.48 | 4.08 | 1.51 |
| BrAr:LOC2770_at | LOC2770 | GNAI1 | 0.004652401 | 6.2 | 5.42 | 0.58 |
| BrAr:LOC55970_at | LOC55970 | GNG12 | 0.002374064 | 7.64 | 6.99 | 0.63 |
| BrAr:LOC57678_at | LOC57678 | GPAM | 0.001956822 | 5.21 | 4.31 | 0.53 |
| BrAr:LOC221914_at | LOC221914 | GPC2 | 0.009569549 | 4 | 4.43 | 1.35 |
| BrAr:LOC166647_at | LOC166647 | GPR125 | 0.009449671 | 3.82 | 3.02 | 0.58 |
| BrAr:LOC29909_at | LOC29909 | GPR171 | 0.00480987 | 4.98 | 6.28 | 2.46 |
| BrAr:LOC84636_at | LOC84636 | GPR174 | 0.002524422 | 4.12 | 5.49 | 2.57 |
| BrAr:LOC8477_at | LOC8477 | GPR65 | 0.00103869 | 4.16 | 5.16 | 2 |
| BrAr:LOC27197_at | LOC27197 | GPR82 | 0.004696185 | 3.18 | 3.82 | 1.55 |
| BrAr:LOC285513_at | LOC285513 | GPRIN3 | 0.009773641 | 5.1 | 5.79 | 1.62 |
| BrAr:LOC63940_at | LOC63940 | GPSM3 | 0.001950781 | 5.47 | 6.41 | 1.92 |
| BrAr:LOC2876_at | LOC2876 | GPX1 | 0.007974153 | 8.32 | 8.93 | 1.52 |
| BrAr:LOC9402_at | LOC9402 | GRAP2 | 0.002136939 | 4.05 | 4.84 | 1.73 |
| BrAr:LOC2885_at | LOC2885 | GRB2 | 0.001904691 | 7.67 | 8.16 | 1.41 |
| BrAr:LOC23708_at | LOC23708 | GSPT2 | 0.006499379 | 4.36 | 4.69 | 1.25 |
| BrAr:LOC2995_at | LOC2995 | GYPC | 0.001913948 | 8.65 | 9.4 | 1.69 |
| BrAr:LOC3001_at | LOC3001 | GZMA | 0.003090567 | 8.03 | 9.39 | 2.57 |
| BrAr:LOC3002_at | LOC3002 | GZMB | 0.000184806 | 5.15 | 7.01 | 3.62 |
| BrAr:LOC2999_at | LOC2999 | GZMH | 0.004465152 | 6 | 7.53 | 2.88 |
| BrAr:LOC3003_at | LOC3003 | GZMK | 0.003988143 | 5.82 | 7.7 | 3.67 |
| BrAr:LOC3004_at | LOC3004 | GZMM | 0.000223193 | 3.17 | 3.62 | 1.37 |
| BrAr:LOC3055_at | LOC3055 | HCK | 0.002709241 | 5.07 | 5.88 | 1.75 |
| BrAr:LOC3059_at | LOC3059 | HCLS1 | 0.008970756 | 6.33 | 7.25 | 1.9 |
| BrAr:LOC10870_at | LOC10870 | HCST | 0.001539626 | 5.38 | 6.37 | 1.99 |
| BrAr:LOC3081_at | LOC3081 | HGD | 0.001200099 | 7.79 | 5.93 | 0.28 |
| BrAr:LOC8348_at | LOC8348 | HIST1H2BO | 0.002966899 | 2.15 | 2.51 | 1.28 |
| BrAr:LOC3133_at | LOC3133 | HLA-E | 0.001498294 | 8.91 | 9.53 | 1.54 |
| BrAr:LOC3141_at | LOC3141 | HLCS | 0.001753289 | 4.39 | 3.92 | 0.72 |
| BrAr:LOC6928_at | LOC6928 | HNF1B | 0.001049148 | 6.53 | 5.01 | 0.35 |
| BrAr:LOC3226_at | LOC3226 | HOXC10 | 0.002953491 | 6.98 | 5.74 | 0.42 |
| BrAr:LOC9956_at | LOC9956 | HS3ST2 | 0.00370855 | 3.39 | 4.27 | 1.85 |
| BrAr:LOC3291_at | LOC3291 | HSD11B2 | 0.008439525 | 4.81 | 3.67 | 0.45 |
| BrAr:LOC3326_at | LOC3326 | HSP90AB1 | 0.002039686 | 10.96 | 10.49 | 0.72 |
| BrAr:LOC3304_at | LOC3304 | HSPA1B | 0.007974407 | 9.08 | 8.56 | 0.7 |
| BrAr:LOC26353_at | LOC26353 | HSPB8 | 0.009342901 | 6.58 | 5.55 | 0.49 |
| BrAr:LOC79663_at | LOC79663 | HSPBAP1 | 0.007672001 | 5.31 | 5.86 | 1.46 |
| BrAr:LOC3329_at | LOC3329 | HSPD1 | 0.00697964 | 10.96 | 10.49 | 0.72 |
| BrAr:LOC3385_at | LOC3385 | ICAM3 | 0.003007494 | 6.8 | 7.62 | 1.76 |
| BrAr:LOC3400_at | LOC3400 | ID4 | 0.009458867 | 5.41 | 4.28 | 0.46 |

TABLE 7A-continued

Genes From an Analysis of Tumor Biopsies With >1.2-fold or <0.8-fold Differences Between Treatment Groups Before and After Treatment.

| Probeset (BrainArray v.10) | ENTREZ Gene ID | HUGO Gene Symbol | P value for Response v. No Response at C2D8 | No Response: Mean RMA value at C2D8 | Response: Mean RMA value at C2D8 | Response v. No response: Fold difference at C2D8 |
|---|---|---|---|---|---|---|
| BrAr:LOC9592_at | LOC9592 | IER2 | 0.009528222 | 7.39 | 7.85 | 1.37 |
| BrAr:LOC25900_at | LOC25900 | IFFO1 | 0.000639277 | 3.46 | 3.85 | 1.3 |
| BrAr:LOC3458_at | LOC3458 | IFNG | 1.86189E−05 | 2.71 | 4.13 | 2.68 |
| BrAr:LOC3480_at | LOC3480 | IGF1R | 0.00679354 | 5.74 | 5 | 0.6 |
| BrAr:LOC10320_at | LOC10320 | IKZF1 | 0.008042369 | 5.26 | 6.15 | 1.86 |
| BrAr:LOC22806_at | LOC22806 | IKZF3 | 0.008271122 | 4.95 | 6.37 | 2.68 |
| BrAr:LOC3586_at | LOC3586 | IL10 | 0.002863799 | 2.59 | 2.97 | 1.3 |
| BrAr:LOC3587_at | LOC3587 | IL10RA | 0.001372236 | 3.37 | 4.05 | 1.6 |
| BrAr:LOC3600_at | LOC3600 | IL15 | 0.001625719 | 3.14 | 3.76 | 1.55 |
| BrAr:LOC3603_at | LOC3603 | IL16 | 0.000845357 | 4.44 | 5.31 | 1.82 |
| BrAr:LOC3559_at | LOC3559 | IL2RA | 0.001475194 | 4.13 | 5.29 | 2.23 |
| BrAr:LOC3614_at | LOC3614 | IMPDH1 | 0.001505322 | 3.89 | 4.4 | 1.43 |
| BrAr:LOC10207_at | LOC10207 | INADL | 0.003879207 | 5.15 | 4.12 | 0.49 |
| BrAr:LOC3631_at | LOC3631 | INPP4A | 0.007352833 | 3.57 | 4.05 | 1.4 |
| BrAr:LOC3635_at | LOC3635 | INPP5D | 0.00112411 | 4.54 | 5.2 | 1.57 |
| BrAr:LOC3640_at | LOC3640 | INSL3 | 0.004655003 | 2.66 | 3 | 1.26 |
| BrAr:LOC3643_at | LOC3643 | INSR | 0.006167598 | 7.17 | 6.21 | 0.51 |
| BrAr:LOC79711_at | LOC79711 | IPO4 | 0.009040723 | 4.97 | 4.43 | 0.68 |
| BrAr:LOC51135_at | LOC51135 | IRAK4 | 0.000346338 | 4.93 | 5.35 | 1.34 |
| BrAr:LOC3659_at | LOC3659 | IRF1 | 0.002554721 | 5.44 | 6.26 | 1.75 |
| BrAr:LOC3660_at | LOC3660 | IRF2 | 0.004250315 | 6.25 | 6.79 | 1.45 |
| BrAr:LOC10379_at | LOC10379 | IRF9 | 0.002270511 | 5.73 | 6.24 | 1.43 |
| BrAr:LOC79190_at | LOC79190 | IRX6 | 0.003746275 | 3.47 | 2.69 | 0.58 |
| BrAr:LOC9636_at | LOC9636 | ISG15 | 0.003943514 | 7.87 | 8.6 | 1.66 |
| BrAr:LOC3669_at | LOC3669 | ISG20 | 0.008015767 | 6.19 | 7.17 | 1.97 |
| BrAr:LOC3676_at | LOC3676 | ITGA4 | 0.007770498 | 5.18 | 5.9 | 1.65 |
| BrAr:LOC3695_at | LOC3695 | ITGB7 | 1.09194E−05 | 4.17 | 4.9 | 1.66 |
| BrAr:LOC3696_at | LOC3696 | ITGB8 | 0.009774541 | 6.32 | 5.6 | 0.61 |
| BrAr:LOC3702_at | LOC3702 | ITK | 0.000614646 | 3.37 | 4.37 | 2 |
| BrAr:LOC9767_at | LOC9767 | JADE3 | 0.004374851 | 5.16 | 4.67 | 0.71 |
| BrAr:LOC3718_at | LOC3718 | JAK3 | 0.003488731 | 3.77 | 4.33 | 1.48 |
| BrAr:LOC152789_at | LOC152789 | JAKMIP1 | 0.000267184 | 2.53 | 3.24 | 1.63 |
| BrAr:LOC126306_at | LOC126306 | JSRP1 | 0.004431839 | 2.8 | 3.16 | 1.28 |
| BrAr:LOC3726_at | LOC3726 | JUNB | 0.000225013 | 5.03 | 5.55 | 1.44 |
| BrAr:LOC8850_at | LOC8850 | KAT2B | 0.007454606 | 5.58 | 6.19 | 1.52 |
| BrAr:LOC84541_at | LOC84541 | KBTBD8 | 0.007562573 | 3.04 | 3.66 | 1.53 |
| BrAr:LOC3738_at | LOC3738 | KCNA3 | 0.0058006 | 4.35 | 5.58 | 2.34 |
| BrAr:LOC8514_at | LOC8514 | KCNAB2 | 4.1508E−05 | 3.38 | 3.99 | 1.53 |
| BrAr:LOC3766_at | LOC3766 | KCNJ10 | 0.002550731 | 2.8 | 3.99 | 2.28 |
| BrAr:LOC54442_at | LOC54442 | KCTD5 | 0.000154004 | 3.4 | 3.76 | 1.29 |
| BrAr:LOC10765_at | LOC10765 | KDM5B | 0.003578740 | 4.95 | 4.42 | 0.69 |
| BrAr:LOC9834_at | LOC9834 | KIAA0125 | 0.009858424 | 3.39 | 4.13 | 1.66 |
| BrAr:LOC80183_at | LOC80183 | KIAA0226L | 0.008468237 | 3.63 | 4.29 | 1.58 |
| BrAr:LOC55196_at | LOC55196 | KIAA1551 | 1.95908E−05 | 7.31 | 8.27 | 1.95 |
| BrAr:LOC85379_at | LOC85379 | KIAA1671 | 0.003044192 | 6.99 | 6.18 | 0.57 |
| BrAr:LOC8462_at | LOC8462 | KLF11 | 0.000172623 | 7.09 | 6.63 | 0.73 |
| BrAr:LOC113730_at | LOC113730 | KLHDC7B | 8.25644E−05 | 3.61 | 4.26 | 1.57 |
| BrAr:LOC55175_at | LOC55175 | KLHL11 | 0.002335786 | 6.5 | 5.96 | 0.69 |
| BrAr:LOC11275_at | LOC11275 | KLHL2 | 0.002161388 | 5.75 | 6.32 | 1.48 |
| BrAr:LOC89857_at | LOC89857 | KLHL6 | 0.002656846 | 4.17 | 5.12 | 1.92 |
| BrAr:LOC10219_at | LOC10219 | KLRG1 | 0.004918882 | 4.43 | 5.26 | 1.79 |
| BrAr:LOC23633_at | LOC23633 | KPNA6 | 0.000721932 | 7.11 | 6.55 | 0.68 |
| BrAr:LOC337985_at | LOC337985 | KRTAP20-3 | 0.000960059 | 2.94 | 3.28 | 1.26 |
| BrAr:LOC3903_at | LOC3903 | LAIR1 | 0.002738539 | 4.9 | 5.73 | 1.78 |
| BrAr:LOC55353_at | LOC55353 | LAPTM4B | 0.001371449 | 8.58 | 7.76 | 0.57 |
| BrAr:LOC51520_at | LOC51520 | LARS | 0.009065446 | 6.6 | 6.23 | 0.78 |
| BrAr:LOC7462_at | LOC7462 | LAT2 | 0.004658386 | 4.1 | 4.73 | 1.55 |
| BrAr:LOC3932_at | LOC3932 | LCK | 3.62704E−05 | 3.64 | 4.63 | 1.99 |
| BrAr:LOC253558_at | LOC253558 | LCLAT1 | 0.000716258 | 6.84 | 6.14 | 0.61 |
| BrAr:LOC3937_at | LOC3937 | LCP2 | 0.001771463 | 7.02 | 8.18 | 2.23 |
| BrAr:LOC3965_at | LOC3965 | LGALS9 | 0.001147339 | 5.37 | 6.21 | 1.79 |
| BrAr:LOC3981_at | LOC3981 | LIG4 | 0.001719114 | 2.71 | 3.09 | 1.3 |
| BrAr:LOC10288_at | LOC10288 | LILRB2 | 0.009625864 | 6.8 | 7.9 | 2.15 |
| BrAr:LOC11006_at | LOC11006 | LILRB4 | 0.001892547 | 4.12 | 5.17 | 2.08 |
| BrAr:LOC10990_at | LOC10990 | LILRB5 | 0.007304563 | 3.53 | 4.12 | 1.5 |
| BrAr:LOC80774_at | LOC80774 | LIMD2 | 0.001004901 | 7.19 | 8.24 | 2.08 |
| BrAr:LOC55957_at | LOC55957 | LIN37 | 0.002341033 | 4.27 | 4.67 | 1.32 |
| BrAr:LOC55327_at | LOC55327 | LIN7C | 0.005757252 | 7.6 | 7.13 | 0.72 |
| BrAr:LOC54072_at | LOC54072 | LINC00158 | 0.001209137 | 2.37 | 3.08 | 1.63 |
| BrAr:LOC100507254_at | LOC100507254 | LINC01013 | 3.62726E−05 | 2.61 | 3.15 | 1.45 |
| BrAr:LOC643418_at | LOC643418 | LIPN | 0.002890607 | 2.09 | 2.49 | 1.33 |

TABLE 7A-continued

Genes From an Analysis of Tumor Biopsies With >1.2-fold or <0.8-fold Differences Between Treatment Groups Before and After Treatment.

| Probeset (BrainArray v.10) | ENTREZ Gene ID | HUGO Gene Symbol | P value for Response v. No Response at C2D8 | No Response: Mean RMA value at C2D8 | Response: Mean RMA value at C2D8 | Response v. No response: Fold difference at C2D8 |
|---|---|---|---|---|---|---|
| BrAr:LOC100286925_at | LOC100286925 | LOC100286925 | 0.001015116 | 3.19 | 3.64 | 1.36 |
| BrAr:LOC100289455_at | LOC100289455 | LOC100289455 | 0.001145861 | 3.29 | 3.65 | 1.29 |
| BrAr:LOC100506748_at | LOC100506748 | LOC100506748 | 0.008166821 | 6.98 | 6.13 | 0.56 |
| BrAr:LOC57121_at | LOC57121 | LPAR5 | 0.00875015 | 4.1 | 4.61 | 1.42 |
| BrAr:LOC54947_at | LOC54947 | LPCAT2 | 0.006481437 | 5.75 | 6.44 | 1.62 |
| BrAr:LOC9404_at | LOC9404 | LPXN | 0.002413256 | 4.47 | 5.35 | 1.85 |
| BrAr:LOC101060069_at | LOC84859 | LRCH3 | 0.006908809 | 4.77 | 5.16 | 1.31 |
| BrAr:LOC57622_at | LOC57622 | LRFN1 | 0.006641146 | 2.64 | 2.98 | 1.27 |
| BrAr:LOC4040_at | LOC4040 | LRP6 | 0.009500312 | 6.44 | 5.84 | 0.66 |
| BrAr:LOC10128_at | LOC10128 | LRPPRC | 0.001448129 | 6.78 | 6.25 | 0.69 |
| BrAr:LOC126364_at | LOC126364 | LRRC25 | 0.007312481 | 4.46 | 4.93 | 1.39 |
| BrAr:LOC57470_at | LOC57470 | LRRC47 | 3.37646E−05 | 8.67 | 8.07 | 0.66 |
| BrAr:LOC84967_at | LOC84967 | LSM10 | 1.7086E−06 | 4.71 | 5.51 | 1.73 |
| BrAr:LOC729862_at | | LSP1 ‖ RP11-14N7.2 ‖ ? ‖ LSP1P3 ‖ ‖ ? | 7.43131E−05 | 7.01 | 7.59 | 1.49 |
| BrAr:LOC4056_at | LOC4056 | LTC4S | 0.002016128 | 2.67 | 3.01 | 1.27 |
| BrAr:LOC4063_at | LOC4063 | LY9 | 0.001081065 | 2.75 | 3.3 | 1.47 |
| BrAr:LOC23643_at | LOC23643 | LY96 | 0.009105973 | 7.33 | 8.38 | 2.07 |
| BrAr:LOC1130_at | LOC1130 | LYST | 0.00025477 | 5.55 | 6.52 | 1.95 |
| BrAr:LOC9935_at | LOC9935 | MAFB | 0.002538157 | 5.98 | 6.96 | 1.97 |
| BrAr:LOC114569_at | LOC114569 | MAL2 | 0.001540039 | 6.23 | 4.47 | 0.3 |
| BrAr:LOC4125_at | LOC4125 | MAN2B1 | 0.000700622 | 6.33 | 7.04 | 1.64 |
| BrAr:LOC389840_at | LOC389840 | MAP3K15 | 0.001025836 | 6.05 | 5.25 | 0.58 |
| BrAr:LOC1326_at | LOC1326 | MAP3K8 | 0.000177401 | 3.32 | 4.02 | 1.63 |
| BrAr:LOC11184_at | LOC11184 | MAP4K1 | 0.005700934 | 4.03 | 4.79 | 1.69 |
| BrAr:LOC55016_at | LOC55016 | MARCH1 | 0.006442113 | 6.49 | 7.27 | 1.71 |
| BrAr:LOC153562_at | LOC153562 | MARVELD2 | 0.003345363 | 5.43 | 4.06 | 0.39 |
| BrAr:LOC64087_at | LOC64087 | MCCC2 | 0.001691149 | 7.47 | 6.66 | 0.57 |
| BrAr:LOC4170_at | LOC4170 | MCL1 | 0.009694025 | 6.18 | 6.53 | 1.27 |
| BrAr:LOC57192_at | LOC57192 | MCOLN1 | 0.002029101 | 5.95 | 6.44 | 1.41 |
| BrAr:LOC4191_at | LOC4191 | MDH2 | 0.009556738 | 9.19 | 8.8 | 0.77 |
| BrAr:LOC90390_at | LOC90390 | MED30 | 0.0097495 | 5.3 | 5.74 | 1.36 |
| BrAr:LOC4210_at | LOC4210 | MEFV | 0.004481657 | 2.61 | 3.18 | 1.48 |
| BrAr:LOC4233_at | LOC4233 | MET | 0.000481401 | 7.62 | 6.5 | 0.46 |
| BrAr:LOC4242_at | LOC4242 | MFNG | 0.000113115 | 4.18 | 4.64 | 1.38 |
| BrAr:LOC388931_at | LOC388931 | MFSD2B | 0.000281083 | 2.46 | 2.82 | 1.29 |
| BrAr:LOC4257_at | LOC4257 | MGST1 | 0.004490845 | 9.01 | 7.75 | 0.42 |
| BrAr:LOC4259_at | LOC4259 | MGST3 | 0.005680745 | 9.84 | 9.33 | 0.7 |
| BrAr:LOC64780_at | LOC64780 | MICAL1 | 0.003883901 | 6.86 | 7.55 | 1.62 |
| BrAr:LOC4277_at | LOC4277 | MICB | 0.000795372 | 3.61 | 4.06 | 1.37 |
| BrAr:LOC4281_at | LOC4281 | MID1 | 0.007325003 | 5.28 | 4.1 | 0.44 |
| BrAr:LOC55320_at | LOC55320 | MIS18BP1 | 0.001818937 | 5.2 | 5.74 | 1.46 |
| BrAr:LOC8569_at | LOC8569 | MKNK1 | 0.002977426 | 4.06 | 4.48 | 1.33 |
| BrAr:LOC84451_at | LOC84451 | MLK4 | 0.002009063 | 6.2 | 4.96 | 0.42 |
| BrAr:LOC79817_at | LOC79817 | MOB3B | 0.002552689 | 5.23 | 4.24 | 0.5 |
| BrAr:LOC51678_at | LOC51678 | MPP6 | 8.46017E−05 | 6.4 | 5.39 | 0.5 |
| BrAr:LOC84689_at | LOC84689 | MS4A14 | 0.004152623 | 2.32 | 2.85 | 1.45 |
| BrAr:LOC10943_at | LOC10943 | MSL3 | 3.96167E−05 | 3.91 | 4.31 | 1.32 |
| BrAr:LOC4481_at | LOC4481 | MSR1 | 0.001295486 | 6.34 | 7.32 | 1.97 |
| BrAr:LOC4498_at | LOC4498 | MT1JP | 0.001398135 | 2.67 | 3.05 | 1.3 |
| BrAr:LOC9219_at | LOC9219 | MTA2 | 0.008631439 | 3.83 | 4.17 | 1.26 |
| BrAr:LOC22823_at | LOC22823 | MTF2 | 0.001229081 | 5.75 | 6.13 | 1.3 |
| BrAr:LOC4600_at | LOC4600 | MX2 | 0.007586531 | 5.04 | 5.97 | 1.9 |
| BrAr:LOC4641_at | LOC4641 | MYO1C | 0.009584045 | 6.8 | 6.36 | 0.74 |
| BrAr:LOC4542_at | LOC4542 | MYO1F | 0.000979651 | 5.66 | 6.76 | 2.14 |
| BrAr:LOC4644_at | LOC4644 | MYO5A | 0.009021092 | 5.97 | 6.52 | 1.46 |
| BrAr:LOC4650_at | LOC4650 | MYO9B | 0.000964454 | 3.23 | 3.66 | 1.35 |
| BrAr:LOC64859_at | LOC64859 | NABP1 | 0.001961157 | 6.56 | 7.54 | 1.97 |
| BrAr:LOC65220_at | LOC65220 | NADK | 0.004024885 | 4.32 | 4.76 | 1.36 |
| BrAr:LOC51172_at | LOC51172 | NAGPA | 0.001472846 | 4.11 | 4.45 | 1.27 |
| BrAr:LOC222236_at | LOC222236 | NAPEPLD | 0.008710095 | 4.78 | 4.28 | 0.71 |
| BrAr:LOC4689_at | LOC4689 | NCF4 | 0.001234053 | 5.42 | 6.56 | 2.21 |
| BrAr:LOC10787_at | LOC10787 | NCKAP1 | 0.000270123 | 8.41 | 7.77 | 0.64 |
| BrAr:LOC23413_at | LOC23413 | NCS1 | 0.002517782 | 5.17 | 4.65 | 0.7 |
| BrAr:LOC81565_at | LOC81565 | NDEL1 | 0.00044912 | 5.23 | 5.77 | 1.45 |
| BrAr:LOC10397_at | LOC10397 | NDRG1 | 0.003695088 | 9.61 | 8.56 | 0.48 |
| BrAr:LOC4753_at | LOC4753 | NELL2 | 0.008992092 | 4.3 | 5.12 | 1.76 |
| BrAr:LOC4756_at | LOC4756 | NEO1 | 0.000155222 | 5.94 | 4.94 | 0.5 |
| BrAr:LOC4763_at | LOC4763 | NF1 | 0.007244465 | 6.56 | 6.22 | 0.79 |
| BrAr:LOC51199_at | LOC51199 | NIN | 0.003683293 | 6.46 | 6.97 | 1.43 |

TABLE 7A-continued

Genes From an Analysis of Tumor Biopsies With >1.2-fold or <0.8-fold Differences Between Treatment Groups Before and After Treatment.

| Probeset (BrainArray v.10) | ENTREZ Gene ID | HUGO Gene Symbol | P value for Response v. No Response at C2D8 | No Response: Mean RMA value at C2D8 | Response: Mean RMA value at C2D8 | Response v. No response: Fold difference at C2D8 |
|---|---|---|---|---|---|---|
| BrAr:LOC4818_at | LOC4818 | NKG7 | 0.000612039 | 6.42 | 7.9 | 2.8 |
| BrAr:LOC4820_at | LOC4820 | NKTR | 0.003766901 | 5.41 | 6.03 | 1.54 |
| BrAr:LOC84166_at | LOC84166 | NLRC5 | 0.000330635 | 4.05 | 5.1 | 2.06 |
| BrAr:LOC22861_at | LOC22861 | NLRP1 | 0.001909588 | 3.31 | 4 | 1.61 |
| BrAr:LOC199713_at | LOC199713 | NLRP7 | 0.006716245 | 2.69 | 3.12 | 1.35 |
| BrAr:LOC64127_at | LOC64127 | NOD2 | 0.002184673 | 2.63 | 3.19 | 1.47 |
| BrAr:LOC55505_at | LOC55505 | NOP10 | 0.002678965 | 7.9 | 8.38 | 1.39 |
| BrAr:LOC51491_at | LOC51491 | NOP16 | 0.008450601 | 6.59 | 6.01 | 0.67 |
| BrAr:LOC80896_at | LOC80896 | NPL | 0.000690308 | 5.67 | 6.94 | 2.41 |
| BrAr:LOC29982_at | LOC29982 | NRBF2 | 0.000389607 | 6.36 | 7 | 1.56 |
| BrAr:LOC375387_at | LOC375387 | NRROS | 4.50837E−05 | 4.04 | 4.69 | 1.57 |
| BrAr:LOC8439_at | LOC8439 | NSMAF | 4.41796E−05 | 4.88 | 5.47 | 1.51 |
| BrAr:LOC84628_at | LOC84628 | NTNG2 | 0.001660303 | 4.93 | 5.68 | 1.68 |
| BrAr:LOC64710_at | LOC64710 | NUCKS1 | 0.005778725 | 8.86 | 8.48 | 0.77 |
| BrAr:LOC10482_at | LOC10482 | NXF1 | 0.003244475 | 6.15 | 6.63 | 1.39 |
| BrAr:LOC8638_at | LOC8638 | OASL | 0.00362918 | 3.97 | 4.9 | 1.91 |
| BrAr:LOC57489_at | LOC57489 | ODF2L | 0.000757399 | 5.21 | 5.97 | 1.69 |
| BrAr:LOC56957_at | LOC56957 | OTUD7B | 0.009648978 | 4.8 | 4.4 | 0.76 |
| BrAr:LOC92106_at | LOC92106 | OXNAD1 | 0.006226342 | 6.8 | 7.38 | 1.5 |
| BrAr:LOC10606_at | LOC10606 | PAICS | 0.000951329 | 8.18 | 7.46 | 0.61 |
| BrAr:LOC10298_at | LOC10298 | PAK4 | 0.002616248 | 5.34 | 4.84 | 0.7 |
| BrAr:LOC53354_at | LOC53354 | PANK1 | 0.003924872 | 7.01 | 5.72 | 0.41 |
| BrAr:LOC167153_at | LOC167153 | PAPD4 | 0.007179274 | 5.69 | 6.17 | 1.39 |
| BrAr:LOC56288_at | LOC56288 | PARD3 | 2.62632E−05 | 5.31 | 4.64 | 0.63 |
| BrAr:LOC165631_at | LOC165631 | PARP15 | 0.000597574 | 2.41 | 3.18 | 1.71 |
| BrAr:LOC79668_at | LOC79668 | PARP8 | 0.001033904 | 5.58 | 6.21 | 1.55 |
| BrAr:LOC64098_at | LOC64098 | PARVG | 3.02295E−07 | 4.78 | 5.58 | 1.74 |
| BrAr:LOC197135_at | LOC197135 | PATL2 | 5.2694E−05 | 3.01 | 3.59 | 1.5 |
| BrAr:LOC5076_at | LOC5076 | PAX2 | 0.003571547 | 4.67 | 3.83 | 0.56 |
| BrAr:LOC80714_at | LOC80714 | PBX4 | 0.000750992 | 3.36 | 3.92 | 1.48 |
| BrAr:LOC5096_at | LOC5096 | PCCB | 0.006027555 | 5.97 | 5.3 | 0.63 |
| BrAr:LOC56122_at | LOC56122 | PCDHB14 | 0.008482753 | 4.79 | 4.29 | 0.71 |
| BrAr:LOC51449_at | LOC51449 | PCYOX1 | 0.000871422 | 7.51 | 6.8 | 0.61 |
| BrAr:LOC80380_at | LOC80380 | PDCD1LG2 | 0.00249208 | 4.57 | 5.67 | 2.14 |
| BrAr:LOC5140_at | LOC5140 | PDE3B | 0.007301599 | 3.96 | 4.5 | 1.45 |
| BrAr:LOC5142_at | LOC5142 | PDE4B | 0.004457634 | 3.67 | 4.65 | 1.98 |
| BrAr:LOC5148_at | LOC5148 | PDE6G | 8.94693E−05 | 3.82 | 4.3 | 1.39 |
| BrAr:LOC5152_at | LOC5152 | PDE9A | 0.009685654 | 4.38 | 3.52 | 0.55 |
| BrAr:LOC23089_at | LOC23089 | PEG10 | 0.004556464 | 4.76 | 3.48 | 0.41 |
| BrAr:LOC5217_at | LOC5217 | PFN2 | 0.002114964 | 6.37 | 5.72 | 0.63 |
| BrAr:LOC10857_at | LOC10857 | PGRMC1 | 0.006475701 | 9.61 | 9.02 | 0.66 |
| BrAr:LOC9489_at | LOC9489 | PGS1 | 0.000369132 | 2.7 | 3.03 | 1.26 |
| BrAr:LOC51131_at | LOC51131 | PHF11 | 0.00019631 | 5.68 | 6.25 | 1.48 |
| BrAr:LOC84457_at | LOC84457 | PHYHIPL | 0.009902214 | 4.94 | 3.93 | 0.5 |
| BrAr:LOC8554_at | LOC8554 | PIAS1 | 0.002603807 | 6.34 | 6.76 | 1.33 |
| BrAr:LOC5293_at | LOC5293 | PIK3CD | 0.000699768 | 3.49 | 4.16 | 1.6 |
| BrAr:LOC5294_at | LOC5294 | PIK3CG | 0.00795533 | 5.21 | 6.01 | 1.74 |
| BrAr:LOC23533_at | LOC23533 | PIK3R5 | 0.001975664 | 4.73 | 5.62 | 1.86 |
| BrAr:LOC200576_at | LOC200576 | PIKFYVE | 0.004438308 | 5.12 | 5.45 | 1.26 |
| BrAr:LOC57095_at | LOC57095 | PITHD1 | 0.000620788 | 6.64 | 7.08 | 1.35 |
| BrAr:LOC9033_at | LOC9033 | PKD2L1 | 7.38701E−05 | 3.89 | 4.98 | 2.13 |
| BrAr:LOC8502_at | LOC8502 | PKP4 | 0.003912211 | 6.87 | 6.12 | 0.6 |
| BrAr:LOC23659_at | LOC23659 | PLA2G15 | 0.000750241 | 4.57 | 4.9 | 1.26 |
| BrAr:LOC26279_at | LOC26279 | PLA2G2D | 0.007862004 | 3.33 | 4.02 | 1.61 |
| BrAr:LOC5329_at | LOC5329 | PLAUR | 0.002226155 | 5.31 | 6.56 | 2.38 |
| BrAr:LOC5330_at | LOC5330 | PLCB2 | 0.001006462 | 2.75 | 3.19 | 1.35 |
| BrAr:LOC23207_at | LOC23207 | PLEKHM2 | 0.004949319 | 4.19 | 4.56 | 1.29 |
| BrAr:LOC51177_at | LOC51177 | PLEKHO1 | 0.003165895 | 8.41 | 9.1 | 1.61 |
| BrAr:LOC80301_at | LOC80301 | PLEKHO2 | 0.005664231 | 6.43 | 7.1 | 1.59 |
| BrAr:LOC10154_at | LOC10154 | PLXNC1 | 0.007188456 | 5.22 | 6.01 | 1.74 |
| BrAr:LOC134359_at | LOC134359 | POC5 | 0.007629631 | 3.29 | 3.76 | 1.38 |
| BrAr:LOC5425_at | LOC5425 | POLD2 | 0.005541595 | 6.74 | 6.09 | 0.64 |
| BrAr:LOC10891_at | LOC10891 | PPARGC1A | 0.002105868 | 6.16 | 4.32 | 0.28 |
| BrAr:LOC8496_at | LOC8496 | PPFIBP1 | 0.005135014 | 6.39 | 5.74 | 0.64 |
| BrAr:LOC132160_at | LOC132160 | PPM1M | 0.000392111 | 4.9 | 5.67 | 1.71 |
| BrAr:LOC26051_at | LOC26051 | PPP1R16B | 0.006257791 | 3.87 | 4.45 | 1.5 |
| BrAr:LOC170954_at | LOC170954 | PPP1R18 | 0.008008247 | 6.81 | 7.44 | 1.55 |
| BrAr:LOC80316_at | LOC80316 | PPP1R2P9 | 1.60391E−05 | 2.09 | 2.43 | 1.27 |
| BrAr:LOC55607_at | LOC55607 | PPP1R9A | 0.001723064 | 5.18 | 3.96 | 0.43 |
| BrAr:LOC55012_at | LOC55012 | PPP2R3C | 0.000340239 | 6.33 | 7.07 | 1.66 |
| BrAr:LOC5533_at | LOC5533 | PPP3CC | 5.36619E−05 | 5.77 | 6.53 | 1.69 |

TABLE 7A-continued

Genes From an Analysis of Tumor Biopsies With >1.2-fold or <0.8-fold Differences Between Treatment Groups Before and After Treatment.

| Probeset (BrainArray v.10) | ENTREZ Gene ID | HUGO Gene Symbol | P value for Response v. No Response at C2D8 | No Response: Mean RMA value at C2D8 | Response: Mean RMA value at C2D8 | Response v. No response: Fold difference at C2D8 |
|---|---|---|---|---|---|---|
| BrAr:LOC22870_at | LOC22870 | PPP6R1 | 0.000456639 | 6.15 | 6.72 | 1.49 |
| BrAr:LOC57580_at | LOC57580 | PREX1 | 0.002348002 | 4.45 | 5.25 | 1.74 |
| BrAr:LOC5551_at | LOC5551 | PRF1 | 0.000633167 | 4.5 | 5.7 | 2.3 |
| BrAr:LOC5563_at | LOC5563 | PRKAA2 | 0.001193036 | 4.89 | 3.79 | 0.47 |
| BrAr:LOC55119_at | LOC55119 | PRPF38B | 0.002925833 | 6.13 | 6.47 | 1.27 |
| BrAr:LOC260429_at | LOC260429 | PRSS33 | 0.00349208 | 2.29 | 2.9 | 1.52 |
| BrAr:LOC9051_at | LOC9051 | PSTPIP1 | 4.32976E−05 | 3.41 | 4.3 | 1.86 |
| BrAr:LOC5729_at | LOC5729 | PTGDR | 0.000425807 | 2.38 | 2.81 | 1.34 |
| BrAr:LOC5734_at | LOC5734 | PTGER4 | 0.000452488 | 4.44 | 5.24 | 1.74 |
| BrAr:LOC5747_at | LOC5747 | PTK2 | 0.009028965 | 6.15 | 5.62 | 0.7 |
| BrAr:LOC2185_at | LOC2185 | PTK2B | 0.001623169 | 3.98 | 4.6 | 1.54 |
| BrAr:LOC5771_at | LOC5771 | PTPN2 | 0.006868732 | 4.77 | 5.11 | 1.27 |
| BrAr:LOC26191_at | LOC26191 | PTPN22 | 0.000805615 | 3.2 | 4.36 | 2.23 |
| BrAr:LOC5774_at | LOC5774 | PTPN3 | 0.003383111 | 5.36 | 4.39 | 0.51 |
| BrAr:LOC5777_at | LOC5777 | PTPN6 | 0.004965746 | 7.06 | 7.82 | 1.68 |
| BrAr:LOC5778_at | LOC5778 | PTPN7 | 0.000995185 | 2.67 | 3.12 | 1.37 |
| BrAr:LOC5788_at | LOC5788 | PTPRC | 0.004701448 | 7.25 | 8.28 | 2.05 |
| BrAr:LOC5790_at | LOC5790 | PTPRCAP | 0.00029735 | 5.16 | 6.35 | 2.29 |
| BrAr:LOC5792_at | LOC5792 | PTPRF | 0.003117004 | 6.94 | 6.1 | 0.56 |
| BrAr:LOC10744_at | LOC10744 | PTTG2 | 0.001807529 | 3.24 | 3.88 | 1.56 |
| BrAr:LOC79037_at | LOC79037 | PVRIG | 3.84156E−06 | 6.58 | 8.12 | 2.91 |
| BrAr:LOC29108_at | LOC29108 | PYCARD | 0.002026411 | 4.93 | 5.49 | 1.47 |
| BrAr:LOC149628_at | LOC149628 | PYHIN1 | 0.000408398 | 4.51 | 5.61 | 2.14 |
| BrAr:LOC5858_at | LOC5858 | PZP | 0.000216348 | 3.19 | 4.09 | 1.86 |
| BrAr:LOC26056_at | LOC26056 | RAB11FIP5 | 0.004593636 | 6.64 | 6.01 | 0.65 |
| BrAr:LOC64284_at | LOC64284 | RAB17 | 0.006172675 | 7.39 | 5.88 | 0.35 |
| BrAr:LOC5873_at | LOC5873 | RAB27A | 0.000947493 | 6.09 | 6.84 | 1.68 |
| BrAr:LOC10966_at | LOC10966 | RAB40B | 0.002689147 | 7.65 | 6.79 | 0.55 |
| BrAr:LOC9910_at | LOC9910 | RABGAP1L | 0.000351958 | 6.99 | 7.85 | 1.81 |
| BrAr:LOC64792_at | LOC64792 | RABL5 | 0.008308224 | 6.37 | 5.72 | 0.64 |
| BrAr:LOC5880_at | LOC5880 | RAC2 | 0.001759421 | 6.1 | 7.38 | 2.42 |
| BrAr:LOC5898_at | LOC5898 | RALA | 0.003482967 | 7.81 | 8.31 | 1.41 |
| BrAr:LOC5900_at | LOC5900 | RALGDS | 5.09268E−06 | 4.17 | 4.94 | 1.71 |
| BrAr:LOC5906_at | LOC5906 | RAP1A | 0.005950215 | 9 | 9.4 | 1.32 |
| BrAr:LOC5922_at | LOC5922 | RASA2 | 0.000504636 | 4.86 | 5.55 | 1.61 |
| BrAr:LOC64926_at | LOC64926 | RASAL3 | 1.47228E−05 | 4.37 | 5.38 | 2.02 |
| BrAr:LOC158158_at | LOC158158 | RASEF | 0.002425894 | 5.87 | 4.62 | 0.42 |
| BrAr:LOC10235_at | LOC10235 | RASGRP2 | 0.001039747 | 2.92 | 3.68 | 1.69 |
| BrAr:LOC115727_at | LOC115727 | RASGRP4 | 0.007288134 | 3.02 | 3.73 | 1.64 |
| BrAr:LOC11186_at | LOC11186 | RASSF1 | 0.001331649 | 3.94 | 4.32 | 1.31 |
| BrAr:LOC83593_at | LOC83593 | RASSF5 | 0.001158920 | 4.31 | 5.22 | 1.87 |
| BrAr:LOC166863_at | LOC166863 | RBM46 | 2.68055E−05 | 2.01 | 2.34 | 1.26 |
| BrAr:LOC92241_at | LOC92241 | RCSD1 | 0.004611303 | 6.15 | 6.88 | 1.66 |
| BrAr:LOC84957_at | LOC84957 | RELT | 0.001573556 | 3.57 | 4.12 | 1.46 |
| BrAr:LOC5973_at | LOC5973 | RENBP | 0.000886528 | 2.38 | 2.75 | 1.29 |
| BrAr:LOC266747_at | LOC266747 | RGL4 | 2.53719E−05 | 3.62 | 4.51 | 1.86 |
| BrAr:LOC5996_at | LOC5996 | RGS1 | 0.000948891 | 4.25 | 5.94 | 3.24 |
| BrAr:LOC10287_at | LOC10287 | RGS19 | 0.001238043 | 5.56 | 6.38 | 1.77 |
| BrAr:LOC6007_at | LOC6007 | RHD | 0.005520962 | 2.64 | 3.01 | 1.29 |
| BrAr:LOC391_at | LOC391 | RHOG | 0.001998079 | 5.78 | 6.39 | 1.53 |
| BrAr:LOC85415_at | LOC85415 | RHPN2 | 0.004672418 | 6.05 | 4.84 | 0.43 |
| BrAr:LOC11035_at | LOC11035 | RIPK3 | 0.000107974 | 2.49 | 2.82 | 1.26 |
| BrAr:LOC79621_at | LOC79621 | RNASEH2B | 0.000141017 | 5.85 | 6.52 | 1.6 |
| BrAr:LOC7844_at | LOC7844 | RNF103 | 0.005704234 | 7.92 | 7.59 | 0.8 |
| BrAr:LOC79589_at | LOC79589 | RNF128 | 0.006163854 | 6.73 | 5.53 | 0.43 |
| BrAr:LOC115992_at | LOC115992 | RNF166 | 2.77285E−05 | 3.38 | 3.84 | 1.37 |
| BrAr:LOC55599_at | LOC55599 | RNPC3 | 0.000969762 | 5.01 | 5.72 | 1.64 |
| BrAr:LOC6195_at | LOC6195 | RPS6KA1 | 0.004714766 | 4.72 | 5.27 | 1.46 |
| BrAr:LOC126638_at | LOC126638 | RPTN | 0.002032449 | 1.89 | 2.23 | 1.26 |
| BrAr:LOC91543_at | LOC91543 | RSAD2 | 0.008745842 | 5 | 6.13 | 2.18 |
| BrAr:LOC154075_at | LOC154075 | SAMD3 | 0.005964418 | 3.88 | 4.66 | 1.71 |
| BrAr:LOC219285_at | LOC219285 | SAMD9L | 0.009330304 | 6.01 | 6.84 | 1.78 |
| BrAr:LOC64092_at | LOC64092 | SAMSN1 | 0.000102994 | 5.55 | 6.97 | 2.68 |
| BrAr:LOC54440_at | LOC54440 | SASH3 | 0.00085679 | 4.4 | 5.5 | 2.14 |
| BrAr:LOC6303_at | LOC6303 | SAT1 | 0.000105426 | 9.5 | 10.19 | 1.62 |
| BrAr:LOC132320_at | LOC132320 | SCLT1 | 0.003975976 | 5.67 | 6.13 | 1.37 |
| BrAr:LOC9672_at | LOC9672 | SDC3 | 0.002541208 | 5.41 | 6.14 | 1.66 |
| BrAr:LOC6385_at | LOC6385 | SDC4 | 0.000890801 | 8.12 | 6.99 | 0.46 |
| BrAr:LOC10993_at | LOC10993 | SDS | 0.006668039 | 4.91 | 5.91 | 2 |
| BrAr:LOC81929_at | LOC81929 | SEH1L | 0.001200528 | 6.64 | 6.12 | 0.7 |
| BrAr:LOC6404_at | LOC6404 | SELPLG | 1.27077E−05 | 3.91 | 4.81 | 1.87 |

TABLE 7A-continued

Genes From an Analysis of Tumor Biopsies With >1.2-fold or <0.8-fold Differences Between Treatment Groups Before and After Treatment.

| Probeset (BrainArray v.10) | ENTREZ Gene ID | HUGO Gene Symbol | P value for Response v. No Response at C2D8 | No Response: Mean RMA value at C2D8 | Response: Mean RMA value at C2D8 | Response v. No response: Fold difference at C2D8 |
|---|---|---|---|---|---|---|
| BrAr:LOC57556_at | LOC57556 | SEMA6A | 0.00940132 | 6.51 | 5.48 | 0.49 |
| BrAr:LOC57337_at | LOC57337 | SENP7 | 0.003067422 | 4.38 | 4.86 | 1.39 |
| BrAr:LOC1731_at | LOC1731 | SEPT1 | 0.000805403 | 3.89 | 4.82 | 1.91 |
| BrAr:LOC653509_at | LOC653509 | SFTPA1 | 0.000239394 | 1.97 | 2.84 | 1.83 |
| BrAr:LOC729238_at | LOC729238 | SFTPA2 | 0.001051605 | 2.33 | 3 | 1.59 |
| BrAr:LOC6440_at | LOC6440 | SFTPC | 0.000220741 | 2.41 | 2.85 | 1.35 |
| BrAr:LOC166929_at | LOC166929 | SGMS2 | 0.001113196 | 4.98 | 4.48 | 0.71 |
| BrAr:LOC4068_at | LOC4068 | SH2D1A | 0.001779304 | 3.5 | 4.83 | 2.51 |
| BrAr:LOC9047_at | LOC9047 | SH2D2A | 0.000366782 | 2.79 | 3.45 | 1.58 |
| BrAr:LOC23616_at | LOC23616 | SH3BP1 | 0.00025747 | 3.77 | 4.32 | 1.47 |
| BrAr:LOC30011_at | LOC30011 | SH3KBP1 | 0.005587272 | 5.36 | 5.95 | 1.51 |
| BrAr:LOC92799_at | LOC92799 | SHKBP1 | 1.06036E−05 | 4.07 | 4.56 | 1.4 |
| BrAr:LOC27181_at | LOC27181 | SIGLEC8 | 0.004624284 | 3.14 | 3.92 | 1.72 |
| BrAr:LOC27180_at | LOC27180 | SIGLEC9 | 0.008896966 | 3.48 | 4.24 | 1.69 |
| BrAr:LOC6494_at | LOC6494 | SIPA1 | 0.00010627 | 4.4 | 4.97 | 1.49 |
| BrAr:LOC55423_at | LOC55423 | SIRPG | 0.001013902 | 3.77 | 5.02 | 2.37 |
| BrAr:LOC27240_at | LOC27240 | SIT1 | 0.009541619 | 4.21 | 5.25 | 2.07 |
| BrAr:LOC6503_at | LOC6503 | SLA | 0.003691368 | 6.12 | 7.19 | 2.09 |
| BrAr:LOC84174_at | LOC84174 | SLA2 | 4.01901E−05 | 3.44 | 4.37 | 1.9 |
| BrAr:LOC114836_at | LOC114836 | SLAMF6 | 0.001206283 | 3.67 | 5.07 | 2.64 |
| BrAr:LOC51296_at | LOC51296 | SLC15A3 | 0.008843878 | 5.28 | 5.94 | 1.57 |
| BrAr:LOC10165_at | LOC10165 | SLC25A13 | 0.004725296 | 5.28 | 4.57 | 0.61 |
| BrAr:LOC79085_at | LOC79085 | SLC25A23 | 0.00261534 | 6.15 | 5.24 | 0.53 |
| BrAr:LOC11309_at | LOC11309 | SLCO2B1 | 0.004740526 | 4.67 | 5.2 | 1.44 |
| BrAr:LOC342618_at | LOC342618 | SLFN14 | 0.000448431 | 2.11 | 2.5 | 1.31 |
| BrAr:LOC60682_at | LOC60682 | SMAP1 | 0.008833996 | 5.88 | 6.2 | 1.25 |
| BrAr:LOC64744_at | LOC64744 | SMAP2 | 0.000548688 | 6.58 | 7.54 | 1.95 |
| BrAr:LOC333929_at | LOC333929 | SNAI3 | 6.31401E−05 | 3.45 | 3.86 | 1.33 |
| BrAr:LOC684959_at | LOC684959 | SNORA25 | 0.000701791 | 5.18 | 6.92 | 3.35 |
| BrAr:LOC677793_at | LOC677793 | SNORA2A | 0.004141989 | 2.47 | 2.89 | 1.33 |
| BrAr:LOC619569_at | LOC619569 | SNORA41 | 0.005258597 | 4.34 | 5.33 | 1.98 |
| BrAr:LOC112574_at | LOC112574 | SNX18 | 0.005169055 | 4.89 | 5.34 | 1.37 |
| BrAr:LOC124460_at | LOC124460 | SNX20 | 3.26962E−06 | 2.68 | 3.02 | 1.26 |
| BrAr:LOC55553_at | LOC55553 | SOX6 | 0.006451258 | 4.9 | 3.77 | 0.46 |
| BrAr:LOC6662_at | LOC6662 | SOX9 | 0.009655204 | 6.9 | 5.72 | 0.44 |
| BrAr:LOC6672_at | LOC6672 | SP100 | 0.001727009 | 6.96 | 7.45 | 1.4 |
| BrAr:LOC6688_at | LOC6688 | SPI1 | 0.008822213 | 4.24 | 4.76 | 1.43 |
| BrAr:LOC6708_at | LOC6708 | SPTA1 | 1.16906E−06 | 2.38 | 3.23 | 1.81 |
| BrAr:LOC6711_at | LOC6711 | SPTBN1 | 0.008787825 | 7.9 | 7.37 | 0.69 |
| BrAr:LOC55133_at | LOC55133 | SRBD1 | 7.08163E−05 | 5.76 | 6.1 | 1.27 |
| BrAr:LOC57522_at | LOC57522 | SRGAP1 | 0.003087421 | 5.55 | 5.17 | 0.77 |
| BrAr:LOC5552_at | LOC5552 | SRGN | 0.00272892 | 8.12 | 9.19 | 2.1 |
| BrAr:LOC6728_at | LOC6728 | SRP19 | 0.003493429 | 7.37 | 7.85 | 1.39 |
| BrAr:LOC54434_at | LOC54434 | SSH1 | 0.005981539 | 4.52 | 4.85 | 1.26 |
| BrAr:LOC6775_at | LOC6775 | STAT4 | 0.005220669 | 4.41 | 5.34 | 1.9 |
| BrAr:LOC6793_at | LOC6793 | STK10 | 0.009263738 | 4.53 | 5.12 | 1.51 |
| BrAr:LOC6789_at | LOC6789 | STK4 | 0.00450869 | 7.93 | 8.48 | 1.47 |
| BrAr:LOC8676_at | LOC8676 | STX11 | 0.00051139 | 3.55 | 4.29 | 1.68 |
| BrAr:LOC252983_at | LOC252983 | STXBP4 | 0.001970596 | 5.31 | 4.7 | 0.65 |
| BrAr:LOC84144_at | LOC84144 | SYDE2 | 0.003504369 | 4.13 | 3.2 | 0.52 |
| BrAr:LOC6856_at | LOC6856 | SYPL1 | 0.001398608 | 9.2 | 8.65 | 0.68 |
| BrAr:LOC23118_at | LOC23118 | TAB2 | 0.008891674 | 7.08 | 7.48 | 1.33 |
| BrAr:LOC10579_at | LOC10579 | TACC2 | 0.004608709 | 4.74 | 3.94 | 0.57 |
| BrAr:LOC117289_at | LOC117289 | TAGAP | 0.000123968 | 4.2 | 5.36 | 2.24 |
| BrAr:LOC51347_at | LOC51347 | TAOK3 | 0.007575933 | 6.88 | 7.21 | 1.26 |
| BrAr:LOC374403_at | LOC374403 | TBC1D10C | 3.27706E−06 | 3.27 | 4.3 | 2.05 |
| BrAr:LOC55357_at | LOC55357 | TBC1D2 | 0.003377907 | 4.63 | 5.44 | 1.75 |
| BrAr:LOC29110_at | LOC29110 | TBK1 | 0.004923804 | 6.36 | 6.71 | 1.27 |
| BrAr:LOC79718_at | LOC79718 | TBL1XR1 | 0.000559181 | 8.66 | 8.14 | 0.7 |
| BrAr:LOC57057_at | LOC57057 | TBX20 | 7.90703E−05 | 3.2 | 3.93 | 1.66 |
| BrAr:LOC30009_at | LOC30009 | TBX21 | 0.007593459 | 3.96 | 4.8 | 1.79 |
| BrAr:LOC7003_at | LOC7003 | TEAD1 | 1.21964E−05 | 7.54 | 6.73 | 0.57 |
| BrAr:LOC9840_at | LOC9840 | TESPA1 | 0.001195878 | 3.32 | 4.15 | 1.79 |
| BrAr:LOC29844_at | LOC29844 | TFPT | 0.000897111 | 8.52 | 8.96 | 1.35 |
| BrAr:LOC80764_at | LOC80764 | THAP7 | 0.005395763 | 2.81 | 3.13 | 1.25 |
| BrAr:LOC387357_at | LOC387357 | THEMIS | 0.001717274 | 4.43 | 5.77 | 2.52 |
| BrAr:LOC9473_at | LOC9473 | THEMIS2 | 0.002444402 | 4.13 | 4.95 | 1.76 |
| BrAr:LOC79896_at | LOC79896 | THNSL1 | 0.005476544 | 3.76 | 3.29 | 0.72 |
| BrAr:LOC7072_at | LOC7072 | TIA1 | 0.00561477 | 5.85 | 6.3 | 1.36 |
| BrAr:LOC201633_at | LOC201633 | TIGIT | 0.001834122 | 3.26 | 4.23 | 1.95 |
| BrAr:LOC9414_at | LOC9414 | TJP2 | 0.007201227 | 6.02 | 5.42 | 0.66 |

TABLE 7A-continued

Genes From an Analysis of Tumor Biopsies With >1.2-fold or <0.8-fold Differences Between Treatment Groups Before and After Treatment.

| Probeset (BrainArray v.10) | ENTREZ Gene ID | HUGO Gene Symbol | P value for Response v. No Response at C2D8 | No Response: Mean RMA value at C2D8 | Response: Mean RMA value at C2D8 | Response v. No response: Fold difference at C2D8 |
|---|---|---|---|---|---|---|
| BrAr:LOC140711_at | LOC140711 | TLDC2 | 0.008125954 | 3.2 | 3.53 | 1.26 |
| BrAr:LOC7099_at | LOC7099 | TLR4 | 0.006243027 | 6.74 | 7.4 | 1.58 |
| BrAr:LOC10333_at | LOC10333 | TLR6 | 0.006729152 | 3.05 | 3.52 | 1.39 |
| BrAr:LOC54106_at | LOC54106 | TLR9 | 0.004792073 | 2.51 | 2.83 | 1.25 |
| BrAr:LOC53346_at | LOC53346 | TM6SF1 | 0.001782749 | 4.48 | 5.11 | 1.56 |
| BrAr:LOC147138_at | LOC147138 | TMC8 | 0.001322432 | 3.09 | 3.58 | 1.41 |
| BrAr:LOC201799_at | LOC201799 | TMEM154 | 0.006931541 | 3.57 | 4.69 | 2.17 |
| BrAr:LOC132332_at | LOC132332 | TMEM155 | 0.002173193 | 2.02 | 2.96 | 1.91 |
| BrAr:LOC80008_at | LOC80008 | TMEM156 | 0.003752351 | 2.89 | 3.68 | 1.73 |
| BrAr:LOC23731_at | LOC23731 | TMEM245 | 0.004802032 | 6.91 | 6.32 | 0.66 |
| BrAr:LOC84302_at | LOC84302 | TMEM246 | 0.004460952 | 5.12 | 4.03 | 0.47 |
| BrAr:LOC144110_at | LOC144110 | TMEM86A | 0.000526517 | 4.01 | 4.51 | 1.41 |
| BrAr:LOC252839_at | LOC252839 | TMEM9 | 0.006039341 | 6.71 | 6.2 | 0.7 |
| BrAr:LOC7126_at | LOC7126 | TNFAIP1 | 0.003724845 | 6.07 | 5.59 | 0.72 |
| BrAr:LOC7127_at | LOC7127 | TNFAIP2 | 0.007086897 | 3.8 | 4.2 | 1.33 |
| BrAr:LOC79626_at | LOC79626 | TNFAIP8L2 | 0.005171815 | 5.38 | 6.27 | 1.86 |
| BrAr:LOC8764_at | LOC8764 | TNFRSF14 | 0.000685645 | 4.93 | 5.3 | 1.29 |
| BrAr:LOC10673_at | LOC10673 | TNFSF13B | 0.000330647 | 7.04 | 8.27 | 2.33 |
| BrAr:LOC944_at | LOC944 | TNFSF8 | 0.000583173 | 3.78 | 4.65 | 1.82 |
| BrAr:LOC10040_at | LOC10040 | TOM1L1 | 0.006200064 | 7.15 | 6.13 | 0.49 |
| BrAr:LOC9804_at | LOC9804 | TOMM20 | 0.003122245 | 8.31 | 7.83 | 0.72 |
| BrAr:LOC163590_at | LOC163590 | TOR1AIP2 | 0.005250439 | 5.01 | 4.46 | 0.68 |
| BrAr:LOC9760_at | LOC9760 | TOX | 0.009969532 | 2.93 | 3.71 | 1.72 |
| BrAr:LOC58476_at | LOC58476 | TP53INP2 | 0.002403891 | 6.48 | 5.84 | 0.64 |
| BrAr:LOC28755_at | LOC28755 | TRAC | 0.003798506 | 6.57 | 8.11 | 2.9 |
| BrAr:LOC7185_at | LOC7185 | TRAF1 | 0.002177656 | 3.39 | 4 | 1.53 |
| BrAr:LOC80342_at | LOC80342 | TRAF3IP3 | 0.000221585 | 4.47 | 5.34 | 1.83 |
| BrAr:LOC28737_at | LOC28737 | TRAJ18 | 0.000140457 | 2.62 | 3.48 | 1.82 |
| BrAr:LOC9881_at | LOC9881 | TRANK1 | 0.000942584 | 4.84 | 5.54 | 1.63 |
| BrAr:LOC10131_at | LOC10131 | TRAP1 | 0.009156509 | 7.5 | 6.81 | 0.62 |
| BrAr:LOC50852_at | LOC50852 | TRAT1 | 0.003755808 | 4.24 | 5.69 | 2.73 |
| BrAr:LOC28688_at | LOC28688 | TRAY5 | 2.09643E−06 | 2.61 | 3.4 | 1.73 |
| BrAr:LOC28638_at | LOC28638 | TRBC2 | 0.006293187 | 8.36 | 9.86 | 2.83 |
| BrAr:LOC23321_at | LOC23321 | TRIM2 | 0.000863602 | 6.54 | 5.4 | 0.46 |
| BrAr:LOC6737_at | LOC6737 | TRIM21 | 0.003545744 | 6.49 | 7.02 | 1.45 |
| BrAr:LOC10346_at | LOC10346 | TRIM22 | 0.000567832 | 7.55 | 8.35 | 1.74 |
| BrAr:LOC140691_at | LOC140691 | TRIM69 | 0.008249896 | 2.96 | 3.37 | 1.33 |
| BrAr:LOC83707_at | LOC83707 | TRPT1 | 0.002909746 | 5.65 | 6.16 | 1.42 |
| BrAr:LOC51393_at | LOC51393 | TRPV2 | 0.002776554 | 4.44 | 4.97 | 1.45 |
| BrAr:LOC23554_at | LOC23554 | TSPAN12 | 0.008216589 | 8.56 | 7.09 | 0.36 |
| BrAr:LOC164118_at | LOC164118 | TTC24 | 0.000150934 | 2.42 | 2.89 | 1.38 |
| BrAr:LOC23331_at | LOC23331 | TTC28 | 0.00335618 | 5.76 | 5 | 0.59 |
| BrAr:LOC7286_at | LOC7286 | TUFT1 | 0.005760063 | 3.8 | 3.26 | 0.69 |
| BrAr:LOC7289_at | LOC7289 | TULP3 | 0.007323623 | 6.12 | 5.62 | 0.71 |
| BrAr:LOC11344_at | LOC11344 | TWF2 | 0.001857556 | 5.47 | 6.02 | 1.47 |
| BrAr:LOC7305_at | LOC7305 | TYROBP | 0.002745226 | 9.37 | 10.17 | 1.75 |
| BrAr:LOC199746_at | LOC199746 | U2AF1L4 | 0.003606119 | 4.42 | 5 | 1.5 |
| BrAr:LOC283991_at | LOC283991 | UBALD2 | 0.005670187 | 4.96 | 5.5 | 1.45 |
| BrAr:LOC53347_at | LOC53347 | UBASH3A | 2.71583E−05 | 2.78 | 3.2 | 1.34 |
| BrAr:LOC56061_at | LOC56061 | UBFD1 | 0.001588397 | 7.25 | 6.62 | 0.65 |
| BrAr:LOC7372_at | LOC7372 | UMPS | 0.007796438 | 6.4 | 5.96 | 0.74 |
| BrAr:LOC7391_at | LOC7391 | USF1 | 0.001182734 | 3.98 | 4.43 | 1.36 |
| BrAr:LOC9958_at | LOC9958 | USP15 | 0.000863058 | 6.45 | 7 | 1.46 |
| BrAr:LOC158880_at | LOC158880 | USP51 | 0.002422567 | 3.63 | 3.3 | 0.79 |
| BrAr:LOC6843_at | LOC6843 | VAMP1 | 0.000736222 | 2.86 | 3.27 | 1.32 |
| BrAr:LOC9217_at | LOC9217 | VAPB | 8.55226E−05 | 6.91 | 6.38 | 0.69 |
| BrAr:LOC7409_at | LOC7409 | VAV1 | 0.000186062 | 4.59 | 5.72 | 2.19 |
| BrAr:LOC7716_at | LOC7716 | VEZF1 | 0.001044696 | 6.93 | 6.53 | 0.76 |
| BrAr:LOC7443_at | LOC7443 | VRK1 | 0.002220519 | 6.75 | 7.33 | 1.5 |
| BrAr:LOC284415_at | LOC284415 | VSTM1 | 6.7987E−05 | 2.86 | 3.67 | 1.76 |
| BrAr:LOC7454_at | LOC7454 | WAS | 0.000745019 | 4.52 | 5.31 | 1.73 |
| BrAr:LOC8976_at | LOC8976 | WASL | 6.45542E−05 | 5.9 | 5.26 | 0.64 |
| BrAr:LOC7456_at | LOC7456 | WIPF1 | 0.0016442 | 7.26 | 8.05 | 1.72 |
| BrAr:LOC26118_at | LOC26118 | WSB1 | 0.004722578 | 8.36 | 9 | 1.56 |
| BrAr:LOC23286_at | LOC23286 | WWC1 | 9.72052E−05 | 7.29 | 5.56 | 0.3 |
| BrAr:LOC25937_at | LOC25937 | WWTR1 | 0.000418593 | 8.84 | 8.39 | 0.73 |
| BrAr:LOC63929_at | LOC63929 | XPNPEP3 | 0.00882263 | 5.45 | 5 | 0.73 |
| BrAr:LOC9942_at | LOC9942 | XYLB | 0.000620581 | 5.24 | 4.4 | 0.56 |
| BrAr:LOC10413_at | LOC10413 | YAP1 | 0.000471948 | 6.52 | 5.7 | 0.57 |
| BrAr:LOC7535_at | LOC7535 | ZAP70 | 2.17013E−05 | 3.26 | 3.87 | 1.53 |
| BrAr:LOC79413_at | LOC79413 | ZBED2 | 0.002690869 | 3.04 | 4.13 | 2.13 |

TABLE 7A-continued

Genes From an Analysis of Tumor Biopsies With >1.2-fold or <0.8-fold DifferencesBetween Treatment Groups Before and After Treatment.

| Probeset (BrainArray v.10) | ENTREZ Gene ID | HUGO Gene Symbol | P value for Response v. No Response at C2D8 | No Response: Mean RMA value at C2D8 | Response: Mean RMA value at C2D8 | Response v. No response: Fold difference at C2D8 |
|---|---|---|---|---|---|---|
| BrAr:LOC81030_at | LOC81030 | ZBP1 | 0.001365506 | 3.1 | 3.63 | 1.44 |
| BrAr:LOC65986_at | LOC65986 | ZBTB10 | 6.24155E−05 | 6.03 | 5.22 | 0.57 |
| BrAr:LOC29068_at | LOC29068 | ZBTB44 | 0.006051218 | 8.48 | 7.94 | 0.69 |
| BrAr:LOC340152_at | LOC340152 | ZC3H12D | 0.002391622 | 2.94 | 3.29 | 1.28 |
| BrAr:LOC92092_at | LOC92092 | ZC3HAV1L | 0.002285154 | 7 | 6.14 | 0.55 |
| BrAr:LOC79670_at | LOC79670 | ZCCHC6 | 0.00012791 | 6.4 | 7.13 | 1.67 |
| BrAr:LOC84243_at | LOC84243 | ZDHHC18 | 0.009930106 | 4.15 | 4.66 | 1.42 |
| BrAr:LOC7538_at | LOC7538 | ZFP36 | 0.002038195 | 5.92 | 6.66 | 1.67 |
| BrAr:LOC346171_at | LOC346171 | ZFP57 | 0.006254335 | 2.86 | 3.22 | 1.28 |
| BrAr:LOC9372_at | LOC9372 | ZFYVE9 | 0.00211562 | 5.54 | 5.01 | 0.69 |
| BrAr:LOC84619_at | LOC84619 | ZGPAT | 0.004266495 | 4.55 | 4.92 | 1.29 |
| BrAr:LOC222882_at | LOC222882 | ZHX2 | 0.001424882 | 9.54 | 8.88 | 0.63 |
| BrAr:LOC7586_at | LOC7586 | ZKSCAN1 | 0.003281465 | 5.98 | 5.51 | 0.72 |
| BrAr:LOC84225_at | LOC84225 | ZMYND15 | 0.000116904 | 2.69 | 3.14 | 1.36 |
| BrAr:LOC94039_at | LOC94039 | ZNF101 | 0.000182538 | 4.92 | 5.85 | 1.9 |
| BrAr:LOC7566_at | LOC7566 | ZNF18 | 0.001440453 | 3.13 | 3.54 | 1.33 |
| BrAr:LOC286101_at | LOC286101 | ZNF252P | 0.000891302 | 5.82 | 5.18 | 0.64 |
| BrAr:LOC10308_at | LOC10308 | ZNF267 | 0.009630783 | 6.54 | 7.13 | 1.5 |
| BrAr:LOC92822_at | LOC92822 | ZNF276 | 0.001512078 | 3.48 | 3.87 | 1.32 |
| BrAr:LOC63925_at | LOC63925 | ZNF335 | 0.000953752 | 2.98 | 3.42 | 1.36 |
| BrAr:LOC84124_at | LOC84124 | ZNF394 | 0.000427762 | 5.04 | 5.4 | 1.29 |
| BrAr:LOC58499_at | LOC58499 | ZNF462 | 6.00777E−05 | 6.84 | 5.92 | 0.53 |
| BrAr:LOC144348_at | LOC144348 | ZNF664 | 0.001903398 | 7.66 | 7.2 | 0.73 |
| BrAr:LOC79970_at | LOC79970 | ZNF767 | 0.000764983 | 3.37 | 3.97 | 1.52 |
| BrAr:LOC128611_at | LOC128611 | ZNF831 | 2.84292E−05 | 2.91 | 3.3 | 1.31 |
| BrAr:LOC84937_at | LOC84937 | ZNRF1 | 0.005882736 | 4.42 | 4.79 | 1.29 |
| BrAr:LOC84133_at | LOC84133 | ZNRF3 | 0.00270792 | 3.31 | 2.57 | 0.6 |
| BrAr:LOC79699_at | LOC79699 | ZYG11B | 0.009608898 | 5.57 | 5.13 | 0.74 |

TABLE 7B

Normalization of select genes presented in Table 7A relative to the mean of all values measured at baseline.

| Categorization of response | NKG7 | PVRIG | SPI1 | CLEC2B | TNFSF13B | CTLA4 | TIGIT | NKTR | CD244 | PDCD1LG2 | TNFRSF14 | TNFSF8 |
|---|---|---|---|---|---|---|---|---|---|---|---|---|
| ≥20% decrease | 8.63 | 8.43 | 4.87 | 9.19 | 8.96 | 4.88 | 4.48 | 6.93 | 4.19 | 5.73 | 6.06 | 5.48 |
| ≥20% decrease | 8.60 | 7.98 | 5.44 | 8.56 | 8.62 | 5.51 | 4.79 | 5.74 | 4.59 | 4.63 | 5.24 | 4.40 |
| ≥20% decrease | 7.91 | 8.28 | 5.88 | 8.64 | 8.35 | 3.55 | 4.17 | 6.21 | 4.93 | 6.42 | 5.44 | 5.55 |
| ≥20% decrease | 7.39 | 7.38 | 4.49 | 8.69 | 7.80 | 3.61 | 3.58 | 5.78 | 3.38 | 4.57 | 4.75 | 3.59 |
| ≥20% decrease | 7.50 | 7.69 | 4.80 | 8.18 | 9.29 | 4.69 | 4.60 | 5.75 | 4.00 | 6.58 | 5.60 | 5.43 |
| ≥20% decrease | 9.71 | 10.07 | 5.69 | 8.30 | 8.97 | 5.50 | 6.50 | 6.28 | 5.38 | 6.77 | 6.18 | 5.95 |
| ≥20% decrease | 9.23 | 10.06 | 4.63 | 8.99 | 8.25 | 5.20 | 5.17 | 6.09 | 4.68 | 5.51 | 5.08 | 5.69 |
| RMA intensity value at C2D8 | | | | | | | | | | | | |
| ≥20% decrease | 7.72 | 7.14 | 3.82 | 6.65 | 6.67 | 3.27 | 3.06 | 5.38 | 3.52 | 4.08 | 5.20 | 3.21 |
| ≥20% decrease | 8.19 | 7.94 | 4.96 | 7.62 | 8.50 | 4.51 | 4.67 | 5.38 | 3.92 | 6.36 | 5.19 | 4.90 |
| ≥20% decrease | 8.02 | 7.16 | 4.67 | 8.58 | 8.61 | 4.86 | 4.39 | 5.99 | 4.39 | 5.88 | 5.58 | 4.60 |
| ≥20% decrease | 6.79 | 7.88 | 4.10 | 8.86 | 8.42 | 4.89 | 2.97 | 5.20 | 3.28 | 4.89 | 5.04 | 3.85 |
| <20% decrease | 6.79 | 6.49 | 4.06 | 8.25 | 7.14 | 3.34 | 2.93 | 5.62 | 3.10 | 3.68 | 5.14 | 3.36 |
| <20% decrease | 4.68 | 5.55 | 4.30 | 6.34 | 6.77 | 2.92 | 2.36 | 5.10 | 3.44 | 3.64 | 5.16 | 4.01 |
| <20% decrease | 6.28 | 5.96 | 3.74 | 7.83 | 6.95 | 3.83 | 3.47 | 6.92 | 3.09 | 4.85 | 5.49 | 4.03 |
| <20% decrease | 5.39 | 6.65 | 4.91 | 7.34 | 7.29 | 3.05 | 2.68 | 6.39 | 3.29 | 4.16 | 5.03 | 3.75 |
| <20% decrease | 6.34 | 6.64 | 3.96 | 6.80 | 7.32 | 3.53 | 3.45 | 5.69 | 2.90 | 3.98 | 4.78 | 3.23 |
| <20% decrease | 6.54 | 7.37 | 4.07 | 6.44 | 6.70 | 3.36 | 3.39 | 4.42 | 3.38 | 3.46 | 5.12 | 3.43 |
| <20% decrease | 6.89 | 7.46 | 4.44 | 8.00 | 8.80 | 3.31 | 3.17 | 5.00 | 3.46 | 5.20 | 4.92 | 4.46 |
| <20% decrease | 6.37 | 6.54 | 4.23 | 6.27 | 5.66 | 2.89 | 2.83 | 5.10 | 3.18 | 3.25 | 5.16 | 3.64 |
| <20% decrease | 5.27 | 5.15 | 4.10 | 7.67 | 6.47 | 3.62 | 3.07 | 5.40 | 2.77 | 4.14 | 5.37 | 3.48 |
| <20% decrease | 4.59 | 5.94 | 3.99 | 6.75 | 5.30 | 2.83 | 2.60 | 5.80 | 3.05 | 2.70 | 4.16 | 3.12 |
| <20% decrease | 7.67 | 6.63 | 4.83 | 8.36 | 8.46 | 3.83 | 3.74 | 5.16 | 4.12 | 5.33 | 4.81 | 4.47 |
| <20% decrease | 8.24 | 7.99 | 4.63 | 7.68 | 8.21 | 5.43 | 4.86 | 6.03 | 4.02 | 6.50 | 5.10 | 4.62 |
| <20% decrease | 7.00 | 8.06 | 5.09 | 7.52 | 8.55 | 3.60 | 3.90 | 5.48 | 3.66 | 5.90 | 4.69 | 4.52 |
| <20% decrease | 5.76 | 6.93 | 4.07 | 7.11 | 7.76 | 3.19 | 3.19 | 5.83 | 3.41 | 4.34 | 4.46 | 3.67 |
| <20% decrease | 7.54 | 7.58 | 5.25 | 7.91 | 9.05 | 5.87 | 4.07 | 5.60 | 4.49 | 7.66 | 5.03 | 4.88 |
| <20% decrease | 8.99 | 8.04 | 4.06 | 8.20 | 8.32 | 4.15 | 4.71 | 4.56 | 4.77 | 5.42 | 5.69 | 5.20 |
| <20% decrease | 5.02 | 5.87 | 4.19 | 8.98 | 6.97 | 3.26 | 2.83 | 4.69 | 2.98 | 3.35 | 5.32 | 3.10 |
| <20% decrease | 5.90 | 5.52 | 3.64 | 6.50 | 5.98 | 2.93 | 2.71 | 6.18 | 2.97 | 3.37 | 4.72 | 3.80 |
| <20% decrease | 8.00 | 7.89 | 4.93 | 7.82 | 7.21 | 3.97 | 4.73 | 5.95 | 6.14 | 6.66 | 5.29 | 4.98 |

TABLE 7B-continued

Normalization of select genes presented in Table 7A relative to the mean of all values measured at baseline.

| Categorization of response | NKG7 | PVRIG | SPI1 | CLEC2B | TNFSF13B | CTLA4 | TIGIT | NKTR | CD244 | PDCD1LG2 | TNFRSF14 | TNFSF8 |
|---|---|---|---|---|---|---|---|---|---|---|---|---|
| <20% decrease | 9.31 | 8.89 | 5.11 | 8.16 | 8.88 | 6.05 | 5.40 | 4.94 | 5.01 | 6.70 | 5.26 | 4.42 |
| <20% decrease | 8.61 | 8.77 | 5.65 | 8.67 | 9.15 | 6.36 | 5.51 | 5.86 | 4.80 | 6.46 | 5.45 | 5.71 |
| <20% decrease | 5.63 | 6.19 | 4.13 | 6.83 | 5.67 | 2.97 | 2.67 | 4.97 | 3.38 | 3.86 | 4.98 | 3.34 |
| <20% decrease | 5.76 | 5.83 | 4.19 | 8.96 | 7.22 | 3.51 | 3.04 | 5.47 | 3.36 | 4.04 | 4.51 | 3.83 |
| <20% decrease | 5.81 | 5.99 | 3.99 | 6.82 | 6.10 | 3.09 | 2.97 | 5.08 | 3.06 | 3.44 | 4.91 | 3.64 |
| <20% decrease | 7.69 | 7.78 | 5.09 | 8.05 | 9.12 | 5.70 | 5.12 | 5.77 | 3.70 | 7.03 | 5.21 | 5.14 |
| <20% decrease | 5.58 | 6.08 | 4.50 | 6.54 | 6.28 | 3.36 | 3.17 | 4.64 | 3.06 | 3.20 | 4.08 | 3.38 |
| <20% decrease | 5.37 | 5.70 | 4.48 | 6.98 | 6.55 | 2.95 | 2.71 | 5.69 | 3.26 | 3.44 | 4.71 | 3.75 |
| <20% decrease | 8.28 | 7.38 | 4.28 | 8.21 | 8.34 | 5.34 | 4.73 | 5.88 | 3.56 | 6.34 | 5.06 | 4.72 |
| <20% decrease | 5.95 | 6.50 | 4.12 | 7.18 | 6.79 | 3.14 | 2.61 | 4.73 | 2.94 | 3.95 | 4.53 | 3.64 |
| <20% decrease | 6.11 | 6.16 | 4.55 | 8.67 | 7.66 | 2.94 | 2.63 | 5.19 | 2.96 | 3.63 | 4.96 | 3.74 |
| <20% decrease | 6.57 | 5.80 | 4.19 | 6.50 | 6.54 | 2.79 | 3.19 | 5.56 | 3.72 | 4.76 | 4.99 | 4.55 |
| <20% decrease | 5.76 | 5.62 | 4.13 | 7.45 | 6.58 | 3.97 | 2.97 | 5.45 | 3.06 | 4.65 | 4.82 | 3.74 |
| <20% decrease | 5.37 | 6.19 | 4.40 | 6.48 | 5.81 | 3.08 | 2.86 | 5.21 | 3.31 | 3.70 | 4.84 | 2.91 |
| <20% decrease | 6.87 | 8.10 | 4.95 | 7.71 | 8.74 | 4.59 | 5.23 | 5.09 | 3.58 | 5.40 | 5.47 | 4.40 |
| <20% decrease | 7.36 | 6.77 | 4.50 | 7.77 | 6.96 | 3.29 | 3.68 | 6.04 | 3.67 | 3.70 | 5.09 | 4.05 |
| <20% decrease | 5.45 | 5.48 | 4.01 | 7.17 | 7.00 | 2.85 | 2.44 | 4.80 | 3.24 | 3.58 | 4.86 | 3.18 |
| <20% decrease | 6.85 | 5.88 | 4.65 | 7.76 | 7.91 | 3.90 | 3.62 | 5.84 | 3.63 | 4.66 | 4.56 | 4.10 |
| <20% decrease | 6.35 | 6.35 | 3.80 | 6.14 | 7.44 | 3.26 | 2.96 | 5.00 | 3.25 | 4.70 | 4.95 | 3.51 |
| <20% decrease | 7.97 | 7.90 | 4.69 | 8.11 | 7.63 | 3.94 | 3.80 | 4.47 | 3.68 | 5.68 | 4.70 | 4.33 |
| <20% decrease | 6.52 | 6.41 | 3.77 | 7.13 | 6.56 | 3.68 | 3.89 | 6.20 | 3.27 | 3.90 | 5.33 | 3.76 |
| <20% decrease | 7.86 | 7.34 | 4.62 | 8.57 | 8.59 | 4.67 | 4.54 | 5.30 | 4.59 | 5.88 | 5.03 | 4.09 |
| <20% decrease | 6.32 | 6.35 | 5.10 | 8.83 | 6.72 | 3.23 | 2.92 | 5.22 | 3.01 | 4.58 | 4.90 | 3.71 |
| <20% decrease | 5.54 | 6.21 | 3.67 | 6.42 | 6.37 | 3.34 | 2.87 | 6.31 | 2.98 | 3.92 | 4.49 | 3.37 |
| <20% decrease | 7.12 | 5.46 | 3.42 | 6.46 | 5.73 | 2.74 | 2.69 | 4.42 | 3.52 | 3.85 | 5.66 | 3.10 |
| Mean RMA, all Patients | 6.89 | 6.97 | 4.47 | 7.66 | 7.48 | 3.89 | 3.66 | 5.50 | 3.67 | 4.80 | 5.06 | 4.12 |
| Mean RMA, Responders | 8.15 | 8.18 | 4.85 | 8.39 | 8.40 | 4.59 | 4.40 | 5.88 | 4.21 | 5.58 | 5.40 | 4.79 |
| Fold-difference in Mean values | 2.40 | 2.31 | 1.30 | 1.65 | 1.89 | 1.62 | 1.67 | 1.30 | 1.45 | 1.72 | 1.26 | 1.59 |
| Expression relative to Mean of all values at C2D8 | | | | | | | | | | | | |
| <20% decrease | 3.35 | 2.74 | 1.32 | 2.87 | 2.78 | 1.99 | 1.76 | 2.69 | 1.43 | 1.90 | 2.01 | 2.56 |
| <20% decrease | 3.27 | 2.01 | 1.96 | 1.86 | 2.19 | 3.06 | 2.19 | 1.18 | 1.89 | 0.89 | 1.13 | 1.21 |
| <20% decrease | 2.03 | 2.47 | 2.66 | 1.96 | 1.82 | 0.79 | 1.43 | 1.63 | 2.39 | 3.07 | 1.30 | 2.69 |
| <20% decrease | 1.42 | 1.33 | 1.02 | 2.04 | 1.24 | 0.82 | 0.95 | 1.21 | 0.82 | 0.85 | 0.81 | 0.70 |
| <20% decrease | 1.52 | 1.64 | 1.26 | 1.43 | 3.49 | 1.74 | 1.92 | 1.18 | 1.25 | 3.43 | 1.45 | 2.48 |
| <20% decrease | 7.08 | 8.60 | 2.33 | 1.55 | 2.80 | 3.04 | 7.15 | 1.71 | 3.27 | 3.92 | 2.17 | 3.57 |
| >20% decrease | 5.06 | 8.49 | 1.12 | 2.51 | 1.70 | 2.48 | 2.84 | 1.50 | 2.00 | 1.63 | 1.02 | 2.97 |
| >20% decrease | 1.78 | 1.12 | 0.64 | 0.49 | 0.57 | 0.65 | 0.66 | 0.92 | 0.90 | 0.61 | 1.11 | 0.53 |
| >20% decrease | 2.46 | 1.96 | 1.40 | 0.97 | 2.02 | 1.53 | 2.02 | 0.92 | 1.18 | 2.94 | 1.10 | 1.72 |
| >20% decrease | 2.20 | 1.14 | 1.15 | 1.89 | 2.18 | 1.96 | 1.66 | 1.40 | 1.65 | 2.11 | 1.43 | 1.39 |
| >20% decrease | 0.93 | 1.88 | 0.77 | 2.29 | 1.92 | 1.99 | 0.62 | 0.81 | 0.76 | 1.07 | 0.99 | 0.83 |
| <20% decrease | 0.94 | 0.72 | 0.75 | 1.50 | 0.79 | 0.68 | 0.60 | 1.09 | 0.67 | 0.46 | 1.06 | 0.59 |
| <20% decrease | 0.22 | 0.37 | 0.89 | 0.40 | 0.61 | 0.51 | 0.41 | 0.76 | 0.85 | 0.45 | 1.08 | 0.93 |
| <20% decrease | 0.65 | 0.50 | 0.60 | 1.12 | 0.69 | 0.96 | 0.88 | 2.66 | 0.67 | 1.04 | 1.35 | 0.94 |
| <20% decrease | 0.35 | 0.80 | 1.36 | 0.80 | 0.88 | 0.56 | 0.51 | 1.84 | 0.76 | 0.64 | 0.98 | 0.77 |
| <20% decrease | 0.68 | 0.79 | 0.70 | 0.55 | 0.89 | 0.78 | 0.87 | 1.13 | 0.59 | 0.57 | 0.82 | 0.54 |
| <20% decrease | 0.78 | 1.32 | 0.76 | 0.43 | 0.58 | 0.69 | 0.83 | 0.47 | 0.82 | 0.40 | 1.04 | 0.62 |
| <20% decrease | 1.00 | 1.41 | 0.98 | 1.26 | 2.49 | 0.67 | 0.71 | 0.71 | 0.86 | 1.32 | 0.91 | 1.27 |
| <20% decrease | 0.70 | 0.74 | 0.85 | 0.38 | 0.28 | 0.50 | 0.56 | 0.75 | 0.71 | 0.34 | 1.08 | 0.72 |
| <20% decrease | 0.32 | 0.28 | 0.77 | 1.00 | 0.50 | 0.83 | 0.66 | 0.93 | 0.53 | 0.63 | 1.24 | 0.64 |
| <20% decrease | 0.20 | 0.49 | 0.72 | 0.53 | 0.22 | 0.48 | 0.48 | 1.23 | 0.65 | 0.23 | 0.54 | 0.50 |
| <20% decrease | 1.71 | 0.79 | 1.28 | 1.62 | 1.97 | 0.96 | 1.05 | 0.79 | 1.36 | 1.45 | 0.84 | 1.28 |
| <20% decrease | 2.56 | 2.03 | 1.12 | 1.01 | 1.65 | 2.90 | 2.29 | 1.44 | 1.27 | 3.26 | 1.03 | 1.42 |
| <20% decrease | 1.08 | 2.13 | 1.54 | 0.90 | 2.10 | 0.82 | 1.18 | 0.98 | 0.99 | 2.15 | 0.78 | 1.32 |
| <20% decrease | 0.46 | 0.97 | 0.76 | 0.68 | 1.21 | 0.62 | 0.72 | 1.25 | 0.83 | 0.73 | 0.66 | 0.74 |
| <20% decrease | 1.57 | 1.52 | 1.72 | 1.19 | 2.95 | 3.94 | 1.33 | 1.07 | 1.76 | 7.26 | 0.98 | 1.70 |
| <20% decrease | 4.29 | 2.10 | 0.75 | 1.45 | 1.78 | 1.20 | 2.07 | 0.52 | 2.13 | 1.54 | 1.55 | 2.11 |
| <20% decrease | 0.27 | 0.47 | 0.82 | 2.49 | 0.70 | 0.64 | 0.56 | 0.57 | 0.62 | 0.37 | 1.20 | 0.49 |
| <20% decrease | 0.50 | 0.37 | 0.56 | 0.45 | 0.35 | 0.51 | 0.52 | 1.60 | 0.61 | 0.37 | 0.79 | 0.80 |
| <20% decrease | 2.15 | 1.89 | 1.37 | 1.11 | 0.83 | 1.05 | 2.10 | 1.36 | 5.53 | 3.64 | 1.18 | 1.81 |
| <20% decrease | 5.36 | 3.77 | 1.55 | 1.40 | 2.63 | 4.45 | 3.33 | 0.68 | 2.52 | 3.72 | 1.15 | 1.23 |
| <20% decrease | 3.30 | 3.47 | 2.27 | 2.00 | 3.18 | 5.54 | 3.62 | 1.28 | 2.19 | 3.16 | 1.31 | 3.01 |
| <20% decrease | 0.42 | 0.58 | 0.79 | 0.56 | 0.28 | 0.53 | 0.50 | 0.69 | 0.81 | 0.52 | 0.94 | 0.58 |
| <20% decrease | 0.46 | 0.45 | 0.82 | 2.45 | 0.83 | 0.77 | 0.65 | 0.97 | 0.81 | 0.59 | 0.69 | 0.82 |
| <20% decrease | 0.47 | 0.51 | 0.72 | 0.56 | 0.38 | 0.57 | 0.62 | 0.74 | 0.65 | 0.39 | 0.90 | 0.72 |
| <20% decrease | 1.74 | 1.76 | 1.54 | 1.31 | 3.11 | 3.49 | 2.75 | 1.20 | 1.02 | 4.69 | 1.11 | 2.03 |
| <20% decrease | 0.40 | 0.54 | 1.02 | 0.46 | 0.43 | 0.69 | 0.71 | 0.55 | 0.65 | 0.33 | 0.51 | 0.60 |
| <20% decrease | 0.35 | 0.41 | 1.01 | 0.62 | 0.52 | 0.52 | 0.52 | 1.14 | 0.75 | 0.39 | 0.78 | 0.77 |
| <20% decrease | 2.61 | 1.33 | 0.88 | 1.46 | 1.81 | 2.73 | 2.10 | 1.29 | 0.93 | 2.91 | 1.00 | 1.52 |
| <20% decrease | 0.52 | 0.72 | 0.78 | 0.72 | 0.62 | 0.59 | 0.48 | 0.58 | 0.60 | 0.55 | 0.69 | 0.72 |
| <20% decrease | 0.58 | 0.57 | 1.06 | 2.01 | 1.13 | 0.52 | 0.49 | 0.80 | 0.61 | 0.44 | 0.94 | 0.77 |
| <20% decrease | 0.80 | 0.44 | 0.83 | 0.45 | 0.52 | 0.46 | 0.72 | 1.04 | 1.04 | 0.97 | 0.96 | 1.35 |

TABLE 7B-continued

Normalization of select genes presented in Table 7A relative to the mean of all values measured at baseline.

| Categorization of response | NKG7 | PVRIG | SPI1 | CLEC2B | TNFSF13B | CTLA4 | TIGIT | NKTR | CD244 | PDCD1LG2 | TNFRSF14 | TNFSF8 |
|---|---|---|---|---|---|---|---|---|---|---|---|---|
| <20% decrease | 0.46 | 0.39 | 0.79 | 0.86 | 0.54 | 1.05 | 0.62 | 0.96 | 0.65 | 0.90 | 0.85 | 0.77 |
| <20% decrease | 0.35 | 0.58 | 0.95 | 0.44 | 0.31 | 0.57 | 0.58 | 0.82 | 0.78 | 0.46 | 0.86 | 0.43 |
| <20% decrease | 0.98 | 2.19 | 1.40 | 1.03 | 2.39 | 1.63 | 2.96 | 0.75 | 0.94 | 1.51 | 1.33 | 1.21 |
| <20% decrease | 1.38 | 0.87 | 1.02 | 1.07 | 0.69 | 0.66 | 1.01 | 1.45 | 0.99 | 0.47 | 1.03 | 0.96 |
| <20% decrease | 0.37 | 0.36 | 0.73 | 0.71 | 0.71 | 0.48 | 0.43 | 0.61 | 0.74 | 0.43 | 0.87 | 0.52 |
| <20% decrease | 0.98 | 0.47 | 1.13 | 1.07 | 1.34 | 1.00 | 0.97 | 1.26 | 0.97 | 0.91 | 0.71 | 0.99 |
| <20% decrease | 0.69 | 0.65 | 0.63 | 0.35 | 0.97 | 0.64 | 0.62 | 0.70 | 0.74 | 0.93 | 0.92 | 0.66 |
| <20% decrease | 2.12 | 1.90 | 1.16 | 1.36 | 1.10 | 1.03 | 1.10 | 0.49 | 1.00 | 1.83 | 0.78 | 1.16 |
| <20% decrease | 0.78 | 0.68 | 0.62 | 0.69 | 0.53 | 0.86 | 1.17 | 1.62 | 0.76 | 0.54 | 1.21 | 0.78 |
| <20% decrease | 1.95 | 1.30 | 1.11 | 1.87 | 2.16 | 1.71 | 1.84 | 0.87 | 1.88 | 2.11 | 0.98 | 0.98 |
| <20% decrease | 0.67 | 0.65 | 1.55 | 2.24 | 0.59 | 0.63 | 0.60 | 0.82 | 0.63 | 0.86 | 0.90 | 0.75 |
| <20% decrease | 0.39 | 0.59 | 0.58 | 0.42 | 0.46 | 0.68 | 0.58 | 1.75 | 0.62 | 0.54 | 0.67 | 0.59 |
| <20% decrease | 1.17 | 0.35 | 0.48 | 0.43 | 0.30 | 0.45 | 0.51 | 0.47 | 0.90 | 0.52 | 1.51 | 0.50 |

TABLE 8A

Genes From an Analysis of Tumor Biopsies With >1.2-fold or <0.8-fold Differences Between Treatment Groups Before and After Treatment Comparing the Fold Change in Responsive and Non-Responsive Subjects.

| Probeset (BrainArray v.10) | ENTREZ Gene ID | HUGO Gene Symbol | P value for change upon treatment differing between response groups | No Response: Mean RMA value at baseline | Response: Mean RMA value at baseline | No Response: Mean RMA value at C2D8 | Response: Mean RMA value at C2D8 | No Response: Change upon treatment | Response: Change upon treatment |
|---|---|---|---|---|---|---|---|---|---|
| BrAr:LOC140_at | LOC140 | ADORA3 | 0.003217778 | 5.64 | 5.85 | 5.65 | 6.72 | 1 | 1.83 |
| BrAr:LOC1645_at | LOC1645 | AKR1C1 | 0.001911057 | 7.79 | 7.23 | 7.78 | 5.96 | 0.99 | 0.41 |
| BrAr:LOC1646_at | LOC1646 | AKR1C2 | 0.000754158 | 6.14 | 5.69 | 6.33 | 4.63 | 1.14 | 0.48 |
| BrAr:LOC57101_at | LOC57101 | ANO2 | 0.000361197 | 2.77 | 2.58 | 2.61 | 3.32 | 0.9 | 1.67 |
| BrAr:LOC7984_at | LOC7984 | ARHGEF5 | 0.00010372 | 7.21 | 6.99 | 7.18 | 5.88 | 0.98 | 0.46 |
| BrAr:LOC115761_at | LOC115761 | ARL11 | 0.003149723 | 2.94 | 3.13 | 2.99 | 3.59 | 1.04 | 1.38 |
| BrAr:LOC445_at | LOC445 | ASS1 | 0.000728649 | 6.91 | 6.42 | 6.87 | 5.75 | 0.97 | 0.63 |
| BrAr:LOC23743_at | LOC23743 | BHMT2 | 0.00056076 | 7.41 | 7.11 | 7.44 | 5.77 | 1.02 | 0.39 |
| BrAr:LOC80114_at | LOC80114 | BICC1 | 0.003236408 | 6.65 | 6.16 | 6.48 | 5.37 | 0.89 | 0.58 |
| BrAr:LOC55337_at | LOC55337 | C19ORF66 | 0.001415972 | 5.39 | 5.32 | 5.39 | 5.83 | 1 | 1.42 |
| BrAr:LOC26005_at | LOC26005 | C2CD3 | 0.003271581 | 3.3 | 3.36 | 3.24 | 3.74 | 0.96 | 1.3 |
| BrAr:LOC718_at | LOC718 | C3 | 0.000510688 | 10.78 | 10.93 | 10.95 | 10.04 | 1.12 | 0.54 |
| BrAr:LOC64170_at | LOC64170 | CARD9 | 0.001441216 | 4.24 | 4.46 | 4.38 | 5.22 | 1.1 | 1.69 |
| BrAr:LOC50937_at | LOC50937 | CDON | 0.005728583 | 4.65 | 4.23 | 4.45 | 3.52 | 0.87 | 0.61 |
| BrAr:LOC55501_at | LOC55501 | CHST12 | 0.000722334 | 3.51 | 3.58 | 3.47 | 4.04 | 0.97 | 1.38 |
| BrAr:LOC146223_at | LOC146223 | CMTM4 | 0.000872911 | 5.68 | 5.63 | 5.54 | 4.84 | 0.91 | 0.58 |
| BrAr:LOC1759_at | LOC1759 | DNM1 | 0.000278896 | 4.86 | 5.14 | 4.7 | 3.89 | 0.9 | 0.42 |
| BrAr:LOC1956_at | LOC1956 | EGFR | 0.007012678 | 7.36 | 6.8 | 7.23 | 5.74 | 0.92 | 0.48 |
| BrAr:LOC100131897_at | LOC100131897 | FAM196B | 0.002546233 | 3.74 | 3.93 | 3.72 | 4.27 | 0.99 | 1.27 |
| BrAr:LOC2195_at | LOC2195 | FAT1 | 0.009212583 | 9.67 | 9.47 | 9.47 | 8.45 | 0.87 | 0.49 |
| BrAr:LOC115290_at | LOC115290 | FBXO17 | 0.001904392 | 6 | 5.74 | 5.9 | 5 | 0.93 | 0.6 |
| BrAr:LOC11328_at | LOC11328 | FKBP9 | 0.008901288 | 6.75 | 6.49 | 6.64 | 6.04 | 0.93 | 0.73 |
| BrAr:LOC8321_at | LOC8321 | FZD1 | 0.001761088 | 7.19 | 6.83 | 7.17 | 6.39 | 0.99 | 0.73 |
| BrAr:LOC2581_at | LOC2581 | GALC | 6.17362E−05 | 5.63 | 5.6 | 5.7 | 6.18 | 1.05 | 1.5 |
| BrAr:LOC57678_at | LOC57678 | GPAM | 0.001774483 | 4.9 | 4.95 | 5.21 | 4.31 | 1.24 | 0.64 |
| BrAr:LOC3226_at | LOC3226 | HOXC10 | 0.003809884 | 6.97 | 6.76 | 6.98 | 5.74 | 1.01 | 0.49 |
| BrAr:LOC9956_at | LOC9956 | HS3ST2 | 0.003715771 | 3.53 | 3.7 | 3.39 | 4.27 | 0.9 | 1.49 |
| BrAr:LOC79190_at | LOC79190 | IRX6 | 0.000738422 | 3.31 | 3.07 | 3.47 | 2.69 | 1.12 | 0.77 |
| BrAr:LOC3766_at | LOC3766 | KCNJ10 | 0.007473696 | 2.48 | 2.67 | 2.8 | 3.99 | 1.24 | 2.49 |
| BrAr:LOC100289455_at | LOC100289455 | LOC100289455 | 0.001954644 | 3.27 | 3.13 | 3.29 | 3.65 | 1.01 | 1.44 |
| BrAr:LOC4125_at | LOC4125 | MAN2B1 | 0.007502126 | 6.22 | 6.64 | 6.33 | 7.04 | 1.08 | 1.32 |
| BrAr:LOC22823_at | LOC22823 | MTF2 | 0.00018303 | 5.73 | 5.74 | 5.75 | 6.13 | 1.02 | 1.31 |
| BrAr:LOC51172_at | LOC51172 | NAGPA | 0.001020819 | 4.18 | 4.04 | 4.11 | 4.45 | 0.96 | 1.33 |
| BrAr:LOC10787_at | LOC10787 | NCKAP1 | 0.009526855 | 8.51 | 8.26 | 8.41 | 7.77 | 0.93 | 0.71 |
| BrAr:LOC23413_at | LOC23413 | NCS1 | 0.00077159 | 5.16 | 5.07 | 5.17 | 4.65 | 1.01 | 0.75 |
| BrAr:LOC4820_at | LOC4820 | NKTR | 0.005837122 | 5.46 | 5.54 | 5.41 | 6.03 | 0.97 | 1.41 |
| BrAr:LOC80896_at | LOC80896 | NPL | 0.003423516 | 5.66 | 6.09 | 5.67 | 6.94 | 1 | 1.81 |
| BrAr:LOC375387_at | LOC375387 | NRROS | 0.001100607 | 4.17 | 4.25 | 4.04 | 4.69 | 0.91 | 1.36 |
| BrAr:LOC79668_at | LOC79668 | PARP8 | 0.001671059 | 5.48 | 5.7 | 5.58 | 6.21 | 1.07 | 1.43 |
| BrAr:LOC197135_at | LOC197135 | PATL2 | 6.9616E−05 | 3.06 | 2.98 | 3.01 | 3.59 | 0.97 | 1.53 |
| BrAr:LOC9033_at | LOC9033 | PKD2L1 | 0.004494258 | 3.82 | 4.2 | 3.89 | 4.98 | 1.05 | 1.72 |
| BrAr:LOC5729_at | LOC5729 | PTGDR | 0.002150214 | 2.38 | 2.33 | 2.38 | 2.81 | 1 | 1.4 |
| BrAr:LOC10235_at | LOC10235 | RASGRP2 | 0.003641911 | 3.05 | 3.12 | 2.92 | 3.68 | 0.92 | 1.48 |
| BrAr:LOC5973_at | LOC5973 | RENBP | 0.009590131 | 2.31 | 2.38 | 2.38 | 2.75 | 1.05 | 1.29 |

TABLE 8A-continued

Genes From an Analysis of Tumor Biopsies With >1.2-fold or <0.8-fold Differences Between Treatment Groups Before and After Treatment Comparing the Fold Change in Responsive and Non-Responsive Subjects.

| Probeset (BrainArray v.10) | ENTREZ Gene ID | HUGO Gene Symbol | P value for change upon treatment differing between response groups | No Response: Mean RMA value at baseline | Response: Mean RMA value at baseline | No Response: Mean RMA value at C2D8 | Response: Mean RMA value at C2D8 | No Response: Change upon treatment | Response: Change upon treatment |
|---|---|---|---|---|---|---|---|---|---|
| BrAr:LOC55599_at | LOC55599 | RNPC3 | 0.003973794 | 5.09 | 5.03 | 5.01 | 5.72 | 0.94 | 1.61 |
| BrAr:LOC57337_at | LOC57337 | SENP7 | 0.001110208 | 4.54 | 4.43 | 4.38 | 4.86 | 0.9 | 1.35 |
| BrAr:LOC166929_at | LOC166929 | SGMS2 | 0.002683966 | 5.19 | 5.12 | 4.98 | 4.48 | 0.87 | 0.64 |
| BrAr:LOC11309_at | LOC11309 | SLCO2B1 | 0.006057789 | 4.53 | 4.85 | 4.67 | 5.2 | 1.1 | 1.28 |
| BrAr:LOC6708_at | LOC6708 | SPTA1 | 0.005000147 | 2.36 | 2.55 | 2.38 | 3.23 | 1.01 | 1.6 |
| BrAr:LOC7003_at | LOC7003 | TEAD1 | 0.00098282 | 7.6 | 7.23 | 7.54 | 6.73 | 0.96 | 0.71 |
| BrAr:LOC144110_at | LOC144110 | TMEM86A | 0.009256951 | 3.91 | 4.12 | 4.01 | 4.51 | 1.07 | 1.31 |
| BrAr:LOC944_at | LOC944 | TNFSF8 | 0.002299197 | 3.68 | 4.05 | 3.78 | 4.65 | 1.07 | 1.51 |
| BrAr:LOC10413_at | LOC10413 | YAP1 | 0.005339969 | 6.55 | 6.26 | 6.52 | 5.7 | 0.98 | 0.68 |
| BrAr:LOC65986_at | LOC65986 | ZBTB10 | 0.002210855 | 6.11 | 5.72 | 6.03 | 5.22 | 0.95 | 0.71 |
| BrAr:LOC9372_at | LOC9372 | ZFYVE9 | 0.005927672 | 5.63 | 5.39 | 5.54 | 5.01 | 0.94 | 0.77 |
| BrAr:LOC79970_at | LOC79970 | ZNF767 | 0.004796367 | 3.5 | 3.58 | 3.37 | 3.97 | 0.91 | 1.31 |

TABLE 8B

Normalization of select genes presented in Table 8A relative to the mean of all values measured at baseline.

| Categorization of response | RMA intensity value at Baseline | | RMA intensity value at C2D8 | | Fold change on treatment | |
|---|---|---|---|---|---|---|
| | NKTR | TNFSF8 | NKTR | TNFSF8 | NKTR | TNFSF8 |
| ≥20% decrease | 3.96 | 2.68 | 5.20 | 3.85 | 2.4 | 2.3 |
| ≥20% decrease | 5.18 | 5.08 | 5.38 | 4.90 | 1.2 | 0.9 |
| ≥20% decrease | 5.71 | 4.57 | 5.75 | 5.43 | 1.0 | 1.8 |
| ≥20% decrease | 5.17 | 3.48 | 5.78 | 3.59 | 1.5 | 1.1 |
| ≥20% decrease | 5.44 | 4.57 | 5.99 | 4.60 | 1.5 | 1.0 |
| ≥20% decrease | 4.57 | 5.12 | 6.09 | 5.69 | 2.9 | 1.5 |
| ≥20% decrease | 6.38 | 5.38 | 6.21 | 5.55 | 0.9 | 1.1 |
| ≥20% decrease | 5.61 | 3.55 | 6.28 | 5.95 | 1.6 | 5.3 |
| ≥20% decrease | 6.70 | 4.32 | 6.93 | 5.48 | 1.2 | 2.2 |
| <20% decrease | 4.76 | 3.42 | 4.42 | 3.10 | 0.8 | 0.8 |
| <20% decrease | 4.10 | 3.38 | 4.42 | 3.43 | 1.3 | 1.0 |
| <20% decrease | 5.16 | 2.99 | 4.47 | 4.33 | 0.6 | 2.5 |
| <20% decrease | 5.10 | 5.33 | 4.56 | 5.20 | 0.7 | 0.9 |
| <20% decrease | 5.65 | 4.10 | 4.69 | 3.10 | 0.5 | 0.5 |
| <20% decrease | 4.57 | 2.77 | 4.80 | 3.18 | 1.2 | 1.3 |
| <20% decrease | 4.45 | 3.31 | 4.94 | 4.42 | 1.4 | 2.2 |
| <20% decrease | 5.36 | 3.56 | 4.97 | 3.34 | 0.8 | 0.9 |
| <20% decrease | 5.14 | 2.61 | 5.00 | 3.51 | 0.9 | 1.9 |
| <20% decrease | 5.01 | 4.92 | 5.00 | 4.46 | 1.0 | 0.7 |
| <20% decrease | 5.10 | 3.23 | 5.08 | 3.64 | 1.0 | 1.3 |
| <20% decrease | 4.85 | 3.83 | 5.09 | 4.40 | 1.2 | 1.5 |
| <20% decrease | 5.57 | 3.25 | 5.10 | 3.64 | 0.7 | 1.3 |
| <20% decrease | 5.03 | 4.56 | 5.10 | 4.01 | 1.0 | 0.7 |
| <20% decrease | 4.81 | 3.90 | 5.16 | 4.47 | 1.3 | 1.5 |
| <20% decrease | 5.64 | 4.28 | 5.19 | 3.74 | 0.7 | 0.7 |
| <20% decrease | 3.96 | 3.36 | 5.21 | 2.91 | 2.4 | 0.7 |
| <20% decrease | 5.01 | 3.38 | 5.22 | 3.71 | 1.2 | 1.3 |
| <20% decrease | 5.47 | 3.58 | 5.30 | 4.09 | 0.9 | 1.4 |
| <20% decrease | 4.84 | 4.15 | 5.47 | 3.83 | 1.5 | 0.8 |
| <20% decrease | 5.69 | 4.97 | 5.48 | 4.52 | 0.9 | 0.7 |
| <20% decrease | 5.25 | 4.44 | 5.56 | 4.55 | 1.2 | 1.1 |
| <20% decrease | 6.66 | 3.94 | 5.60 | 4.88 | 0.5 | 1.9 |
| <20% decrease | 5.57 | 3.85 | 5.77 | 5.14 | 1.2 | 2.5 |
| <20% decrease | 5.38 | 3.12 | 5.80 | 3.12 | 1.3 | 1.0 |
| <20% decrease | 5.68 | 3.51 | 5.83 | 3.67 | 1.1 | 1.1 |
| <20% decrease | 5.68 | 4.37 | 5.84 | 4.10 | 1.1 | 0.8 |
| <20% decrease | 5.36 | 4.47 | 5.86 | 5.71 | 1.4 | 2.4 |
| <20% decrease | 5.37 | 4.25 | 5.88 | 4.72 | 1.4 | 1.4 |
| <20% decrease | 6.00 | 5.36 | 6.03 | 4.62 | 1.0 | 0.6 |
| <20% decrease | 6.33 | 4.30 | 6.18 | 3.80 | 0.9 | 0.7 |

TABLE 8B-continued

Normalization of select genes presented in Table 8A relative to the mean of all values measured at baseline.

| Categorization of response | RMA intensity value at Baseline | | RMA intensity value at C2D8 | | Fold change on treatment | |
|---|---|---|---|---|---|---|
| | NKTR | TNFSF8 | NKTR | TNFSF8 | NKTR | TNFSF8 |
| <20% decrease | 6.82 | 3.42 | 6.31 | 3.37 | 0.7 | 1.0 |
| <20% decrease | 5.85 | 3.60 | 6.39 | 3.75 | 1.4 | 1.1 |

D. Safety Analysis

All recorded AEs were listed and tabulated by system organ class, preferred term, treatment group, and dose, and coded according to the most current version of the Medical Dictionary for Regulatory Activities (MedDRA; version 17.1 at database lock). The incidence of AEs was tabulated and reviewed for significance and clinical importance. Summaries of select AEs regardless of causality were created and frequency distributions were tabulated by dose.

III. Results

A. Patient Population

Patients were enrolled from September 2011 to September 2012 at 14 participating US and non-US centers. In total, 92 patients were assigned to study treatment, 91 of whom were treated (FIG. 2). The median age of patients was 61 years, 67% were male, and 96% had undergone previous surgery on the primary tumor (Table 9). Baseline characteristics were similar between previously treated patients (n=67), who were assigned to nivolumab 0.3, 2.0, or 10 mg/kg, and treatment-naïve (n=24) patients, who were assigned to nivolumab 10 mg/kg every 3 weeks (Table 9).

TABLE 9

Baseline Patient Characteristics and Demographics.

| | Previously Treated, Nivolumab 0.3, 2, and 10 mg/kg (n = 67) | Treatment-naïve, Nivolumab 10 mg/kg (n = 24) | Total (n = 91) |
|---|---|---|---|
| Median age, years | 61.0 | 63.5 | 61.0 |
| Sex, n (%) | | | |
| Male | 46 (69) | 15 (63) | 61 (67) |
| Female | 21 (31) | 9 (38) | 30 (33) |
| Previous therapy, n (%) | | | |
| Surgery | 64 (96) | 23 (96) | 87 (96) |
| Radiotherapy | 25 (37) | 5 (21) | 30 (33) |
| Previous systemic therapy | 67 (100) | 0 | 67 (74) |
| Therapy for metastatic disease | 60 (90) | 0 | 60 (66) |
| Adjuvant therapy | 5 (7) | 0 | 5 (6) |
| Neoadjuvant therapy | 5 (7) | 0 | 5 (6) |

B. Clinical Efficacy

Responses were evaluated in 91 patients who received at least one dose of nivolumab. The ORR was 15% (95% confidence interval (CI), 8.7-24.5) overall; ORRs for individual dose groups are shown in Table 10. Stable disease was observed in 46% of patients overall (Table 10). Twenty one patients met the criterion of at least 20% maximal reduction in Tumor Burden sustained for 2 evaluations (used for analysis of the association between Response and gene expression).

TABLE 10

Clinical Efficacy.

| | Previously Treated (n = 67) | | | Treatment-naïve | |
|---|---|---|---|---|---|
| | Nivolumab 0.3 mg/kg (n = 22) | Nivolumab 2.0 mg/kg (n = 22) | Nivolumab 10 mg/kg (n = 23) | Nivolumab 10 mg/kg (n = 24) | Total (n = 91)[a] |
| ORR, n (%)[b] | 2 (9) | 4 (18) | 5 (22) | 3 (13) | 14 (15) |
| 95% CI | 1.1-29.2 | 5.2-40.3 | 7.5-43.7 | 2.7-32.4 | 8.7-24.5 |
| Best response, n (%) | | | | | |
| CR | 0 | 0 | 0 | 2 (8) | 2 (2) |
| PR | 2 (9) | 4 (18) | 5 (22) | 1 (4) | 12 (13) |
| Stable disease | 8 (36) | 10 (46) | 11 (48) | 13 (54) | 42 (46) |
| Progressive disease | 9 (41) | 5 (23) | 6 (26) | 7 (29) | 27 (30) |
| Unable to determine | 3 (14) | 3 (14) | 1 (4) | 1 (4) | 8 (9) |
| PFS rate, % (95% CI) | | | | | |
| At 24 weeks | NE | 44 (23-63) | 58 (35-76) | 50 (28-68) | 43 (32-53) |
| At 48 weeks | NE | NE | 32 (13-52) | 39 (18-59) | 25 (16-35) |
| OS rate, % (95% CI) | | | | | |
| At 12 months | 71 (47-86) | 72 (48-86) | 74 (48-88) | 81 (57-92) | 75 (64-83) |
| At 24 months | 44 (22-64) | 61 (36-78) | 51 (27-71) | 76 (51-89) | 58 (46-68) |
| Median OS, months (95% CI) | 16.4 (10.1-NR) | NR | 25.2 (12.0-NR) | NR | — |

Note
ORR, objective response rate; CR, complete response; NE, not evaluated; NR, not reached; PR, partial response; PFS, progression free survival; OS, overall survival.
[a] All treated patients were evaluated for response.
[b] Confirmed response only.

Progression-free survival (PFS) rates were 43% (95% CI, 32-53) at 24 weeks and 25% (95% CI, 16-35) at 48 weeks overall; PFS rates for individual dose groups are shown in Table 10.

Overall survival (OS) rates were 75% (95% CI, 64-83) at 12 months and 58% (95% CI, 46-68) at 24 months overall; OS rates for individual dose groups are shown in Table 10 and FIG. 3. Median OS (95% CI) was 16.4 months (95% CI, 10.1—not reached (NR)) for Arm 1 (0.3 mg/kg nivolumab), NR for Arm 2 (2 mg/kg nivolumab), 25.2 months (95% CI, 12.0—NR) for Arm 3 (10 mg/kg nivolumab), and NR for Arm 4 (10 mg/kg nivolumab) patients (Table 10; FIG. 3).

C. Tumor-Associated Lymphocytes

Immunohistochemistry (IHC) of tissue from serial tumor biopsies was performed to evaluate whether frequencies of tumor-associated lymphocytes increased with nivolumab treatment. On-treatment biopsies showed enrichment of CD3+, CD4+, and CD8+ cells from baseline to cycle 2 day 8 (FIG. 4A-FIG. 5G). For all nivolumab-treated patients combined with baseline and cycle 2 day 8 values (N=36), median changes from baseline to cycle 2 day 8 in the proportion of CD3+, CD4+, and CD8+ cells were 9.83%, 0.44%, and 2.64%, respectively, with a majority of patients experiencing increases (FIG. 4E-FIG. 4G). Baseline percentages and increases from baseline were greater for CD3+ and CD8+ than for CD4+ cells. Most patients had very low or undetectable levels of CD4+ at baseline, and only modest changes from baseline. Fourteen patients had both baseline percentages and changes from baseline values <0.45%. Increases were observed across all baseline levels. These results did not appear to vary with nivolumab dose or previous treatment status (data not shown).

Distributions of the proportion of CD3+, CD4+, and CD8+ cells and their relationships to each other are shown in FIG. 5A-FIG. 5F. Changes in the proportion of CD3+ and CD8+ cells were highly associated (FIG. 5B), while changes in the proportion of CD4+ cells did not appear to be associated with changes in CD3+(FIG. 5A) or CD8+(FIG. 5C) cells. Changes in the proportion of CD3+ cells were nearly always greater than changes in the proportion of CD4+(FIG. 5A) or CD8+(FIG. 5B) cells. Expression analysis of RNA from tumor biopsies obtained in parallel showed that CD3 (FIG. 5G) and CD8 (FIG. 5H), but not CD4 (FIG. 5J), transcripts significantly increased post-treatment (1.7-fold for gene CD3D, p=0.006 [FIG. 5G]; 1.7-fold for gene CD8A, p=0.002 [FIG. 5H]; 1.2-fold for gene CD4, p=0.175 [FIG. 5J]). These changes did not appear to depend on nivolumab dose or previous treatment.

D. Receptor Occupancy

Nivolumab occupancy of the PD-1 receptor in peripheral T cells varied negligibly with dose or previous treatment status. Peak median receptor occupancy was 99% (range, 55%-117%) at cycle 1 day 1 at 1 hour after treatment infusion for all patients combined (FIG. 6A-FIG. 6D). Median receptor occupancy at cycle 1 day 1 was 99% for Arm 1 (0.3 mg/kg nivolumab; FIG. 6A), 99% for Arm 2 (2 mg/kg nivolumab; FIG. 6B), and 96% for Arm 3 (10 mg/kg nivolumab; FIG. 6C), and 97% for all previously treated patients combined; and 102% for treatment-naïve patients (Arm 4; 10 mg/kg nivolumab; FIG. 6D). Median PD-1 occupancy was sustained through cycle 8 day 1 for all treatment groups (≥97%) except the 10 mg/kg previously treated group, where a slight decrease in median occupancy to 83% (range, 56%-90%) was observed at cycle 8 day 1 (FIG. 6A-FIG. 6D).

E. PD-L1 Expression and Objective Response

The association between ORR and PD-L1 expression was assessed in fresh biopsies obtained at baseline (Table 11; n=56). The ORR was higher in tumors with ≥5% PD-L1 expression than in tumors with <5% PD-L1 expression (4/18 [22%] and 3/38 [8%], respectively). In view of the limited number of patients, the relevance of PD-L1 expression status in RCC tumor cells is to be further investigated.

TABLE 11

Objective Response Rate by PD-L1 Expression.

| Fresh tumor samples | PD-L1 Expression[a] | |
|---|---|---|
| | ≥5% | <5% |
| Objective response rate | 4/18 (22%) | 3/38 (8%) |
| 95% CI | 0-60.2% | 0-70.8% |

Note
[a]Expression is based on tumor membrane staining of tumor biopsies prior to first dose; CI, confidence interval.

F. Gene Expression Profiling

Figure 7A:
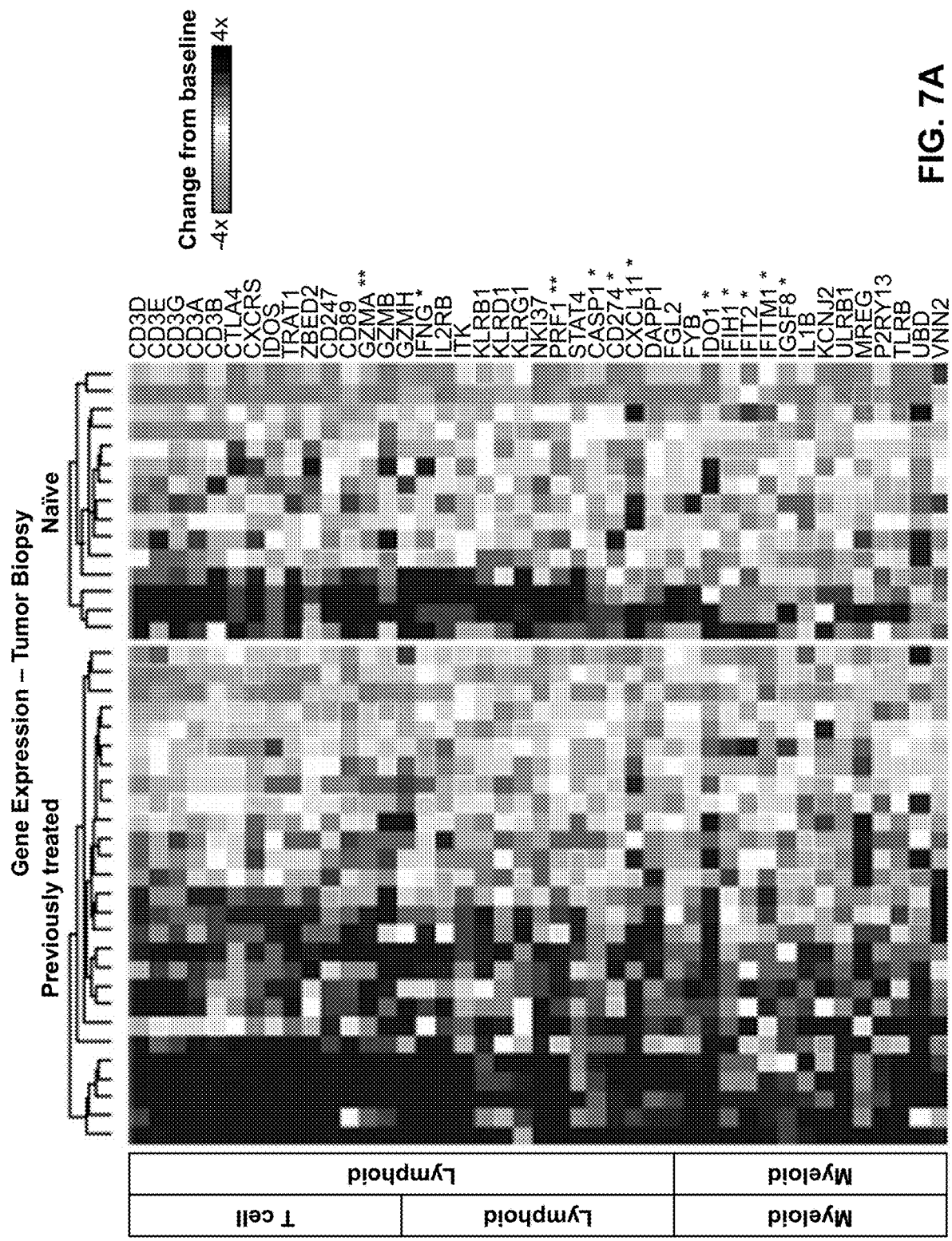
FIG. 7A is a heat map representing microarray expression data, which shows the fold change of the expression level in tumor biopsies of 43 regulated transcripts (>1.3 fold, $p<0.01$) that are specifically associated with either the lymphoid or myeloid immune lineage. Within the lymphoid lineage, 10 transcripts indicated are specific to T cells. Data are included from 42 patients with measures at both time points, separated by their previous treatment status. Genes, listed on the right, labeled by a (**) are members of interferon-regulated transcription modules collated by the BRi2 consortium (Chaussabel et al. (2008) *Immunity* 29:150-64). Markers of immune cytolytic activity are labeled by a (*).

To gain additional insight into the immunological changes in tumors during nivolumab treatment, gene expression profiling was undertaken on baseline and post-treatment tumor biopsies (N=59 at baseline, 55 at cycle 2 day 8, with 42 patients having matched samples). In total, expression of 108 transcripts changed over time based on the significance criteria (>1.3-fold change in mean expression, p<0.01; Table 2, above), including 71 previously associated with immune lineages (Abbas et al. (2005) *Genes Immun* 6:319-31) (p<0.001), all of which increased at cycle 2 day 8. Of these 71 transcripts, 43 were defined as lymphoid—lineage specific (CD3D, CD3E, CD3G, CD8A, CD8B, CTLA-4, CXCR6, ICOS, TRAT1, ZBED2, CD247, CD69, GZMA, GZMB, GZMH, IFNG, IL2RB, ITK, KLRB1, KLRD1, KLRG1, NKG7, PRF1, STAT4) or myeloid-lineage specific (CASP1, IL1B, CXCL11, IFIH1, UBD, CD274, DAPP1, FGL2, FYB, IDO1, IFIT2, IFITM1, IGSF6, KCNJ2, LILRB1, MREG, P2RY13, TLR8, VNN2) (FIG. 7A). In the lymphoid lineage, an increase was observed for CD8A/B and CD3D/E/G, markers of activated T cells such as CTLA-4 and ICOS, and markers of cytolytic activity such as granzyme A (GZMA) and perforin (PRF1). Transcripts associated with the myeloid lineage include the dendritic cell-associated genes UBD, IFIH1, and CXCL11, the PD-1 ligand PD-L1 (CD274), and the immunomodulatory enzyme IDO1. Sixteen of the 108 transcripts were previously identified as interferon-regulated (Chaussabel et al. (2008) *Immunity* 29:150-64), including CXCL9 (MIG). Interferon-γ was the only interferon represented in the 108 genes. Pathway analysis of the 108 genes identified significant effects (p<0.001) on interferon signaling, T cell signaling, and major histocompatibility complex class I antigen presentation processes. In particular with reference to major histocompatibility complex class I antigen presentation we observed up-regulation of the immunoproteasome component PSMB9 and the immunopeptide transporter TAP1, and the T cell components VAV1, TRAC, FYB, CD8A, CD8B, CD3G, CD3D, CD3E, CD274 (PDL1) and CD247. The roles of these components are outlined in FIG. 7B.

To evaluate whether similar transcriptional changes were observed in the periphery, microarray analysis was performed on whole blood samples (N=82 at cycle 1 day 1 and N=74 at cycle 1 day 2, with 70 patients having matched samples; N=73 at cycle 2 day 8). Expression of 59 transcripts changed from baseline to cycle 1 day 2 according to the significance criteria (>1.2-fold, p<0.01; Table 3, above), including 30 previously associated with immune lineages (CCR7, CD27, CD3G, IL7R, NFATC3, P2RY8, RORA, TRAC, TRBC2, AIM2, DDX60L, FBXO6, GBP1, GBP5, IFI35, IFI44, IFI6, IFIH1, IFIT1, IFIT2, IFIT3, IRF7, PARP14, PARP9, SAMD9L, SCO2, STAT1, TAP1, TNFAIP6, and TYMP; Abbas et al. (2005) *Genes Immun*

Figure 7B:
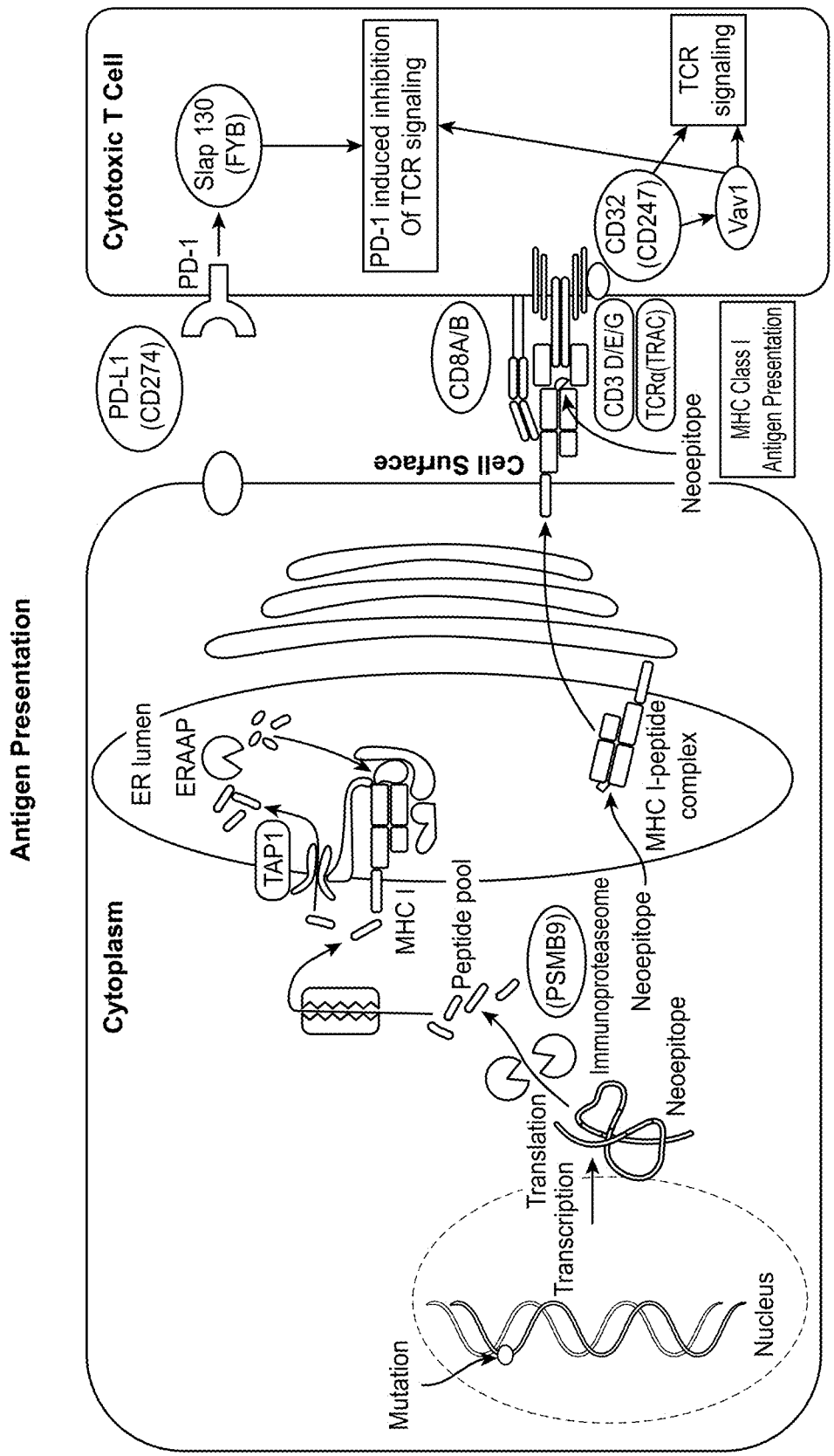
FIG. 7B is a schematic representation of the components of antigen presentation regulated by PD-1.
Figure 7C:
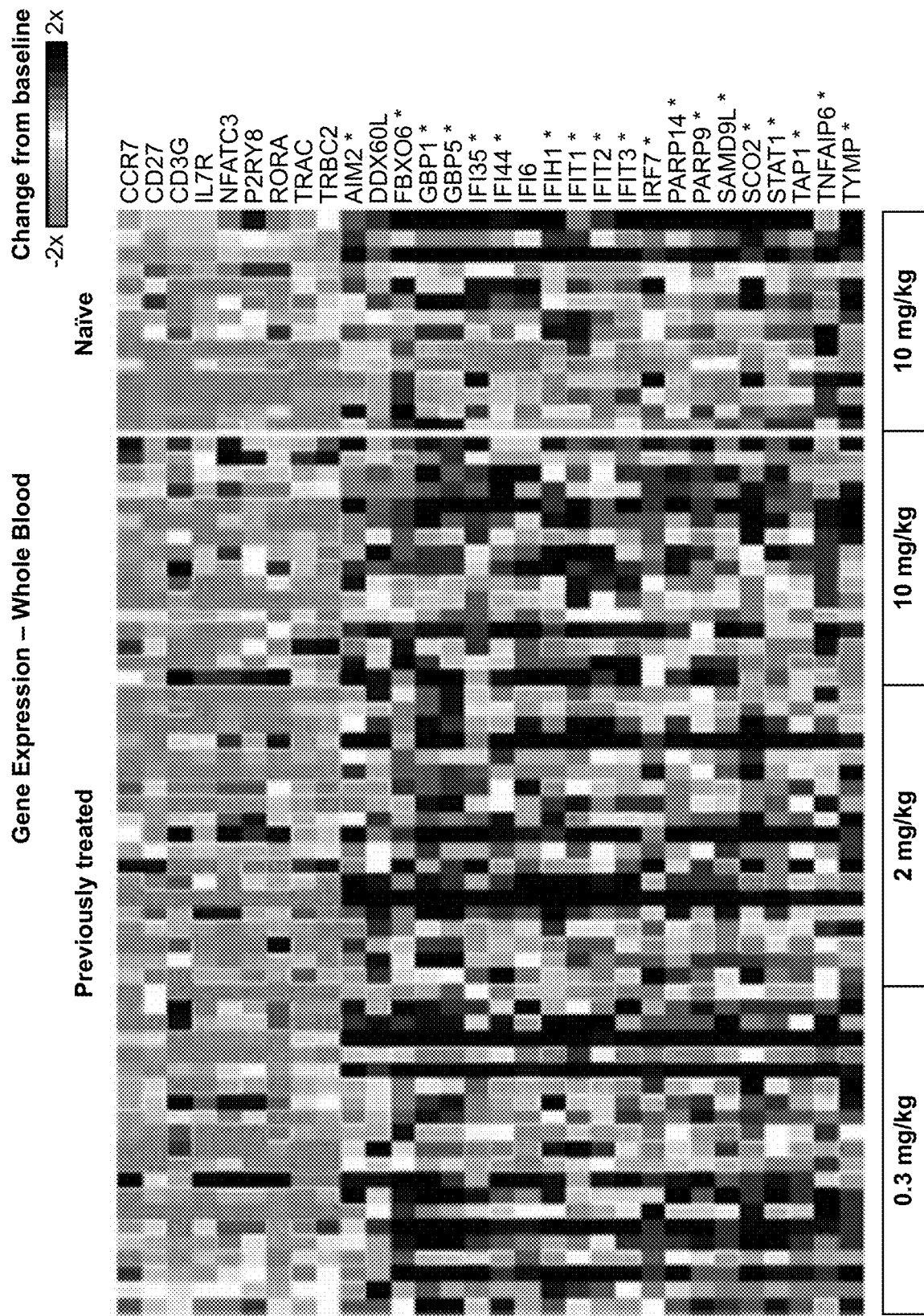
FIG. 7C is a heat map representing microarray expression data, which show the fold change of 30 transcripts in peripheral blood associated with immune lineages and significantly regulated (>1.2-fold, $p<0.01$) in all treatment groups at cycle 1 day 2. Data are included from 70 patients with measures at both time points, separated by treatment group. Genes labeled by a (*) are members of interferon-regulated transcription modules collated by the BRi2 consortium (Chaussabel et al. (2008) *Immunity* 29:150-64).

6:319-31) (p<0.001; FIG. 7C). These included transcripts for T cell receptor α and β subunits and the CD3 γ subunit, which decreased relative to baseline. The 59 transcripts included 29 previously identified as interferon-regulated (Chaussabel et al. (2008) *Immunity* 29:150-64), all of which increased (indicated by an *; FIG. 7C). No transcripts from interferon genes were regulated or detectable in blood.

With two exceptions, the above transcriptional effects were similar between nivolumab dose groups and between previously treated and treatment-naïve patients (p>0.01 for interaction between time and dose group or previous treatment status). Results of analysis for pharmacodynamic transcriptional effects that differ between treatment groups are presented in Table 7 and Table 8, above. Consistent with the efficacy and IHC results described above, this analysis of gene expression did not identify a large effect of dose or previous treatment.

An analysis of the association between gene expression and Response to nivolumab was performed, with evaluable data for 69 patients. 54 patients had <20% reduction in tumor burden (N=43 at baseline and 44 at cycle 2 day 8 with 33 patients having matched samples) and 15 patients had a ≥20% reduction in tumor burden (N=13 at baseline and 11 at cycle 2 day 8, with 9 patients having matched samples). In the gene expression data obtained at baseline, 311 transcripts were found to be differentially expressed (P<0.01, >1.3× difference, and a false discovery rate <16%) in patients who displayed a ≥20% reduction in tumor burden as compared to those patients with a <20% reduction in tumor burden (FIG. 8A, Table 4). Genes observed to have lower expression levels in those patients with a ≥20% reduction in tumor burden included several involved in establishment of protein localization ($P<10^{-5}$), negative regulation of epithelial cell proliferation involved in lung morphogenesis ($P<10^{-4}$), and genes previously identified to be downregulated by ipilimumab in melanoma ($P<10^{-4}$; see, e.g., Ji et al. (2012) *Cancer Immunol. Immunother.* 61:1019-31). Genes with higher expression levels included several upregulated by ipilimumab in melanoma ($P<10^{-23}$; see, e.g., Ji et al. (2012) *Cancer Immunol. Immunother.* 61:1019-31), various immune system genes ($P<10^{-7}$; 45 genes, e.g., IL15RA, IL1R2, and IRF1), including known myeloid lineage genes (e.g., IL1A, LINC00158, PRAM1, and SPI1), and known lymphoid lineage genes (e.g., CD3E, AIM2, GZMB, NKG7, CD7, and CTSW). In particular, the baseline expression levels of MICB, PVRIG NKG7, SPI1 and CLEC2B were significantly higher in patients exhibiting a ≥20% reduction in tumor burden as compared to those with <20% reduction.

In the gene expression data obtained on treatment at Cycle 2 day 8, a total of 779 genes were found to be differentially expressed (P<0.01, >1.3-fold difference, and a false discovery rate <16%) in patients who displayed a ≥20% reduction in tumor burden as compared to those patients with ≤20% reduction (FIG. 8B, Table 5). Genes observed to have lower expression levels in those patients with a ≥20% reduction in tumor burden included an over-representation of cellular component organization genes ($P<10^{-18}$), signaling genes ($P<10^{-16}$), and genes previously identified to be downregulated by ipilimumab in melanoma ($P<10^{-5}$; see, e.g., Ji et al. (2012) *Cancer Immunol. Immunother.* 61:1019-31). Genes with higher expression levels included over-representation of those upregulated by ipilimumab in melanoma ($P<10^{-135}$; see, e.g., Ji et al. (2012) *Cancer Immunol. Immunother.* 61:1019-31), various immune system genes ($P<10^{-82}$; 188 genes), known myeloid lineage genes (51 genes, e.g., CD68, CD86, CASP1, and CSF3R), known lymphoid lineage genes (more than 65 genes, e.g., TCRα/β, CD3D, CD8A, and CD28), cytolytic function genes (e.g., KLRG1, granzymes, and PRF1), interferon regulated genes (24 genes, e.g., AIM2, CASP1, CCL8, and IRF9), and immune checkpoint molecules (e.g., TIGIT, CTLA-4, PD-L2, and IL10RA). In particular, the on treatment expression levels of [ ] CTLA4, PD-L2 (PDCD1LG2), TIGIT, PVRIG, NKG7, SPI1, CLEC2B, CD244, NKTR, TNFSF8, TNFSF13B and TNFRSF14 were significantly higher in patients exhibiting a ≥20% reduction in tumor burden as compared to those with <20% reduction (see, e.g., FIG. 8C-FIG. 8E). Note that PVRIG, NKG7, SPI1, CLEC2B are also among the 311 genes differentially expressed at baseline in patients who displayed a ≥20% reduction in tumor burden. Also, NKTR and TNFSF8, are among the subset (from the 779 genes) of 56 genes that also showed >1.25-fold change in expression upon treatment in patients who displayed a ≥20% reduction in tumor burden, with that change upon treatment being significantly different (P<0.01) from any change upon treatment in those patients with <20% reduction.

G. Interferon-γ-Related Chemokines

Figure 9E:
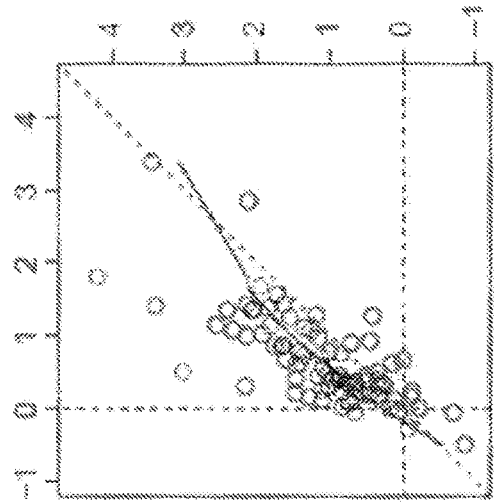
Figure 9F:
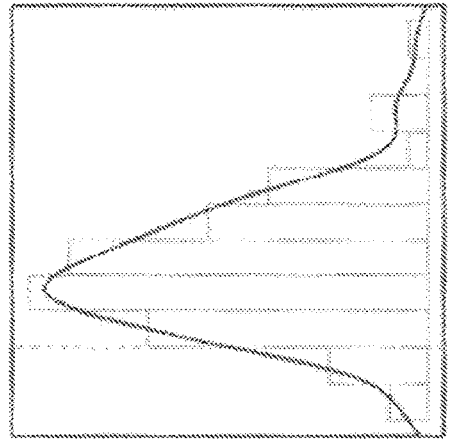
Figure 9G:
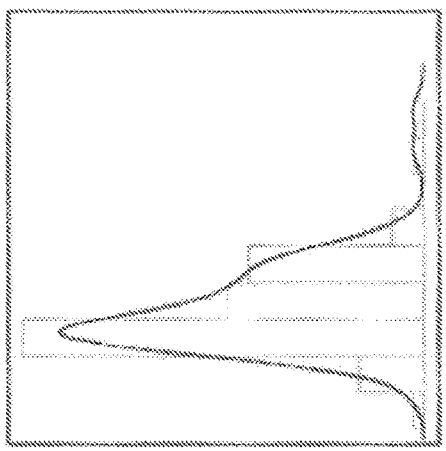
Figure 9H:
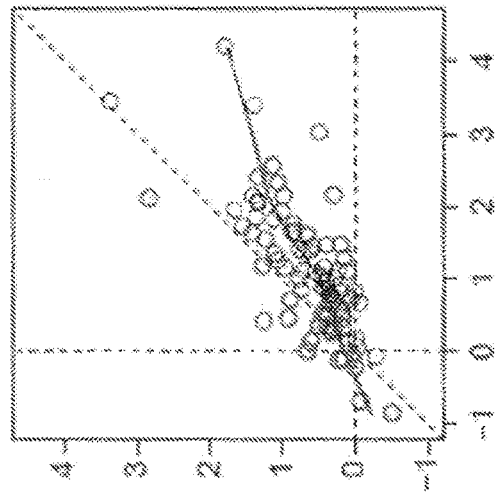
Figure 9J:
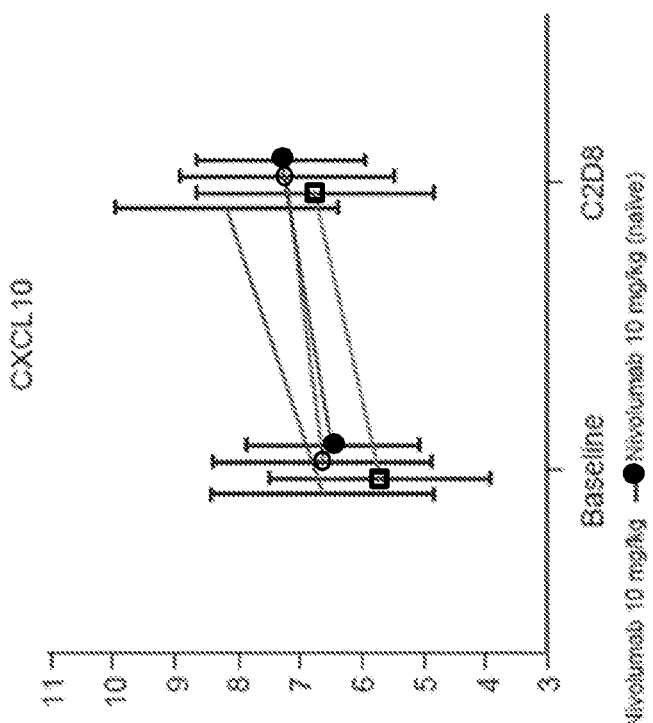
Figure 9K:
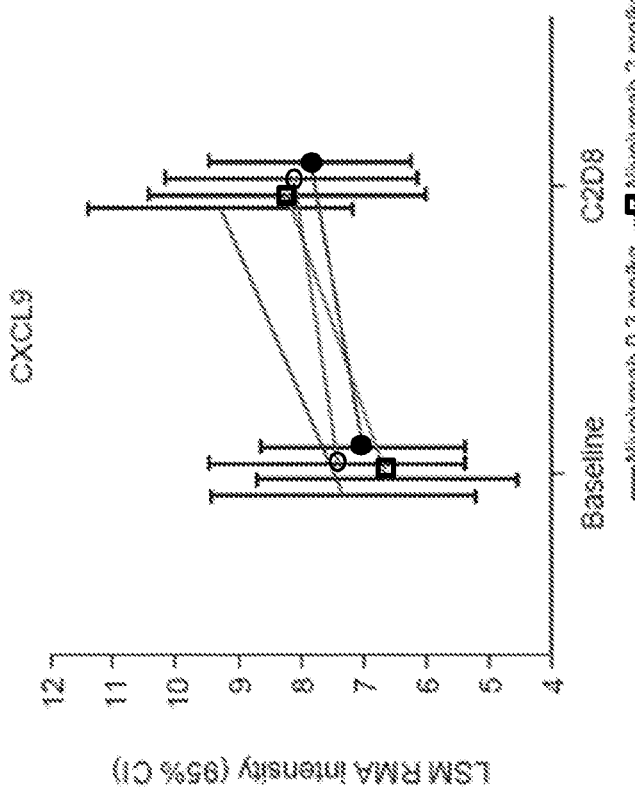

As the observed increases in interferon-γ-regulated chemokine transcripts in tumor could potentially result in an increase in circulating chemokines in the periphery, serum levels of a number of serum-soluble factors were quantified (Table 12). FIG. 9A and FIG. 9B summarize overall survival as a function of levels of select serum chemokines at baseline, and as a function of the corresponding changes from baseline. In serum, increases were noted in CXCL9 (MIG) and CXCL10 (IP-10), with median changes of 1861 pg/ml (range, -2,000 to 22,890) and 157 (range, -398 to 3.930), respectively, from baseline to cycle 2 day 8 (N=85). Median percent change from baseline of these chemokines were 90% (range, -451% to 1,730%) and 37% (range, -30% to 936%), respectively. Most patients had increases in both CXCL9 and CXCL10 and these increases were observed across all baseline values (FIG. 9C and FIG. 9D). Within-patient changes in CXCL9 (FIG. 9E) tended to be greater than within-patient changes in CXCL10 (FIG. 9H). Changes between CXCL9 and CXCL10 were highly associated (FIG. 9F and FIG. 9G). In tumor, mean levels of CXCL9 (FIG. 9J) and CXCL10 (FIG. 9K) transcripts increased from baseline to cycle 2 day 8 (2.4-fold for 4283 at/CXCL9, p=0.0008 [FIG. 9G]; 2-fold for 3627 at/CXCL10, p=0.011 [FIG. 9K]). These observed changes were not associated with nivolumab dose or previous treatment status (data not shown). At cycle 2 day 8, serum levels of CXCL9 and CXCL10 were associated with their mRNA transcript levels obtained from a corresponding biopsy from the same patient (Partial correlation 0.369 for CXCL9, p=0.006 [FIG. 9L]; Partial correlation 0.298 for CXCL10, p=0.029 [FIG. 9M]).

TABLE 12

| List of Serum-soluble Factors Quantified | |
|---|---|
| Stem cell factor | Vascular epithelial growth factor-3 |
| Brain-derived neurotrophic factor | Vascular epithelial growth factor |
| Vascular epithelial growth factor-2 | RANTES |
| Vitamin D binding protein | Von Willebrand factor |
| α-2 macroglobulin | ICAM-1 |
| MCP-1 (CCL2) | α-1 antitrypsin |
| CXCL 10 (IP10) | VCAM-1 |
| Eotaxin | TNF RII |
| Haptoglobin | TIMP-1 |
| Ferritin | IL2-RA |
| MMP-3 | C reactive protein |
| IL-18 | Factor VII |

TABLE 12-continued

List of Serum-soluble Factors Quantified

| β-2-microglobulin | Complement 3 |
|---|---|
| CXCL9 (MIG) | MIP-1 β (CCL4) |

H. T-Cell Receptor

T-cell sequencing was used to determine the T-cell receptor (TCR) repertoire in patients pre- and on treatment with nivolumab (FIG. 10A-FIG. 10C). Tumor T-cell frequency increased from an average log (HR) score of about −0.75 pre-treatment to about −0.4 on treatment, with an increased hazard ration (95% CI) from 0.5 (0.2, 0.9) to 0.7 (0.3, 1.3) (FIG. 10D). Tumor clonality of T-cells increased from an average log (HR) score of about −0.5 pre-treatment to about −0.3 on treatment, with a decreased hazard ration (95% CI) from 0.7 (0.3, 1.2) to 0.8 (0.5, 1.4) (FIG. 10E). Blood clonality of T-cells decreased from an average log (HR) score of about 0.2 to 0.1, with a decreased hazard ration (95% CI) from 1.2 (0.8, 1.7) to 1.1 (0.8, 1.6) (FIG. 10F).

IV. Discussion

This is the first translational study involving analysis of both pretreatment and on-treatment biopsies aimed specifically at understanding the immunomodulatory activity of an anti-PD-1 antagonist, e.g., nivolumab, seeking to identify cellular signals associated with T cell reactivation in mRCC. Nivolumab demonstrated an immunomodulatory effect of PD-1 inhibition through multiple lines of evidence across all doses studied.

Clinical activity was observed in both treatment-naïve and previously treated patients at each dose. Median OS was 16.4-25.2 months for previously treated patients, similar to that seen in another recent randomized dose-ranging phase 2 study of nivolumab (Motzer et al. (2014) *J Clin Oncol* 33:1430-37). Median OS was not reached for treatment-naïve patients.

The IHC analysis of tumor-associated lymphocyte markers (i.e., CD3+, CD4+, CD8+) showed increased lymphocytic presence in biopsies at cycle 2 day 8 of treatment. These data suggest that nivolumab either increased the tumor trafficking or infiltration of T cells in post-treatment biopsies, facilitated the expansion of T cells already within the tumor microenvironment, or both. A recent study examining mutations and response in lung cancer showed that specific CD8+ T cell responses to the anti-PD-1 therapy pembrolizumab paralleled tumor regression (Rizvi et al. (2015) *Science* 348:124-28), suggesting that the observed increases in tumor-associated lymphocytes could contribute to the clinical effects of nivolumab. Furthermore, a study in metastatic melanoma showed immune infiltrates only in pembrolizumab responders (Tumeh et al. (2014) *Nature* 515:568-71). The results from the current nivolumab biomarker study in mRCC are not consistent with these findings in melanoma, potentially due to a difference in tumor biology. In the current nivolumab study, some level of induction of tumor-associated lymphocytes was noted in the majority of patients on study across all nivolumab doses.

Nivolumab demonstrated high, sustained PD-1 receptor occupancy on circulating T cells from baseline to cycle 8 day 1 at all dose levels, with no notable differences between previously treated and treatment-naïve patients. Even 0.3 mg/kg nivolumab was sufficient to achieve near-complete saturation of the PD-1 receptor in previously treated patients (>90%). This was higher than the PD-1 receptor occupancy reported in a recent nivolumab study (median, 64%-70%) for a mixed population of patients with various solid tumors (Topalian et al. (2012) *N Engl J Med* 366:2443-54), suggesting either potential differences between patients with different solid tumors or variations between techniques.

There was a lack of concordance in PD-L1 expression in the fresh and archived samples. In this nivolumab study, objective responses appeared to be more frequent in patients whose fresh biopsies showed ≥5% PD-L1 expression, similar to findings from another study in patients with RCC (Motzer et al. (2014) *J Clin Oncol* 33:1430-37). Archived samples were typically obtained from patients at diagnosis, suggesting that the tumor biology may change over time and that association with clinical response may be better assessed in samples taken proximal to the latest treatment. Clinical responses to PD-L1 blockade have been observed in patients with tumors expressing high levels of PD-L1, especially when PD-L1 was expressed by tumor-associated lymphocytes (Herbst et al. (2014) *Nature* 515:563-67). Several patients in the present study classified as showing <5% PD-L1 expression demonstrated objective responses to nivolumab. This is consistent with data previously reported in RCC (Motzer et al. (2014) *J Clin Oncol* 33:1430-37), melanoma (Robert et al. (2015) *N Engl J Med* 372:320-30), and squamous cell non-small-cell lung cancer (Carbone et al. (2014) *J Clin Oncol* 32:Abstract TPS8128). Recognition of the tumor by T cells during the adaptive immune response mediates interferon-γ production and release. Thus, nivolumab-induced T cell reactivation was expected to increase interferon-γ-regulated transcripts and proteins in tumors and potentially elsewhere. Using gene expression profiling in tumor biopsies, interferon-γ transcripts and interferon-regulated transcripts were found to have increased in tumors, while only interferon-regulated transcripts rapidly and transiently increase in whole blood following nivolumab treatment. Transcripts for T cell receptor subunits (CD3γ, TCRα, TCRβ) rapidly and transiently decreased in whole blood after treatment with nivolumab, suggesting that treatment with nivolumab may prompt T cells to exit the periphery. These effects in the blood were concurrent with a transient decrease in levels of CD27 transcript, an immune cell marker important for long-term maintenance of T cell immunity (DeBarros et al. (2011) *Eur J Immunol* 41:195-201). In tumor biopsies, expression of genes from lymphoid- and myeloid-specific lineages was elevated at cycle 2 day 8 of study treatment, indicating that both cell types have an increased presence upon treatment. These effects are in line with observations from previous studies that demonstrated enhanced T cell activation and increased expression of interferon-γ at the tumor site, resulting from PD-L1/PD-L2 blockade or PD-1 inhibition (Brown et al. (2003) *J Immunol* 170:1257-66; Rodig et al. (2003) *Eur J Immunol* 33:3117-26; Peng et al. (2012) *Cancer Res* 72:5209-18).

Chemokines are known to guide the trafficking behavior of T cells as part of the immune response against tumors. In this study, increased transcription of genes for the key chemokines CXCL9 and CXCL10 at the tumor site was observed following treatment with nivolumab, potentially induced through interferon-γ production. Furthermore, high serum concentrations of CXCL9 and CXCL10 at cycle 2 day 8, in the absence of their transcripts in whole blood at cycle 1 day 2 or cycle 2 day 8, suggest that the tumor is the source of these chemoattractants (Ji et al. (2012) *Cancer Immunol. Immunother.* 61:1019-31). Nearly all patients on study showed some induction of these chemokines. These findings were consistent with the transcriptional changes in the tumor and peripheral blood.

The type and frequency of AEs were similar in both previously treated and treatment-naïve patients, and the pattern and type of AEs were also consistent with previous reports of nivolumab in mRCC, advanced metastatic melanoma, colorectal cancer, castrate-resistant prostate cancer, and non-small-cell lung cancer (Brahmer et al. (2010) *J Clin Oncol* 28:3167-75; Drake et al. (2013) *J Clin Oncol* 31:Abstract 4514; Motzer et al. (2014) *J Clin Oncol* 33:1430-37). There was no obvious dose-dependent relationship, and the rate of severe AEs was low. Overall, nivolumab was well tolerated.

Nivolumab monotherapy demonstrated immunomodulation consistent with PD-1 inhibition in the majority of patients, as evidenced by serial analysis of tumor-associated lymphocytes, genome-wide RNA profiling, and analysis of chemokines and related cell markers. The analysis of the tumor microenvironment in pretreatment versus on-treatment patient biopsies afforded key insights beyond the scope of xenograft models and the limited number of biomarker studies that exist for anti-PD-1 therapies in mRCC, which used only pretreatment biopsies to evaluate treatment responses. These on-treatment changes in tumor and peripheral blood gene expression and serum immune markers were not dose dependent and were similar between previously treated and treatment-naïve patients. In particular, data presented here and elsewhere continue to point to the critical role of Th1 response factors such as CXCL9 and CXCL10 in the anti-tumor activity observed with checkpoint inhibitors (Ji et al. (2012) *Cancer Immunol. Immunother.* 61:1019-31). This study also adds to the growing evidence that nivolumab is effective in tumors regardless of PD-L1 expression.

The genes provided in Tables 6, 7, and 8 suggest mechanistic hypotheses for sensitivity to nivolumab therapy involving the presence of both myeloid and lymphoid cell types, and their interaction. In patients exhibiting a ≥20% reduction in tumor burden as compared to those with <20% reduction, an increased presence of NK cells is indicated by transcripts including PVRIG and NKG7 (at baseline) and PVRIG, TIGIT, NKG7, NKTR and CD244 (upon treatment), and an increased presence of myeloid cells is indicated by transcripts including SPI1 and CLEC2B (at baseline and on treatment).

One mechanism of sensitivity may involve differential activation of the cytolytic response of NK and NKT cells. Prior to therapy, MICB and CLEC2B transcripts are elevated in RCC patients exhibiting a ≥20% reduction in tumor burden as compared to those with <20% reduction. Enhanced tumor expression of ligands that bind the NKG2D/KLRK1 receptor (i.e. MICB, MICA, RAET1E, RAET1G, ULBP2, ULBP1, RAET1L, and ULBP3) or NKp80/KLRF1 (i.e. CLEC2B) would enhance NK cell cytolytic activity. Upon therapy, NKTR, CD244, TNFRSF14, PVRIG and TIGIT transcripts are elevated in RCC patients exhibiting a ≥20% reduction in tumor burden as compared to those with <20% reduction. NKTR and CD244 proteins are considered likely to positively modulate the cytolytic activity triggered by nivolumab, TNFRSF14 has both inhibitory and activating roles, whereas PVRIG and TIGIT are considered to be co-inhibitory receptors and in this context the latter may serve in the feedback inhibition that ultimately controls the immune response unleashed by nivolumab.

Another mechanism of sensitivity may involve differential effects upon adaptive immunity. Upon therapy, TNFSF8 and TNFSF13B transcripts are elevated in RCC patients exhibiting a ≥20% reduction in tumor burden as compared to those with <20% reduction. TNFSF13B/BAFF plays an important role in the proliferation and differentiation of B cells, and engagement of TNFSF8 expressed by human IgD-positive IgM-positive B cells was reported to inhibit class switch DNA recombination and antibody production.

Another mechanism of sensitivity may involve differential effects on antigen presentation. We have noted increased transcripts for 12 proteins involved in Class I antigen presentation among the 108 genes significantly regulated by nivolumab treatment (Table 2; FIG. 7B). Responders to nivolumab therapy may posses intrinsic differences in number or type of antigenic peptides available for presentation through Class I (e.g. neo-epitopes arising from mutational burden of their tumor), and this may further intersect with components represented in Table 6A and Table 7A.

What is claimed is:

1. A method for treating a subject afflicted with a tumor derived from a renal cell carcinoma (RCC) comprising:
    (i) administering to the subject a first dose of an antibody or an antigen-binding portion thereof that binds specifically to a Programmed Death-1 receptor (PD-1) and inhibits PD-1 activity ("anti-PD-1 antibody") or an antibody or an antigen-binding portion thereof that binds specifically to a Programmed Death-Ligand 1 (PD-L1) and inhibits PD-L1 activity ("anti-PD-L1 antibody"); and
    (ii) administering a second dose of the anti-PD-1 antibody or the anti-PD-L1 antibody to the subject, wherein a tumor sample obtained from the subject exhibits an increased expression level of cytotoxic T-lymphocyte antigen ("CTLA-4"), T-cell immunoreceptor with Ig and ITIM domains ("TIGIT"), Programmed Death-Ligand 2 ("PD-L2"), or any combination thereof after (i) relative to the expression level of CTLA-4, TIGIT, PD-L2, or any combination thereof, prior to (i).

2. The method of claim 1, wherein after the administration of the first dose, the subject further exhibits an increased T cell count in the tumor.

3. The method of claim 1, wherein the first dose of the anti-PD-1 antibody comprises more than one dose, and wherein the first dose of the anti-PD-1 antibody is administered at a dose of about 1 mg/kg body weight once about every three weeks.

4. The method of claim 1, wherein the first dose of the anti-PD-L1 antibody is administered at a flat dose of at least about 1200 mg.

5. The method of claim 1, wherein the expression of CTLA-4, TIGIT, PD-L2, or any combination thereof is a protein expression measured by an immunohistochemistry, an ELISA, a western blot, a protein array or any combination thereof.

6. The method of claim 1, wherein the expression of CTLA-4, TIGIT, PD-L2, or any combination thereof is a nucleotide expression measured by an in situ hybridization, a DNA or RNA array or polynucleotide hybridization technique, a tumor sequencing technique, a quantitative polymerase chain reaction (PCR), or any combination thereof.

7. The method of claim 1, wherein the tumor further expresses PD-L1.

8. The method of claim 1, wherein the anti-PD-1 antibody is nivolumab.

9. The method of claim 1, wherein the anti-PD-1 antibody is pembrolizumab.

10. The method of claim 8, wherein the first dose comprises more than one dose, and wherein the first dose is administered at a dose of about 240 mg once about every 2 weeks.

11. The method of claim 1, wherein the anti-PD-L1 antibody is BMS-936559, MPDL3280A, MEDI4736, or MSB0010718C.

12. The method of claim 1, which further comprises administering one or more additional anti-cancer agents.

13. The method of claim 12, wherein the anti-cancer agent is selected from the group consisting of an antibody or antigen-binding portion thereof that binds specifically to CTLA-4 and inhibits CTLA-4 activity ("anti-CTLA-4 antibody or antigen-binding portion thereof"), a chemotherapy, a platinum-based doublet chemotherapy, a tyrosine kinase inhibitor, an anti-VEGF inhibitor, and any combination thereof.

14. The method of claim 13, wherein the anti-cancer agent is an anti-CTLA-4 antibody or antigen-binding portion thereof.

15. The method of claim 14, wherein the anti-cancer agent is ipilimumab.

* * * * *